US007566558B2

(12) United States Patent
Sherman et al.

(10) Patent No.: US 7,566,558 B2
(45) Date of Patent: Jul. 28, 2009

(54) NUCLEIC ACIDS AND POLYPEPTIDES INVOLVED IN THE PRODUCTION OF CRYPTOPHYCIN

(75) Inventors: David H. Sherman, Ann Arbor, MI (US); Zachary Q. Beck, Ann Arbor, MI (US); Yousong Ding, Ann Arbor, MI (US)

(73) Assignee: Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 11/830,656

(22) Filed: Jul. 30, 2007

(65) Prior Publication Data

US 2008/0090277 A1    Apr. 17, 2008

Related U.S. Application Data

(60) Provisional application No. 60/820,715, filed on Jul. 28, 2006.

(51) Int. Cl.
C12N 9/10     (2006.01)
C12N 9/00     (2006.01)
C12N 15/00    (2006.01)
C12N 1/20     (2006.01)
C12N 1/00     (2006.01)
C12P 21/06    (2006.01)
C07H 21/04    (2006.01)

(52) U.S. Cl. ...................... 435/193; 435/183; 435/69.1; 435/320.1; 435/252.3; 435/254.11; 536/23.2

(58) Field of Classification Search ........................ None
See application file for complete search history.

(56) References Cited

U.S. PATENT DOCUMENTS

| | | | |
|---|---|---|---|
| 4,683,195 A | 7/1987 | Mullis et al. |
| 4,683,202 A | 7/1987 | Mullis |
| 4,800,159 A | 1/1989 | Mullis et al. |
| 4,845,085 A | 7/1989 | Sesin |
| 4,845,086 A | 7/1989 | Sesin |
| 4,874,748 A | 10/1989 | Katz et al. |
| 4,965,188 A | 10/1990 | Mullis et al. |
| 5,063,155 A | 11/1991 | Cox et al. |
| 5,098,837 A | 3/1992 | Beckmann et al. |
| 5,149,639 A | 9/1992 | Katz et al. |
| 5,672,491 A | 9/1997 | Khosla et al. |
| 5,712,146 A | 1/1998 | Khosla et al. |
| 5,830,750 A | 11/1998 | Khosla et al. |
| 5,843,718 A | 12/1998 | Khosla et al. |
| 5,945,315 A | 8/1999 | Moore et al. |
| 5,952,298 A | 9/1999 | Moore et al. |
| 5,962,290 A | 10/1999 | Khosla et al. |
| 6,013,626 A | 1/2000 | Moore et al. |
| 6,022,731 A | 2/2000 | Khosla et al. |
| 6,090,601 A | 7/2000 | Gustafsson et al. |
| 6,399,789 B1 | 6/2002 | Santi et al. |
| 6,492,562 B1 | 12/2002 | Ashley et al. |
| 6,524,841 B1 | 2/2003 | McDaniel et al. |
| 6,589,968 B2 | 7/2003 | Arslanian et al. |
| 6,660,862 B2 | 12/2003 | Reeves et al. |
| 2002/0065261 A1 | 5/2002 | Corbett et al. |
| 2003/0219872 A1 | 11/2003 | Hucul et al. |

FOREIGN PATENT DOCUMENTS

| | | |
|---|---|---|
| WO | WO 95/08548 | 3/1995 |
| WO | WO 96/40968 | 12/1996 |
| WO | WO 97/02358 | 1/1997 |
| WO | WO 98/27203 | 6/1998 |
| WO | WO 98/49315 | 11/1998 |
| WO | WO 93/13663 | 7/2003 |

OTHER PUBLICATIONS

Whisstock et al., Prediction of protein function from protein sequence. Q. Rev. Biophysics., 2003, vol. 36 (3): 307-340.*
Guo et al., Protein tolerance to random amino acid change. PNAS., 2004, vol. 101 (25): 9205-9210.*
Broun et al., Catalytic plasticity of fatty acid modification enzymes underlying chemical diversity of plant lipids. Science, 1998, vol. 282: 1315-1317.*
Witkowski et al., Conversion of b-ketoacyl synthase to a malonyl decarboxylase by replacemnt of the active-site cysteine with glutamine. Biochemistry, 1999, vol. 38: 11643-11650.*
Seffernick et al., Melamine deaminase and Atrazine chlorohydrolase: 98 percent identical but functionally different. J. Bacteriol.,2001, vol. 183 (8): 2405-2410.*
Chang et al., Biosynthetic pathway and gene cluster analysis of Curacin A, an antitubulin natural product from tropical marine Cyanobacterium Lyngbya majuscula. J. Nat. Prod., 2004, vol. 67: 1356-1367.*
"NiceZyme View of Enzyme: EC 1.3.99.15," [online]. [retrieved on Nov. 7, 2007]. Retrieved from the Internet: <URL: www.expasy.org/cgi-bin/niceyme.pl?1.3.99.15>, 1 page.
Altschul et al., "Gapped Blast and PSI-Blast: a new generation of protein database search programs," *Nucleic Acids Res.*, 1997, 25(17):3389-3402.
Boddy et al., "Epothilone C Macrolactonization and Hydrolysis Are Catalyzed by the Isolated Thioesterase Domain of Epothilone Polyketide Synthase," *J. Am. Chem. Soc.*, 2003, 125:3428-3429.
Challis et al., "Predictive, structure-based model of amino acid recognition by nonribosomal peptide synthetase adenylation domains," *Chem. Biol.*, 2000, 7:211-224.
Chiu et al., "Molecular cloning and sequence analysis of the complestatin biosynthetic gene cluster," *Proc. Natl. Acad. Sci. USA*, 2001, 98(15):8548-8553.

(Continued)

*Primary Examiner*—Richard Hutson
*Assistant Examiner*—Ganapathirama Raghu
(74) *Attorney, Agent, or Firm*—Fish & Richardson P.C.

(57) ABSTRACT

The present invention provides polypeptides involved in cryptophycin biosynthesis and the nucleic acid molecules that encode such polypeptides. The nucleic acid molecules and polypeptides of the invention or variants thereof can be used in the methods of the invention to produce cryptophycins.

5 Claims, 47 Drawing Sheets

OTHER PUBLICATIONS

Dayhoff et al., "A Model of Evolutionary Change in Proteins," *Atlas of Protein Sequence and Structure*, 1978, vol. 5, suppl. 3, 345-352, The National Biomedical Research Foundation, Silver Spring, MD.

Eaton, "Organization and Evolution of Naphthalene Catabolic Pathways: Sequence of the DNA Encoding 2-Hydroxychromene-2-Carboxylate Isomerase and *trans-o*-Hydroxybenzylidenepyruvate Hydratase-Aldolase from NAH7 Plasmid," *J. Bacteriol.*, 1994, 176(24):7757-7762.

Fu et al., "Engineered Biosynthesis of Novel Polyketides: Stereochemical Course of Two Reactions Catalyzed by a Polyketide Synthase," *Biochemistry*, 1994, 33:9321-9326.

Eggen et al., "Total Synthesis of Cryptophycin-24 (Arenastatin A) Amenable to Structural Modifications in the C16 Side Chain," *J. Org. Chem.*, 2000, 65:7792-7799.

Golakoti et al., "Structure Determination, Conformational Analysis, Chemical Stability Studies, and Antitumor Evaluation of the Cryptophycins. Isolation of 18 New Analogs from *Nostoc* sp. Strain GSV 224," *J. Am. Chem. Soc.*, 1995, 117:12030-12049.

Golakoti et al., "Total Structures of Cryptophycins, Potent Antitumor Depsipeptides from the Blue-Green Alga *Nostoc* sp. Strain GSV 224," *J. Am. Chem. Soc.*, 1994, 116:4729-4737.

Ishikawa and Hotta, "FramePlot: a new implementation of the Frame analysis for predicting protein-coding regions in bacterial DNA with high G+C content," *FEMS Microbiol. Lett.*, 1999, 174:251-253.

Jacobsen et al., "Spindly, a tetratricopeptide repeat protein involved in gibberellin signal transduction in *Arabidopsis*," *Proc. Natl. Acad. Sci. USA*, 1996, 93:9292-9296.

Kim et al., "Evidence for the role of 2-hydroxychromene-2-carboxylate isomerase in the degradation of anthracene by *Sphingomonas yanoikuyae* B1," *FEMS Microbiol. Lett.*, 1997, 153(2):479-484.

Kinzie et al., "Posttranslation Hydroxylation of Human Phenylalanine Hydroxylase Is a Novel Example of Enzyme Self-Repair within the Second Coordination Sphere of Catalytic Iron," *J. Am. Chem. Soc.*, 2003, 125(16):4710-4711.

Kneller et al., "Improvements in Protein Secondary Structure Prediction by An Enhanced Neural Network," *J. Mol. Biol.*, 1990, 214:171-182.

Kohli et al., "Biomimetic synthesis and optimization of cyclic peptide antibiotics," *Nature*, 2002, 418:658-661.

Kohli et al., "Chemoenymatic Route to Macrocyclic Hybrid Peptide/Polyketide-like Molecules," *J. Am. Chem. Soc.*, 2003, 125:7160-7161.

Lamb et al., "Tetratrico peptide repeat interactions: to TPR or not to TPR?" *Trends Biosci.*, 1995, 20:257-259.

Landegren et al., "A Ligase-Mediated Gene Detection Technique," *Science*, 1988, 241:1077-1080.

Leahy et al., "A Method for Attachment of Peptides to Solid Surface with Enhanced Immunoreactivity," *BioTechniques*, 1992, 13(5):738-743.

Littlechild, "Haloperoxidases and their role in biotransformation reactions," *Curr. Opin. Chem. Biol.*, 1999, 3:28-34.

Magarvey et al., "Biosynthetic Characterization and Chemoenzymatic Assembly of the Cryptophycins. Potent Anticancer Agents from *Nostoc* Cyanobionts," *ACS Chem. Biol.*, 2006, 1(12):766-779.

Marahiel et al., "Modular Peptide Synthetases Involved in Nonribosomal Peptide Synthesis," *Chem. Rev.*, 1997, 97:2651-2673.

Martinez et al., "A Structural Approach into Human Tryptophan Hydroxylase and its Implications for the Regulation of Serotonin Biosynthesis," *Curr. Med. Chem.*, 2001, 8(9):1077-1091.

McDaniel et al., "Engineered Biosynthesis of Novel Polyketides," *Science*, 1993, 262:1546-1550.

Nakazawa et al., "UV and skin cancer: Specific p53 gene mutation in normal skin as a biologically relevant exposure measurement," *Proc. Natl. Acad. Sci. USA*, 1994, 91:360-364.

Neilan et al., "Nonribosomal Peptide Synthesis and Toxigenicity of Cyanobacteria," *J. Bacteriol.*, 1999, 181(13):4089-4097.

Patten et al., "Applications of DNA shuffling to pharmaceuticals and vaccines," *Curr. Opin. Biotechnol.*, 1997, 8:724-733.

Ramjee et al., "*Eschericia coli* $_L$-aspartate-$\alpha$-decarboxylase: preprotein processing and observation of reaction intermediates by electrospray mass spectrometry," *Biochem. J.*, 1997, 323:661-669.

Rohr, "Combinatorial Biosynthesis—An Approach in the Near Future?" *Angew. Chem. Int. Ed. Engl.*, 1995, 34(8):881-885.

Ryle et al., "Interconversion of two oxidized forms of taurine/$\alpha$-ketoglutarate dioxygenase, a non-heme iron hydroxylase: Evidence for bicarbonate binding," *Proc. Natl. Acad. Sci. USA*, 100(7):3790-3795.

Saitoh et al., "Mammalian thioredoxin is a direct inhibitor of apoptosis signal-regulating kinase (ASK) 1," *EMBO J.*, 1998, 17(9):2596-2606.

Sambrook et al., *Molecular Cloning: A Laboratory Manual*, 1989, 2nd ed., §§ 7.37-7.57, 9.47-9.57, 11.7-11.8, 11.45-11.57, Cold Springs Harbor Laboratory Press, Cold Spring Harbor, NY.

Schwarzer et al., "Nonribosomal peptides: from genes to products," *Nat. Prod. Rep.*, 2003, 20:275-287.

Sikorski et al., "TPR Proteins as Essential Components of the Yeast Cell Cycle," *Cold Springs Harbor Symp. Quant. Biol.*, 1991, 56:663-673.

Smith and Johnson, "Single-step purification of polypeptides expressed in *Escherichia coli* as fusions with glutathione S-transferase," *Gene*, 1988, 67:31-40.

Solomon et al., "Non-heme iron enzymes: Contrasts to heme catalysis," *Proc. Natl. Acad. Sci. USA*, 2003, 100(7):3589-3594.

Subbaraju et al., "Three New Cryptophycins from *Nostoc* sp. GSV 224," *J. Nat. Prod.*, 1997, 60:302-305.

Tang et al., "Cloning and Heterologous Expression of the Epothilone Gene Cluster," *Science*, 2000, 287:640-642.

van Pée and Unversucht, "Biological dehalogenation and halogenation reactions," *Chemosphere*, 2003, 52:299-312.

Waugh and Long, "Prospects for generating new antibiotics," *Science Progress*, 2002, 85(1):73-88.

Williamson and Brown, "Purification and Properties of $_L$-Asparte-$\alpha$-decarboxylase, an Enzyme That Catalyzes the Formation of $\beta$-Alanine in *Eschericia coli*," *J. Biol. Chem.*, 1979, 254(16):8074-8082.

Wilson et al., "Analysis of Promoters Recognized by PvdS, an Extracytoplasmic-Function Sigma Factor Protein from *Pseudomonas aeruginosa*," *J. Bacteriol.*, 2001, 183(6):2151-2155.

Wu et al., "Biomimetic Synthesis of Gramicidin S and Analogues by Enzymatic Cyclization of Linear Precursors on Solid Support," *Org. Lett.*, 2003, 5(10):1749-1752.

\* cited by examiner

Cryptophycin 1
$C_{35}H_{43}ClN_2O_8$
Exact Mass: 654.27
Mol. Wt.: 655.18
Predominant compound produced by
Nostoc sp ATCC 53789

Cryptophycin 52
$C_{36}H_{45}ClN_2O_8$
Exact Mass: 668.29
Mol. Wt.: 669.20
Synthetic compound chosen
for clinical evaluation

FIG. 5-1

```
PDAM163
TGATATTAGATGTTTAATATCTTAGGAAATTTTGATAAACAGGAAAGCTTATGACTGTCAGTTGCGAGAAC
GGTAAATTTTTAAACATATTTGCTCAACTTTCTCAACCACCAAATACTTTGCCTTCAGCTTAAAAAGCAAA
TATACTTCTTATTCGCTTTGGATATAACGAAAGTTCATATCCCCCTTGTAGCCAGAAGCTTTCGCAAGATC
CTTAAAGTTTTGCACGCCGGTATACTGATGTCCATTGATAACCCAAGTTGGTACACCTGGACTTTCGCCG
CATTGCACAAGTCTGGGTGGGATTGATACCTCTCTTATCGCACTCAACTTTAATACTGTCGTTGATTATT
TGGTAGGCTTGCTTCCCAAAGATTAACTTTTGTTCGTGACAGTGAGGACACCACCAAGAAACATATTCTTT
TGCCCCGATATACACCAAATGCTTCGCCAAGGCTAGTTCTGCCTTCCCTGAAGTGGTAGTGATTTCCCAAC
CGACTCCGTCTGAGGTCGTTCTTTGGGCAGGAAGAAAATAATCGATGGGGACTTTTGGTTGTCTGTTTGT
TGAGCAATATCTGTCAGTAGTGCAGAGCCAGAACTCGTACCAACACAAATAATGGAGAGCGTTAACAGTGC
AAATAAAAAAGGGTGTTTGATAGCCATATTAAATATATACTTTGATTGAATAGTTGTCGAAGCTAACAATT
GTATGTTTAAGATTGTAGTATTTTGTATAACTGATAATACGAAGCCAGAKRATCCCCATCTTATCTTCGTC
ATAATCGAAATTATCATCACCATGTTCTTCATACCACTTTCTTTCTTCCTCCAAAGCGATTTCTCTCTCGA
TGATTTTTCTTTCTAGAATTTCACTTTCTAGAATTTCACTTTCAAGCTTTTCTCTTTCAAATCTTTCTCTT
TCTATTCTTTCTCTTCTCTGCCTTTCTTTCTCTTCTCTTTCTCTCTCAAGTTGAATTAATCGCTGCTCCAC
TCTCTCACAGTAAAAATCCAAGGCTTTACCAGTGGCTGCTCCGGTAATTGCACCACCAGCCAAAAATATTA
TTACAGTTTTCCAGCCTTGAATGGGATTACCGCTCCACTCCAAACTACCCTCATTGAGCCACACTAGTAGG
AAGTAAACGAGAATTCCAATAACAGTATTGATCGGTGCAAAAACTCTCGGTGTCATCTGGGTTTGACGAAG
TATCAGCCATTGCGCCAGGGTGAGAATCACACCAAAGATTGCCGCAGCAATTCCTGAGAGAATCAGATTAC
CTGGGAAACTAAACGGATCTACTGTAAATCTAATGATTAGCGTGATAATAATCGGGGCAGAGAGCAAAAAG
CTCAGAAGTAAGCTAGCGCTAATCGCAAGAAACCAGTAGCGACCGAGATAACCCAGGCGAAATTCTAACAA
CGACTCTTGTACTTCCAAACAAAGTCATCCAAAATGCAATACTCGCGGTCAAATAATCAAGCATTAGCCGT
TGTTTTACCCGTGTGTTGAAGAGGGTATTTCTAGAATACGCCCAAACAGTATTTTGTTGTTGTGGTGGCT
CTGGTGTGGTGTTTTTTTTTTTGATAATTGCTCTATGAGATTTTTCAATGAGTTTTATATTTGGTAGTGCT
TTAAGGCTGCAAAATATAAAAAGCAACGAAAAACCCCATCCTTCATACAGGTTGGGGGATAGATAAAAAA
CATATATTCCATGATGACACAATTCAATATTTGTTCGACTGCTGTCAGCCTAGAGGTGGGCAATGAACAA
ACCACCATCCAGACGCAAGAAAATTACCCCTGCGACATCTGAGGAACCAAAGCTAGCAACTGACCCTGCTC
AGGAAAATACTTCTTTGCACGAAAATCCAGGGGGAGCAACTATCACGGTGACGGCTGTTGAAGTAACAGAT
TTGACCCAGGAAGAACAAAGCTTACGCCTGCATTTAGAACACCGTGTGGAGAGAGCATTTTTGGAGGCGGG
TCAAGCGTTGATGGAGTTGCGGGACAGACGGCTGTACCGTTCCACGCACCGGACTTTTGAAGAATACTGCC
GCGAACGCTTCAATTATAGTCGTGACGCGGCTTACTTGAAGATTTCGGCTACTGTGGTTTATGAGAATCTT
CAAAAGTTTTTGCCGACCATTGGTCGGCAAATTCCAATGCCGACCAACGAACGACAATTGCGTTTTTTGGC
GAAAGCCGAGTTGGAACCGGCTGTGCAAGCGGATGTATGGCGGCAGGCAGTGGAGCAAGCTGGCAATAAGA
TTCCATCCGGTCGCATAGTGAAAGATGTTGTAGATAGGATACGCGAAAGGACGAAAGTACCCAATCCTTAC
CACGTTGGGGAGATATGCGTTCTTCTACCCAAAGATAATGCAGACTTGAGAGGTAAAGCGGGTTATTGGGG
CGTGGTCAGCCATGTTGGAGAATACAGTTGTACACTCCAGATATGGGACGGTGACTATACCGTAAAAATCG
AACACCTGAAATCACTGGAATTACTTGATGAAGATTGCCAATTCATGCAGCAGTTATGTGTGAGGTTACGG
CAGTTGCATCAAGTGGACAGGCGTGACGAGGCTGTGGATTGGCTGTTGCAGTGGTTGGGGAAACAGGCCAA
ACCTTATCTGTCATCCTTGCAGTCAAAGCTGCTGGCGTTGTTGAGAGAGAGTACAACCTGGTTTGGAAGC
AGCAGAAGTGATGAGATAGCTAGTAAACAATAGGTTAATCCAACAAATACACAATGCAACAATTAACTCAT
TGCATGAAAGCGGTAAGCGATCGCGGAGGGTCTGGTAGAGTTGCCATGCTGGAAGGCTTATCGGTTCAAGA
AGAAATCTGAGTAGGTCATGGGAGTGTCCTTTTATAGCCGCCATAACCGGACAGTTACCATTTTTCCCTC
ATGACATAGCACTAAATCTTACCAGCACTTCAAATTAAAGGTAAAGCAGTGCTAGTCATCAGTCACGATGA
TAAATATTTCCATTTAGCATCTCGCATTGTAAGGCTGGATTACGGACATCTTAAGTATGAGTCATGAAAAT
TATGTATTCCAAACCCGACAACTTACTGCATCCACTGTACCCAATCAGGCGCAGATGTCATCAATTGACTA
AACTTATCAGTGTAAGTATCGTCAAACTCTAGCATCACTCCCCATCGCTCATCACTCGTGAATCGGAAAAT
TGGAACTGAAGCCGATGCAGAGGAACATAACCGCCACAAAGCTGAAGTAAGCGCAGCAGATGATTAGCTCT
ACGATCCAGCCCTCTCAATATTGACAAATAGTACACTATGTGAGTTTTCTAAGAAGGTAAGACTAAAACTG
CACTTAAGCGCTTATGTTATCTCCCCTATTTGATGCTTTTGTAGAGGCAAGCCCCGTCAGTGTAATGATGC
GAGTCCTAATGGAAAACATTTTTAATTCCTCGCGAATGAATCAAATATTTGATACATCAAGCGTTCGCCAA
TACTCTCAAGAGCTACTGTTTTCGACTCAGGTGGATTTGATGAGTCTAGTAGTGTGTGGATGTATCCCTC
GGTTCATGCAGCCTATCAGAAGAAGGCAGTGGAGGTAAGTGTCAGCGCCACAGCGTTATACAACAAACTGC
AACGGATTGAACTGCCTGTAAGTCGGGCATTAGTGCATGAGACAGCATCTGACCTCCAGCAGTTGCTGTTG
```

FIG. 5-2

```
ATGTTGAATGTGGAACGCCCCAGTCCTCTAGGAAAACAATATCGGTTGCGGATTGTAGATGGCAGTTGTTT
AGCCGGAACCGAACGCAGACTAGCAGCGCTGCGCCCCATGCAGCCAAACCATTACCCGGAAAAACAATCG
CCATTCTCGACCCAGGGACAAAACTGGTGGTTGATGTGATTCCTTGTGAAGACGGTCATTCCCAAGAACGC
TCCAAGTTTCATCAGGTTTTGGCACAAGTGCAACCCCAACAGGTATGGATTGCAGACCGTAACTTTTGTAC
CGCAGGATTTCTCCATACTATTGCCAAACTTGGAGCGTTTTTTGTGATTCGTCAACACGGGGTTTAGGAT
ACGAGCCTTTTGGTGAGTTACAAGCTGTTGGGTTGTGCCAAACAGGAACTGTGTTTGAACAACAGGTGGAA
ATTGTCCATGAGGGAGGGACTTTTCGGTGTCGCCGTATCGTAGTTAAGTTGACTCGTCCCACCCGTGACCA
ACAGTGGGAAATTGCCATTTTTACCAACTTACCACCCACTGACGCAGACGGCATTCTGGTGCCACAACTCT
ATCAAGGGCGGTGGAGTGTGGAAACTTTATTCCAAACTGTGACCCAAAACTTTCATGGAGAAATTGAAACC
CTAGCTTATCCTAAAGCTGCCTTATTCTCCTACTGCATGGCACTGTCAGCCTACAACCTTTTAGCGACACT
TAAAGCAGTTCTTGGCAGTGTACATGGGGTAGACAAAATCGATATTGGGCTATCCGATTTTTACCTAGTAG
ATGATATCCATTCCATCTATCGGGGCATGATGATTGCTATTCCTCCGGTTCATTGGCAATTCTTTGAGGAG
TTTACCAACATTCAGATGGTAGACGTTCTCCAGCATCTAGCAACCAAAGTACATCTCAAATCTTTTCGCAA
ACACCCCAGAAGTCCCAAAAAGAAACGACCACCACTCTCTGTTGATGGCAAACATTCCCACTGTTCCACTA
CTCGAAAGCTCAAGCAATACAAAGCAGCTCTTGATGCTATCCCGTGAAGCAATTTCATAAAATATGTTATT
TGTCAATATTGAGAGGGCTGGCTCTACGATCCTAACGTGGCAAAACTTACTAGAGAAGAGTAAAAATCCTG
TAATCTTGACCTTGTAGCGAAATAATGGTGCGAAAACTTGGCATGAAATTGTCTAAAACCAGAGGCAACAT
CGTTTGAAGTACTCGATTGTGTTCAAAAAAAATGCCCTTCGTGCGGTCAAGCAATGTGGAATGAATACAAT
AATCCTCGACATATAAGAACGTTAAACGGGGTAGTAGAACTACAACTAAAAATTCGTCGATGTCAAAATAA
TTCATGTCTGCGGTACAAAAAAGCATATCGACCAGAGCAAGAAGGGTCACTCGCTCTACCACAAAACGAAT
TTGGTTTGGATGTGATTTTATAAGGAGCATTACGCTACCAGGAACATAGAAGTGTTCCCCAAATACACGCT
CACCTCGAATTAAAAGGTATATGTATAAGTCAACGAACGGTCACGCACCTAATTGACAGATATGACGAGTT
ACTTTCTTTATGGCTAAAAGACCATAAAAGGTTAAAAGCAATAGTGGCTAATCAAGGACGGGTTATATTAG
CGATCGATGGAATGCAGCCAGAAATTGGACATGAGGTATTATGTATGCTTTGAATCATAATGTGAGAAAAA
TTTTGATCCATAAATTAGAAAAAAGTTAACGAAAATTCAGGCTTTCGTGCTAATCAAAAATTAAAACTTTG
AATCAAATTATGAGTGAGAGTTGAAATTCTGAATCATAACTAGAGAATGAGTTGAAAAAACACAATTGGAC
AAAACTTGCACAAAAAATCCCTGACAAAATTTCTCTAACTTAAACTTTCAATTCAGAATATGGTTCAAATA
CCAATGTTATGGTTCAAAACTTTTACACAAGCTGTTAGGGTAGCATTACTTAGTATTGCTCATGGTTTATG
TCATTATCATTACCTGAAGGAAGCAATTAAACCCATATATGAGGCGGATCGACATGCAAAAAAGGAATAAA
AAAAAGGTTAGAGGATTACGAGACATTGAATGTAGTGTTGTCAATGAAGATCAGAAAATGGCGACTATTA
TTGAAGATTATTGCTCGGCAGTACGTAGTTCTATAACCAATGATGGTCAAACCAATTCGCAATTGACAATT
CGCAATTCGCAGTTGAATTCAAAGTTAGCTCTGAACCCACCCCTGAATTGAGTCTACTGATTTAGAGAATC
AGAGTTAGCTCTGAGACCCATTAATTAACAATTCAACAATTAAGTAATTTCTTGTCTTTAATTGCGAATTG
CGAATTGACAATTGTTTCGGTCATCCACCGTTAGAGGCATCTGGATTAAAGTTACAAGAAAATTTGACGTT
GATAGAACAAAGCTTAGAACGGATGGAAAAAAGTGCTWTACCACCACCTTTAGTCAACCTAAAATACTGA
TAGCCAAGGGATTATCTGCGACTGTATCTTTATTTTCACTTGTTAGGGTTGCATATCAGTGGGTTGATAAA
GCTAGTTATATTCTCAACAATAAAATAGCTTTTGATGCTGCTGGAGTCAAACAAAGTTATCAACAACTGTT
AACAGAAATGTCCCAACAAAATAGAAAGCTGGTACACTGAATACCGCAATCGATAACTTTATAAAAACCA
CCCATAACTACTCGTCTAGACTTTTTCATTGTTACGAAATTGAAGATTTTCCAGAACTAATAATGACTTA
GAACATGCTTTTGGTATGTTACGTCATCATCAACGTCGTTGTACTGGTCGTAAGGTTGCTCCCTCATCCCT
CGTTATTCGTGGCTCTGTCAAACTTGCCTGTGCGTAGGCGTAGCCCGTCGTAGACATCGCTACTAAGCTTC
ACTCTTTTACCGCATCTGATTTAGCACAAGTTGATATTCATACTTGGCTCGAATTACGATCTCAACTGCAA
AAACACCACAAAGCCAGAATTGAACAATATCGATTTCTCAGAGACCCCAAGGGGTTACTTGGCTAATTTAGA
GAGTCGTCTTCTCTAGTAAGTTTTACCATACTAGGTTTTTCTTGTTCTCAAATCCTGTTGCCATGACTCGG
ATCTTGCAGCTAGATGGTAAGAATTATACCCTAGCTCGCATAGTGCCACTTTCAACCCGACGTTGCAGTTC
AGGTAAGTCCGCTTGTCAATAGGGTTTGAGACGCGCTAACCCTGGGGTATGAACACTTAAACGATCATGAA
CAATTACGTCATGACAAGATGTTCGTCTTGGCGAGCAGCATCGCATAAATTTTACCATTTTTAGTATTTC
CAGGCTCTAAGTGTGGAGCAAAGAGTTTCTTTGGAGAGGGATTACCTGTACCAATCCTAATTTTGGCTGAG
TTGTAACATATAGACCATCAACTGCCCCAACTGCCGATAGTATGGAAAATCCCTCGACTGCATTGAAAAAC
TGGGCATTTGTCTTCATTACCTCGTTACCTTTTCCCTTTCGATTGCCAACGCCTGCTTGTCTTGCCTAAT
GCTGTGGCTTGACTGAATCCGCTGAGACATCTCTGCCATAACAAAATCGGCAATCCCTCCTTAGCGTCCT
CCAAGTCCTCGACGCCGGACACCAGATTCAAGAATGCTAGCTTTAGGTTAGAACTGCCGAAGTCACGGCGA
CTAAGCCGTTGTGCCTCCCAGAAATAGGAATCCTTGCCACGGTTTTGATCGTAGAAGGCTGATACGAACAC
TAAGAAACGCAAATAAGCCTGCCGATAGCTCTGATCGTAGAAAGAAGCAGCTTGTGACTCAGTCACCTCGC
```

FIG. 5-3

```
CACGTATAACACTTGTGATACTGGCTGCGGCTAACAAAGCGCTATAAGTAGCAAGATGCACCCCACTCGAT
AGTAGGGGGTCTAGGAAGCAAGCAGCGTCTCCCGATATGAAGTAGGCTGGTCCTGAAAAGGAGTCGGAAGT
GTAAGAGTAATCTTGCTCAACTTTCACGTCTGAGACTAGCTCCCCTAGTGCAACCAGATCCGCTATCAAGG
GACACTCTGCAATCGCCTCCACGTAGATATCCTTCAAGTTCTTAGTCAGTCTCTCCTTGTAGGTTGACTTA
TGCATCACTACACCAACGCTCATAATTTCCTCATCCAAAGGAATTCCCCACACCCAACCATCTGGAATGGA
GCCCAAGGCAATCGCACCCGACTGACCTTTAGGTAGTCTCAAGGCGTTTTTCCAGTACCCCCAGATGCCAA
CATTCTGGAATACGTCGTGTAGACGGCGGTTTTTCAGATACTCCGTCGCCATGATCCCAGCACGACCTGAA
GCGTCAATCATAAAGTCAAAAGAAATCTCCCCGGTAGTATCATTTGATTGTGACCAAGTAGCGCTGCGCGG
GCGATCGCCATCAAAAGACAACTGGCGAATTTTAGTCCCTTCAAAAACCTTCACACCCTGGCTCTTTGAAT
GCTCTAAAAGCAAGTGGTCGAATTCGTCACGGCGAACTTGGAAGCTGTAGGTGTTGTCCCCCGTAAGTTCC
CCAAAATTGAGGCTCCACTTTTCCGTTCCCCATTCTATGTACGCTCCAGGTTTACGCTGAAAGCCATAAGC
TTCAATTTTCTCGCGTACGCCAAGCAGGTCAAAAATTTCTAAAGCAGAGGGCAAAAGAGATTCCCCAACGT
GGTAACGCGGGAATACCTCTCGTTCTAACAGCGTTACATCAAAGCCCTCACGAGCCAATAGGGTAGCAGCA
GTAGATCCAGAAGGTCCCCCTCCGATAATTAGAATCTGTGTGGAATTAGGCAGTGTAGACATTGCAGGTTT
CTTCTCCAAAAGATACAGTATTTTCGCAACAATGGCGGTTGTGTCGCCTAGGGACAAACAATCTGTCTTAC
TCGTGTGGCATTAAGCGACAACTCCAAAGATTTCTTTGATAAACTTGGCTTGAGCTACACTGTTCCCGGC
CGATAAAGATACTTCCACTCCCCTTTAACTTGGATGTAAGTTTCGTCTACCCGCCATGAATCATTCGTCTG
CTTCAAATAAATGAGGACGAATCCGAAATCCAGTTCCAAGCCGCATTTCAACACCCATCAATTCAGGGTGG
AATGATCCACGTCTATGCCTCGCTCCTACATCATCTCCTCCAAGTCCCAATAGAACAACGAGCGGCAGTAC
CAACGCACATTAAGCAGGATGATTTCTGGCAAAAGGTGACGCCATTTGAACAGGGAGCGAGTGGAAATGGA
AAGCTAAGAGCCTGTCAAGAAACAACTTTTACAATTTATTATCTAGAAAGCTTACTGAGAAAGCATTTCTA
GCTCAAAAGAGGCAAGGTTGTTACATGACAAGCTCTAAGCATTAACGACAAGGATTTCCTACCCTGCACTA
TCTCACTCAGCTTTTTGCGACACAACCTTTAAAAGCACACTTTTAAAATGCGATGGGCTTACGCCTTACAG
GTACTTGAGAAACTTGTTGTTTTCATCCACGATAATTTTTTTCGGTTCCTTGATTTCGTCAGTTACCTCGA
ATGCTAGCAATGTGATAAGGTCTCCTGAATTGACTAGGTGGGCGGAGCCACCGTTCATACAGATTACCCCG
GAATTTTCCTCACCTTCTAGGACATAGGTTTCTAGACGATTACCATTAGTGTTGTCCACCACCATAACCTT
TTCACCCGGTAGTATGTCTGCCTTTTCCATCAGAACTTTGTCTACTGTAATACTTCCGATGTAGTTAACGT
TGGCTTCCGTCACCGTCGCTCTGTGAATTTTCGACTTCAACATAATACGCATCGTTTCTTTCCTCATGTGG
CTTTAAATTTCAATTGAGTTGACTGAGAAATATCTGAGCCTATATCTATTTGAGATGGCTGATACTTTTA
GCAAATAAACTCAAGTTTTTGGGGCTATAGAAATACCAAACTTTAAATTTATAATATCAGATTGTCCATC
AAACCAAAGTCGATTTAGTAGCCTATACTCTTGTTTGGAAAATGCAGTTCTTCCATGCAAAACTCTAGTAT
TATCTACAATAATTATTTGGTTTTGTGCAAGTTTAAAAATTACTTGATTGTCAGGATTATTTACAAAGTTT
TCAAATGATTTAAATGCCGCAAAACTTTTCGATTCAACCGAAACATGAGCTGCATTATCTGCTCTAAACCT
TACAATAAGCCCAGCATGATGTTCTTCAAAAATAGGTTTAGTTGCTTTTTTATTATCTCTTTTGACTGTAA
TCGCATCAGGATTAAACAAAGTTAACAATCCAACTGGGTTTGTCCGCTTTAGATGTTCATATACCAGCTTG
CCATCAATAAGCTTGGTGAACCCGCCATTTGCAGCAGCAATCTGGCACTGCATTGCCATTACTTTTGGTGG
AGTAATTGTGAACGCTCCATCCGTATGTAACGATAAATCTGTAGTTGTAGTATTTACATATTCTGGATAAC
TATCAACAGGACTGATGGGAACAATTCCCTGTGAATCAGAATGTTCGTGCTGAATAATTGTTCCAAAATAA
TCAGACAATTTTAATAAGTTATTCTTAGGTGTTGCTGAAGGTTCGTGTTCTAGTATTACGAATCCAAACTC
ATTAAATTTATTTGCCATCTCAGCTTCTTTAGAAACTGGCATTTCTAATACACTTTTCACTCTAATTATTA
GATTTTCAATTTTATTGAATACATTTTAATTTCTCCTGGATGTCACTGCTCTGCTACAACTAGCTTAA
TTTTTTTAGAATTCTCATGTTTACAATAAATACGTTTTCAAAAAAATACTATAAGTCTTGCTGATATAGG
TTGTAAATCCCTCGATATAGCTAGGTAATAATCAAACATAAAATTAAATGCCTCTATTGCATGTTTATTTA
GAGCATGATAAGTATGTTTAAACAGAATTATTTACATTCAGTAGACCAAAAAGCTTTCCAAAAGACTTACC
AGCTATTGATTTTCCTTGGGAATGCAATAATCCGCCGATATAAGCTTTTAAGAGGATGTTTAAAAAATTGG
GAGTTGAGTAAAAATATTTTAAACATCCTCTAATAGTTTAAAATTCAGTTTTTTACAATACAACCATTTT
TAATCCACCTTGAGGATAAATTGAGAAAATATCTCGTACTGGTTTTAAAGGAGGTTTGCCTACCAATTCCA
ATTGCCAATTCCGCAAAATATTAGCCAATACTAACTTCATTTAAACTGAGCAAATGCCATACCAATGCAA
GTTCGGTTACCGCCACCGAAAGGGAAATACTCATAATTTAAAAATTTATTATCTAGAAAACGTTCTGGCTT
AAACTGTTTAGAGTTAGGATATAGTTCTTCCCGGTGGTGAATTAGATAAATACATGGATAAAGACAAGTTC
CTACCTCAAATTGATGACCTCCAATTTCTATTGGCGATTTTACAATTCGAGGAAAAGTAGTTAGACCAACT
GGATATATTCTCAAGGTTTCAGCACAAACTGCATTGAGATAAGGTAATTTGCTTATTTCCGTTGGGTCTGG
ATTATCTCCTAACTCATCTAATTCTTGCAATAACTTGGCTCTTATCTCTGGTAAGTAATGAATCCAATAAT
ATGCCCATGTTATTGCTGCAGATGTAGTTTCATATCCAGAAAAGATAAGTGTCATTAACTCATCTTGCAAC
```

FIG. 5-4

```
TCCTCATCTGTCATTTTTCCTCCATTTTCATCTCGTGCTGCCATCAGCATACTGAGGATATCATTGTTGTA
ATTGTTACAATTTTCTCTACGTTCTTTGATTTCTGCAGAAATGATATTTGCAATCTGACGTTGGCAACGTA
AAAGATTACCCCAGGCACTCCAAGAACCCCAGTCTCTTCTAAACACATTGAAGAAAAGAGAGCTAGAAGCA
AAGGGATTAGTTATAGTGGATACTATTTGATTAACTATCAATTTGAGTTGTTGATAACGTTCCGTTTTATC
TGAACCCAGTAAAACCGTTAACATCGCTCGCAGCGTAATTTCTTTGACTTCCTTGTAAATAATCAATCTTT
GACCAGGTTGCCAATTAGAAGTAACCTGCTTCGTTGCATGGCATATTAGTTCTCCATAGTTAGATATATTT
TGACCATGAAAGCAGGCATCAGTAGTTTACGCTGTCGTTTATGACTACTTCCATCAAGCAAGGTGACGGA
ATTGTTGCCTAAAAAAAATCCTGCTAAATCGTTAGCTTTAGCTTTTCCACTGTCAAAATACTTGTGTTTAT
CAAAAATTTCTTTTATATCCTTAGGATTACTAATAAGTACTAAAGGTTCAAAACCAATAGCTTTGAAGGTA
AAAGTGTCTCCATAGCGTGCTCGACACTCTTCCAAAAATTCACAAGGATTATTAAGCCATTGCAATAAGTT
CCACCAAGATGGTGTAGTGGGACCAGGAAGTAATGAGGATTTAGCAGTATTAATCATTTTAGTTATGCTGG
ATTTGGCGTAAATTTACTAATTAGACTTTGGACACTATTGAATTTCATTTTTCCAATTGATGGGTTTTCTG
TGCTTGTTCAAGAGATATTTGCATTTGTTGAGCCAATACCTTGACATGAGGCTCACTCAGCATTGAAACAT
GATTACCCGGAACTATATGGATTTCCACTTCTCCATCAGAAAACTGATTCCAACCCCATGTTGGCTCTTGG
AAAATGTGAGAATAACTTTCTTGCTCTGGATTTATCTCCTCGCACAAAACAAAGTGATTGGAGTTTTATA
AGTCTTTTCCGGTTCATACTTAATTTGACATTGAGTTTGGAAAACTTGTAATAAACCACGAACAATTTTGA
TATCTGTTTGAGCAGGCAAAAAACCAACTATTTCTAACTTTTGCTTGAAATAATTTAATTGTTGCTCCCAA
GTTAGAGAAGTTAGAGTTTCATAAGATAAAAATAGATTTTCTCCAACAATATCTTCAATAACCTCAGCCAT
TCGACATATCCACTTTGCATTATCCCAGTTAGAAAAATCATTCTGATGATTAGCTTGAGAAGTTGGTGCAG
GAGTATCTAAAATTCCAACATAAGCAACAGACTTTCCAATAAGTTGTAGTTGATTCGCCATTTCAAATACT
ACATGACTGCCAAAGGAATGACCAGCCAAGAAGTAAGGACCAACTGGTTGAACTGTTTGAATTGCTTTAAT
GTGTTGGGAGGCTATTTCTTCAACACTTTTATGAGGTTCGGTTTCACCATCAAGACCTTGTGCTTGTAAAC
CGTATAACGGTTGATTATTTCCAAGATATTGTGCTAAGTGGTGGAAGTAGAGAACATTTCCACCTGCTCCT
GGTACACAGAACAAAGGTGGTAATGAACCGTTTTGTTGAATTGGTACTAATGGAGACCAAAGTTCGGCTCC
GGAATCGGAACCAACAAGAAGTGCTAGTCGTTCAATGGTGGGATTTTGAAAAAGAGTGGCTAAAGGTAAAT
TTTTCTGGAATTGTTGTTGAATCTCGGACATTAGACGGACAGCTAGAAGGGAATGTCCTCCTAAGCTAAAG
AAGTTGTCATGAATACCAATAGAGGGTAGATTGAGAACTTCTTGGAAAATCTCAACTAACTGACGTTCTGT
TTGATTCCGTGGTTTTGTCTGCTCAGAAGTATTCAAACCTCCATATATAGCAGCAATTTGTTCCCGATTAA
TTTCTCCTCTTTGAGTAAGGGGTATTTGTTCAAGTTGGACAAAGTTAATTTGATTGGGTATCCCAAAGCGA
TCGTGTAGTTGTAACTCTTGTAAGGAGAGTGCAGCAAGTTCTGGTGTGGGAGAGGTGAAGTAAGCAGTTAA
TTTCTGCTTGGGCTGACAATCACGAATCAAATGTTCAACATTTGTTTTAGTTCCATCCAATCCGATTAATA
GATTATGTTCCGAACCAGATAAAGCTGCTAAAAATGAGTAAAATCCTTGTTGAGGAGTAATAATAAAATAG
CCCTTAGCACGACTGAGTTCTTGGAATTGATAGCCATGACTTATTCCGGTTTCATTCCACATACTCCAAGA
GCAGCAATAGCTTTGGAAACCGTTTGTTGTTGATAATCGCTCCATGCTGACTGAAAACTATTTGCTGCAC
TATAAGCTGCAACATTGGTTCCTCCAAAGAAACCATTTACAGAACAAAAGTGGACAAATAAAGCATTTTCT
TTATCCTTGAGCAATTGATGCAATACCCAAGTACCGCTAACTTTAGGACGTAAAACAGCAGCGATATTTCC
TGGGGTTTCTTTCTCGATTGGCGTTTCCTGAATAATCCCAGCCATATGAAATACCCCATCAAGTTGAGTCC
TCCATTCTTGTGTTGCTTTTTCTACTACCTGTTGTAAACCTACTAAATCACAAATATCTACAGTTTGATAA
ATTATTGAACCTGGTAGTTTTTCTAATTCTTGATACCTCTGCAATTTGTGCTAGCTTCCTCATTATTATC
TTCAATTTGAGTTCTACCAACTAATATTAAATTTGCTTGATAATGTTCTAATAAGTACTTTGCAATAACAG
TCCCAATTCCTCCAAGCCCTCCTGTAAGTAGATACGTTCCTCCTGGTAGAATCGGAATTTTTGTTTTTCC
TTAGCAGTCATATCTACTGGTTCCAGACCAGACACAAAACGTTCTCTATTGCGTATAGCAACTTCCAATTC
TTTATCAGCAGAATACAGTTCTTGCCAAATATAACTATTGTTGAGTTCTGGTGCTAATGGTAAATCTAAAT
GACGAGTAGTTAACCAAGGCATTTCTTGACTAACAGTTTTAAGTAAGCCTAAAACAGTGGATTTTTCGGGT
TGAATTTTATCTGTGGGATGAACTAATTGGCTTTGATTAGCAATCCATAATAATTTGACTGCTTGCTGTTT
GCCTTGAATTTCTTCTAAAGCTTGTACTAAAAATAGTAAACTGTAAATTCCTTGTTGTTGAGTGGACTCTA
AATTTTCCAAGCTAGAAATTTTTTCAGTCTGCTCGTTGTAGTTCCAAAGATGAAGAATTTGACTAATTACT
TGGCTATTTTGCCTCAAAGAATCAATTAACAAGCGATAGTGTTGTGGATTTCCAGGAACAACAGAATAATG
ATTTGGGCTAATTTGAGCAAAATTTGAACCAATAGTAACTTGAGCATATGGTTGAACAGTTTGGGACATTC
CTCGGTTATCTTGTTGCCAACCCAAATTATCTGTAAATATTAGGGTTAAAGTTTTCTGAGAAGAATAATTG
AGTAAAGTATTTTTACTTTCTTTAATTTGCCATACTTTACGGTAAAACCAGTTGGGAATAGTATTAGTATT
ATCAAGCAACAAGTCTACACGCTGTCTGAGAGATTTAAACTCACCACATTCAAAACGTTGCTTAAGGAGGG
AACGTTGAATTTTACCGATGGAAGTTTTGGGAATCAGTTCTTTATCTATGGGTATTAAATAACTTGGATTT
ATCCCGCAGTATTTTATAACTTGTTCCCTAACCTTTTTCAAAAGCTCTAATAATTGATTCTTCTCAGATAC
```

FIG. 5-5

```
ATACGGAGTGAAAAAGATTACTAATTCTTCGGTATTATTGCTAGCAACGCAGACTCCACAGGCTGCGGTAT
AAGAAACTTCAACCTCTCCTAATTCTTCAACAACAGCTTCTATTTCATGACTATAATAATTAACTCCATTA
ATAATAATGATATCTTTTTGTCGTCCTGTAATCGTTAAGCATCCATCTTTTATAAATCCTAAATCACCTGT
ATTAAACCAACCATCTTCGGTAAATGCTTCCTTATTTGCTTTTGGATTTTGATAATAACCAGAAGTAACGG
TTAATCCTTTGACCTGAAGTAAACCAATTTCACCTTCTGATAATACTTCCATGTCTTGATTGACTATTCTC
AGACAAGTACCCCTAATCGGTTTTCCAAGATTTACAAAGGAATTATCATCTGAACTTGATAAGAGTGAAAA
ATTGTCAGAATAAGTAATACCAGAGGAAACCTCAGCCATTCCCAAGATGGAGTCATAGCATCCCCAGGTA
AGCCAAAGGGAGCAAGTAATTTCAAAAAACGTCTTGCTGTTGCTGCAACAATTTGTTCCGCACCATTTAAC
ATCAAGCGAATAGAAGATAAATTCCAATTCTGCTTTTCTATTTCTTGAACAAAATCATTAATTAAACTATA
AGCAAAGTTAGGAGCAAAAGTAACAGTGACACCAAAAGTATCAATCCAATCCAACCATCTTAAAGGTTTTT
CAATCACTAATTGACTAGTAGCATGAATTTGTTTACATCCTAAATAAATATCCCGGATATGAAAATATATT
AAACCTGCAACATGGTCTAAGGGCATCCAATTTAAGGTTATATCTTCTGGGGTAAAATTATTCATTTGTAT
TGAACCAATAGTCCTACTCAGTAGATTTAAATGGCTCAACTGTACCACCTTAGACATACCTGTACTACCGG
AAGTAAGCATGAACAGTGCTAAATCTTCTGGTTGGGCATTATAGTAATCTTTATCTGTTGAGAACTTTTGT
AAACTTTCAATAGTTTCTAACTTAAAGTTGTCGTCATTTAGATTTGAGACCATTTCTTTAGTTCTGACAA
TGATTTTTTATCTGTTAAAATCAAAGGTCTTTCTAACATCTGCCAACTATTTTGTAATTTATTTAGATTGA
CATTGGGCTGGTCATAGCTTACAGGAATTACAACGGGTACGGAATAAAGCCTCCCAACACACAACCCCAA
AAAGCACTAATAAAATCTTTATTTTCTTTTAATTGCAAAATAACTTTATCTTGTGGCTTAATTCCCAGTTT
TCTGAAGCCACCTAGAATTCTTTGAGCATCTTCTAATAACTGGGCATATGATTGAACTTGTCGGAACCAT
CAGAGTTAATATAAGTGATTCCTTTGTGAGGAAATTTCCCAGCAGTTTTTTGCAGCATCTCCCCTAAAGTT
TCTGGAGATGATTCTGGAAAGATTAATACTTCTTCGTGGCTGATGGCAGGTGATTTATTTCTAATAGGGA
ACTACTCTCTTTTCCCCTAGCAGTTCTGGGAGTTTCAACTGGAGTAGAACCTTGATTGAAAATAGCTTGGA
TTGATGGTAAAAGTTCTTCTAAATGTATCGGAGAAATCGTTTTTACATTTGGCTCAATAAAAACAGCAACT
TTATCAATTTCCGCCTGAGAACCTATTTGTTCTTCCCAAGTGTTAATTAACTCAGAATCAATTATGCTAAT
AGAAGCTAAACCTACTTCATCAACTTCTCCAAAACTTGTCAATGGTAAAGCAGATACTGGTACATAGATGC
AGGGTAATGGGTATCCAGGTAACTGAGATTTTAAATAATGGTGTAAAAACTCCCTAGCCCAAGAACCATCT
TTGACTACGTAAGCGACTAATTTTTGATTGCGTACCATTACATAGCAATCTTCTACCCCTTTCGCTGTTTG
TAAAGCTTGTTCAATACGTTGTAGGTTAATTCGTTGTCCATTAACTGTGACAATTCGATGCTCTTTTCCTA
GCAATTCCAGAGAACCATCGACTCGACGACAACCCCATTCCCCTGTTTTAATAACTTACCCAGTTGGGTA
TGTTCTATGAACTTATAAATTTTTCTGGTTCTGGATGTAACTTGTCTGGGAGTAAATCGCAATTCCCCAA
ATAAATTTCTCCTTCTACACTCAAAGGAACTAATTGTTGATGGTTATCTAAAATGTAAATTTGTAAATTAT
TTGAACTCAGGAAATGAACATATTTATCCAGCAGGTAAGTTGTAGCGATGTTATTGTAACTGTGCAGTACC
TGCTCTTGCTCAGAATCTGTGAATAATGGTAATTCACTTATCTTTTGTTGGGGATTTTCTACAATCGCGCT
ACACAGATTCTGGAAATGAGCAGTCATGCGCTCAATAGTTGACCCATCAAATAAGTCAGTGTTGTATTCCC
ATGAACCCACTAGTGCTTCGGAAGTTTGCTGCATTGATACTGTTAAATCAAACCGGGCTGTTTCTGTTTGA
GAACTCAATAAATTAAGGGTCACACCAGGTAATTCTAATTCACCCATGGGTGCATTCTGCAACACAAACAT
TACCTGGAATAAGGGTGCATAACTCAAAGAGCGTTGTGGTTGTAGTACTTCAACTACCTGTTCAAAAGGCA
CATCCTGATGTTCATAAGCTTCAAGTGTAGTTTCCCTAACTTGTGCCAGCAAATTCTCAAAACTGGGATTA
TCTTCAAAACGGGTTTTCAATACCAAAGTATTGGCAAAAAAGCCAATCAAAGACTCAATTTCACTGCAGTT
GCGATTGGCAATGGGTGAACCAATTAAAATATCTAATTGACCGCTGTAGCGATAGAGTAAAGTGGCAAACG
CTGCGTGCAGGGTCATAAATAAGGTAGTACCCGAGTTCCGAGACAGGGTTTGCAACTTCTCTTTTAAATCA
GTATTTAAACTAAAACTTTGAGTAGTACCCCGGAAAGTTTGCACGGTTGGACGAGGACGGTCAGTAGGTAA
TTGTAACAATTCTGGTGCACCCTCTAACTGAGAAAGCCAGTAATTGAGTTGAGTTTCTAGTACCTTTCCAC
TTAACCATTGTCTTTGCCAAACTGCAAAGTCTGCATACTGGATTGGTAATTCTGCCAAGGGGGATGGTTTT
CCTGCACTAAAAGCTTGATATAAAGTAGATAGTTCTTGGCTGAATATCCCCATTGACCAACCATCAGAGAC
AATGTGGTGCATCGTCAGTAATAACACATATTCTCTGGCATCTAACTGCAATAAACTACACCTGATTAGTG
GTGCAGTTTCTAAGTCAAAGGGGGTAATTGCTGCAAGTTGTGCTTGTTGGTGAAGGACACTTTCCCGTTCT
GTTGCTTCTAGTTGCTGTAAGTCCGCCACACTGATGTTCATGGTGGCTTCTGGGTGAATTACCTGTATTGG
TGTGCCATTCACAGTTCGGAAGCTGGTCGTAGTACTTCATGACGGCGGACTATTTCTGATAATGCTTGTT
GCAAGGCATTAATATCCAACTTTCCAGTGACACGAATTGCTCCTGGCATGTTATAAGTGGCACTTGACCCT
TCAAGTTGGTTGAGGAACCACAACCGGTCTTGTGCAAAAGATAGGGGTAATTGTTGGTTCTGTGTTCTTGG
CTGAATGGGGGGAAGACTTAATGCGCTATTAGTAGTACGTAATTGGGTTAATGTTTGCTCTAATTGAGCTA
CAGTGGGAGAGGAAAAGACTGCACTTAGTTCTATTTCTACTTCAAAGGCAACTCTGAGTCGGGAAATTAAT
CGGGTTGCTAGTAGGGAATGTCCTCCCAATTCAAAGAAGTTGTCATGGATTCCAACATTTTGCACACCTAG
```

FIG. 5-6

```
AATAGAAGCGAAGATGTTGGCTATTATTTCTTCACCCGATGTACGTGGTGGGACATATTCATGTTCTCGGC
TAATTTCTCCATCAGGTGCTGGAAGGGCTTTACGGTCTATTTTACCGCTGGGTGTCAACGGTAAGGTGTCT
AAGATGACAAAGGCACTGGGCATCATGTATTCTGGTAGCTTTTGTTTGAGGAATTCACGCAGGTGATAGGT
ACTTAGTGATTCATCCTCACAGACTATGTAGGCTACTAAACGTTTGCTACCTGGAATATCTTCTATGGCAA
TGACAACGACTTGTTGGATTTGGGGGTGGGTACTGAGGACTGCTTCGATTTCTCCAAGTTCAATGCGGAAG
CCCCGCACCTTCACTTGGTGATCGATACGCCCACAAATTCGATATTACCATCCGGCAGCCAGCGGGCTAG
GTCTCCAGTCCTAAACAATCTTTCTGCTTGTGCCTTTTTACTTTTCCCCCTGTCCTTCACAAACGGGTTGG
GGATAAACTTTTCCCGCGTTAACTCGGGCAGATTTAAATACCCTTTTGCAAGCCCATCTCCGCCGACGTAT
AGCTCACCCGTAACACCAGGTGGCAAAAGATCGCCATACTTGTCGAGGATGTAAATTTGTGTGTTTGAAAT
CGGTTTTCCAATCGGAATCGTATTTCTTTTCAGATATTCTTCTAGAGCTTCTCCTAAATCTGCTCTTCGCT
CGTCTGCCAACTGCAAATGTATTATTTCTTTATGCAGGACAGCAGTTTCCCTATCCCCTGAGCCACTAGGA
AGATTTTTTAAAGCATCAAGTTTCTCTTTACTTTTTGCTTCAATTTGATTTGCGATTCTCAGTTGACTTC
AAAGCATGTAACATCAGCGGCAACTTCTGAAGAGCCGTAGAGATTGAACAATCTGGCAGAGCTGATTTCT
GGTGAAATTCCTTAGCCAAGGTTAGCGGTAAGACTTCACCGCTGCAAAACACATATTTGAGATATCGAAGT
TTTGTCAGTTGTTGGGGCGCATTTTCCAGTATCGCTTTTAATAGCGATGGAACGAGAACAATTCTAGTTAC
CTTTCGATCGCTCAACAGGCTCATTAGCCTGGGAATATTGCCCCGTATATCATCTGGAACGATCACAAGGG
GAATTCCTTTGAGAAGGGGAGAAAATATTTCCGCAACATGATCGCCAAAATTGATGGATGTTTCTGAGAG
CAAATCTCATCTGCCCCAAATGGTAGCATTTCCCAGATCCAATGCAAGCGATTGACAATGCCGCGAAGCGT
GCCGAGAACGGCTTTGGGTTTTCCAGTAGAACCAGACGTATAGATTGCGTATGCAAGGTCATCCAGTGTTG
TTTGCCGATCCAGATTTTCAACGCCTTCCCTAGCAATGACATCCCTATCCCTGTCCAGGCAAACGATATGG
GCATTTGAGGGGAAATCTTTTCGAGCAGAGGCTGCTGGGTCAATATGATATGCACATTGGAATCTTCCTG
CATGAACGCCAGTCGTTCTTGCGGATAGTTCGGATCTAACGGCACATATACACCACCAGCTTTAAGTATCC
CCAACAGTCCTACAATCATATCAATGGAGTATTCTATGCAAATACCCACCAGCACTTCTGGTTTCACTCCC
AGAGTTTGTAGATAATGTGCTAATTGGTTCGCTTTTTGATTTAATTGTTGGTAGGTTGATTGTTCTTCTTC
AAACACCACTGCTATGGAGTTGGGGTTTTTTCTACCTGTTGCTCAAATAACTGATGAATACATTTATCAG
ATGGGTAATCCGTTGCAGTGTTATTCCACTCAACCAATAACTGATGACGTTCTACTTCACTTAATAAAGGT
AATTGAGCTACCTTATGTGAAGGATTTTCCACAATTGCAATTGCTGATAAAACAGTTTGCAGATATCCTAA
AATCCACTCAATAGTATTTGAAGAGAAACGAGCAGTATCGTAACTAATCCTAACTGACAACTTATCCCCAG
GAACTGCAACTAAAGTTAGTGGATAATTAGTTTGTTCAAAAACCTCTATATCACCTAAGTGTAATGAACCT
TCTTCATTCAACAAAGAATTATCAATTGGATAATTCTCAAACACCACAATGCTCTCAAACAAAGGTATTCC
ACCTGGTATCTCAGAAGTAGCTTGAATATCAACAAGAGGAGTATAAAAATACTCTTGTAATTCAACCATTG
ACTGTTGTATTTTTTGCAACCAAGGTATGAGTTGCTCCTGGGTGGATACTTGTACTCGTAAGGGAAGGGTG
TTAATAAACAGTCCTACCATATTTTCTATCTCAGAGAGGCTAGGAGGACGACCAGAAACAGTCACACCAAA
TACTACATCTTTCTCACCACTATAACGACTCAATAGTAAAGCCCAAGCAGCTTGTACTACAGTTGATAAAG
TCACATGATGTTGTTGTGCTATATGAAGTAACTTCTGAGTGCATTCAGGGGATAAACTACTTGTTCTCTCC
TGATAATCCGCAGTTTTATACTGTTGCTCTTTCAGAAATTGAGTTTTATCCATTACCAATGGAGTGGGAGC
ACTAAAACCTTGTAAAGTTTGTTGCCAAAACTCAATTGCTGCTGATTTGTCTTGAGAATTCAACCAAGCAA
TATAATCCTGGTAAGGACGTGGTTTTGGCAATTGGCAATTTTCACCAAGCAGATGTGCTTTATAGAAAATT
AAAATTTCTTTAAAAATAATTGATAAACACCATCCATCCATAAGGATGTGGTGATGACTCCAGATAAATTT
GTAATTATCTTCGCCTAGCCTGACTAACGTACACCGCATTAATGGTGCTTGGGATAAGTTAAAACCTTGTT
CTCTTTGTGTTTGCAATAATTGTTTTAATTGTTGTTGTTGATCATTAGAAGAAAGTTCTCGCCAATCAAGA
GTATTCCAAGGAACATTAACCTGTTTTAGTACTACTTGTAATGGAGTTTGGCGATTTTCCCAAACAAAAAA
TGTACGTAGAATTGAATGTCTATCTAAAACTTTTTGCCAAGCTCTTTCAAAAGCAGCAACATTGATATTCC
CCTTCAAACCCCAGGTCATCTGTTCAAGATATACCCCACTATAAGGTGCATAAAGACTGTGGAACAGCATC
CCTTGTTGCATGGGAGAAAGTGGATAAATTGAAGAGATATTTCTTCTAATTTCTTCGTTGCTCATTGTTCT
CTCTTTTTTTATCTATATTTTTTATATTTACACTATTTGCCCAAGTTTTTTAATAACTCATCAAGTTCTAA
TTGATTTAACTGTGCATCTGGGAAATCACTAGCTGTATATCCAAAACCATTTTCTGACTGGCAATGTTCTA
TTATTGACTTAATTGCTTGAATATAGCTTTGTGTCAAATTTTTTACTGTATCATGAGTATGAAAATTACTA
CTATAAGTCCAATCAATTTGTAATTCACCTTCTACCACCAGACTATTAATCTCTAATAGATGGTGACGAGT
TTGCTTTGAACTATGATTATCTCCAGTAGATTCTGGCGCAAATTTCCAACCCGTTTCCGATTGTATTTGGT
CAAATTGTCCTAGGTAGTTAAAACTAATTTCTGGAGTAGGAATTGTCTGTAGTTTTGGGTTACAGTAGTA
TCTTCACACAAGTAACGCAATATACCAAAGCCAATACCACGATGGGGAATCTCTCGTAATTGTTCTTTAAT
TGACTTGATAACTTCTGCTGGTTGTTTATCGTCTGGTAATCGCAATAATACTGGGAATAAACTGGTAAACC
AACCTATTGTTCTTGATAAGTCTACATCTGAAAATAGTTCTTCTCTGCCATGTCCTTCTAGGTCAATTAGT
```

FIG. 5-7

```
ACTTTTGAATCTCCCGTCCACTCTGCCAAGGAAACTACTAATGCACTGAGGAGGATATCGTTAATTTGTGT
GTTATAAGCTGAGTTTACTGACCCCAGCAAAGCGCGGGTTTCTTCTGGACTCAATTTCACTCTATAATTAA
TCGCACTATCAACTGTTTTTTCTGCTTGAGTGTGAGCAGAATCTAATGGTAGTGGTGTTGTTTCTGACCAA
GGTTGGTTGAGCCAATAGTCTAACTCTTGTTTGATTTTTTCTGATTGTGCATAATTTTTCAATTTCTCTGC
CCAATCAATAAATGCTGTTGTTTTCGCATTTAGCTGTATTGATTGTTGAGCGATTAGTTGTTGATAGATTG
TTTCTAAGTCTGATAGTAAAATTCGCCAACTCACACCATCTACTGCTAGGTGATGAATAATAATCAGTAAA
CGGGCATCAACTTCACTACCTAAGTTAAACATCACCACTTGCATTAAAGGTCCCTCTGAGAGGTTTAAACT
TGCTTGATATTCCGTGGCGATCTGTGATAAAGCTTGTGGTTGTTCAATGACAGGAGTTGATGATAAATCAA
CTACAGTAAATGCTACGGGATCATCAAAGCCATGGTTTATTTGTTTGTACTCAGATGCAACTGATGTGAAT
CGTAAACGCAGAGCATCGTGATGCTCTAATAATTTTTTCAAGGCTGTTTCGATTAATTCAGTTTGCAGATG
ATTGGGAATCTGCAATAAAACTGATTGGTTGTAATGGTGTGCTTCTTGGCTATTTTGTGCAAAGAACCACT
GTTGAATTGGTGTTAGGGGTGCAACTCCAGTAACTATACCTTGGTTAGCACTGACAGTAACTGTTGTATTG
GCTACTAATGCTAGTTTGGCGATGGTTTCATTTTGGAATATTTGTTTGGGAGTGATTTGTATTCCTAAGTT
TTTGGCACGAGAAACTACTTGAATACCAAGGATGGAGTCGCCACCAATTTCAAAGAAGTTGTCATGGATGC
TGACTTGTTCTTTAAGGAGCAGTTCWTGCCAAATGTTGGTTAAGATTTGTTCTATTTCTGTGCGTGGTGCG
ACATATTCATCCTCTCGGCTAACTTCCCCATCAGGTGCACTTAGGGCTTGCGGTCTACTTTACCGTTGGG
TGTCAACGGTAGGGTGTCTAAGATGACAAAGCTAGAGGGGAGCATATATTCTGGCAATTTAGACTTTAGGT
AGGAGCGCAATTCATTGCTACTCAGTACCTTACGTTCAGGCTTTGACTTATTAATTGTGTAATCTTCTAGA
TTATTTTCAGCAAACAATCGTTGATAAAAGGGTTTTGCTTAAACAATTGTTTCCAATGATATGAGATGTA
TTCAAACTCAATCTCTTTTCCAGTTTTTTTTAAAAGACGACCTCGAAGAGTATAATCTGGATTCAAATTAT
TTTCACAAAGCGTTCTCGTACAAACAGCTTCGATGATATCTCCTTCATTTACATAAATTCCTGGTTCAAAC
ACTGGAAGATAAACTGGTAACCAGCAATGTTCATTTTCTAAAATATCTATACATTCTCCTTCAATTGTGTG
TAAGTTTAATCCCACTGAAAAACCATCTAATCTTCCTGATTTTTCAATAGTTAATTTAATTTGGTGAGTAG
ATTCTGTGCTAACAAGCTTGCTAAAGTCTAAATCCTCAAAAACTCCTCGATTGGACAACCAGTTTACTTGA
TTTAATCCTTTAATACATACTCGTAAATCAAAAGGATATCCAACTTGCTCAAATATCTTCTGGGTATAATA
ACCTGAAACTTTTGTAAATTGGGGTTGATTTAGTAATTCATCAGGAAGAGTTACTGCAATAATTTGAGTCA
CACTTCTTTGGGGAATCATTACACCATCTGATTTGAGAAATCTTCTGGCGTTGTTGATAATTACTGCTGCT
CCTTCAGATCCACCAATGGGTCCCACAATTTCAGAAACACATACATCAACTTCTTCTGGTAAGTTGGCTGT
AGTAGCGTCTCCATGTATGATTTGAATTTGTTCTGATAACCCCAACTCTTGCACGCAAGCTGAAGCTAACT
TACTGGTTTGCTCGTCTCTCAATTGCGTAGACTTTCTTAGCACCTGCTTCTGCACAAAATCTGGCTATA
ATTGCATCCTTGCCCGTGCCAATTTCAACAACTACTTTATCTTTAACCATTTGATTAATTGCGACTTGGTA
ACTCTGGTTTCGACGATGATCATTGGTCATCGCATAGTACAAGAGCTCATCATAAACGTAGAATTCTGCTA
CTGAGGGCCAAAGTTCAATTCCTGTCTGGGGCTGGGGATCTTTTTCTTTTGACTGAAGAGGAACTAAATAT
GCTACCAACCGTTTGTGACCCGGAGTATCTTCCCTTTCGGTGACTGCGACTTGCTGTACTTGAGGATGGGT
ACTCAGAACTGATTCTATTTCTCCTAGTTCTATGCGGAACCACGTATTTTCACCTGGTTATCAAGACGAC
CAAGAAACTCAATATTACCATCTGGTAAGTATCGAGCTAAATCTCCAGTTTTATATAGTTTTGATCTGCTA
TTGAAGGGGTTAGGGATGAATTTCTCTAAAGTTAATTCCGGTCGGTTGAGGTAACCTCTGGCTAAGCCATA
ACCTCCGATGTATAATTCTCCGGATACACTTATGGGTACTGGTTCTAAGTGCTTATCTAAGATATAGATTT
GGGTGTTTGCAATGGGCGACCGATAGTAACTTTCTCGCTACCATGGCTGATTTGAGCCACTGCAGCACCA
ATAGTAGACTCAGTAGGCCCATAACCATTAAACAAACGACGACCAACAGACCACTGATTGGCCAATTCKAM
WYTASAAGSWTCCCCTGCCACAATTATCTGACCCAAGGCTGGAAATTCATCAGTAGCTAGTACTGCCAGGG
CAGAGGGAGGTAACGTAACATGAGTTACACATCTTTCTTGTAAAATTTGCTTTAAATCCGAACCCGGGATT
AACTCAGAAGCTATAGCCAAAATTAGCATTGCTCCAGAAGTCAAAGCGATAAATATTTCCGAAACTGAAGC
ATCAAAACTTATAGAAGCAAATTGAAGAACACGACTATTTGGTTCTAGATAAAATAAATTTTTCTGTGCTT
GAATAAGGTTGCACAAAGAAAAATGTTCAATCCCAACCCCCTTGGGAACTCCAGTAGAACCAGAAGTATAA
ATCACATAAGCCAAATTATCTGAACATACCCCAACATCAAGATTCTCCTGACTGTGTTGCTCAATCACTCC
CCAATCACTATCCAAACAAACCACCTGTGCAGTATGTGACGGCAAAGATTCCAGTAGGGACTTTTGAGCCA
ACAACACCTCAACACCTGAATCCGCCAACATATAACTCAACCGTTCTTGGGGATAATTGGGGTCAAGGGGT
ACATAAGCCCCACCAGCCTTGAGTATCCCCAAGAGCCCTACCACCATTTCAAAAGAACGCTCCACGTAAAT
CCCTACCAGCACCTCTGGTTCGACTCGCAAGGAAAGCAGGTGATGTGCTAGTTGGTTGGCTTTTTGATTTA
ATTGTTGGTAGGTTAACTGCTGATTCTCAAATACCACCGCGACTGCATCCGGTGTTCTCTACCTGCTCT
TCAAACAATTGATGGATACATTTACTGGGATATTCCCTTGCTGTATCATTCCACTCCACCAACAACTGATG
CCGTTCTACTTCACTCAATAGGGGTGATTCACTTACCTTTTGTTGAGGATTTTCCACAATCGCTGACAATA
AATTCTGGAAATGACCAGCCATGCGCTCAATGGTTGACTCATCAAACAAGTCAGTGTTGTACTTAAAAACC
```

FIG. 5-8

```
CCAAAAACAGATGAACTCCCCTCCACCATTTCTAAACCTAAATCTAACTGACCTTCCTGTTGAGGTATTTC
ATAAGGTTTTATCTTCAATTCTCCCCAATCAACATAGGTTTCTATTTGATTTACAAACAACTTCTGTATAT
CTTGAGATTTTTGGAACTGCAGTAGAGAAAAAGAAGCCTGAAAAATCGGCGAACGACTGGGGTCGCGGTGT
GGCTGTAGCTTTTCTACCAATAGAGCAAATGGGTAATCTTGATGAGCAAGTGCTTCCAATACGGTTTGGCG
TACTTGGGCGAGGAAATCTTTGAAACTGGGATTTCCCGATAAATTTGCTCGCATAACAACAGGATCAACAA
AGTAGCCCAAGATCGAAGCAAACTTAGCTTGACTCCTACCTGAGGTGGGAGAACCGACTAAAATATCCTCC
TGGCCTGTGTAACGATACAAAAACACCTGAAAAGTTGCTAAGAGCATCATGTAAAGTGTTGCTCCCGAGTT
TAAAGCCAGCTCCTTGAGTTGCTTAGTGAGCTTGTCAGATAATTTGAAGTGATGGGAAGCACCATTATAAG
TTTTTATCGGTGGTCGCTGTCTTGAGGTTGCTAGGTTTAGTGCTGGCAAATCGCCTGTCAGTTTTGCTGC
CAGTAGTTCCAGAGTCTTTCCCCTTCAGTCTCCTGCAAAATATTCCTCTGCCAACGAACGTAATCTTGGTA
AGAATGCTTTAGAGGAGAAAGGGGTGTCTTAAAATCAGCCCATTGTACTTGGTAGAGTTGTGGCAACTCCT
GTATTAACATATCTAAAGACCAGGCATCGCAAGCAATGTGGTGTATGGTTAGCAACAGGACATGTTCTTTC
TTGGAACGAGTAAACCACCGAACTCGCATAACAGGCCCTCGTTCGAGGTCAAAATATTGTTGATGGCTCTC
AATCACTTTCCCTTTCAGTTCATCTTCACTCCAAGCAGAAGCATCAATTTGCAAGAAATTTAATTCCTGAA
AATTATTTACCTGTTGGATTGACTCAGATCCGAGTTTGGGATAATTTGTACGCAATATCGGATGCCGTTCT
ATTAGTTTCTCAAATGCCTTTTGCATTGCTGTAATATCTACTGTTGAGCAAATACGAGCGACAAATGATAC
GTTATAAGCATGACTTTCTGGTGCTAATTGCCACAAAAACCAAAGTGCCCGTTGACCGTAAGAAAGGGGAT
AGACGTTTAAAATATCTGGGCGATCGCGCAGCAATTGTAATATTTCGGTTTTGTATTGTTTCAGTTGAGCT
AATACTAAAGCAGTTGATTCTTCTTGAGGAGCATCGTAACAAAGCCGTTCGCCCTCACTCCACACTTGCCA
ACCTTTTATTGAAATATCTTGTAAAAATTCGATTAAATTCATAATTCACCTCTTATCCGCTCGTTTTCTTT
CCTATTGCTTTGGTAGAGTTGCCCATTATTTTCTGACTCAACTCCTTGATTCTGAGCAACTTGGCTCAGTT
GCTCATTCACTTCAGTGGCTAAATCAACGATACTGATATCTTCTATAAATTTGACTATAGATATATCCACG
AGCAAGTCAGTTTGAAGCCTATTGTGCAATTCCACAGCCATTAGAGAATCAAGCCCCATAGTGTTCAGGGG
CTGTTGCATATCAATTTGAGAAGTGCTCAAAGAAAGTACTTGAGAAATTTCATCTTTAATGTAAATTATCA
AAAGCTTTTCTCTTTCTCTTGGTAAAGCAGCTTTTAGCTGTTCTAAAAATTCATTGTGCTTTGTCTTTGTT
TTGAGGGCTTTTTGCTGTGATTTGCTTTCTTTTACCAATTGGGACAGCAATGGTATTTGATTACCAAAACT
AAATTGCTCTTGGAACACTGACCATTGAATTGGTAGGACTCCTACTTGTGGTATGGATTGTTCGAGTAATT
GTCCTAGAACCTGCAATCCCTGTTCTGAAGACAAAAAAGTCATTCCCTTGGACACCATTCTATCTTGATGA
GGACTATCCAAATTTGCTGCCATTCCCTCTTGTGCCCATGGTCCCCAGTTAATGCTCAAGCCAGGTAAACC
CATACCCCGTCGATGATGGGCTAAACCATCCATGAAAGCATTAGCAGCAGCATAATTCCCTTGACCAGGCG
AACCCAATATTGAAGCCATAGAGGAAAAACAAACAAAAAAGTCCAAAGGTAGATTCTGAGTCAAATTATGC
AAATGCCAAGCCCCTTGTACTTTTGGTGCCATCACCTGTGTAAATTTTTCCCAATTCATGTTTAACAGCAA
ACCATCATCCAATATCCCAGCAGCATGAATTATTCCTCGTAATGCTGGCAAAGATACTTTGATTGACTCTA
TAATTCTTGCCACATTTTCTTGTTGGGAAATATCTCCACACAGGACTAATACTTGCGCTCCTGCCTTCTGT
AATTGTTCAATGGTTTGTTGAGCTTTTGCTGATGGCTGCCTACGTCCGGTAAGTACTAAATATTTGACCCC
TTGTTGTACCATCCACTCAGCGGTTTTTAACCCCAGTGCTCCCAGACCTCCGGTAATTAAGTAACTGGCTT
CGGCTTGGATTAGGTTGTCTAAAGACTTATATTCTGATAGCTTCAGTTGAAATGGTTGTTGCGAGGAAATT
TGTAATCCGGACTGTGTAGATGTACTCATTTTTTGTTGCCGCTCTAACCGGGCAACGTGACGTACCCCTTG
ACAGTAAGCAATTTGGTTTTCATCACCAGGAGATAATAGTTCCTCTAACAAAGCAGCTACTGTTTGGGAAT
CTTCCATAGTTGGATCTAAGTCTAAACACCGGCATTGTAATTCCCTATGTTCCTGGGCAATTACTCGACCT
AACCCCCATAAAGGTGTTTGTTGGAATTGTATAGGAAGGGACTCATTACCCACAGATTGTGAGCCTTGAGT
CACTAACCATAATGGGGCACTTTCCATATCTTGATTTTTTACTAAGCCTTGGACTAAATGAAGTACGCTGC
CACAGCCCAGTTCTTGGGATTTTTGCAACTCCTGTGCCCCAGTCCTTAGTGCTATTGTTGAGTCCAAACTC
CACAGGTGAATAATTCCTCGTAATGGGGGTTGCTGCTCCAAGCTTGATTGCAATAGGTGCAGGAATTCCTC
AGGATGGTTGGGGTTGATTTGATAATGTTGAGATTCTAACTGCTGGTAATTTTCCCCTGGTGTTACTAATA
TACAATGCCAACCTTGTTGTTCTAAGGATTCTACCAGATGTTTGCCTATACCTGTGGGTGGGGAAAACAAT
AACCAGCTACCTGATTTTGTTAAGTCAATTGATTGGTTATGGGGTGAAATTGATTGGGTTTGCCAATGGAT
TTGATATAACCAATTATTAAATTTTGGTTCAATATTACGCAACAAAGCCTCGCGAGAAGTACGTAATAAAG
TTAAACCTTCAACTCTTGCTACTACTATTCCTTGTTCATCCAATAAACAAACTTTACCGCTCAAAGTTTGT
TTATTAGTTTCTGTTGCACCTATCTCTACTTGAGTCCACAAACTATTACTACCACTCCGATAAATTTGTAG
TCGTTTTATTTCCAATGGCAAATAAGTTTCTTGGTTGTCCGTTTTACCCATAACTGCTGCTAACACCTGGA
AGCTAGCATCTAAAAGAATTGGGTGCAGTTGGTATAAAGTTGCAACATTCACCTCAGTTTCTGGTAACTGA
ATTTCACCTAGTGCTTTTCCTTCGCTGTGCCACAGTTGTTTAACGGCTTGGAAAGAAGAACCGTAATTAAG
ACCCCATTCTTCAAATTTTTGGTAGAATTCAGTAGCTAATATCTGTTGGTTATACTCGTCTTTAATCGCTT
```

FIG. 5-9

```
TTAAGTTTGTTGTTTCTAATTGGGGGTCTTTATTACCTACTAATATTTTTCCTTCAATATGTAGAATCCAT
TTAGGTTCTGAAGAATTAGTGTTTATATCCAAACTGAAAATTTGGAATTTATAGCTTTGTACTAACTGTAA
ATTTAAAACTATCTGAATTGTATTAATTTCATCCTTTGATAAAATTAATACTTTTTGGATTGCTATATCTT
CTAGGATTAAATCATCTGAATTGAATAAAATTGAACCTGCTGCTAAGGCTATTTCCAAGTAAGCTGCTGCT
GGGAAAACAGGTTGAGAAAAAACACAGTGGTGTTGCAGGTAAGTTGGTTGAGAAGCACTAATTTGACATTC
AAAACGAATTTGCTGTTCTAAGGCTGCTAAATGTAATCTTTGACCGAGTAGAGGGTGAAGATTTTTATGAT
TTGATAAAACTGTTTTTGATGTATTAGATTATTATTTGTCTCAATCCAATAACGTTGCCGTTGAAAGGGA
TAAGTCGGCAATACTACCTTGCTACGAGAATAATCTTTATCAAACCCTAACCAATCAACTTTAACTCCATG
CACATATAGTTCAGCCAAACTTTGTAGCATTTGCTGCCAGTCTTCTTGACCTGGTTTCAAAGAAGGCAACC
AAACTCCCACATCTTCTGGCAAGCACTGTCTTCCCATGCCTAACAAAGTTGGTTTGGGTCCAATTTCTAAG
AAGATGGAATAACCTTCTTGCTGTAATGTGTCCATACTTTGGGCAAATTTCACCGGTTGCCGGACATGATT
TACCCAATAGCTTGCTGTGGCAATACTATTCTCTGCCCTAGCTCCCGTTACATTTGATACTAATGGAATAT
TTGGTTGATTGTAGGTTATTTCTGATGCTACTGCTTCAAAGTCCGCCAACATTGGTTCCATCAAATGTGAA
TGGAATGCGTGGATACTTGCAGTCGTTTTGTCTTAATGTCTTCTGCTTCTAAGCTATTTTGAACCGCTCC
AATTGCTTCTGCCTCACCAGAAATGACAATGCTTTGGGGTCCGTTAATCGATGCGATCGCTACTTTTTGAG
AGTATGGTGCAATTAGTTGATTTACCTTTTCAATTGAAGCCATTACAGATAACATTTCACCCCCAGAGGGT
AACTGTTGCATTAGTCTTCCTCTATGAGCAATCAGTTTTAAACCATCTTCTAAACTAAATATTCCTGCTAC
TGTGGCTGCCACATATTCCCCAGCACTATGCCCCATAACCACATCCGGTTTTATTCCCCAGGATTCCCATA
GTTTATAAAGAGCATATTCTATTGCAAATAAAGCTACTTGGGTATAGGCGGTTTGAGCTAGGACATTTTCC
TGTACTTGAGCCACATCAAGTATTTCTAATAAAGGTTTGTCTAAGTAGTTTTCTAATATTTGGGCACATTG
ATCGCTAGTACCTCTCCATAAAACTTGGTATACGCAACTAATTGCTTCACCAATTCCGGTTGATACTTTAA
TATTCCTGCGTCTACCACCGCAACTATTTTCTTCGGCTTTGTCTCCTCATCTGCCGAAATTACTTGCGCTA
GCGTCGGGTTTTTCAACTCAAATAAATTTGGGTGAAGTAAATCTCATAGTTAAAAGTAACCGAAACACGT
TGATGAATTAATCTATTTTTTGCTTGATGTCAACTATCATATTTTGCAGGTATATCTAAAAGTGCAGTA
CTATTCAAAGCTTCAAGGAAAACCTCAACCGAGTGAGAACCATTTACCTTGACTTGATTATTCATGATGAA
AAACGGCACGCTGTTGATGCCATTTAAGCGAGCAAATGCCGATTCAGCAACAACTGTATCAACGACATCGC
GATCGTTTAATTGCAACTTTAATTCGGTAGCATCCATCTGGTATGCTGTACCGATGGCAACAATAACGTTA
ATATCTCCAATATTCAAACCCTCTTCAAAGTAAGCTCTATAAATAGCTTCAACGACATCATTTTTATGTT
TGTCGGTGCTAATGCAATCAGTTGGTGAGCAAGCTTAGTATTGACAGCCAAACGGATTTTTTCAAAATCTA
GCTTAACCCCAGCCGCCTCCCCTGCGCGTTGCGTATAATCAAACATCTGTTGCATTTCTGGCGCTTTAATG
CCTTTTCTATTTTGCATAAAGCTACTAAATTCGTACCCCTCAGCAGGAACAGTATCATCCAGAAGAAAGGG
ATGCCATCGGATATTTACTTCTTGTTCTTGCCATTGTGCCAGTGCATCAAATAGATGTTTTTTCCCAATTC
TGCACCAAGGGCAAACGGTATCATGAAAGATATCTATCAGCATAGTTTTGTCACTCAAATGCTAATATTT
GTGTGCATCTGGGGTTTAAAATCTCGTTGCAGAGCCGTTGTATTTAAAGGCTGGAGAAAACTATTAATTTT
CTCTTCAAAAAAACTTTGAGTATTTTCAAACTCTTTAATTAATGCCTCTCTATCCTTCCTAGCCACCAGTC
TAGCCAATCGGCTGTAAGTTTTAGCTAAAAAGCTAATAGCATTACACCTTTCTTCAGTCGCTAGCATAATA
TCAACGCATAAATTAGGATTTTGCGAAAATAAACGTTTTACAATATCAATCTCTTGACGATAGTTAGGAGT
TGACATTGTTAAACTCTGCTCTATCTCTACTCTTGATTGTGCTAAGAAAACACCAAGACTAAATCTACAGA
AATGCTGCGTGGCTTGAATAATCACCATCATT (SEQ ID NO:1)
```

FIG. 6-1

(crpA)

```
ATGGGGCATAGTGCTGGGGAATATGTGGCAGCCACAGTAGCAGGAATATTTAGTTTAGAAGATGGTTTAAA
ACTGATTGCTCATAGAGGAAGACTAATGCAACAGTTACCCTCTGGGGGTGAAATGTTATCTGTAATGGCTT
CAATTGAAAAGGTAAATCAACTAATTGCACCATACTCTCAAAAAGTAGCGATCGCATCGATTAACGGACCC
CAAAGCATTGTCATTTCTGGTGAGGCAGAAGCAATTGGAGCGGTTCAAAATAGCTTAGAAGCAGAAGACAT
TAAGACAAAACGACTGCAAGTATCCCACGCATTCCATTCACATTTGATGGAACCAATGTTGGCGGACTTTG
AAGCAGTAGCATCAGAAATAACCTACAATCAACCAAATATTCCATTAGTATCAAATGTAACGGAGCTAGG
GCAGAGAATAGTATTGCCACAGCAAGCTATTGGGTAAATCATGTCCGGCAACCGGTGAAATTTGCCCAAAG
TATGGACACATTACAGCAAGAAGGTTATTCCATCTTCTTAGAAATTGGACCCAAACCAACTTTGTTAGGCA
TGGGAAGACAGTGCTTGCCAGAAGATGTGGGAGTTTGGTTGCCTTCTTTGAAACCAGGTCAAGAAGACTGG
CAGCAAATGCTACAAAGTTTGGCTGAACTATATGTGCATGGAGTTAAAGTTGATTGGTTAGCGTTTGATAA
AGATTATTCTCGTAGCAAGGTAGTATTGCCGACTTATCCCTTTCAACGGCAACGTTATTGGATTGAGACAA
ATAATAATCTAATACATCAAAAACAGTTTTTATCAAATCATAAAAATCTTCACCCTCTACTCGGTCAAAGA
TTACATTTAGCAGCCTTAGAACAGCAAATTCGTTTTGAATGTCAAATTAGTGCTTCTCAACCAACTTACCT
GCAACACCACTGTGTTTTTTCTCAACCTGTTTTCCCAGCAGCAGCTTACTTGGAAATAGCCTTAGCAGCAG
GTTCAATTTTATTCAATTCAGATGATTTAATCCTAGAAGATATAGCAATCCAAAAAGTATTAATTTTATCA
AAGGATGAAATTAATACAATTCAGATAGTTTTAAATTTACAGTTAGTACAAAGCTATAAATTCCAAATTTT
CAGTTTGGATATAAACACTAATTCTTCAGAACCTAAATGGATTCTACATATTGAAGGAAAATATTAGTAG
GTAATAAAGACCCCCAATTAGAAACAACAAACTTAAAAGCGATTAAAGACGAGTATAACCAACAGATATTA
CCTACTGAATTCTACCAAAAATTTGAAGAATGGGGTCTTAATTACGGTTCTTCTTTCCAAGCCGTTAAACA
ACTGTGGCACAGCGAAGGAAAAGCACTAGGTGAAATTCAGTTACCAGAAACTGAGGTGAATGTTGCAACTT
TATACCAACTGCACCCAATTCTTTTAGATGCTAGCTTCCAGGTGTTAGCAGCAGTTATGGGTAAAACGGAC
AACCAAGAAACTTATTTGCCATTGGAAATAAAACGACTACAAATTTATCGGAGTGGTAGTAATAGTTTGTG
GACTCAAGTACACATAGGTGCAACAGAAACTAATAAACAAACTTTGAGCGGTAAAGTTTCTTTATTGGATG
AACAAGGAATAGTAGTAGCAAGAGTTGAAGGTTTAACTTTATTACGTACTTCTCGCGAGGCTTTGTTGCGT
AATATTGAACCAAAATTTAATAATTGGTTATATCAAATCCATTGGCAAACCCAATCAATTTCACCCCATAA
CCAATCAATTGACTTAACAAAATCAGGTAGCTGGTTATTGTTTTCCCCACCCACAGGTATAGGCAAACATC
TGGTAGAATCCTTAGAACAACAACGTTGGCATTGTATATTAGTAACACCAGGGGAAAATTACCAGCAGTTA
GAATCTCAACATTATCAAATCAACCCCAACCATCCTGAGGAATTCCTGCACCTATTGCAATCAAGCTTGGA
GCAGCAACCCCCATTACGAGGAATTATTCACCTGTGGAGTTTGGACTCAACAATAGCACTAAGGACTGGGG
CACAGGAGTTGCAAAAATCCCAAGAACTGGGCTGTGGCAGCGTACTTCATTTAGTCCAAGCCTTAGTAAAA
AATCAAGATATGGAAAGTGCCCCATTATGGTTAGTGACTCAAGGCTCACAATCTGTGGGTAATGAGTCCCT
TCCTATACAATTCCAACAAACACCTTTATGGGGGTTAGGTCGAGTAATTGCCCAGGAACATAGGGAATTAC
AATGCCGGTGTTTAGACTTAGATCCAACTATGGAAGATTCCCAAACAGTAGCTGCTTTGTTAGAGGAACTA
TTATCTCCTGGTGATGAAAACCAAATTGCTTACTGTCAAGGGGTACGTCACGTTGCCCGGTTAGAGCGGCA
ACAAAAAATGAGTACATCTACACAGTCCGGATTACAAATTTCCTCGCAACAACCATTTCAACTGAAGCTAT
CAGAATATAAGTCTTTAGACAACCTAATCCAAGCCGAAGCCAGTTACTTAATTACCGGAGGTCTGGGAGCA
CTGGGGTTAAAAACCGCTGAGTGGATGGTACAACAAGGGGTCAAATATTTAGTACTTACCGGACGTAGGCA
GCCATCAGCAAAAGCTCAACAAACCATTGAACAATTACAGAAGGCAGGAGCGCAAGTATTAGTCCTGTGTG
GAGATATTTCCCAACAAGAAAATGTGGCAAGAATTATAGAGTCAATCAAAGTATCTTTGCCAGCATTACGA
GGAATAATTCATGCTGCTGGGATATTGGATGATGGTTTGCTGTTAAACATGAATTGGGAAAAATTTACACA
GGTGATGGCACCAAAAGTACAAGGGGCTTGGCATTTGCATAATTTGACTCAGAATCTACCTTTGGACTTTT
TTGTTTGTTTTTCCTCTATGGCTTCAATATTGGGTTCGCCTGGTCAAGGGAATTATGCTGCTGCTAATGCT
TTCATGGATGGTTTAGCCCATCATCGACGGGGTATGGGTTTACCTGGCTTGAGCATTAACTGGGGACCATG
GGCACAAGAGGGAATGGCAGCAAATTTGGATAGTCCTCATCAAGATAGAATGGTGTCCAAGGGAATGACTT
TTTTGTCTTCAGAACAGGGATTGCAGGTTCTAGGACAATTACTCGAACAATCCATACCACAAGTAGGAGTC
CTACCAATTCAATGGTCAGTGTTCCAAGAGCAATTTAGTTTTGGTAATCAAATACCATTGCTGTCCCAATT
GGTAAAAGAAAGCAAATCACAGCAAAAAGCCCTCAAAACAAAGACAAAGCACAATGAATTTTTAGAACAGC
TAAAAGCTGCTTTACCAAGAGAAAGAGAAAAGCTTTTGATAATTTACATTAAAGATGAAATTTCTCAAGTA
CTTTCTTTGAGCACTTCTCAAATTGATATGCAACAGCCCCTGAACACTATGGGGCTTGATTCTCTAATGGC
TGTGGAATTGCACAATAGGCTTCAAACTGACTTGCTCGTGGATATATCTATAGTCAAATTTATAGAAGATA
TCAGTATCGTTGATTTAGCCACTGAAGTGAATGAGCAACTGAGCCAAGTTGCTCAGAATCAAGGAGTTGAG
TCAGAAAATAATGGGCAACTCTACCAAAGCAATAGGAAAGAAAACGAGCGGATAAGAGGTGAATTATCA
(SEQ ID NO:2)
```

FIG. 6-2

(CrpA)
MGHSAGEYVAATVAGIFSLEDGLKLIAHRGRLMQQLPSGGEMLSVMASIEKVNQLIAPYSQKVAIASINGP
QSIVISGEAEAIGAVQNSLEAEDIKTKRLQVSHAFHSHLMEPMLADFEAVASEITYNQPNIPLVSNVTGAR
AENSIATASYWVNHVRQPVKFAQSMDTLQQEGYSIFLEIGPKPTLLGMGRQCLPEDVGVWLPSLKPGQEDW
QQMLQSLAELYVHGVKVDWLGFDKDYSRSKVVLPTYPFQRQRYWIETNNNLIHQKQFLSNHKNLHPLLGQR
LHLAALEQQIRFECQISASQPTYLQHHCVFSQPVFPAAAYLEIALAAGSILFNSDDLILEDIAIQKVLILS
KDEINTIQIVLNLQLVQSYKFQIFSLDINTNSSEPKWILHIEGKILVGNKDPQLETTNLKAIKDEYNQQIL
PTEFYQKFEEWGLNYGSSFQAVKQLWHSEGKALGEIQLPETEVNVATLYQLHPILLDASFQVLAAVMGKTD
NQETYLPLEIKRLQIYRSGSNSLWTQVEIGATETNKQTLSGKVCLLDEQGIVVARVEGLTLLRTSREALLR
NIEPKFNNWLYQIHWQTQSISPHNQSIDLTKSGSWLLFSPPTGIGKHLVESLEQQGWHCILVTPGENYQQL
ESQHYQINPNHPEEFLHLLQSSLEQQPPLRGIIHLWSLDSTIALRTGAQELQKSQELGCGSVLHLVQALVK
NQDMESAPLWLVTQGSQSVGNESLPIQFQQTPLWGLGRVIAQEHRELQCRCLDLDPTMEDSQTVAALLEEL
LSPGDENQIAYCQGVRHVARLERQQKMSTSTQSGLQISSQQPFQLKLSEYKSLDNLIQAEASYLITGGLGA
LGLKTAEWMVQQCVKYLVLTGRRQPSAKAQQTIEQLQKAGAQVLVLCGDISQQENVARIIESIKVSLPALR
GIIHAAGILDDGLLLNMNWEKFTQVMAPKVQGAWHLHNLTQNLPLDFFVCFSSMASILGSPGQGNYAAANA
FMDGLAHHRRGMGLPGLSINWGPWAQEGMAANLDSPHQDRMVSKGMTFLSSEQGLQVLGQLLEQSIPQVGV
LPIQWSVFQEQFSFGNQIPLLSQLVKESKSQQKALKTKTKHNEFLEQLKAALPREREKLLIIYIKDEISQV
LSLSTSQIDMQQPLNTMGLDSLMAVELHNRLQTDLLVDISIVKFIEDISIVDLATEVNEQLSQVAQNQGVE
SENNGQLYQSNRKENERIRGEL (SEQ ID NO:3)

crpC
ATGAATTTAATCGAATTTTTACAAGATATTTCAATAAAAGGTTGGCAAGTGTGGAGTGAGGGCGAACGGCT
TGTTACGATGCTCCTCAAGAAGAATCAACTGCTTTAGTATTAGCTCAACTGAAACAATACAAAACCGAAA
TATTACAATTGCTGCGCGATCGCCCAGATATTTTAAACGTCTATCCCCTTTCTTACGGTCAACGGGCACTT
TGGTTTTTGTGGCAATTAGCACCAGAAAGTCATGCTTATAACGTATCATTTGTCGCTCGTATTTGCTCAAC
AGTAGATATTACAGCAATGCAAAAGGCATTTGAGAAACTAATAGAACGGCATCCGATATTGCGTACAAATT
ATCCCAAACTCGGATCTGAGTCAATCCAACAGGTAAATAATTTTCAGGAATTAAATTTCTTGCAAATTGAT
GCTTCTGCTTGGAGTGAAGATGAACTGAAAGGGAAAGTGATTGAGAGCCATCAACAATATTTTGACCTCGA
ACGAGGGCCTGTTATGCGAGTTCGGTGGTTTACTCGTTCAAGAAAGAACATGTCCTGTTGCTAACCATAC
ACCACATTGCTTGCGATGCCTGGTCTTTAGATATGTTAATACAGGAGTTGCCACAACTCTACCAAGTACAA
TGGGCTGATTTTAAGACACCCCTTTCTCCTCAAAGCATTCTTACCAAGATTACGTTCGTTGGCAGAGGAA
TATTTTGCAGGAGACTGAAGGGGAAAGACTCTGGAACTACTGGCAGCAAAAACTGACAGGCGATTTGCCAG
CACTAAACCTAGCAACCTCAAGACAGCGACCACCGATAAAAACTTATAATGGTGCTTCCCATCACTTCAAA
TTATCTGACAAGCTCACTAAGCAACTCAAGGAGCTGGCTTTAAACTCGGGAGCAACACTTTACATGATGCT
CTTAGCAACTTTTCAGGTGTTTTTGTATCGTTACACAGGCCAGGAGGATATTTTAGTCGGTTCTCCCACCT
CAGGTAGGAGTCAAGCTAAGTTTGCTTCGATCTTCGGCTACTTTGTTGATCCTGTTGTTATGCGAGCAAAT
TTATCGGGAAATCCCAGTTTCAAAGATTTCCTCGCCCAAGTACGCCAAACCGTATTGGAAGCACTTGCTCA
TCAAGATTACCCATTTGCTCTATTGGTAGAAAAGCTACAGCCACACCGCGACCCCAGTCGTTCGCCGATTT
TTCAGGCTTCTTTTTCTCTACTGCAGTTCCAAAAATCTCAAGATATACAGAAGTTGTTTGTAAATCAAATA
GAAACCTATGTTGATTGGGGAGAATTGAAGATAAAACCTTATGAAATACCTCAACAGGAAGGTCAGTTAGA
TTAGGTTTAGAAATGGTGGAGGGGAGTTCATCTGTTTTTGGGGTTTTTAAGTACAACACTGACTTGTTTG
ATGAGTCAACCATTGAGCGCATGGCTGGTCATTTCCAGAATTTATTGTCAGCGATTGTGGAAAATCCTCAA
CAAAAGGTAAGTGAATCACCCCTATTGAGTGAAGTAGAACGGCATCAGTTGTTGGTGGAGTGGAATGATAC
AGCAAGGGAATATCCCAGTAAATGTATCCATCAATTGTTTGAAGAGCAGGTAGAGAGAACACCGGATGCAG
TCGCGGTGGTATTTGAGAATCAGCAGTTAACCTACCAACAATTAAATCAAAAAGCCAACCAACTAGCACAT
CACCTGCTTTCCTTGCGAGTCGAACCAGAGGTGCTGGTAGGGATTTACGTGGAGCGTTCTTTTGAAATGGT
GGTAGGGCTCTTGGGCATACTCAAGGCTGGTGCGGCTTATGTACCCCTTGACCCCAATTATCCCCAAGAAC
GGTTGAGTTATATGTTGGCGGATTCAGGTGTTGAGGTGTTGTTGGCTCAAAAGTCCCTACTGGAATCTTTG
CCGTCACATACTGCACAGGTGGTTTGTTTGGATAGTGATTGGGGAGTGATTGAGCAACACAGTCAGGAGAA
TCTTGATGTTGGGGTATGTTCAGATAATTTGGCTTATGTGATTTATACTTCTGGTTCTACTGGAGTTCCCA
AGGGGGGTTGGGATTGAACATTTTTCTTGTGCAACCTTATTCAAGCACAGAAAATTTATTTTATCTAGAA
CCAAATAGTCGTGTTCTTCAATTTGCTTCTATAAGTTTTGATGCTTCAGTTTCGGAAATATTTATCGCTTT
GACTTCTGGAGCAATGCTAATTTTGGCTATAGCTTCTGAGTTAATCCCGGGTTCGGATTTAAAGCAAATTT
TACAAGAAAGATGTGTAACTCATGTTACGTTACCTCCCTCTGCCCTGGCAGTACTAGCTACTGATGAATTT

FIG. 6-3

CCAGCCTTGGGTCAGATAATTGTGGCAGGGGAWSCTTSTAYWMTKGAATTGGCCAATCAGTGGTCTGTTGG
TCGTCGTTTGTTTAATGGTTATGGGCCTACTGAGTCTACTATTGGTGCTGCAGTGGCTCAAATCAGCCATG
GTAGCGAGAAAGTTACTATCGGTCGCCCCATTGCAAACACCCAAATCTATATCTTAGATAAGCACTTAGAA
CCAGTACCCATAAGTGTATCCGGAGAATTATACATCGGAGGTTATGGCTTAGCCAGAGGGTTACCTCAACCG
ACCGGAATTAACTTTAGAGAAATTCATCCCTAACCCCTTCAATAGCAGATCAAAACTATATAAAACTGGAG
ATTTAGCTCGATACTTACCAGATGGTAATATTGAGTTTCTTGGTCGTCTTGATAACCAGGTGAAAATACGT
GGTTTCCGCATAGAACTAGGAGAAATAGAATCAGTTCTGAGTACCCATCCTCAAGTACAGCAAGTCGCAGT
CACCGAAAGGGAAGATACTCCGGGTCACAAACGGTTGGTAGCATATTTAGTTCCTCTTCAGTCAAAAGAAA
AAGATCCCCAGCCCCAGACAGGAATTGAACTTTGGCCCTCAGTAGCAGAATTCTACGTTTATGATGAGCTC
TTGTACTATGCGATGACCAATGATCATCGTCGAAACCAGAGTTACCAAGTCGCAATTAATCAAATGGTTAA
AGATAAAGTAGTTGTTGAAATTGGCACGGGCAAGGATGCAATTATAGCCAGATTTTGTGCAGAAGCAGGTG
CTAAGAAAGTCTACGCAATTGAGAGAGACGAGCAAACCAGTAAGTTAGCTTCAGCTTGCGTGCAAGAGTTG
GGGTTATCAGAACAAATTCAAATCATACATGGAGACGCTACTACAGCCAACTTACCAGAAGAAGTTGATGT
ATGTGTTTCTGAAATTGTGGGACCCATTGGTGGATCTGAAGGAGCAGCAGTAATTATCAACAACGCCAGAA
GATTTCTCAAATCAGATGGTGTAATGATTCCCCAAAGAAGTGTGACTCAAATTATTGCAGTAACTCTTCCT
GATGAATTACTAAATCAACCCCAATTTACAAAAGTTTCAGGTTATTATACCCAGAAGATATTTGAGCAAGT
TGGATATCCTTTTGATTTACGAGTATGTATTAAAGGATTAAATCAAGTAAACTGGTTGTCCAATCGAGGAG
TTTTTGAGGATTTAGACTTTAGCAAGCTTGTTAGCACAGAATCTACTCACCAAATTAAATTAACTATTGAA
AAATCAGGAAGATTAGATGGTTTTTCAGTGGGATTAAACTTACACACAATTGAAGGAGAATGTATAGATAT
TTTAGAAAATGAACATTGCTGGTTACCAGTTTATCTTCCAGTGTTTGAACCAGGAATTTATGTAAATGAAG
GAGATATCATCGAAGCTGTTTGTACGAGAACGCTTTGTGAAAATAATTTGAATCCAGATTATACTCTTCGA
GGTCGTCTTTTAAAAAAAACTGGAAAAGAGATTGAGTTTGAATACATCTCATATCATTGGAAACAATTGTT
TAAGCAAAACCCTTTTTATCAACGATTGTTTGCTGAAAATAATCTAGAAGATTACACAATTAATAAGTCAA
AGCCTGAACGTAAGGTACTGAGTAGCAATGAATTGCGCTCCTACCTAAAGTCTAAATTGCCAGAATATATG
CTCCCCTCTAGCTTTGTCATCTTAGACACCCTACCGTTGACACCCAACGGTAAGTAGACCGCAAAGCCCT
AAGTGCACCTGATGGGAAGTTAGCCGAGAGGATGAATATGTCGCACCACGCACAGAAATAGAACAAATCT
TAACCAACATTTGGCAWGAACTGCTCCTTAAAGAACAAGTCAGCATCCATGACAACTTCTTTGAAATTGGT
GGCGACTCCATCCTTGGTATTCAAGTAGTTTCTCGTGCCAAAAACTTAGGAATACAAATCACTCCCAAACA
AATATTCCAAAATCAAACCATCGCCAAACTAGCATTAGTAGCCAATACAACAGTTACTGTCAGTGCTAACC
AAGGTATAGTTACTGGAGTTGCACCCCTAACACCAATTCAACAGTGGTTCTTTGCACAAAATAGCCAAGAA
GCACACCATTACAACCAATCAGTTTTATTGCAGATTCCCAATCATCTGCAAACTGAATTAATCGAAACAGC
CTTGAAAAAATTATTAGAGCATCACGATGCTCTGCGTTTACGATTCACATCAGTTGCATCTGAGTACAAAC
AAATAAACCATGGCTTTGATGATCCCGTAGCATTTACTGTAGTTGATTTATCATCAACTCCTGTCATTGAA
CAACCACAAGCTTTATCACAGATCGCCACGGAATATCAAGCAAGTTTAAACCTCTCAGAGGGACCTTTAAT
GCAAGTGGTGATGTTTAACTTAGGTAGTGAAGTTGACGCCGTTTACTGATTATTATTCATCACCTAGCAG
TAGATGGTGTGAGTTGGCGAATTTTACTATCAGACTTAGAAACAATCTATCAACAACTAATCGCTCAACAA
TCAATACAGCTAAATGCGAAAACAACAGCATTTATTGATTGGGCAGAGAAATTGAAAAATTATGCACAATC
AGAAAAAATCAAACAAGAGTTAGACTATTGGCTCAACCAACCTTGGTCAGAAACAACACCACTACCATTAG
ATTCTGCTCACACTCAAGCAGAAAAAACAGTTGATAGTGCGATTAATTATAGAGTGAAATTGAGTCCAGAA
GAAACCCGCGCTTTGCTGGGGTCAGTAAACTCAGCTTATAACACACAAATTAACGATATCCTCCTCAGTGC
ATTAGTAGTTTCCTTGGCAGAGTGGACGGGAGATTCAAAAGTACTAATTGACCTAGAAGGACATGGCAGAG
AAGAACTATTTTCAGATGTAGACTTATCAAGAACAATAGGTTGGTTTACCAGTTTATTCCCAGTATTATTG
CGATTACCAGACGATAAACAACCAGCAGAAGTTATCAAGTCAATTAAAGAACAATTACGAGAGATTCCCCA
TCGTGGTATTGGCTTTGGTATATTGCGTTACTTGTGTGAAGATACTACTGTAACCCAAAAACTACAGACAA
TTCCTACTCCAGAAATTAGTTTTAACTACCTAGGACAATTTGACCAAATACAATCGGAAACGGGTTGGAAA
TTTGCGCCAGAATCTACTGGAGATAATCATAGTTCAAAGCAAACTCGTCACCATCTATTAGAGATTAATAG
TCTGGTGGTAGAAGGTGAATTACAAATTGATTGGACTTATAGTAGTAATTTTCATACTCATGATACAGTAA
AAAATTTGACACAAAGCTATATTCAAGCAATTAAGTCAATAATAGAACATTGCCAGTCAGAAAATGGTTTT
GGATATACAGCTAGTGATTTCCCAGATGCACAGTTAAATCAATTAGAACTTGATGAGTTATTAAAAAACTT
GGGCAAATAG (SEQ ID NO:4)

CrpC
MNLIEFLQDISIKGWQVWSEGERLCYDAPQEESTALVLAQLKQYKTEILQLLRDRPDILNVYPLSYGQRAL
WFLWQLAPESHAYNVSFVARICSTVDITAMQKAFEKLIERHPILRTNYPKLGSESIQQVNNFQELNFLQID

FIG. 6-4

ASAWSEDELKGKVIESHQQYFDLERGPVMRVRWFTRSKKEHVLLLTIHHIACDAWSLDMLIQELPQLYQVQ
WADFKTPLSPLKHSYQDYVRWQRNILQETEGERLWNYWQQKLTGDLPALNLATSRQRPPIKTYNGASHHFK
LSDKLTKQLKELALNSGATLYMMLLATFQVFLYRYTGQEDILVGSPTSGRSQAKFASILGYFVDPVVMRAN
LSGNPSFKDFLAQVRQTVLEALAHQDYPFALLVEKLQPHRDPSRSPIFQASFSLLQFQKSQDIQKLFVNQI
ETYVDWGELKIKPYEIPQQEGQLDLGLEMVEGSSSVFGVFKYNTDLFDESTIERMAGHFQNLLSAIVENPQ
QKVSESPLLSEVERHQLLVEWNDTAREYPSKCIHQLFEEQVERTPDAVAVVFENQQLTYQQLNQKANQLAH
HLLSLRVEPEVLVGIYVERSFEMVVGLLGILKAGGAYVPLDPNYPQERLSYMLADSGVEVLLAQKSLLESL
PSHTAQVVCLDSDWGVIEQHSQENLDVGVCSDNLAYVIYTSGSTGVPKGVGIEHFSLCNLIQAQKNLFYLE
PNSRVLQFASISFDASVSEIFIALTSGAMLILAIASELIPGSDLKQILQERCVTHVTLPPSALAVLATDEF
PALGQIIVAGXXXXXELANQWSVGRRLFNGYGPTESTIGAAVAQISHGSEKVTIGRPIANTQIYILDKHLE
PVPISVSGELYIGGYGLARGYLNRPELTLEKFIPNPFNSRSKLYKTGDLARYLPDGNIEFLGRLDNQVKIR
GFRIELGEIESVLSTHPQVQQVAVTEREDTPGHKRLVAYLVPLQSKEKDPQPQTGIELWPSVAEFYVYDEL
LYYAMTNDHRRNQSYQVAINQMVKDKVVVEIGTGKDAIIARFCAEAGAKKVYAIERDEQTSKLASACVQEL
GLSEQIQIIHGDATTANLPEEVDVCVSEIVGPIGGSEGAAVIINNARRFLKSDGVMIPQRSVTQIIAVTLP
DELLNQPQFTKVSGYYTQKIFEQVGYPFDLRVCIKGLNQVNWLSNRGVFEDLDFSKLVSTESTHQIKLTIE
KSGRLDGFSVGLNLHTIEGECIDILENEHCWLPVYLPVFEPGIYVNEGDIIEAVCTRTLCENNLNPDYTLR
GRLLKKTGKEIEFEYISYHWKQLFKQNPFYQRLFAENNLEDYTINKSKPERKVLSSNELRSYLKSKLPEYM
LPSSFVILDTLPLTPNGKVDRKALSAPDGEVSREDEYVAPRTEIEQILTNIWXELLLKEQVSIHDNFFEIG
GDSILGIQVVSRAKNLGIQITPKQIFQNQTIAKLALVANTTVTVSANQGIVTGVAPLTPIQQWFFAQNSQE
AHHYNQSVLLQIPNHLQTELIETALKKLLEHHDALRLRFTSVASEYKQINHGFDDPVAFTVVDLSSTPVIE
QPQALSQIATEYQASLNLSEGPLMQVVMFNLGSEVDARLLIIIHHLAVDGVSWRILLSDLETIYQQLIAQQ
SIQLNAKTTAFIDWAEKLKNYAQSEKIKQELDYWLNQPWSETTPLPLDSAHTQAEKTVDSAINYRVKLSPE
ETRALLGSVNSAYNTQINDILLSALVVSLAEWTGDSKVLIDLEGHGREELFSDVDLSRTIGWFTSLFPVLL
RLPDDKQPAEVIKSIKEQLREIPHRGIGFGILRYLCEDTTVTQKLQTIPTPEISFNYLGQFDQIQSETGWK
FAPESTGDNHSSKQTRHHLLEINSLVVEGELQIDWTYSSNFHTHDTVKNLTQSYIQAIKSIIEHCQSENGF
GYTASDFPDAQLNQLELDELLKNLGK (SEQ ID NO:5)

crpD
ATGAGCAACGAAGAAATTAGAAGAAATATCTCTTCAATTTATCCACTTTCTCCCATGCAACAAGGGATGCT
GTTCCACAGTCTTTATGCACCTTATAGTGGGGTATATCTTGAACAGATGACCTGGGGTTTGAAGGGGAATA
TCAATGTTGCTGCTTTTGAAAGAGCTTGGCAAAAAGTTTTAGATAGACATTCAATTCTACGTACATTTTTT
GTTTGGGAAAATCGCCAAACTCCATTACAAGTAGTACTAAAACAGGTTAATGTTCCTTGGAATACTCTTGA
TTGGCGAGAACTTTCTTCTAATGATCAACAACAACAATTAAAACAATTATTGCAAACACAAAGAGAACAAG
GTTTTAACTTATCCCAAGCACCATTAATGCGGTGTACGTTAGTCAGGCTAGGCGAAGATAATTACAAATTT
ATCTGGAGTCATCACCACATCCTTATGGATGGATGGTGTTTATCAATTATTTTTAAAGAAATTTTAATTTT
CTATAAAGCACATCTGCTTGGTGAAAATTGCCAATTGCCAAAACCACGTCCTTACCAGGATTATATTGCTT
GGTTGAATTCTCAAGACAAATCAGCAGCAATTGAGTTTTGGCAACAAACTTTACAAGGTTTTAGTGCTCCC
ACTCCATTGGTAATGGATAAAACTCAATTTCTGAAAGAGCAACAGTATAAAACTGCGGATTATCAGGAGAG
AACAACTAGTTTATCCCCTGAATGCACTCAGAAGTTACTTCATATAGCACAACAACATCATGTGACTTTAT
CAACTGTAGTACAAGCTGCTTGGGCTTTACTATTGAGTCGTTATAGTGGTGAGAAAGATGTAGTATTTGGT
GTGACTGTTTCTGGTCGTCCTCCTAGCCTCTCTGAGATAGAAAATATGGTAGGACTGTTTATTAACACCCT
TCCCTTACGAGTACAAGTATCCACCCAGGAGCAACTCATACCTTGGTTGCAAAAAATACAACAGTCAATGG
TTGAATTACAAGAGTATTTTTATACTCCTCTTGTTGATATTCAAGCTACTTCTGAGATACCAGGTGGAATA
CCTTTGTTTGAGAGCATTGTGGTGTTTGAGAATTATCCAATTGATAATTCTTTGTTGAATGAAGAAGGTTC
ATTACACTTAGGTGATATAGAGGTTTTTGAACAAACTAATTATCCACTAACTTTAGTTGCAGTTCCTGGGG
ATAAGTTGTCAGTTAGGATTAGTTACGATACTGCTCGTTTCTCTTCAAATACTATTGAGTGGATTTTAGGA
TATCTGCAAACTGTTTTATCAGCAATTGCAATTGTGGAAAATCCTTCACATAAGGTAGCTCAATTACCTTT
ATTAAGTGAAGTAGAACGTCATCAGTTATTGGTTGAGTGGAATAACACTGCAACGGATTACCCATCTGATA
AATGTATTCATCAGTTATTTGAGCAACAGGTAGAAAAAACCCCAACTCCATAGCAGTGGTGTTTGAAGAA
GAACAATCAACCTACCAACAATTAAATCAAAAGCGAACCAATTAGCACATTATCTACAAACTCTGGGAGT
GAAACCAGAAGTGCTGGTGGGTATTTGCATACAATACTCCATTGATATGATTGTAGGACTGTTGGGGATAC
TTAAAGCTGGTGGTGTATATGTGCCGTTAGATCCGAACTATCCGCAAGAACGACTGGCGTTCATGCAGGAA
GATTCCAATGTGCATATCATATTGACCCAGCAGCCTCTGCTCGAAAAGATTTCCCCTCAAAATGCCCATAT
CGTTTGCCTGGACAGGGATAGGGATGTCATTGCTAGGGAAGGCGTTGAAAATCTGGATCGGCAAACAACAC

FIG. 6-5

```
TGGATGACCTTGCATACGCAATCTATACGTCTGGTTCTACTGGAAAACCCAAAGCCGTTCTCGGCACGCTT
CGCGGCATTGTCAATCGCTTGCATTGGATCTGGGAAATGCTACCATTTGGGGCAGATGAGATTTGCTCTCA
GAAAACATCCATCAATTTTGGCGATCATGTTGCGGAAATATTTTCTCCCCTTCTCAAAGGAATTCCCCTTG
TGATCGTTCCAGATGATATACGGGGCAATATTCCCAGGCTAATGAGCCTGTTGAGCGATCGAAAGGTAACT
AGAATTGTTCTCGTTCCATCGCTATTAAAAGCGATACTGGAAAATGCGCCCAACAACTGACAAAACTTCG
ATATCTCAAATATGTCTTTTGCAGCGGTGAAGTCTTACCGCTAACCTTGGCTAAGGAATTTCACCAGAAAA
TCAGCTCTGCCAGATTGTTCAATCTCTACGGCTCTTCAGAAGTTGCCGCTGATGTTACATGCTTTGAAGTC
AAACTGAGAATCGCAAATCAAATTGAAGCAAAAAGTAAAGAGAAACTTGATGCTTTAAAAAATCTTCCTAG
TGGCTCAGGGGATAGGGAAACTGCTGTCCTGCATAAAGAAATAATACATTTGCAGTTGGCAGACGAGCGAA
GAGCAGATTTAGGAGAAGCTCTAGAAGAATATCTGAAAAGAAATACGATTCCGATTGGAAAACCGATTTCA
AACACACAAATTTACATCCTCGACAAGTATGGCGATCTTTTGCCACCTGGTGTTACGGGTGAGCTATACGT
CGGCGGAGATGGGCTTGCAAAAGGGTATTTAAATCTGCCCGAGTTAACGCGGGAAAAGTTTATCCCCAACC
CGTTTGTGAAGGACAGGGGGAAAAGTAAAAAGGCACAAGCAGAAAGATTGTTTAGGACTGGAGACCTAGCC
CGCTGGCTGCCGGATGGTAATATCGAATTTGTAGGGCGTATCGATCACCAAGTGAAGGTGCGGGGCTTCCG
CATTGAACTTGGAGAAATCGAAGCAGTCCTCAGTACCCACCCCCAAATCCAACAAGTCGTTGTCATTGCCA
TAGAAGATATTCCAGGTAGCAAACGTTTAGTAGCCTACATAGTCTGTGAGGATGAATCACTAAGTACCTAT
CACCTGCGTGAATTCCTCAAACAAAAGCTACCAGAATACATGATGCCCAGTGCCTTTGTCATCTAGACAC
CTTACCGTTGACACCCAGCGGTAAAATAGACCGTAAAGCCCTTCCAGCACCTGATGGAGAAATTAGCCGAG
AACATGAATATGTCCCACCACGTACATCGGGTGAAGAAATAATAGCCAACATCTTCGCTTCTATTCTAGGT
GTGCAAAATGTTGGAATCCATGACAACTTCTTTGAATTGGGAGGACATTCCCTACTAGCAACCCGATTAAT
TTCCCGACTCAGAGTTGCCTTTGAAGTAGAAATAGAACTAAGTGCAGTCTTTTCCTCTCCCACTGTAGCTC
AATTAGAGCAAACATTAACCCAATTACGTACTACTAATAGCGCATTAAGTCTTCCCCCCATTCAGCCAAGA
ACACAGAACCAACAATTACCCCTATCTTTTGCACAAGACCGGTTGTGGTTCCTCAACCAACTTGAAGGGTC
AAGTGCCACTTATAACATGCCAGGAGCAATTCGTGTCACTGGAAAGTTGGATATTAATGCCTTGCAACAAG
CATTATCAGAAATAGTCCGCCGTCATGAAGTACTACGCACCAGCTTCCGAACTGTGAATGGCACACCAATA
CAGGTAATTCACCCAGAAGCCACCATGAACATCAGTGTGGCGGACTTACAGCAACTAGAAGCAACAGAACG
GGAAAGTGTCCTTCACCAACAAGCACAACTTGCAGCAATTACCCCCTTTGACTTAGAAACTGCACCACTAA
TCAGGTGTAGTTTATTGCAGTTAGATGCCAGAGAATATGTGTTATTACTGACGATGCACCACATTGTCTCT
GATGGTTGGTCAATGGGGATATTCAGCCAAGAACTATCTACTTTATATCAAGCTTTTAGTGCAGGAAAACC
ATCCCCCTTGGCAGAATTACCAATCCAGTATGCAGACTTTGCAGTTTGGCAAAGACAATGGTTAAGTGGAA
AGGTACTAGAAACTCAACTCAATTACTGGCTTTCTCAGTTAGAGGGTGCACCAGAATTGTTACAATTACCT
ACTGACCGTCCTCGTCCAACCGTGCAAACTTTCCGGGGTACTACTCAAAGTTTTAGTTTAAATACTGATTT
AAAAGAGAAGTTGCAAACCCTGTCTCGGAACTCGGGTACTACCTTATTTATGACCCTGCACGCAGCGTTTG
CCACTTTACTCTATCGCTACAGCGGTCAATTAGATATTTTAATTGGTTCACCCATTGCCAATCGCAACTGC
AGTGAAATTGAGTCTTTGATTGGCTTTTTTGCCAATACTTTGGTATTGAAAACCCGTTTTGAAGATAATCC
CAGTTTTGAGAATTTGCTGGCACAAGTTAGGGAAACTACACTTGAAGCTTATGAACATCAGGATGTGCCTT
TTGAACAGGTAGTTGAAGTACTACAACCACAACGCTCTTTGAGTTATGCACCCTTATTCCAGGTAATGTTT
GTGTTGCAGAATGCACCCATGGGTGAATTAGAATTACCTGGTGTGACCCTTAATTTATTGAGTTCTCAAAC
AGAAACAGCCCGGTTTGATTTAACAGTATCAATGCAGCAAACTTCCGAAGCACTAGTGGGTTCATGGGAAT
ACAACACTGACTTATTTGATGGGTCAACTATTGAGCGCATGACTGCTCATTTCCAGAATCTGTGTAGCGCG
ATTGTAGAAAATCCCCAACAAAGATAAGTGAATTACCATTATTCACAGATTCTGAGCAAGAGCAGGTACT
GCACAGTTACAATAACATCGCTACAACTTACCTGCTGGATAAATATGTTCATTTCCTGAGTTCAAATAATT
TACAAATTTACATTTTAGATAACCATCAACAATTAGTTCCTTTGAGTGTAGAAGGAGAAATTTATTTGGGG
AATTGCGATTTACTCCCAGACAAGTTACATCCAGAACCAGAAAAATTTATAAGTTTCATAGAACATACCCA
ACTGGGTAAGTTATTAAAAACAGGGGAATGGGGTTGTCGTCGAGTCGATGGTTCTCTGGAATTGCTAGGAA
AAGAGCATCGAATTGTCACAGTTAATGGACAACGAATTAACCTACAACGTATTGAACAAGCTTTACAAACA
GCGAAAGGGGTAGAAGATTGCTATGTAATGGTACGCAATCAAAAATTAGTCGCTTACGTAGTCAAAGATGG
TTCTTGGGCTAGGGAGTTTTTACACCATTATTTAAAATCTCAGTTACCTGGATACCCATTACCCTGCATCT
ATGTACCAGTATCTGCTTTACCATTGACAAGTTTTGGAGAAGTTGATGAAGTAGGTTTAGCTTCTATTAGC
ATAATTGATTCTGAGTTAATTAACACTTGGGAAGAACAAATAGGTTCTCAGGCGGAAATTGATAAAGTTGC
TGTTTTTATTGAGCCAAATGTAAAAACGATTTCTCCGATACATTTAGAAGAACTTTTACCATCAATCCAAG
CTATTTTCAATCAAGGTTCTACTCCAGTTGAAACTCCCAGAACTGCTAGGGGAAAAGAGAGTAGTTCCCTA
TTAGAAATAAAATCACCTGCCATCAGCCACGAAGAAGTATTAATCTTTCCAGAATCATCTCCAGAAACTTT
AGGGGAGATGCTGCAAAAAACTGCTGGGAAATTTCCTCACAAAGGAATCACTTATATTAACTCTGATGGTT
```

FIG. 6-6

```
CCGAACAAGTTCAATCATATGCCCAGTTATTAGAAGATGCTCAAAGAATTCTAGGTGGCTTCAGAAAACTG
GGAATTAAGCCACAAGATAAAGTTATTTTGCAATTAAAAGAAAATAAAGATTTTATTAGTGCTTTTTGGGG
TTGTGTGTTGGGAGGCTTTATTCCCGTACCCGTTGTAATTCCTGTAAGCTATGACCAGCCCAATGTCAATC
TAAATAAATTACAAAATAGTTGGCAGATGTTAGAAAGACCTTTGATTTTAACAGATAAAAAATCATTGTCA
GAACTAAAGAAATGGTCTCAAAATCTAAATGACGACAACTTTAAGTTAGAAACTATTGAAAGTTTACAAAA
GTTCTCAACAGATAAAGATTACTATAATGCCCAACCAGAAGATTTAGCACTGTTCATGCTTACTTCCGGTA
GTACAGGTATGTCTAAGGTGGTACAGTTGAGCCATTTAAATCTACTGAGTAGGACTATTGGTTCAATACAA
ATGAATAATTTTACCCCAGAAGATATAACCTTAAATTGGATGCCCTTAGACCATGTTGCAGGTTTAATATA
TTTTCATATCCGGGATATTTATTTAGGATGTAAACAAATTCATGCTACTAGTCAATTAGTGATTGAAAAAC
CTTTAAGATGGTTGGATTGGATTGATACTTTTGGTGTCACTGTTACTTTTGCTCCTAACTTTGCTTATAGT
TTAATTAATGATTTTGTTCAAGAAATAGAAAAGCAGAATTGGAATTTATCTTCTATTCGCTTGATGTTAAA
TGGTGCGGAACAAATTGTTGCAGCAACAGCAAGACGTTTTTGAAATTACTTGCTCCCTTTGGCTTACCTG
GGGATGCTATGACTCCATCTTGGGGAATGGCTGAGGTTTCCTCTGGTATTACTTATTCTGACAATTTTCA
CTCTTATCAAGTTCAGATGATAATTCCTTTGTAAATCTTGGAAAACCGATTAGGGGTACTTGTCTGAGAAT
AGTCAATCAAGACATGGAAGTATTATCAGAAGGTGAAATTGGTTTACTTCAGGTCAAAGGATTAACCGTTA
CTTCTGGTTATTATCAAAATCCAAAAGCAAATAAGGAAGCATTTACCGAAGATGGTTGGTTTAATACAGGT
GATTTAGGATTTATAAAAGATGGATGCTTAACGATTACAGGACGACAAAAAGATATCATTATTATTAATGG
AGTTAATTATTATAGTCATGAAATAGAAGCTGTTGTTGAAGAATTAGGAGAGGTTGAAGTTTCTTATACCG
CAGCCTGTGGAGTCTGCGTTGCTAGCAATAATACCGAAGAATTAGTAATCTTTTTCACTCCGTATGTATCT
GAGAAGAATCAATTATTAGAGCTTTTGAAAAAGGTTAGGGAACAAGTTATAAAATACTGCGGGATAAATCC
AAGTTATTTAATACCCATAGATAAAGAACTGATTCCCAAAACTTCCATCGGTAAAATTCAACGTTCCCTCC
TTAAGCAACGTTTTGAATGTGGTGAGTTAAATCTCTCAGACAGCGTGTAGACTTGTTGCTTGATAATACT
AATACTATTCCCAACTGGTTTTACCGTAAAGTATGGCAAATTAAAGAAAGTAAAAATACTTTACTCAATTA
TTCTTCTCAGAAAACTTTAACCCTAATATTTACAGATAATTTGGGTTGGCAACAAGATAACCGAGGAATGT
CCCAAACTGTTCAACCATATGCTCAAGTTACTATTGGTTCAAATTTTGCTCAAATTAGCCCAAATCATTAT
TCTGTTGTTCCTGGAAATCCACAACACTATCGCTTGTTAATTGATTCTTTGAGGCAAAATAGCCAAGTAAT
TAGTCAAATTCTTCATCTTTGGAACTACAACGAGCAGACTGAAAAAATTTCTAGCTTGGAAAATTTAGAGT
CCACTCAACAACAAGGAATTTACAGTTTACTATTTTTAGTACAAGCTTTAGAAGAAATTCAAGGCAAACAG
CAAGCAGTCAAATTATTATGGATTGCTAATCAAAGCCAATTAGTTCATCCCACAGATAAAATTCAACCCGA
AAAATCCACTGTTTTAGGCTTACTTAAAACTGTTAGTCAAGAAATGCCTTGGTTAACTACTCGTCATTTAG
ATTTACCATTAGCACCAGAACTCAACAATAGTTATATTTGGCAAGAACTGTATTCTGCTGATAAAGAATTG
GAAGTTGCTATACGCAATAGAGAACGTTTTGTGTCTGGTCTGGAACCAGTAGATATGACTGCTAAGGAAAA
ACAAAAAATTCCGATTCTACCAGGAGGAACGTATCTACTTACAGGAGGGCTTGGAGGAATTGGGACTGTTA
TTGCAAAGTACTTATTAGAACATTATCAAGCAAATTTAATATTAGTTGGTAGAACTCAAATTGAAGATAAT
AATGAGGAAGCTAGCACAAAATTGCAGAGGTATCAAGAATTAGAAAAACTACCAGGTTCAATAATTTATCA
AACTGTAGATATTTGTGATTTAGTACGTTTACAACACGTAGTAGAAAAAGCAACACAAGAATGGAGCACTC
AACTTGATGGGGTATTTCATATGGCTGGGATTATTCAGGAAACGCCAATCGAGAAAGAAACCCCAGGAAAT
ATCGCTGCTGTTTTACGTCCTAAAGTTAGCGGTACTTGGGTATTGCATCAATTGCTCAAGGATAAAGAAAA
TGCTTTATTTGTCCACTTTTGTTCTGTAAATGGTTTCTTTGGAGGAACCAATGTTGCAGCTTATAGTGCAG
CAAATAGTTTTCAGTCAGCATGGAGCGATTATCAACAACAAAACGGTTTCCAAAGCTATTGCTGCTCTTGG
AGTATGTGGAATGAAACCGGAATAAGTCATGGCTATCAATTCCAAGAACTCAGTCGTGCTAAGGGCTATTT
TATTATTACTCCTCAACAAGGATTTTACTCATTTTTAGCAGCTTTATCTGGTTCGGAACATAATCTATTAA
TCGGATTGGATGGAACTAAAACAAATGTTGAACATTTGATTCGTGATTGTCAGCCCAAGCAGAAATTAACT
GCTTACTTCACCTCTCCCACACCAGAACTTGCTGCACTCTCCTTACAAGAGTTACAACTACACGATCGCTT
TGGGATACCCAATCAAATTAACTTTGTCCAACTTGAACAAATACCCCTTACTCAAAGAGGAGAAATTAATC
GGGAACAAATTGCTGCTATATATGGAGGTTTGAATACTTCTGAGCAGACAAAACCACGGAATCAAACAGAA
CGTCAGTTAGTTGAGATTTTCCAAGAAGTTCTCAATCTACCCTCTATTGGTATTCATGACAACTTCTTTAG
CTTAGGAGGACATTCCCTTCTAGCTGTCCGTCTAATGTCCGAGATTCAACAACAATTCCAGAAAAATTTAC
CTTTAGCCACTCTTTTTCAAAATCCCACCATTGAACGACTAGCACTTCTTGTTGGTTCCGATTCCGGAGCC
GAACTTTGGTCTCCATTAGTACCAATTCAACAAAACGGTTCATTACCACCTTTGTTCTGTGTACCAGGAGC
AGGTGGAAATGTTCTCTACTTCCACCACTTAGCACAATATCTTGGAAATAATCAACCGTTATACGGTTTAC
AAGCACAAGGTCTTGATGGTGAAACCGAACCTCATAAAAGTGTTGAAGAAATAGCCTCCCAACACATTAAA
GCAATTCAAACAGTTCAACCAGTTGGTCCTTACTTCTTGGCTGGTCATTCCTTTGGCAGTCATGTAGTATT
TGAAATGGCGAATCAACTACAACTTATTGGAAAGTCTGTTGCTTATGTTGGAATTTTAGATACTCCTGCAC
```

FIG. 6-7

```
CAACTTCTCAAGCTAATCATCAGAATGATTTTTCTAACTGGGATAATGCAAAGTGGATATGTCGAATGGCT
GAGGTTATTGAAGATATTGTTGGAGAAAATCTATTTTTATCTTATGAAACTCTAACTTCTCTAACTTGGGA
GCAACAATTAAATTATTTCAAGCAAAGTTAGAAATAGTTGGTTTTTTGCCTGCTCAAACAGATATCAAAA
TTGTTCGTGGTTTATTACAAGTTTTCCAAACTCAATGTCAAATTAAGTATGAACCGGAAAAGACTTATAA
ACTCCAATCACTTTGTTTTGTGCGAGGGAGATAAATCCAGAGCAAGAAAGTTATTCTCACATTTTCCAAGA
GCCAACATGGGGTTGGAATCAGTTTTCTGATGGAGAAGTGGAAATCCATATAGTTCCGGGTAATCATGTTT
CAATGCTGAGTGAGCCTCATGTCAAGGTATTGGCTCAACAAATGCAAATATCTCTTGAACAAGCACAGAAA
ACCCATCAATTGGAAAAATGA (SEQ ID NO:6)
```

CrpD

```
MSNEEIRRNISSIYPLSPMQQGMLFHSLYAPYSGVYLEQMTWGLKGNINVAAFERAWQKVLDRHSILRTFF
VWENRQTPLQVVLKQVNVPWNTLDWRELSSNDQQQQLKQLLQTQREQGFNLSQAPLMRCTLVRLGEDNYKF
IWSHHHILMDGWCLSIIFKEILIFYKAHLLGENCQLPKPRPYQDYIAWLNSQDKSAAIEFWQQTLQGFSAP
TPLVMDKTQFLKEQQYKTADYQERTSSLSPECTQKLLHIAQQHHVTLSTVVQAAWALLLSRYSGEKDVVFG
VTVSGRPPSLSEIENMVCLFINTLPLRVQVSTQEQLIPWLQKIQQSMVELQEYFYTPLVDIQATSEIPGGI
PLFESIVVFENYPIDNSLLNEEGSLHLGDIEVFEQTNYPLTLVAVPGDKLSVRISYDTARFSSNTIEWILG
YLQTVLSAIAIVENPSHKVAQLPLLSEVERHQLLVEWNNTATDYPSDKCIHQLFEQQVEKNPNSIAVVFBE
EQSTYQQLNQKANQLAHYLQTLGVKPEVLVGICIEYSIDMIVGLLGILKAGGVYVPLDPNYPQERLAFMQE
DSNVHIILTQQPLLEKISPQNAHIVCLDRDRDVIAREGVENLDRQTTLDDLAYAIYTSGSTGKPKAVLGTL
RGIVNRLHWIWEMLPFGADEICSQKTSINFGDHVAEIFSPLLKGIPLVIVPDDIRGNIPRLMSLLSDRKVT
RIVLVPSLLKAILENAPQQLTKLRYLKYVFCSGEVLPLTLAKEFHQKISSARLFNLYGSSEVAADVTCFEV
KLRIANQIEAKSKEKLDALKNLPSGSGDRETAVLHKEIIHLQLADERRADLGEALEEYLKRNTIPIGKPIS
NTQIYILDKYGDLLPPGVTGELYVGGDGLAKGYLNLPELTREKFIPNPFVKDRGKSKKAQAERLFRTGDLA
RWLPDGNIEFVGRIDHQVKVRGFRIELGEIEAVLSTHPQIQQVVVIAIEDIPGSKRLVAYIVCEDESLSTY
HLREFLKQKLPEYMMPSAFVILDTLPLTPSGKIDRKALPAPDGEISREHEYVPPRTSGEEIIANIFASILG
VQNVGIHDNFFELGGHSLLATRLISRLRVAFEVETELSAVFSSPTVAQLEQTLTQLRTTNSALSLPPIQPR
TQNQQLPLSFAQDRLWFLNQLEGSSATYNMPGAIRVTGKLDINALQQALSEIVRRHEVLRTSFRTVNGTPI
QVIHPEATMNISVADLQQLEATERESVLHQQAQLAAITPFDLETAPLIRCSLLQLDAREYVLLLTMHHIVS
DGWSMGIFSQELSTLYQAFSAGKPSPLAELPIQYADFAVWQRQWLSGKVLETQLNYWLSQLEGAPELLQLP
TDRPRPTVQTFRGTTQSFSLNTDLKEKLQTLSRNSGTTLFMTLHAAFATLLYRYSGQLDILIGSPIANRNC
SEIESLIGFFANTLVLKTRFEDNPSFENLLAQVRETTLEAYEHQDVPFEQVVEVLQPQRSLSYAPLFQVMF
VLQNAPMGELELPGVTLNLLSSQTETARFDLTVSMQQTSEALVGSWEYNTDLFDGSTIERMTAHFQNLCSA
IVENPQQKISELPLFTDSEQEQVLHSYNNIATTYLLDKYVHFLSSNNLQIYILDNHQQLVPLSVEGEIYLG
NCDLLPDKLHPEPEKFISFIEHTQLGKLLKTGEWGCRRVDGSLELLGKEHRIVTVNGQRINLQRIEQALQT
AKGVEDCYVMVRNQKLVAYVVKDGSWAREFLHHYLKSQLPGYPLPCIYVPVSALPLTSFGEVDEVGLASIS
IIDSELINTWEEQIGSQAEIDKVAVFIEPNVKTISPIHLEELLPSIQAIFNQGSTPVETPRTARGKESSSL
LEIKSPAISHEEVLIFPESSPETLGEMLQKTAGKFPHKGITYINSDGSEQVQSYAQLLEDAQRILGGFRKL
GIKPQDKVILQLKENKDFISAFWGCVLGGFIPVPVVIPVSYDQPNVNLNKLQNSWQMLERPLILTDKKSLS
ELKKWSQNLNDDNFKLETIESLQKFSTDKDYYNAQPEDLALFMLTSGSTGMSKVVQLSHLNLLSRTIGSIQ
MNNFTPEDITLNWMPLDHVAGLIYFHIRDIYLGCKQIHATSQLVIEKPLRWLDWIDTFGVTVTFAPNFAYS
LINDFVQEIEKQNWNLSSIRLMLNGAEQIVAATARRFLKLLAPFGLPGDAMTPSWGMAEVSSGITYSDNFS
LLSSSDDNSFVNLGKPIRGTCLRIVNQDMEVLSEGEIGLLQVKGLTVTSGYYQNPKANKEAFTEDGWFNTG
DLGFIKDGCLTITGRQKDIIIINGVNYYSHEIEAVVEELGEVEVSYTAACGVCVASNNTEELVIFFTPYVS
EKNQLLELLKKVREQVIKYCGINPSYLIPIDKELIPKTSIGKIQRSLLKQRFECGEFKSLRQRVDLLLDNT
NTIPNWFYRKVWQIKESKNTLLNYSSQKTLTLIFTDNLGWQQDNRGMSQTVQPYAQVTIGSNFAQISPNHY
SVVPGNPQHYRLLIDSLRQNSQVISQILHLWNYNEQTEKISSLENLESTQQQGIYSLLFLVQALEEIQGKQ
QAVKLLWIANQSQLVHPTDKIQPEKSTVLGLLKTVSQEMPWLTTRHLDLPLAPELNNSYIWQELYSADKEL
EVAIRNRERFVSGLEPVDMTAKEKQKIPILPGGTYLLTGGLGGIGTVIAKYLLEHYQANLILVGRTQIEDN
NEEASTKLQRYQELEKLPGSIIYQTVDICDLVGLQQVVEKATQEWRTQLDGVFHMAGIIQETPIEKETPGN
IAAVLRPKVSGTWVLHQLLKDKENALFVHFCSVNGFFGGTNVAAYSAANSFQSAWSDYQQQNGFQSYCCSW
SMWNETGISHGYQFQELSRAKGYFIITPQQGFYSFLAALSGSEHNLLIGLDGTKTNVEHLIRDCQPKQKLT
AYFTSPTPELAALSLQELQLHDRFGIPNQINFVQLEQIPLTQRGEINREQIAAIYGGLNTSEQTKPRNQTE
RQLVEIFQEVLNLPSIGIHDNFFSLGGHSLLAVRLMSEIQQQFQKNLPLATLFQNPTIERLALLVGSDSGA
ELWSPLVPIQQNGSLPPLFCVPGAGGNVLYFHHLAQYLGNNQPLYGLQAQGLDGETEPHKSVEEIASQHIK
```

FIG. 6-8

AIQTVQPVGPYFLAGHSFGSHVVFEMANQLQLICKSVAYVGILDTPAPTSQANHQNDFSNWDNAKWICRMA
EVIEDIVGENLFLSYETLTSLTWEQQLNYFKQKLEIVGFLPAQTDIKIVRGLLQVFQTQCQIKYEPEKTYK
TPITLFCAREINPEQESYSHIFQEPTWGWNQFSDGEVEIHIVPGNHVSMLSEPHVKVLAQQMQISLEQAQK
THQLEK (SEQ ID NO:7)

crpE
ATGATTAATACTGCTAAATCCTCATTACTTCCTGGTCCCACTACACCATCTTGGTGGAACTTATTGCAATG
GCTTAATAATCCTTGTGAATTTTTGGAAGAGTGTCGAGCACGCTATGGAGACACTTTTACCTTCAAAGCTA
TTGGTTTTGAACCTTTAGTACTTATTAGTAATCCTAAGGATATAAAAGAAATTTTTGATAAACACAAGTAT
TTTGACAGTGGAAAAGCTAAAGCTAACGATTTAGCAGGATTTTTTTTAGGCAACAATTCCGTCACCTTGCT
TGATGGAAGTAGTCATAAACGACAGCGTAAACTACTGATGCCTGCTTTTCATGGTCAAAATATATCTAACT
ATGGAGAACTAATATGCCATGCAACGAAGCAGGTTACTTCTAATTGGCAACCTGGTCAAGATTGATTATT
TACAAGCAAGTCAAAGAAATTACGCTGCGAGCGATGTTAACGGTTTTACTGGGTTCAGATAAAACGGAACG
TTATCAACAACTCAAATTGATAGTTAATCAAATAGTATCCACTATAACTAATCCCTTTGCTTCTAGCTCTC
TTTTCTTCAATGTGTTTAGAAGAGACTGGGGTTCTTGGAGTGCCTGGGGTAATCTTTTACGTTGCCAACGT
CAGATTGCAAATATCATTTCTGCAGAAATCAAAGAACGTAGAGAAAATTGTAACAATTACAACAATGATAT
CCTCAGTATGCTGATGGCAGCACGAGATGAAAATGGAGGAAAAATGACAGATGAGGAGTTGCAAGATGAGT
TAATGACACTTATCTTTTCTGGATATGAAACTACATCTGCAGCAATAACATGGGCATATTATTGGATTCAT
TACTTACCAGAGATAAGAGCCAAGTTATTGCAAGAATTAGATGAGTTAGGAGATAATCCAGACCCAACGGA
AATAAGCAAATTACCTTATCTCAATGCAGTTTGTGCTGAAACCTTGAGAATATATCCAGTTGGTCTAACTA
CTTTTCCTCGAATTGTAAAATCGCCAATAGAAATTGGAGGTCATCAATTTGAGGTAGGAACTTGTCTTTAT
CCATGTATTTATCTAATTCACCACCGGGAAGAACTATATCCTAACTCTAAACAGTTTAAGCCAGAACGTTT
TCTAGATAATAAATTTTTAAATTATGAGTATTTCCCTTTCGGTGGCGGTAACCGAACTTGCATTGGTATGG
CATTTGCTCAGTTTAAAATGAAGTTAGTATTGGCTAATATTTTGCGGAATTGGCAATTGGAATTGGTAGGC
AAACCTCCTTTAAAACCAGTACGAGATATTTTCTCAATTTATCCTCAAGGTGGATTAAAAATGGTTGTATT
GTAA (SEQ ID NO:8)

CrpE
MINTAKSSLLPGPTTPSWWNLLQWLNNPCEFLEECRARYGDTFTFKAIGFEPLVLISNPKDIKEIFDKHKY
FDSGKAKANDLAGFFLGNNSVTILLDGSSHKRQRKLLMPAFHGQNISNYGELICHATKQVTSNWQPGQRLII
YKEVKEITLRAMLTVLLGSDKTERYQQLKLIVNQIVSTITNPFASSSLFFNVFRRDWGSWSAWGNLLRCQR
QIANIISAEIKERRENCNNYNNDILSMLMAARDENGGKMTDEELQDELMTLIFSGYETTSAAITWAYYWIH
YLPEIRAKLLQELDELGDNPDPTEISKLPYLNAVCAETLRIYPVGLTTFPRIVKSPIEIGGHQFEVGTCLY
PCIYLIHHREELYPNSKQFKPERFLDNKFLNYEYFPFGGGNRTCIGMAFAQFKMKLVLANILRNWQLELVG
KPPLKPVRDIFSIYPQGGLKMVVL (SEQ ID NO:9)

crpF
ATGTATTCAATAAAAATTGAAAATCTAATAATTAGAGTGAAAAGTGTATTAGAAATGCCAGTTTCTAAAGA
AGCTGAGATGGCAAATAAATTTAATGAGTTTGGATTCGTAATACTAGAACACGAACCTTCAGCAACACCTA
AGAATAACTTATTAAAATTGTCTGATTATTTTGGAACAATTATTCAGCACGAACATTCTGATTCACAGGGA
ATTGTTCCCATCAGTCCTGTTGATAGTTATCCAGAATATGTAAATACTACAACTACAGATTTATCGTTACA
TACGGATGGAGCGTTCACAATTACTCCACCAAAAGTAATGGCAATGCAGTGCCAGATTGCTGCTGCAAATG
GCGGGTTCACCAAGCTTATTGATGGCAAGCTGGTATATGAACATCTAAAGCGGACAAACCCAGTTGGATTG
TTAACTTTGTTTAATCCTGATGCGATTACAGTCAAAAGAGATAATAAAAAAGCAACTAAACCTATTTTTGA
AGAACATCATGCTGGGCTTATTGTAAGGTTTAGAGCAGATAATGCAGCTCATGTTTCGGTTGAATCGAAAA
GTTTTGCGGCATTTAAATCATTTGAAAACTTTGTAAATAATCCTGACAATCAAGTAATTTTTAAACTTGCA
CAAAACCAAATAATTATTGTAGATAATACTAGAGTTTTGCATGGAAGAACTGCATTTTCCAAACAAGAGTA
TAGGCTACTAAATCGACTTTGGTTTGATGGACAATCTGATATTATAAATTTAAAGTTTGGTATTCTATAG
CCCCAAAAAACTTGAGTTTATTTGCTAAAAAGTATCAGCCATCTCAAATAGATATAGGCTCAGATATTTCT
CAGTCAACTCAATTGAAATTTAAAGCCACATGA (SEQ ID NO:10)

CrpF
MYSIKIENLIIRVKSVLEMPVSKEAEMANKFNEFGFVILEHEPSATPKNNLLKLSDYFGTIIQHEHSDSQG
IVPISPVDSYPEYVNTTTTDLSLHTDGAFTITPPKVMAMQCQIAAANGGFTKLIDGKLVYEHLKRTNPVGL

FIG. 6-9

LTLFNPDAITVKRDNKKATKPIFEEHHAGLIVRFRADNAAHVSVESKSFAAFKSFENFVNNPDNQVIFKLA
QNQIIIVDNTRVLHGRTAFSKQEYRLLNRLWFDGQSDIINLKFCISIAPKNLSLFAKKYQPSQIDIGSDIS
QSTQLKFKAT (SEQ ID NO:11)

crpG
ATGTTGAAGTCGAAAATTCACAGAGCGACGGTGACGGAAGCCAACGTTAACTACATCGGAAGTATTACAGT
AGACAAAGTTCTGATGGAAAAGGCAGACATACTACCGGGTGAAAAGGTTATGGTGGTGGACAACACTAATG
GTAATCGTCTAGAAACCTATGTCCTAGAAGGTGAGGAAAATTCCGGGGTAATCTGTATGAACGGTGGCTCC
GCCCACCTAGTCAATTCAGGAGACCTTATCACATTGCTAGCATTCGAGGTAACTGACGAAATCAAGGAACC
GAAAAAAATTATCGTGGATGAAAACAACAAGTTTCTCAAGTACCTGTAA (SEQ ID NO:12)

CrpG
MLKSKIHRATVTEANVNYIGSITVDKVLMEKADILPGEKVMVVDNTNGNRLETYVLEGEENSGVICMNGGS
AHLVNSGDLITLLAFEVTDEIKEPKKIIVDENNKFLKYL (SEQ ID NO:13)

crpH
ATGTCTACACTGCCTAATTCCACACAGATTCTAATTATCGGAGGGGGACCTTCTGGATCTACTGCTGCTAC
CCTATTGGCTCGTGAGGGCTTTGATGTAACGCTGTTAGAACGAGAGGTATTCCCGCGTTACCACGTGGGG
AATCTCTTTTGCCCTCTGCTTTAGAAATTTTTGACCTGCTTGGCGTACGCGAGAAAATTGAAGCTTATGGC
TTTCAGCGTAAACCTGGAGCGTACATAGAATGGGGAACGGAAAAGTGGAGCCTCAATTTTGGGGAACTTAC
GGGGGACAACACCTACAGCTTCCAAGTTCGCCGTGACGAATTCGACCACTTGCTTTTAGAGCATTCAAAGA
GCCAGGGTGTGAAGGTTTTTGAAGGGACTAAAATTCGCCAGTTGTCTTTTGATGGCGATCGCCCGCGCAGC
GCTACTTGGTCACAATCAAATGATACTACCGGGGAGATTTCTTTTGACTTTATGATTGACGCTTCAGGTCG
TGCTGGGATCATGGCGACGGAGTATCTGAAAAACCGCCGTCTACACGACGTATTCCAGAATGTTGGCATCT
GGGGGTACTGGAAAAACGCCTTGAGACTACCTAAAGGTCAGTCGGGTGCGATTGCCTTGGGCTCCATTCCA
GATGGTTGGGTGTGGGAATTCCTTTGGATGAGGAAATTATGAGCGTTGGTGTAGTGATGCATAAGTCAAC
CTACAAGGAGAGACTGACTAAGAACTTGAAGGATATCTACGTGGAGGCGATTGCAGAGTGTCCCTTGATAG
CGGATCTGGTTGCACTAGGGGAGCTAGTCTCAGACGTGAAAGTTGAGCAAGATTACTCTTACACTTCCGAC
TCCTTTTCAGGACCAGCCTACTTCATATCGGGAGACGCTGCTTGCTTCCTAGACCCCCTACTATCGAGTGG
GGTGCATCTTGCTACTTATAGCGCTTTGTTAGCCGCAGCCAGTATCACAAGTGTTATACGTGGCGAGGTGA
CTGAGTCACAAGCTGCTTCTTTCTACGATCAGAGCTATCGGCAGGCTTATTTGCGTTTCTTAGTGTTCGTA
TCAGCCTTCTACGATCAAAACCGTGGCAAGGATTCCTATTTCTGGGAGGCACAACGGCTTAGTCGCCGTGA
CTTCGGCAGTTCTAACCTAAAGCTAGCATTCTTGAATCTGGTGTCCGGCGTCGAGGACTTGGAGGACGCTA
AGGAGGGGATTGCCGATTTTGTTATGGCAGAGATGTCTCAGCGGATTCAGTCAAGCCACAGCATTAGGCAA
GACAAGCAGGCGTTGGCAATCGAAAGGGAAAAAGGTAACGAGGTAATGAAGACAAATGCCCAGTTTTTCAA
TGCAGTCGAGGGATTTTCCATACTATCGGCAGTTGGGGCAGTTGATGGTCTATATGTTACAACTCAGCCAA
AATTAGGATTGGTACAGGTAATCCCTCTCCAAAGAAACTCTTTGCTCCACACTTAG (SEQ ID NO:14)

CrpH
MSTLPNSTQILIIGGGPSGSTAATLLAREGFDVTLLEREVFPRYHVGESLLFSALEIFDLLGVREKIEAYG
FQRKPGAYIEWGTEKWSLNFGELTGDNTYSFQVRRDEFDHLLLEHSKSQGVKVFEGTKIRQLSFDGDRPRS
ATWSQSNDTTGEISFDFMIDASGRAGIMATEYLKNRRLHDVFQNVGIWGYWKNALRLPKGQSGAIALGSIP
DGWVWGIPLDEEIMSVGVVMHKSTYKERLTKNLKDIYVEAIAECPLIADLVALGELVSDVKVEQDYSYTSD
SFSGPAYFISGDAACFLDPLLSSGVHLATYSALLAAASITSVIRGEVTESQAASFYDQSYRQAYLRFLVFV
SAFYDQNRGKDSYFWEAQRLSRRDFGSSNLKLAFLNLVSGVEDLEDAKEGIADFVMAEMSQRIQSSHSIRQ
DKQALAIEREKGNEVMKTNAQFFNAVEGFSILSAVGAVDGLYVTTQPKLGLVQVIPLQRNSLLHT (SEQ
ID NO:15)

crpM
ATGTTATCTCCCCTATTTGATGCTTTTGTAGAGGCAAGCCCCGTCAGTGTAATGATGCGAGTCCTAATGGA
AAACATTTTTAATTCCTCGCGAATGAATCAAATATTTGATACATCAAGCGTTCGCCAATACTCTCAAGAGC
TACTGTTTTCGACTCAGGTGGATTTGATGAGTCTAGTAGTGTGTGGGATGTATCCCTCGGTTCATGCAGCC
TATCAGAAGAAGGCAGTGGAGGTAAGTGTCAGCGCCACAGCCGTTATACAACAAACTGCAACGGATTGAACT

FIG. 6-10

```
GCCTGTAAGTCGGGCATTAGTGCATGAGACAGCATCTGACCTCCAGCAGTTGCTGTTGATGTTGAATGTGG
AACGCCCCAGTCCTCTAGGAAAACAATATCGGTTGCGGATTGTAGATGGCAGTTGTTTAGCCGGAACCGAA
CGCAGACTAGCAGCGCTGCGCCCCATGCAGCCAAACCATTACCCGGAAAAACAATCGCCATTCTCGACCC
AGGGACAAAACTGGTGGTTGATGTGATTCCTTGTGAAGACGGTCATTCCCAAGAACGCTCCAAGTTTCATC
AGGTTTTGGCACAAGTGCAACCCCAACAGGTATGGATTGCAGACCGTAACTTTTGTACCGCAGGATTTCTC
CATACTATTGCCAAACTTGGAGCGTTTTTTGTGATTCGTCAACACGGGGGTTTAGGATACGAGCCTTTTGG
TGAGTTACAAGCTGTTGGGTTGTGCCAAACAGGAACTGTGTTTGAACAACAGGTGGAAATTGTCCATGAGG
GAGGGACTTTTCGGTGTCGCCGTATCGTAGTTAAGTTGACTCGTCCCACCCGTGACCAAGAGTGGGAAATT
GCCATTTTTACCAACTTACCACCCACTGACGCAGACGGCATTCTGGTGGCACAACTCTATCAAGGCGGTG
GAGTGTGGAAACTTTATTCCAAACTGTGACCCAAAACTTTCATGGAGAAATTGAAACCCTAGCTTATCCTA
AAGCTGCCTTATTCTCCTACTGCATGGCACTGTCAGCCTACAACCTTTTAGCGACACTTAAAGCAGTTCTT
GGCAGTGTACATGGGGTAGACAAAATCGATATTGGGCTATCCGATTTTTACCTAGTAGATGATATCCATTC
CATCTATCGGGGCATGATGATTGCTATTCCTCCGGTTCATTGGCAATTCTTTGAGGAGTTTACCAACATTC
AGATGGTAGACGTTCTCCAGCATCTAGCAACCAAAGTACATCTCAAATCTTTTCGCAAACACCCCAGAAGT
CCCAAAAAGAAACGACCACCACTCTCTGTTGATGGCAAACATTCCCACTGTTCCACTACTCGAAAGCTCAA
GCAATACAAAGCAGCTCTTGATGCTATCCCGTGA (SEQ ID NO:16)
```

CrpM

```
MLSPLFDAFVEASPVSVMMRVLMENIFNSSRMNQIFDTSSVRQYSQELLFSTQVDLMSLVVCGMYPSVHAA
YQKKAVEVSVSATALYNKLQRIELPVSRALVHETASDLQQLLLMLNVERPSPLGKQYRLRIVDGSCLAGTE
RRLAALRPHAAKPLPGKTIAILDPGTKLVVDVIPCEDGHSQERSKFHQVLAQVQPQQVWIADRNFCTAGFL
HTIAKLGAFFVIRQHGGLGYEPFGELQAVGLCQTGTVFEQQVEIVHEGGTFRCRRIVVKLTRPTRDQEWEI
AIFTNLPPTDADGILVAQLYQGRWSVETLFQTVTQNFHGEIETLAYPKAALFSYCMALSAYNLLATLKAVL
GSVHGVDKIDIGLSDFYLVDDIHSIYRGMMIAIPPVHWQFFEEFTNIQMVDVLQHLATKVHLKSFRKHPRS
PKKKRPPLSVDGKHSHCSTTRKLKQYKAALDAIP (SEQ ID NO:17)
``` crpN

```
ATGAACAAACCACCATCCAGACGCAAGAAAATTACCCCTGCGACATCTGAGGAACCAAAGCTAGCAACTGA
CCCTGCTCAGGAAAATACTTCTTTGCACGAAAATCCAGGGGAGCAACTATCACGGTGACGGCTGTTGAAG
TAACAGATTTGACCCAGGAAGAACAAAGCTTACGCCTGCATTTAGAACACCGTGTGGAGAGAGCATTTTTG
GAGGCGGGTCAAGCGTTGATGCAGTTGCGGGACAGACGGCTGTACCGTTCCACGCACCGGACTTTTGAAGA
ATACTGCCGCGAACGCTTCAATTATAGTCGTGACGCGGCTTACTTGAAGATTTCGGCTACTGTGGTTTATC
AGAATCTTCAAAAGTTTTTGCCGACCATTGGTCGGCAAATTCCAATGCCCGACCAACGAACGACAATTGCGT
TTTTTGGCGAAAGCCGAGTTGGAACCGGCTGTGCAAGCGGATGTATGGCGGCAGGCAGTGGAGCAAGCTGG
CAATAAGATTCCATCCGGTCGCATAGTGAAAGATGTTGTAGATAGGATACGCGAAAGGACGAAAGTACCCA
ATCCTTACCACGTTGGGGAGATATGCGTTCTTCTACCCAAAGATAATGCAGACTTGAGAGGTAAAGCGGGT
TATTGGGGCGTGGTCAGCCATGTTGGAGAATACAGTTGTACACTCCAGATATGGGACGGTGACTATACCGT
AAAAATCGAACACCTGAAATCACTGGAATTACTTGATGAAGATTGCCAATTCATGCAGCAGTTATGTGTGA
GGTTACGGCAGTTGCATCAAGTGGACAGGCGTGACGAGGCTGTGGATTGGCTGTTGCAGTGGTTGGGGAAA
CAGGCCAAACCTTATCTGTCATCCTTGCAGTCAAAGCTGCTGGCGTTTGTTGAGAGAGAGTACAACCTGGT
TTGGAAGCAGCAGAAGTGA (SEQ ID NO:18)
```

CrpN

```
MNKPPSRRKKITPATSEEPKLATDPAQENTSLHENPGGATITVTAVEVTDLTQEEQSLRLHLEHRVERAFL
EAGQALMELRDRRLYRSTHRTFEEYCRERFNYSRDAAYLKISATVVYENLQKFLPTIGRQIPMPTNERQLR
FLAKAELEPAVQADVWRQAVEQAGNKIPSGRIVKDVVDRIRERTKVPNPYHVGEICVLLPKDNADLRGKAG
YWGVVSHVGEYSCTLQIWDGDYTVKIEHLKSLELLDEDCQFMQQLCVRLRQLHQVDRRDEAVDWLLQWLGK
QAKPYLSSLQSKLLAFVEREYNLVWKQQK (SEQ ID NO:19)
``` crpP

```
ATGACGAAGWTAAGATGGGGATRKTCTYGKMTCGWARTATCAGTTATACAAAATACTACAATCTTAAACAT
ACAATTGTTAGCTTCGACAACTATTCAATCAAAGTATATATTTAATATGGCTATCAAACACCCTTTTTTAT
TTGCACTGTTAACGCTCTCCATTATTTGTGTTGGTACGAGTTCTGGCTCTGCACTACTGACAGATATTGCT
CAACAAACAGACAACCAAAAGTCCCCATCGATTATTTTCTTCCTGCCCAAAGAACGACCTCAGACCGGAGT
```

FIG. 6-11

CGGTTGGGAAATCACTACCACTTCAGGGAAGGCAGAACTAGCCTTGGCGAAGCATTTGGTGTATATCGGGG
CAAAAGAATATGTTTCTTGGTGGTGTCCTCACTGTCACGAACAAAAGTTAATCTTTGGGAAGCAAGCCTAC
CAAATAATCAACGACAGTATTAAAGTTGAGTGCGATAAGAGAGGTATCAATCCCCACCCAGACTTGTGCAA
TGCGGCGAAAGTCCCAGGTGTACCAACTTGGGTTATCAATGGACATCAGTATACCGGCGTGCAAAACTTTA
AGGATCTTGCGAAAGCTTCTGGCTACAAGGGGGATATGAACTTTCGTTATATCCAAAGCGAATAA (SEQ
ID NO:20)

CrpP
MTKXRWGXSXXXXSVIQNTTILNIQLLASTTIQSKYIFNMAIKHPFLFALLTLSIICVGTSSGSALLTDIA
QQTDNQKSPSIIFFLPKERPQTGVGWEITTTSGKAELALAKHLVYIGAKEYVSWWCPHCHEQKLIFGKQAY
QIINDSIKVECDKRGINPHPDLCNAAKVPGVPTWVINGHQYTGVQNFKDLAKASGYKGDMNFRYIQSE
(SEQ ID NO:21)*** crpU
ATGATACAGTGTAATTTTTCGTTGCCACCTGAGTATGTTCTTCGTAAGGCCAAGCCTTTTGATATGTGGTT
AATAGTATTTTTTGTGTTTAGAGCAAGGCTAGACCCCAGTCAATTAAGATGGCAGCAATTTTGGGTCATTG
AATGTGATGGACATTTAGTAGCCTTCGGGCAGATCCGAAACTTTCACTTAGCACAAGAGCTAGGCAGTTTA
TTTGTTGCACCGACTTGGCGAAACCGTGGTTTAGGGACTGTTTTGATACAGCATTTAATTACTCAAGCTAG
TCAACCGCTTTATTTAAAATGCTTAAAATATCAATTGGTGAATTTTTACATTAAAAGAGGCTTTGTATCCG
TTAATTTTAAAGATTTACCACCATCCCTCAAGCCAAAGTTTGGACTATCCCAATTACGAAAGAGGTTAACG
AAAGCTTTTGTGCTGTTTATGAAGTATGAATATCCCAACTGA (SEQ ID NO:22)

CrpU
MIQCNFSLPPEYVLRKAKPFDMWLIVFFVFRARLDPSQLRWQQFWVIECDGHLVAFGQIRNPHLAQELGSL
FVAPTWRNRGLGTVLIQHLITQASQPLYLKCLKYQLVNFYIKRGFVSVNFKDLPPSLKPKFGLSQLRKRLT
KAFVLFMKYEYPN (SEQ ID NO:23)

crpV
ATGTCAGTGCCAGTTAGCGCACAGATTATACCAGATAAAACACTACCTATTAATTCCAATGTTGAACATGA
AGGTAATACTAACCGCATAGAAGGTGGCACTATAAAAGGGAGCAACTTGTTCCACAGTTTTGAACAATTYT
CCGTGCTTACTGGAAATGAAGCTTACTTTAACAACGATATAAATATCCAAAACATTATTACTCGTATTACT
GGGAAGTCTATTTCTAATATCGATGGCATTCTCAAAGCCAATGGCACGGCTAATTTGTTTCTGCTCAATCC
CAATGGCATTATTTTTGGTAATAATGCCAAACTAAATATTGGTGGTTCATTTCTAGCTACTACTGCAAATC
AAATTAATTTTGCTGATGATACTAAATTTAGTACAAACAATCCCCAACCTAATCCTTTACTGACAGTAAGT
GTGCCTATAGGACTGCAAATTGATAGCAACCCCGGTACAATTCGCATCCAAGGTACAGGTCACAATCTAAT
TGCCCCTCCTTTTTCTCCTCTAATCACAAGTAGTAGCGCCGCAAATTTACAAGTGCAACCAGAAAGAACTG
TAGCAATTGTTGGTGGTGATGTAATTTTAGAGGGAGGTGTGATAACGGCTAGGGGAGGGCGAATTGAATTG
GGTAGCCTCAGCAATGGTTCAGTCAGTATTAATCCTACGACCTCTGGTTGGAAACTGGGCTATGAAAATGT
ACCTTATTTCCAAGATATTAACCTCTCAAAACGCGCTKTAGTTAATACTAGTGGCATTGGCAGTGGATCTA
TACAGATAGAGGGACGCAKAGTTACGCTTACAGATGGCTCAGTAATCTTAAATCAAAATCAAGGAACACTA
CCAGGAGGCACACTAAACGTGAATGCTTCGGAGTCTTTGTCAGTGAGTGGTAGCGATCCAATTGCTAGGAC
AGCTGCTGCTTTGCCGAGCGAAACTTTGGGATTGGCAAAGCTGGAGACATTGCAATTTCAACCAAACAGG
TAATTATTAAAAATGGAGGACAAATAAATAATTTAACCTTTGGTGCTGCAACAAGTGGCAATATAAATGTG
AATGCCTCTGATTCTATACAATTGCTTGGGGTTTCGCCTTTTGACCCTGCTGTTTTTAGTACTATCAGCAC
TGCAACTTTCAATTCTGGAAACGCAAACAATATTACAGTGTCAACAGGACAATTCGTTGCCACGGATGGAG
GTAACTTGTCCTCTTCAACCTTTGGAACTGGTAGAGGAGGAGATGTCACTGTAAGTGCAACTGACTCTATA
GAAATAATAGGAGCTTCACCAATAACCTTTCAGCCAAGTATTTATCTTCCATATCGCTCAATGCTGGCAA
AGCTGGCAGCCTAACAATCAGTACATCAAAGTTGATGGTTCAAGATGGCGGGAGGGTTGACGCTTCTACTT
TAGCAAGTGGGGAGGGCGGTAGTGTTACGATTAACGCCTTTAAATCTGTAGAGGTAAGTGGTAAGATACTT
GGTTTTGGAGAGCCTAGTTTGGTGATCTCCAGTGCTAATATCGTCTCTCCAATCTTGCAAAAGTTATACAG
ACTCCCTTCAGTGCCTTCTGGAAAATCTGGAAACGTGACGATTAATACTGGTCAGTTGAGTGTTACAGACG
GTGCTGAAGTTAACGTGAGAAATGACGGTTCTARCGATGCTGGAACACTCAGAATCAATGCTGTTTCTGTT
TCTTTAAACAAACAAAGTGCCATTACAGCAACTACTGCTAACGGCGAAGGCGGTAATATTTCGTGAATAC
ACGGTATTTGCAGCTAAGTAATTACAGTGTTGTAACGACGACCGCAGGTAGTAGAGGCAATGGCGGTAATA

FIG. 6-12

TAAACATCAATGCAGATATATTAAGTGCTTGGGGGAAGAGCAGTATTGCTGCCAATGCTTTCTATGGGTAT
GGAGGAAATGTACTAATTAATACTAGAGGACTTTTTATTGCTCGTGACAGTCAAATTTCTGCAAGTTCTAA
ATACGGAATTAACGGCACTGTTAGCATTAACAATACTGGTGGTGAAATTTATCCTACTAAACTCAAATCAG
AATCGATTCCAGTAGCTCCTCAAATAGCATCAGTTTGTCAAAAAAATTCAGATATACCAATCAGTAAATTT
GTGAATGTTGGCACCGGTGGACTGCCAGCTAATTCTGATGATATGCCATATATGAATTATGAACAGCAAAA
TAACTCTGTTTCAATCCACAATAATAATAACTTAGAGGCATCGAAGGCATCACAAACTGAAGAACCTATAC
AGATAATAGAAGCTCAGGGTTGGATAATAAATCTTGATGGGGAATGTCGTCTTAACTGCACAAAACAATAC
AGCAACCCCTAA (SEQ ID NO:24)

CrpV
MSVPVSAQIIPDKTLPINSNVEHEGNTNRIEGGTIKGSNLFHSFEQXSVLTGNEAYFNNDINIQNIITRIT
GKSISNIDGILKANGTANLFLLNPNGIIFGNNAKLNICGSFLATTANQINFADDTKFSTNNPQPNPLLTVS
VPIGLQIDSNPGTIRIQCTGHNLIGPPFSPLITSSSAANLQVQPERTVAIVGGDVILEGGVITARCGRIEL
GSLSNGSVSINPTTSGWKLGYENVPYFQDINLSKRAXVNTSGIGSGSIQIEGRXVTLTDGSVILNQNQGTL
PGGTLNVNASESLSVSGSDPIARTAGGLRSETLGXGKAGDIAISTKQVIIKNGGQINNLTFGAATSGNINV
NASDSIQLLGVSPFDPAVFSTISTATFNSGNANNITVSTGQFVATDGGNLSSSTFGTGRGGDVTVSATDSI
EIIGASPITFQPSILSSISLNAGKAGSLTISTSKLMVQDGGRVDASTLASGEGGSVTINAFKSVEVSGKIL
GFGEPSLVISSANIVSPILQKLYRLPSVPSGKSGNVTINTGQLSVTDGAEVNVRNDGSXDAGTLRINAVSV
SLNKQSAITATTANGEGGNIFVNTRYLQLSNYSVVTTTAGSRGNGGNININADILSAWGKSSIAANAFYGY
GGNVLINTRGLFIARDSQISASSKYGINGTVSINNTGGEIYPTKLKSESIPVAPQIASVCQKNSDIPISKF
VNVGTGGLPANSDDMPYMNYEQQNNSVSIHNNNNLEASKASQTEEPIQIIEAQGWIINLDGECRLNCTKQY
SNP (SEQ ID NO:25)

crpX
ATGGTGATTATTCAAGCCACGCAGCATTTCTGTAGATTTAGTCTTGGTGTTTTCTTAGCACAATCAAGAGT
AGAGATAGAGCAGAGTTTAACAATGTCAACTCCTAACTATCGTCAAGAGATTGATATTGTAAAACGTTTAT
TTTCGCAAAATCCTAATTTATGCGTTGATATTATGCTAGCGACTGAAGAAAGGTGTAATGCTATTAGCTTT
TTAGCTAAAAACTTACAGCCGATTGGCTAGACTGGTGGCTAGGAAGGATAGAGACGCATTAATTAAAGAGTT
TGAAAATACTCAAAGTTTTTTTGAAGAGAAAATTAATAGTTTTCTCCAGCCTTTAAATACAACGGCTCTGC
AACGAGATTTTAAACCCCAGATGCACACAAATATTAGCATTTGA (SEQ ID NO:26)

CrpX
MVIIQATQHFCRFSLGVFLAQSRVEIEQSLTMSTPNYRQEIDIVKRLFSQNPNLCVDIMLATEERCNAISF
LAKTYSRLARLVARKDREALIKEFENTQSFFEEKINSFLQPLNTTALQRDFKPQMHTNISI (SEQ ID
NO:27)

crpY
ATGCTGATAGATATCTTTCATGATACCGTTTGCCCTTGGTGCAGAATTGGGAAAAAACATCTATTTGATGC
ACTGGCACAATGGCAAGAACAAGAAGTAAATATCCGATGGCATCCCTTTCTTCTGGATGATACTGTTCCTG
CTGAGGGGTACGAATTTAGTAGCTTTATGCAAAATAGAAAAGGCATTAAAGCCGCCAGAAATGCAACAGATC
TTTGATTATACGCAACGCGCAGGGAGGCGGCTGGGGTTAAGCTACATTTTCAAAAAATCCGTTTGGCTGT
CAATACTAAGCTTGCTCACCAACTGATTGCATTAGCACCGACAAACATAAAAAATGATGTCGTTGAAGCTA
TTTATAGAGCTTACTTTGAAGAGGGTTTGAATATTGGAGATATTAACGTTATTGTTGCCATCGGTACAGCA
TACCAGATGGATGCTACCGAATTAAAGTTGCAATTAAACGATCGCGATGTCGTTGATACAGTTGTTGCTGA
ATCGGCATTTGCTCGCTTAAATGGCATCAACAGCGTGCCGTTTTTCATCATGAATAATCAAGTCAAGGTAA
ATGGTTCTCACTCGGTTGAGGTTTTCCTTGAAGCTTTGAATAGTACTGCACTTTTAGATATACCTGCAAAA
ATATGA (SEQ ID NO:28)

CrpY
MLIDIFHDTVCPWCRIGKKHLFDALAQWQEQEVNIRWHPFLLDDTVPAEGYEFSSFMQNRKGIKAPEMQQM
FDYTQRAGEAAGVKLDFEKIRLAVNTKLAHQLIALAPTNIKNDVVEAIYRAYFEEGLNIGDINVIVAIGTA
YQMDATELKLQLNDRDVVDTVVAESAFARLNGINSVPFFIMNNQVKVNGSHSVEVFLEALNSTALLDIPAK
I (SEQ ID NO:29)

FIG. 6-13 crpZ
ATGATAGTTGACATCAAGCAAAAAAATAGATTAATTCATCAACGTGTTTCGGTTACTTTTAACTATGAGAT
TTACTTCACCCAAAATTTATTTGAGTTGAAAAACCCGACGCTAGCGCAAGTAATTTCGGCAGATGAGGAGA
CAAAGCCGAAGAAAATAGTTGCGGTGGTAGACGCAGGAATATTAAAGTATCAACCGGAATTGGTGAAGCAA
TTAGTTGCGTATACCAAGTTTTATGGAGAGGTACTAGCGATCAATGTGCCCAAATATTAG (SEQ ID
NO:30)

CrpZ
MIVDIKQKNRLIHQRVSVTFNYEIYFTQNLFELKNPTLAQVISADEETKPKKIVAVVDAGILKYQPELVKQ
LVAYTKFYGEVLAINVPKY (SEQ ID NO:31)

FIG. 7-1

```
ATGGGGCATAGAGCTTGGGGATATCTGGGAGGGACAGTCGCAGGTATGTTCACTTTGGAAGATTTTTTAAG
AGTGATTCGTCATACTCGTAGACCAATCGCACAGGTACCCTCAGGAGGCGAAACGTTATCTATAAGGAGTT
CAATCGTAAAGATAAGTGAAGTAATCGCGCCATACGCTCCAAACGTCGCGATCTCATAAATTGACGGGCCC
CCAAGCACTGTCAATTCAGGTGGGCCAGTTGCAATTGGAACGCTTCGAAATCTCTTAGCCGCAGTAGAGAT
TTTGACACGACGACGGGAAGTATCCCGCGCGTTCAATGCATATCCGATGAAACGAACGTTAACGGAGTTTG
AAGCAGCAGCACCAGCCCTAACGTACGATCCACTAAACATACCATCAGTACCAAATGTATCGGGAGCGATT
GCGGAGCAGAGTATAACCTGAGCAAGCGGTTGCCTAATTCATCACCGGCTACCGCAGAAATTTGCGCATAG
TACGGACAGATAACAGCACGAAGGTTAATACCTCTGCGTAGACCTTGGACCAGAACCAGCTTTCTTAAGCG
TGGCAAGACAGTACCCGCCAGAGGACGTGGGTCCTTGGGTGCGATCTGTCATACTAGGACAAGTACACTCG
CATCCAATGCTAGAAACTTAGGCTCAACTTTATGCGCAAGGAGTTAAACATGATTGGTTACGGTTCATTAA
AGATTATTGTGGTAGTACGGAAGTAGTCTCGACTTTTGCCTTCCATCGCCAACGTTATTGGTAGGAGAGAT
ATAATAGTCTCATAGATAAGGAACAGATTTCATAAAATCATATTAATCTCCAAGCTCTAGTCGGTAATAGA
TCACAAGTAGCAGCGTTTGAAAAGTGAATTCGGTTTAAATGCCAAAATGGTGCTTCTCATCCAAGTTACCA
GCTACAGCAGTGAGTCTTTCCTGTACCTCTTTACCAAGCTACAGATTAGTTGGTAATACCCATACCAGGAG
GTACAACTTTATTTAAGTCAGGTGATAGAACCCTATAAGATATTGTAATAGAAAAGGCATGAATTTTATCG
ACGGTTAAAATTCAGAGAATTCAAATAGTGTTAATCTTACGGTTACTACAGAGATATAGATTACATATTTT
TGGTCTGGAAACAAATACTGCTACTTAAGAACCTAGCTGGATACTACATGTTCAAGGATAAATGTTAGTAA
GGAACAAAGTCCCAGAATTAGAGACCACATACTTGAAAGCGGTCAAACAAGGGTATAAGGAAAAGATTTTA
CCTAATGAGTTTTACAAGAAACATGAAGAAAGGCGGCTTTATAACGCTGCTTCTATCTAAGCCGTTGGACA
ACTGAGGCAGAGCGATAGCAAAAGACTAAGTGGAATTTAGTTGCCAAAAACACAGGTCATAGTTGCAAATT
TATGACAACTGCGCCTAAATGTTTAAGATGATATGTTCCAGGTATTTCCAGCTGTTGTGGTTAGAACGGAC
AAGCATGGAGCTTATGTGCACTTGGAAAGAAACCGTCAACAAATATAGCGGACTGTTAGTAATGGTTCGTC
GACAGAAGTATAGGTAGATGTAGCAGAACCTAAGAAAACCACTTTGAGATGTAACGTTGATTCATTATATG
AACGCGGAATAGTATGAGCAAGAATTCAAGCTTAAAGTTTATTATGTAGTTCACGGGAGGCATTGTGTTGT
AGTATCGAGCCGCAAGTTAACAAGGGGTTATAACACATCCAGTGGCAGACCCGATCACTTGCACCACATCA
CGAAACAATTGACTTGACAAACTCAGGTGGCTAGTTTTTGGCTTCACCAGCCACCGGGATAGAGAATCATA
TGGTGGAATCGTTCGCACTGCAAAGCTGACATTGTATATTTGTAGGACCAGGGCAGAACTTCCAGGAGTTA
GAAACTCCACAGTATCATATCGACCGCAATCAACCAGACGAATTCATGGACTTGATGAAAGCACGGTTGGT
GCAGCAACCCCAGGTACCAGCAATTATGCACCTACGGGGTTTCGACTAAACAATATCACTAAAGACTGGTG
CGCAGCACTTGCTAAATTAACGAGTACTCGGTTGTGGCAACGAACTGCATCGAGTCAAGGCCTTCGTAATA
GATCGAGATAAGGAGAGTGCCCCCTTATTGTAAGTGGCTCAAGCCTCTCATTCTGAGGGAAATGAATAACT
ACCGATACCATTCCGACAAGCAACTATGTGCGCGTTATGTGGAGTATTTGCACGGGGCCAAAGGCAATTAG
AAAGCCAGTGTTTAGGCTTACATCCATCTAAGGAAGCTTCCGAAAGATTAGCAGCTATCTTTGAGGGACTA
TTCTCTTCTGCTGATGAGAACGTAAATGCTAACTCTCAATGGTTAAGTCGCGTTCCTGAGTAAGAGAGGCG
ATAAAGAATGAGAACATGTACACATTCCGAATGAGAAATATCGTCGCATCAATCATGTCTACTGCAGCTAG
CAGTATATAGCTCATTGGACACCCTTATCGAACTCGAGGCCATTTACTCAATTGCCGTAAGTCTGAGAGCT
CCGGGCTAAAAAGCCGCTAAGTGGTTGATACCACAAGCGGTAATAAATTTCGTGCTTACTGGACATACGCA
GGCAACAGTAAGAGGTCTGCAAACCCTTGATCAAATACACATGGCAGAAGCGCCAGTGTTATTCATCTGGT
GAGAAATTTCGCATCAAGAGACTGTCGCAAGATTTATAAAGTCCAGCAAAGCATTATTGCGAGCACTATCA
GGAAAAATACAGGCCGCCGGGAAATGGTTGGTGGTCTTCTGTTAGATATCAAGTGGGTTAAAGTTACATA
CGTGGTGGAACATAAACTACATCGGACTTGGTATTTCCAGAATATGACTCTGAATCTGCCTATGGACCTTG
TTTTATGTTTTGCCTCCATTGATTCGATCTTTGGTTCGACTGGTCGCGGGTATTAAGCTGGTGCCATTGAG
TTTATGGGTGGTTTATCCCATAATGGACGTGATATGCGATAACCTGGGTCGAGTATTAAATGGCGATCATG
GCCACTAGAAGCAATGGCTGCAAATATGGGTAGCCGTCTTCGAGATTGAGCGGTGACCAAGGCAATGTCTG
TTATGGTTTCAGAGCAGGGAATGCAGCTTCGAAGTCAAAAACTCTAAGAATCATTAGCACAAGTGGGAGTG
CTTCCAAATGAATGGCCAGTGATCCAAGGGCCATTAAGGTTCGGTGATCAATTAGCATTACTCCTAAAT
GGGCAATGCAAGCAAAACACACCATATAGCCATCGAGACTCAGACACAGTACAATGGGTTCTAAGAACACC
TAAAAGCTGCTGTACAAAGAGTAAGACATAAGATTGTGTTAAATTACGTCAAAGGTGTAATATCTAAACTA
TTTTGTTAGAGCATATCTCGACTTGTTATGGATCACCCCCTCAACACAATCGGTCTAGATTCTTTAAAGGC
CGTCCAAGTGCACACTAGTCTTCGAACTGATTTGCTCCTGAATATGTCGCTAGTCATAATTGTATAAAATA
CCTGTATCGTACATATAGGCTCTGAACTGTATCAGCAAGTGAGCCTAATTACGCAGACTCAATGAGATGAG
TCAGACAATAATGGTAAACTCGACCAAACTAAAAGCAACCATAAAGACCGCATTAGTAGTGGATTACGT
(SEQ ID NO:32)
```

FIG. 7-2

ATGGGGCATTATGCCGGGGAATCTGTGCCAGCCATAGTGGCTGGACTATTTGGTCTAGAAGACGTTTTAAA
CCCGCTTGCTTATATAGGACGACTAATCCATCAATTACCATCTGGGAGTGAGATCTTATCTGTAATTGCAT
CTATTGAACAGCTAAATCAGCTATTTGCATCATACCCTCAGAGAGTAGTGATCGCTTCGATCAACGTACAC
CAATGCATAGTCATCTCTGCTGATGCAGACGCATTTGGACCGGGTCAACATAGCTAAGTAGCACAAGACAG
GAAGACAACACGAGTGCAAATATGCCACCCATTTCATACACATCTGCTGGAATCAAAGTTGGTGGAATTTG
ACGCAGTCGCTTCAGACATAACGTACGATCATCCAACTATTCGATTAGCATGAAATGTATCTGGAGCGAGC
GCAGAGAATCGTTTAGCGACAGCAAGCTCTTTGGGTAATCACGTCTGGCTACCGGTGTAACTTGCCAAAAG
AATGCACAAATTACAGAATGAAGGCTATTACATCATCTTATAAATCGGACCAAAACCTACATTGTAAGGCA
TCAGAAGCCAGTGCATGTCAGAACATGAGGGAGTATGGGTGCCATCATTGAAGCTAGCGCAAGACGACTGA
CGGCACATGCCACGAAGCTTGGCAGAATTATCTGTCCATGGCGTTATAGTTCATTGTTTAGCGTTAGATAA
CGAATATTCTCCTAGAAAGGGAGTATTACCTACTTGTCCCTGTCAATGGCAGCGCTATTGCATTGTGACAG
ATAATCATCTAATTCACCAGAGACAGTTTCAATCAAATCATAAGAGTCTTCATCATCTACTCAGTCATACA
TTACATATAGAAGCATTAGATCAGCATATACGGTTTGAATGACATATTAGTGCATCACTACCAGCTTACGT
TCAACACCGCTGCGTTTTATCACAACCTGTTATCCTAGAAGCTGCTTACTAGGTAATCGCCTTAGGAGCGG
GTACAATATTAATCAATGCAGAGGATTTCATCCTACATGATATATCAAACTAAAAAGTAGTAACTTTATCT
AAAGAAGAAGTTAATACACTTCATAAAGGTTTAAACTTACAGTTTATACAAGGCTATCAATTCCTGATCTT
CAGTATGGCTATAAGCACTAATTGATCCGAACCTAGATGCATTCAACATGTTGAAGGACAGATAATAGTGG
GTAATCAATACCCCGAATTACAAACACCAATCTTCAACGCGATTACAGAGGAGTAGAACTAACGGATACTA
CCTGCTGCATTCTACCGAACATTTGCAGACTGGTGTCTTAACTCCGGTCCTTCGTTCTAAGCCGTTCAACT
ACTGCGGGACAGCGCAGGATAAGCATTAGATGTAATTCCGTTACGAGACACCGAGATGAATGTAACAACTT
CATACTAACTACACCTAATTCGTTTCGATGCTCGCTGCCACGTGTTCGCAGCATTTAGGGGTAACACGCAC
AGCCATGAATCTTATATGCCGATTGCAAATAGAACGATTACGAATTCATCGGACTGCTACTAATCGTTTCTG
GACTCAAGGAGAGATCGGTGCGACACAACCTAGTAAACAAGCTTTGACCGGTCAAGTGCGTTTATTCGCTG
ATCAAGGCATAGGAGTAGGATGAGTTGCAGGTGTAACCGTATTACGTGCTTTTCGCGCGGGTTTGTTGCCT
ATTATTGAAGCAATATGTATTAATTGCTTAGATCACATCCACTGGCTAATCCAATCATTTTCGCCGCATAT
CCAAGCAATCGACTGAACCAAATCAGGTACGTGTCTAGTGTTTTCGGCACCCACACGTAAAGGCCAACTTC
TGGGAGACTCCTTATAACAACAAGCTCGGCATTGTAGACTAGTAACACAACGGGACATTTACCAGGAGCTA
GAACCGCAACATGAACAAATCAACCTCAGCCAACTTGAGGAATTCGGGCACCCATGGCAATCCAGCTCGGA
GGAGTAACCCCCACGACGAGGCATTGTTCACCTGCGGACTTGGTACTCAACCATACCACTAACCACTGGGG
GACACGAGTTGCTACAATCCCATGAGCTGGCCGGTGGCAGCGTACGACATTTAGACGAAGGATTAGTAAAG
ATTCAAGATACGCAAAGTGGGCCATTATGGTAATTGACTCAATGCTGACACTCTGGGGGTAATAACTCCCT
GCATATACAATTGCATCAGACATCTTTACGCGGGTTAGGTCGCGGAATCGCCCAAGAATACAGGGAATTAC
TATTCCGCTTTTTAGACATATATCCAAGTATAGAAGATCCCAAAACAGCAGGTGCTTCGTTATAGGATCTA
TCATCTCATGGTCATGTTAACCAAATAGTTTACTGTCATGAGGTACGTCACTTTACCATGTTAGAGCGGCA
ATAGAGAACGAGTACGTCTATACAGTCGGCATTACCATTTTCCTCGCTACAAGCATATCAGCTGAAGCTAG
CAGCTTACAAGTCTTAAGTCAACCTAGTCCTAGCCGATGCGAGTTACGTAGTTAGCGGATGTCTGGCAGTA
CTGGGGTTAATTACGGCCGAGTGGACGGTAGAACATGGGGTGAGATGTTTAGTACTCACCCGACGTCGGGA
GCGATCAGAAAAGGGTCAACAATCCAGTGAACCATTGCAGAAGCCAGGGGCGGAAATATTAGTCCAGTGGG
GCGGTATTTCCCGACACGAAAGTGTGACAAGGATTCTAGAGACATTCAAAGGATCCTTGCCGGCCTTACGA
GAAATGATTCCTACTGCTGGCATATTAGATCATGATTTGCGGTCAAACATGACTGGGGAACCATTTACACG
GGTAATGGCGCCCAAAGTACTAGGTGCTTGTCATGTGCATACCTTGACTCATAATGTACCGTGGGACTTTG
TTCTTTGTTCTTGCTCTATGCCTTGAATAATCGGTTCGCGTGGCCAAGGGACTAATGCGGCTACTAATGCA
TACATGGTTAGTTTAGCCGATCACCGACGAGGTACGGGCTTAGCTGGCTGGAGGATTATCTGGGAACCATG
GACACGAGCGGAAATGGCACCTAATTTGCATTGTCCTCATCGACATAGTATGCTGTCCATGGGTATGACTA
TTATGTCTATAGAACAGTGATTCCAGCTTATAGGACAGTTACCCGAACAGTCGATACCACGAGTCGCAGTG
CTACCACTTGAATGGTCACTGATCCAAGAACATTTTAGTTGTGGTACTCAAGTACCACTGCGGTCCTAGTT
GGTGACAGAAAGCATATCACGGCACCAAGCCCTCAATTCAAAGACATAGCAGAATGAAGTTATAGGATAGC
TAACAGCAGCTTTACCAGGACAAGGAGCAAAGCATATGATAATGTACATTATAGATGCAGTTTCCCGAGTA
CTATCTCTGAGCAGTTATCAAAGTCATATGCATCAGCTCCTGAGCAGTATGGCCCTTGATTCTCAATTGGC
TGTCCAATTGCACATTACGCTACAAGCTGACATGGCTGGTGGAGATAACTATACTCAGATTTATACCAGATT
TCACTATCGTTGCTATAGCCAGTGATGTCATGAGGAACTGACCCTAGTTGCTTAGCATCAACGAGATGAG
TCAGCATATACCGGGCAACTCTACGATAGCATTAGGTAAGCAAGCGAGCGGATTAGACGTCAATAATGA
(SEQ ID NO:33)

FIG. 7-3

```
ATGGGGCATAGCGCTGGGGAATATGTTGCAGCAACAGTACCATGAATTTTTAGATTAGGAGATGGTTCAAA
ACAGATTGCTCAGAGAGCAAGACTTATGCAACAATTACCGTCTGGCGGTTAAATGTTTTCTGTAAAGGCTT
GAATCGTAAAAGTGAATCAACTCATTGCACTATACTCTCAATAAGTAGCGGTCGCATCGATTGACCGACCT
CAAAGCATTGACATGTCTGGCGAGGCAGTAGCAAATGGAGCGGCTGAAAAAAGCTTGGAACCAGAAGACAT
AAAGACAAAATGACTGCAAGTGTCACAGGCATTCCTTTCACGTTTGTTGGACCCAATGTTAGCGGACATTG
AAGCGGTAGCCTCAGAATTAACCTACAGTCAAGCAAATATTTCATAAGGATCAAATGTAAGGGTAGCTAAG
GCAGCGAATAGTATTTCCAAAGCAACCTATTGGTTATATCGTGTCCGGCAACCGGTGAATTTTGCGCAATG
TATGGTCACAATATAGCAAGAAGATTATTCCTTCTTGTTAGAAATTGCACACAAATCAACTTTGTAAGGCG
TGGGCAGACAGTGCTTGCCAGATGATGTTGTAGTATGGGTGCCTCCGTTGAAACCAGGTCAAGAATACTTG
CAGCAGATGCTCCAAAGTATGGCTTAACCATTTGTGCATGCAGTTTAAGTTGATTGGTTTGGGTTTAATAA
GGATTATTCTCCTAGTAAAGTAGTATGGCCGATTTATCCCTATCAACCGCAACGATATTGGAGTGCGACAA
ATTATAATCTAAAACAGCAGAAACAGCTATTATCAAATCATAAGAATCCTCACCCTCAACTCGGTGAAAGA
TAACATTCTGCAGCCTTAGTACTGCAAATTCATTTTGAGTGTCGAATTAGTGCATCTCAAGCAACTTACCC
GCAACACTACTGGTTTTTTTTCAGCCTCTTTTCTCAGCAGTAGCTTGCTTCGAAAAAGCCTTACCAGCAG
GTGCAATTATATTCAAGTCAGATGATTTCATCCTATAAGGTATAGCAATCCCAAAAGTATTTATTATATGA
AACGATCAAAATAATGCAATTCCGATAGTATTGAAATTACATTTAGTGCAAAGCCATAAATACCAAATTCT
CAGTTTGGATGTAATCACTAGTTCTCCAAAACCCAAATGGATTCTACGTATTGAAAGAAAATTATTAGAAG
GTAGTAAAGCCTCCCAATTAAAAACAACAAACTTAGAAGCGCTTTAAGACGGGTATTACCTACAGATAATA
CCTGCTGAATTCTCCTAAAAATTTGAAGGATGCGGTCTTATTTACGGATCGTCTCTCCAAGCCTTTAAACA
AATGTGGCACACCGAAGTAAAGGCACCAGGTAAAATTCCGTGACCAAAAACTGAGGTAAATGTGGCATCTT
CATACGAACTGCACCCAAATCTATTAGATCCTAGCTTCCGGGTGTTTGCTGCAGTAATGCGTAAATCGGAC
AGCCAAGAAGCTAATTGGCCATTGGAAATACAACGACTACAATTTTATCGCAATGGTGGTAACAGTATGAG
GACTCGAGTAGCGATAGGTGCTACAGAAACTAGTACACAGACTTTAAGCGGCAAGGATTGTTTACTGGATG
AACGAGGAACAGTAGTAACAAGAGTTCAAGGTTTATCTTTATAACGTACTACTCGCCAGGCTTAGTTACGT
GATATTCAACCTAAATTTAATAAATGGTTATGTCAAATGCATAGGCAAACCCGATCAATCTCTCCGCATAA
CCAAACAATTGACTTGACAAATTCAGGAAGGTGGTTATTGTTTCCCCCACTCACAAGTATAGGCAAGCATC
TCGTAGTAACCTTACAACGACAAGGATGGCATTGTGTATTAGCAACACCTGGGGAAGATTAGCACCAGTTA
GAATCACTACATTATCAATTCAACCCCTACCATCCAGAGGGATTCCTGGACCTATAGCAATCCAGCTTGGA
ACAGGAACCGCCATAACGAGGAGTTATTTACCTGTAGAGTTACGACTCAACAATTGCACAAAGGGCTGGGG
CACACGACTTGCTAAATTCCCAAGGAGTGGGCTTTGGCAGCGTGCTTCCTTTAGAGCAAGCCATAGTAGAA
AACCAAGATATGGAAAGTTCCCCATTGTGGTTACTGACACAACGCTCACAGTCTTTGGGTCATGAGTCCCT
TCCTGTACCATTCCAACATACACCGTTATGGGGATTACGTCGGGTAATTGCCTAGGGACATTGGAAATTAC
ATTGCCCGTGTTTTGACTTAGGTCCAACTATATAAGATTGCGAAACAGTAGCTTCTTAGTTAGAGGAAATA
TTATGTCCTGGTTATCAAATCCAAATTGATTACTGGCAAGGGGTGCGTCACGTTTCCCGGTTAGGGCGGCA
ACAACATATGAGTGCATCTACATAGTCAGGATAACTAATTTCCTTGCAACACCCGTTTCTACTGAAGCTAG
CAGAATGTAACTCTTTAGGCAACCTACTCCATGCCGGAGCCAGTTAGTTAATTACAGGACGTCTGGTAGCA
CTGGGGTTGAAAACTGCTGGGTGGATGGTCCAACAAGCGGTTAAATTTTTACTACTTTCCGGTGGTAGCCA
GCCATCTGCAAAAGCTCAACAAAGCATTGTACAATTACGGAAGGCAGGACCGCATGTGTTCGTCATGTGTG
GAGAAAATTGCCAACAAGATAAAGTGGCAGCAATTATATAGTCAAGCAAACTATCTTTGCCACCATTACGT
GGTATAATTCATGCTGGTGGGAAATTGGGTGATGGTATGCTCTTAATCATGAGTTGGGTAAAATTAACACA
GGTGATGGCACAAAAAGTACAGGGGGCCTGGCGTTTGCATTATTTGACTGAGAATGTACGTTACGACTTTT
TTGTGTGTTATTCCGGTATGGTTTCAATATTGGGTACGCCTCGTCAAGGGGATTATTATGCTGCGAATGCT
TCCATGGATGGTTTAGCTCATCGTCGACGGGGTATGCGTTTATTTGGCTTGGGCATTAAGTGCGGACTATG
GCCACAGGAGGGATTGGCAGCGAATTTGCATAGTCCTCAACAAGGTAGAAAGGTGTCCAAGGGAATGAGGT
TCTTGTCATCAGAACAGGGATTCCAGCTTCTAGGTCAAATACTCGAAGAATCTATAACACAAGTACGAGTC
CAACCAGTCCAATGGTGAGTGATCGAAGAGCAATTTAGTTGTGGTAATGAAATACCATAGCTCTCCCGATT
GGAAAGGACAGCATATCTCAGCAAAAACCCTCAAGACCAAGACTAAGCACAATGAGTTTATAGAACAGC
TTAAGGCTGCTTTACCAACAGAAAAGGAAAGCATTTGAAAATTGACACTAAAGATGAAGTTTCTAAAGTG
CTTACTTTGAGCCCTTCTGAAATAGATATGCATCAGCGCCTGAACTCTATGGGGCTTGAATCTCTAATCGC
TGTAGAAGTGCACATTAGCCTTCAGACTGACTTGCTGGTGTATATATCAAGAGTCTAATTTACAGAAAGTA
TCAGTACCGTTGGTTTAGCCACTGATGTGAATGGGCAACCGAGCCAAGCTACTCACAATCAAGGTGTTAAG
TCAGGAAATCAAGGGCAGCTTTACCAAAACAATACGAAAGATAACGTGCGGGTAAGAGGTGAAATATGA
(SEQ ID NO:34)
```

FIG. 7-4

```
ATGGGGCATAGTGGTGGGGAATATATCGCAGCCACTGTAGAAGGAATATTTAGGTTAGAAGATGGCTTAAA
ACTTATTGCACATAGAGGAAGACTAAGGCAACCGTTACCCTCTTGGGGTGAAATATTATCTGTGATGGCTT
CACTTGAAAAGGTAATTCAAATAATTGCACCAGACTCTCAAACAGTAGCGATCGCATTGATTAAAGGACCC
CAAGGCATTGTCACTTCTGTTGAGGCAGAAACAATTGGAGCGGGTCAAAATAGCCTAGAAGCTGAAGACAT
AAAGACAAAGCGACTGCAACTATCCCACGTATTCCATTCAAATTTGATGGAGCCAATGCTGGCGGACTTTT
AAGCAGTAGCAACACAAATAAGCTACAATCACCCAAATATTTCATTAGAATCAAATGTGACCCGACCTCGG
GCAGAGATTAGTATTGCAACAGCAAGCGATTGGGTAACTCATGTCCGTCAACCGGTAAAATTTGCCGAAAG
TATGGCCACATTACATCAAGAAGGTAATTCCATCTTGTTAGAAATTCGACCCAAACTAACTTTGTAAGGCA
TGGGGAGACAGTGCCTGCCAGAAGTTGTGGGAGTATGGTTGCCTGCTTTGAAACCCGGTCAAGAATACTGG
CAGCAAAAGCTACAAAGGTTGGCTGACCTATATGTGCTTGGAGTAAAAGTTGATGGGTTAGGGTCTGATAA
AGTTTATTCTCGAAGCAAGGTAGGATTGCCGACTCATCCCTTTCTACGGCAACGATATTGGATGGAGACAA
ATCATAATCTAATTCATCAAAAAAGTTTTTAGCAAATCATAACAATCTTCACTCTCTACTCGGACAAAGA
TTAGATTTAGCACCCTTAGAACTGCAAATTCGATTTGAATGTGAAATTAGTCCTTCTCAACTAACTTACCT
ACAACACCACGGTGTTTTTCCTCAACCTGTTTTTCCAGCAGCAACTTACTTGGGAATAGCCTTCGCAGCAG
TTTCAATATTATTCAATGCAGATGATTCAATCCTAGATGATATAGCAAACCAAAAAGTGTTAATTTTACCA
AAGGATGTAATTAATACAATACAGATAGTTGTAAATTTACCGTTAGTACAATGCTATAAATACCAAATTTT
GAGTTTGGATCTAAACACTATTTCTTCAAAACCTAAAGGGATTCTACCTATTGAAGGTAAAATATTAATAC
GTAATAGAGACCCCCACTTAGAAACATCAAACTTAAAAGAGATTAAAGAGGAGTATAACCCACAGATATTT
CCTACTGAAATCTACCAAAGATTTGAAGCATGGGGTCTTTATTACGGTTATTCTTTCCAGGCCGTTAACCA
ACTGTGGTACAGCGAAGAAAAAGCACTGGGTGAAATCCAGTTACCTGAAACTGAGGAGAATGTTGCAGCTT
TATCCCAACTGTACCCAATTCTATTAGATGCTGGCTTCCAGGCGTTAGCAGCTGTTATGGGTAAAACAGAC
AACCGAGAAACTTACTTGCCATTGTAAATAAAACAACTACAAATGTATCGGAGTCGTAGTAATATTTGTG
GACACAAGTAGAGGTAGGTGCACCAGAAACTATTAAACAAACATTGAGCGGTGAAGTTTGTTCATTGGATG
ATCAAGGAATAATAGTAGCAAGGGTTGAAGGTCTAACTTTATTACGTACTTCACGCGAGGCTTGGTTGCGT
ACTATTGAACCTAAATTTAAAAATTGGTGATATCAAATCCCTTGGCAAACTCAATCAATATCACCCCATAG
CCAATCAATCGACTTAACAATATCAGGTAGATGGTTATTGTGTTCCCCACCTACAGGTATGGGCAAACATG
TGGTAGAATGCTTAGAACAGCAAGGTTGGGATTGTATATGAGTAACACCGGGGAAAATGACCAGCAGTGA
GAATCTCAGCATTATCAAGTCAACCCCAGCCATCCTGGGGAATTCCGGCACCTATTGGAATCAAGCTGGGA
GCAGCAGCCCCCATTAGGAGGAATTATGCACCTGTGGGGTTTGGACTGAACAATAGCGCTAAGGACGGGGG
CACAGGGGTTGCAAAAGTCCCAAGAACGGGGCTGTGGGAGCGTACTTGATTTAGTCCGAGCCTTAGTGAAA
AATCAAGGTATGGAAAGGGCCCCATTAGGGTTAGTGAGTCAAGGCTCGCAATCTGGGGGTAATGGGTCCCT
TCCGATACAATTCGAACAAACACGTTTATGGGGGGTAGGTCGAGGAATTGCCCAAGAACATAGGAAATTAC
AAAGCCGGTGTTAAGACTTAGAACCAACTATGAAAGATTCCAAAACAGTAGATGCTTTGTTAAAGGAACTA
TAATCTCCTGGAGATGAAAACAAAATTGCTTAATGTCAAGGGATACGTCACGATGCCCGGTAAGAGCGGCA
AAAAAAATGACTACATCTACCCAGTCCGGTTTACAAATTTTCTCGCAACATCCATTTCAATTGAAGCTAT
TAGAATATAATTCTTTAGACTACCTAATCCTAGCCGAAGCTAGTTACTTATTTACCGGAGTTCTGGGAGCT
CTGGGGTTATAAACCGCTCGTGTGGATGGTTCAACAAGGGTTCAAATATCTTGTACTTACTGGACGTAGGTA
GCCATCAGCTAAAGCTCAACTAACCATTGATCAATTACAGTAGGCAGGAGTGCAAGTATTTGTCCTGTGTT
GAGATATTTTCCAACAAGATAATGTGGCTAGAATTATTGAGTCAATCTAAGTATCTTTTCCAGCATTACTA
GGAATATTTCATGCTGTCGGGATATTTGATGATGGTTTGCTGTTAAATATGAATTGGGTAAAATTTAAACA
GGTGATAGCACCAAAAATACAAGGGGATTGGCATTTACATAATTTAACTCAGAATATACCTTTGAACTTTT
TTGTATGTTTTTCCACTATGGCTTAAATATTGGGATCGCCTGGTAAAGGGAATTATGCTGCTGCAAATGCT
TTCAAGGAAGGTTTAGCCAATCATCGACCGGGTATGGGCTTACCTGGCCTGAGCATTACCTGGGGACCCTG
GGCACAACAGGGAATGGCCGCAAATTTCGATAGTCCTCCTCAAGATACAATGGTGTCCCAGGGAATGCCTT
TTTTGTCCTCAGAACACGGATTGCAGCTTCTAGGACCATTACTCGACCAATCCATACCCCAAGTAGCAGTC
CTACCCATTCAATGGCCAGTGTTCCCAGAGCAATTCAGTTTTGGTCATCAAATACCCTTGCTGTCCCCATT
GGTACAAGAAAGCACATCACAGCACAAAGCCCTCCAAACAAAGACCAAGCACAACGAATTTTTAGGACAGC
TAAGAGCTGCTTTGCCAAGAGAAGGAGAAAAGCGTTTGATATTGTACATTAAAGGTGAAATTTGTCAAGTA
CTGTCTTTGAGCGCTTCTCAAAGTGATATGCAGCAGCCCTGGACACTATGGGGTTGATTCGCTAATGGC
TGGGGAATTGCGCAATAGGCTGCAAACTGACGTGCTCGTGGGTATATCTATGGTCAAATTTGTAGAAGATA
GCAGTATCGTGGATTTAGCCGCTGAAGTGAGTGAGCAACTGGGCCAAGTTGGTCAGAATCAGGGAGTTGAG
GCAGAAAATAGTGGGCAACTGTACCAAAGGAATAGGAAAGGAAACGAGCGGGTAAGAGGGGAATTATGA
(SEQ ID NO:35)
```

FIG. 7-5

```
ATGGGGCATGGTGCTGGGGAATATGTGGCAGCCACAGTAGCAGGAATATTAAGTTAAGAAGATTGTTTAAA
ACTGATTGCTCATAGAGGAAGACTCATGCAACAGATACCCTCTGGGGGTAAAATGTTATCTGTAATGGCTT
CAATTGGAAAGGTTAATCAACTAATTGCACCATACTCTCAAAAAGCAGCGATCGCATCGATTAACGGACCC
CGAAGCTTTGTCATTTCTGGTGAGGCAGAAGAAATTGGAGCGCTTCAAAAAAGCTTAGAAGCAGAAGACAT
TAAGACAAAACGACTGCAAGTAACCCGCGCATTCCTTTCACATTTGATGGAACCAATGTTCGCGGCCTTTG
AAGCAGGAGCATCAGAAATAACCTACAATCAACCAAATATTCCATTAGTAACAAATGTAACGGGAGAAAGG
GCAGAGAATAGTATTGCCACAGCAAGCAATTGGGTAAATCATGTCCGGCAACCGGTGAAATTGCCAAAAG
TATGGACACATCACAGCCAGAAGGTTATTCCATCTTCTTAGAAATTGGACCCCAACCACCTTTGTTAGGCA
TGGGAAGACAGTGCTTGCCAGAAGATCTGGGAGTTTGGTTTCCTTCTTTGAATCCAGGTCAAGAACACTGG
CAGCAAATGTTACAATGTTTGGCTGAACTATATGTGCATGGAGTTAAAGTTGATTTGTTAGGGTTTGATAA
AGATTATTCTCGTAGCGAGGTAGTATTGCCGACTTATCCCTTTCAGGGGCAACGTGATTGGATTGAGACAA
ATAATAATCTAATACAGCAAAAACAGTTTTTATCAAAACAAAAAAATCTTCACCCTCTACTCGGACAAAGA
ATACATTTAGCAGCCTTAGAACAGCAAATTCGTATTGAATGTCAAATTAGTGCTTCTCACCCAACTCACCT
GCCACACCACTGTGTTTTTTCTCAACCTGTCTTCCCCGCAGCAGCTTACTTGGAAATAGCCTTAGCAGCAG
GTTCAATTTTATTCGATGCAGATGATTTAATCCTAGAAGATATAGCAATCCAAAAGGTATTAATTGTATCA
AAGGATGAAATTAATACAATTCAGATAGTTTTAGATTTACAGTTAGTATAAAGCTTTAAATTCCAAATTTT
CAGTTTGGATATAAACACTTATTCTTCATAACCTAAATGGATTCTACATATTGAAGGAATAATATTAGTAG
GTGATAAAGACCCCCAATTAGAAACAACAAACTTAAAAGCGAGTAAGGACGAGTATAACCAACAGATATTA
CCTACTGAATTCTAGCAGAAATTAGAAGAATGGGGTCTTAATTACGGTTCTTCTTTCCAAGCCATAAAACA
ACAGTGGCACAGCGAAGGAAAAGCACTAGGTGAAAATCAGTTACCAGAAACAGAGATGAATGTTGCAACTT
TATACCAACTGCACCCAATACTTATAGATGCTAGCTTCCAGGTGTTAGCAGCAGTTATAGGTAAAACGGAC
AACCAAGAAGGGGATTTGCCATTGGAAATAAAACGACTACAAATTTATGGGAGTGGTAGTAATAGTTTGTG
GACTCAAGTAGAGATAGGTGCAACAGAAACTAATAAACAAATTTTGTGTGGTAAAGTTTGTTTATTGGATA
AACAAGGAATAGTTGTATCAAGAGTTGAAGGTTTAACTTTATTACGTACTTCTCGCGAGGCTTTGTTAAAA
AAAATTGAACCAAAATTTAATAATTGGTTATATCAAATCCATTGGCAAACCCAATCAATTTCACCCCATAA
CCAATCAATTGACTTAACAAAATCAGGTAGGGGTTGGTGTTTCCCCACCCACAGGTATAGGCAAACATC
GGGTAGAATCCTTAGAACAACAAGGTTGGCATTGTATATTAGTAACACCAGGGGAAATTTACCAGCATTTA
GAATCTCAACATTATCAAATCAACCCTAACCTTCCTGAGGAATTCCTGCACCTATTGCAATCAAGCTTGGA
GTAGCAACCCCCATAACGAGGAATTATTCACATGTGGAGTTTGAACTCAACAATAGCACTAAGGACTGAGG
CACAGGAGTAGCAAAAATCCCAAGAACTGGGCTGTGGCAGCGTCCTTCATTTAGTCCAAGCCTTAGTACAC
AATCAAGATATGCAACGTGCCCCATTATGGTTAGTGACTCAAGGCTCACAATCTGTGGGTAATGAGTCCCT
TCATATACAATTCCAACAAACACCTTTATGGGAGTTAGGTCAAGTAATTGCCCAGGAACATAGGGAATTAC
AATGCCGGTATTTAGACTTAGATACAACTTTGGAATATTCCCAAACAGTAGCTGCTTTGTTAGAGGAACTA
TTATCTCCTGGTGATGATAACCATATTGCTTACTGTCAAGGTGTACGTCACGTTGCCCGTTTAGAGCGGCA
ACATATAATGAGTACATCTACATAGTCCGGATTACTAATTTCCTCGCAACAACCATTTCAACTGAAGCTAT
CAGAATATAAGTCTTAAGACAACCTAATCCAACCCGAACCCAGTTAATTAATTACCGGACCTCTCGGAGAA
CTGGAGTTAAAAACCGCTGAGTGGATGGTACAACAAGAGGTCAAATATTTAGTACTTACCGGACGTAGGCC
GCCATCAGCAAAAGCCCAACAAACCATTGAACACTTACAGACGGCAGGAGCGCAAGTATTAGTCCTGTGTG
CAAATATTTCCCAAAAAGAAAATGTGGCAAGAATTATAGAGTCAATCAAAGTATCTTTGACAGCATTACAA
GGAATAATTCATGCTGCTGGGAAATTGGATGATGGTTTGCTGTTAAACATGAATTGTGATAAATTTACACA
GGTGATGGCACCTAAAGTACAATGGTCTTGGCATTTGCATAATTTGACTCAGAATCTACCATTGGACTTTA
TTGTTTGTATTACCTCTATGGCTTCAATATTGGGTTCGCCTGGTCAAGGGAATTATGCTGCTGCTAATGCT
TTCATGGATGGTTTAGCCAATCATCGACGGGGTATGGATTTACCAGGCTTGAGCATTAAATGGGGACCATG
AGCACAAGAGGGAATGGCAGCAAATTTGGATAGTCCTCATCAACATAGCATGGTGTCCAAGGGAATGACTC
TTCTGTCTTCAGAACACGGATTGCAGGTTCTAGGACAATTACTCGAACAATCCATACCACAAGTAGCAGTC
CTACCATTTCAATGGTCAGTGTTTCAAGATCAATTTAGTTTTGGTAATCAAATTCCATTGCTGTCCCAATT
GGTAAAAGAAAGCAAATCACAGCAAAAAGCCTTCCAACCAAAGACAAAGCACAATGAACTTTTAGAACAGC
TAAAAGCTGCTTTACCAAGAGAAAGACAACAGCTTTTGATAATTTACATTAAAGATGAAATTTGTCAAGTA
CTTTCTTTGAGCACGTCTCAAATTGATATGCGACAGCCCCTGAACACTAGGGGCTTGATGCTCTAATGGC
TGTGGAATTGCACAATAGGCTACAAACTGACTTGCTCGTGGATAAATCTATAGTCAAATTTATAGAAGATA
TCAATATCGTAGATATAGCCACTGAAGTGAATGAGCAACTGAGCCAAGTTGCTCAGAATCAAGGAGTTGAG
TCAGATAATATTGGGCAACTCTACCTAAGCAATAGGATAGTAAACGAGCGGATAAGAGGTGAATTATGA
(SEQ ID NO:36)
```

FIG. 7-6

```
ATGGGGCATAGTGCTGGGGAATATGTGGCAGCCACAGTAGCAGGAATATTTAGTTTAGAAGATGGTTTAAA
ACTGATTGCTCATAGAGGAAGACTAATGCGACAGTTACCCTCTGGGGGTGAAATGTTATCTGTAATGGCTT
CAATTGAAAAGGTAAATCAACTAATTGCACCATACTCTCAAAAAGTAGCGATCGCATCGATTAACGGACCC
CAAAGCATTGTCATTTCTGGTGAGGCAGAAGCAATTGGAGCGGTTCAAAATAGCTTAGGAGCAGAAGACAT
TAAGACAAAACGACTGGAAGTATCCCACGCATTCCATTCACATTTGATGGAACCAATGTTGGCGGACTTTG
AAGCAGTAGCATCAGAAATAACCTACAATCAACCAAATATTCCATGAGTATCAAATGTAACGGGAGCTACG
GCAGAGAATACTATTGCCACAGCAAGCTATTGGGTAAATCATGTCCGGCAACCCGTGAAATTTGCCCAAAG
TATGGGCACATTACAGCAAGAAGGTTATTCCATCTTCTTAGAAATTGGACCCAAACCAACTTTGTTAGGCA
TGGGAAGACAGTGCTTGCCAGAAGATGTGGGAGGTTGGTTGCCTTCTTTGAAACCAGGTCAAGAAGACTGG
CAGCAAATGCTACAAAGTTTGGCTGAACTATATGTGCATGGAGTTAAAGTTGATTGGTTAGGGTTTGATAA
AGATTATTCTCGTAGCAAGGTAGTATTGCCGACTTATCCCTTTCAACGGCAACGTTATTGGGTTGAGACAA
ATAATAATCTAATACATCAACAACAGTTTTTATCAAATCATAAAAATCTTCACCCTCTACTCGGTCAAAGA
TTACATTTAGCAGCCTTAGAACAGCAAATTCGTTTTGAATGTCAAATTCGTGCTTCTCAACCAACTTACCT
GCAACACCACTGTGTTTTTTCTCAACCTGTTTTCCCAGCAGCAGCTTACTTGGAAATAGCCTTAGCAGCAG
GTTCAACTTTATTCAATTCAGATGATTTAATCCTAGAAGATATAGCAATCCAAAAAGTATTAATTTTATCA
AAGGATGAAATTAATACAATTCAGATAGTTTTAAACTTACAGTTAGTACAAAGCTATAAATTCCAAATTTT
CAGTTTGGATATAAACACTAATTCTTCAGAACCTAAATGGATTCTACATATTGAAGGAAAAATACTAGTAG
GTAATAAAGACCCCCAATTAGAAACAACAAACTTAAAAGCGATTAAAGACGAGTATAACCAACAGATATTA
CCTACTGAATTCTACCAAAAATCTGAAGAATGGGGTCTTAATTACGGTTCTTCTTTCCAAGCCGTTAAACA
ACTGTGGCACAGCGAAGGAAAAGCACTAGGTGAAATTCAGTTACCAGAAACCGAGGTGAATGTTGCAACTT
TATACCAACTGCACCCAATTCTTTTAGATGCTAGCTTCCAGGTGTTAGCAGCAGTTATGGGTAAAACGGAC
AACCAAGAACCTTATTTGCCATTGGAAATAAAACGACTACAAATTTATCGGAGTGGTAGTAATAGTTTGTG
GACTCAAGTAGAGATAGGTGCAACAGAAACTAATAAACCAACTTTGAGCGGTAAAGTTTGTCTATTGGATG
AACAAGGAATAGTAGTAGCAAGAGTTGAAGGTTTAACTTTATTACGTACTTCTCGCGAGGCTTTGTTCCGT
AATATTGAACCAAAATTTAATAATTGGTTATATCAAATCCATTGGCAAACCCAATCAATTTCACCCCATAA
CCAATCAATTGACTTAACAAAATCACGTAGCTGGTTATTGTTTTCCCCACCCACAGGTATAGGCAAACATC
TGGTAGAATCCTTAGAACAACAAGGTTGGCATTGTATATTAGTAACACCAGGGGCAAATTACCAGCAGTTA
GAATCTCAACATTATCAAATCAACCCCAACCATCCTGAGGAATTCCTGCACCTATTGCAATCAAGCTTGGA
GCAGCAACCCCCCTTACGAGGAATTATTCACCTGTGGAGTTTGGACTCAACAATAGCACTAAGGACTGGGG
CACAGGAGTTGCAAAAATCCCAAGAACTGGGCTGTGGCAGCCTACTTCATTTAGTCCAAGCCTTAGTAAAA
AATCAAGATATCGAAAGTGCCCCATTATCGTTAGTGACTCAAGGCTCACAATCTGTGGGTAATGAGTCCCC
TCCTATACAATTCCAACAAACACCTTTATGGGGGTTAGGTCGAGTAATTGCCCAGGAACATAGGGAATTAC
AATGCCGGTGTTTAGACTTAGATCCAACCATGGAAGATTCCCAAACAGTAGCTGCTTTGTTAGAGGAACTA
TTATCTCCTCGTCATGAAAACCAAATTGCTTACTGTCAAGGGGTACGTCACGTTGCCCGGTTAGAGCGCCA
ACAAAAAATGAGTACATCTACACAGTCCGGATTACAAATTTCCTCGCAACAACCATTCCAACTGAAGCTAT
CAGAATATAAGTCTTCAGACAACCTAATCCAAGCCGAAGCCAGTTACTTAATTACCGGAGGTCTGGGAGCA
CTGGGGTTAAAAACCGCTGAGTGGATGGTACAACAAGGGGTCAACTATTTAGTACTTACCGGACGTAGGCA
GCCATCAGCAAAAGCTCAACAAACCATTGAACAATTACAGAAGGCAGGAGCGCAAGTATTAGTCCTGTGTG
GACATATTTCCCAACAAGAAAATGTGGCAAGAATTATAGAGTCAATCAAAGTATCTTTGCCAGCGTTACGA
GGAATAATTCATGCTGCTGGGATATTGGATGCTGGTTTGCTGTTAAACATGAATTGGGAAAAATTTACACA
GGTGATGGCACCAAAAGTACAAGGGGCTTGGCATTTGCATAATTTGACTCAGAATCTACCCTTGGACTTTT
TTGTTTGTTTTTCCTCTATGGCTTCAATATTGGGTTCGCCTGGTCAAGGGAATTATGCTGCTGCTAATGCT
TTCATGGATGGTTTAGCCCATCATCGACGGGGTATGGGTTTACCTGCCTTGAGCATTAACTCGGGACCATG
GGCACAAGAGGGAATGGCCGCAAATTTGGATAGTCCTCATCAAGATACAATGGTGTCCAAGGCAATGACTT
TTTTGTCTTCAGAACAGGGATTGCAGGTTCTAGGACAATTACTCGAACAATCCATACCACAAGTAGGAGTC
CTACCCATTCAATGGTCAGTGTTCCAAGAGCAATTTAGTTTTGGTAATCAAATACCATTGCTGTCCCAATT
GGTAAAAGAAAGCAAATCACAGCAAAAAGCCCTCCAAACAAAGACAAAGCACAATGAATTTTTAGAACAGC
TAAAAGCTGCTTTACCAAGAGAAAGAGAAAAGCTTTTGATAATTTACATTAAAGATGAAATTTCCCAAGTA
CTTTCTTTGAGCACTTCTCAAATTGATATGCAACAGCCCCTGAACACTATGGGGCTTGATTCTCTAATGGC
TGTGGAATTGCACAATAGGCTCCAAACTGACTTGCTCGTGGATATATCTATAGTCAAATTTATAGAAGATA
TCAGTATCGTTGATTTAGCCACTGAAGTGAATGAGCAACTGAGCCAAGTTGCTCAGAATCAAGGAGTTGAG
TCAGAAAATAATGGGCAACTCTACCAAAGCAATAGGAAAGAAAACGAGCGGATAAGAGGTGAATTATGA
(SEQ ID NO:37)
``` aKey a) PyBOP, DIPEA, HSNAC, DMF; b) 4 N HCl/dioxane; c) 50:50:1 TFA:CH$_2$Cl$_2$:Et$_3$SiH; d) 20:1 AcCN:48% aq. HF; e) PyBOP, DIPEA (3.0 eq), 3, and 6 or 9.

| | | | |
|---|---|---|---|
| $k_{cat}$ (s$^{-1}$) | 0.35 ± 0.07 | 0.6 ± 0.1 | 0.39 ± 0.02 |
| $K_M$ (μM) | 550 ± 70 | 620 ± 30 | 310 ± 50 |
| $k_{cat}/K_M$ (mM$^{-1}$s$^{-1}$) | 0.64 | 0.97 | 1.26 |

FIG. 14-1 crpA
ATGATTACACCTTCACATGAAAATTTAGGTGCAAATGTACAAGCACTAAGTAACAGTGGGTATCTGGGTAT
GCCAGCAGATGCTCCAAAAAGTTTGTCAGAAGTTTTACAAAGAGCAGTCAAAAAGCATTCTGGGCGAGGCT
TAACATATATTAACTTGGATGGCTCTGAGTATAATCAATCGTATCAAGATTTACTTGAGGAAGCGCAAAAA
ATCTTGGGAGGGTTAAGGAAACTGGGACTCAAACCCCAAGACAAAGTAATTTTTCAGTTAGAACGAAATCA
AGATTTTATTGCTGGTTTTTGGGGTTGTATTTTAGGAGGTTTTATCCCTATACCAGTTCCTGTGCCAATTA
ATTATGAAGAAGGCAGTAATAGTACTAACAAGCTTCATCATATTTGGCAGCTATTAGAACAATGTTTGATC
CTAACAGATATTAAATCAGTATCGAAAATACGACCTTTGTCAAAACTATTTCAATCAGAGCAGTTTGAGAC
AATCGCCATTGATGAGTTACGAGAGTGCGAACCAGATAAAAACTTGTATGTCAGCCAACCAGAAGATTTAG
CATTGCTAATGCTTACTTCCGGTAGTACAAGTATACCCAAAGCGGTAAAAATCTCTCATCAGAACTTGTTA
AGTATGACGGCAGGCACAATCGTGATGAATGGCTTTAACCGTCAGGATGTAACCTTGAATTGGATGCCGAT
GGATCACGTGGGAGCGCTAGTGTTCCTTAGCATTATGGCAGTGGATTTGGGTTGTCAGCAAGTTCACATAC
CAACGGAATACATTTTGCAAAATCCTCTCAACTGGCTAGATTTGATTACTCGTCACCAAGGAACAATTAGC
TGGGCTCCGAATTTTGCCTTTACCTTATTGTGCGATCGCGCCGAAGAAATTAGCCGTAAACATTGGAATTT
ATCTTCCATGAGGTTTTTGGTAAATGCTGGGGAACCTGTTATCGCCAAAACTGCGCGAAATTTCCTGAAAT
TACTGGGTCAACATGGGTTACCATCCACTGCACTGCACCCAGCTTTTGGTATGTGCGAAACCTGTTCAGGA
ATCACTTGGTCAAATAGTTTCTCTTTGGAAACCACCTCAGACGAGGATACCTTTGTTTCGGTTGGTGGTCC
CATACCCGGAGCATCTGTGCGGATTGTAGATGAAAATCAACAAGTGGTGGAAGAGGGGACAATTGGACAGC
TGCAACTTCAGGGAAATTCAGTAACCATAGGCTACTACCAAAATGAGGAGGCGAACCAAGAAGCTTTTACA
AAAGATGGTTGGTTTAACACAGGTGATTTAGGATTTTTAAAAGGTGGATGTTTAACAATTACAGGACGACA
AAAAGATGTAATTATTGTTAATGGAGTAAATTATTATAGTCATGAGATAGAAGCTGTTGTTGAAGAATTAG
GAGAGGTTGAAGTTTCTTATACCGCTGCTTGTGCAATTTGGAATGAAAATAGAAGTACAGATAGATTAGCT
ATATTTTTTAACACAGAAAAGACTATTGATAATGGTTTAGTGGAGCTAATTAAATCAATTCGCACTCACGT
TGTCAAATCTATTGGGATTAATCCTAATTACTTAATTCCGTTAGAAAAGACAACTATTCCGAAAACTTCTA
TCGGTAAAATTCAAAGAAAACAATTAAAAGAACGGTTTGAAAACGGAGAATTTAAGGAAATTGTTGCTCAA
ATTAGCACAGCTTTGGCTGAATTAAAGGCACAGAATTTTGTTTCGGGGAATGAGTTGGAACGTGATGTAGC
CGAGATTTGGCAAGGAGTATTACAGATTCCGGAAGTGGGGATTCACGATAACTTTTTTGAGTTGGGTGGAC
ATTCTGTAATGCTAGCACAAGTTCACAGTAAGCTACAGGAATTATTTGACACAACCTTGTCAGTTGTAGAT
TTATTTAAATATCCGACAATTCATACAATAGTTGAATATTTGACAAAAAAGATTCATTAGAGGGATCATC
CCAAGACGGAATTGCCCGTGCGAAATTGCGAACATCAGCAGTTAATCAAAGAGATGTAGCGATCATTGGCA
TGGCTTGTCGCTTCCCAGGAGCAGAAAATATTTCTCAATTTTGGCAAAATTTATGTGATGGAGTGGAATCA
ATTTCTTTTTTCTCTAAGGAAGAAGTCCTGAATGAAGGTATTCACAAGCAACGATTGGAGAATAAAAACTA
CGTTAAAGCTGCACCTATTATCAAAACATCGAAGAATTTGATGCCAACTTTTTTGGCTATAGTACACGAG
AGGCGATGATCATAGATCCCCAACAACGCTTATTCCTTGAGTGTGCTTGGGAAGCACTTGAAGATGCTGGT
TACGATGGAAACACCTATGAAGGTGCAATTGGTATGTATGCAGGTGCGGGGATGAATACATACTTCATGCA
CAATTTATTCCCCAATCGGAATCAGTTTAATGCTGAAGATGGACCTAATTTAATGATGCTGGATTCTATGG
GAGGATTCCAAATTCAAATTGCTAATGATAAAGACTATTTACCTACAAGAGTATCTTATAAATTAAATCTC
AAGGGTCCAAGTCTGAATGTACAAACGGCTTGTTCAACTTCTTTAGTAGCGATCCACACAGCTTATCAAAG
TGTGGTCAGTCGGGAGTGCGACATGGCTTTAGCGGGGGACTATCGGTTAGTCTGCCCAAAAAGCAGGTC
ATTTATATGAAGATGGATGATTTGTCTCCTGATGGACATTGTCGCGCCTTTGATGCTAAAGCTCAAGGT
ACGATTTTGGCAATGGTTCAGGAATAGTTTTATTGAAGAGATTGAATGAAGCCATCGCCGATGGGGATCA
TATTTACTGTGTGATTAAAGGGTCAGCCATTAATAATGATGGAGCTATGAAAGTGGGGTATTCTGCTACTA
GCCAGGAAGGCCAAGCTACTGGTGTGACTGAGTCGATTGCTTTAGCAGGAATTAACGCTGAAACTATTACT
TATTTTGAAACTCATGGTACAGGAACTTCCATGGGAGACCCCATTGAAGTGGCAGCTATGACTCAGGCTTT
TAGATCAACTACTAATAAATTAGGCATTTTGTGCTATTCGTTCGGTAAAAACAAATGTAGGACATTTACAAA
TTGCTTCCGGAGTTGCAGGGTTCATAAAAACTGCATTAGCTTTAAAATATAAGAAAATACCACCAATCTTA
CATTTTGACCAACCCAACCCTTTGATTGATTTTGCCAATAGCCCATTTTATGTAAATAAAAAGTTACAAGA
CTGGAAAACTGATGGAATTCCTAGACGTGCAGGGGTTAAATCACTGGGAATTGGTGGTACAAATGCTGTT
TAATTTTGGAAGAACCACCGAATCAAGTCAAAACAGGTCGTGGGGAGGGAAGCAAAAATAATGATTATCAG
GAGCGTTCGCTTCACCTGTTAACTTTGTCAGCTAAAACACCAAAAGCACTCGAAGAGTTGGTCAGTCGTTA
TGAGCATCATCTGGAAAGCAACGTAGAGTTAGAAATAGCACATCTGTTATACAGCTAATACAGGACGTA
GTCATTTTGATCATCGATTAGCAATTATCGCCCCTGACACTCAAGTTTTAACTGATGAATTAGTAAAAATT
AGTGCGAAAGAAGAAATTAATGGTGTATTCACAGGAAAACCTTCTAGTAATAATCAATCATCATTAATTGC

FIG. 14-2

```
CTTCCTGTTTACTGGACAAGGTTCACAGTATATAAATATGGGAAGGCAACTCTATAAAACCCAACCTGTCT
TCCGTCAAACCTTAGAGCAGTGCGAACAAATTCTACAACCATATTTAAAAAAATCGATTTTAGATATTATT
TACCCAGAAGATAATCAAAAATTAAACAGTAGTATTATTGACCAAACCGCCTATACCCAAGTAGCTTTATT
TGCAATAGAATATGCTCTTTATAAACTATGGGAATCCTGGGGAATAAAACCGGATGTGGTGATGGGGCATA
GTGCTGGGGAATATGTGGCAGCCACAGTAGCAGGAATATTTAGTTTAGAAGATGGTTTAAAACTGATTGCT
CATAGAGGAAGACTAATGCAACAGTTATCCTCTGGGGGTGAAATGTTATCTGTAATGGCTTCAATTGAAAA
GGTAAATCAACTAATTGCACCATACTCTCAAAAAGTAGCGATCGCATCGATTAACGGACCCCAAAGCATTG
TCATTTCTGGTGAGGCAGAAGCAATTGGAGCGGTTCAAAATAGCTTAGAAGCAGAAGACATTAAGACAAAA
CGACTGCAAGTATCTCACGCATTCCATTCACATTTGATGGAACCAATGTTGGCGGACTTTGAAGCAGTAGC
ATCAGAAATAACCTACAATCAACCAAATATTCCATTAGTATCAAATGTAACGGGAGCTAGGGCAGAGAATA
GTATTGCCACAGCAAGCTATTGGGTAAATCATGTCCGGCAACCGGTGAAATTTGCCCAAAGTATGGACGCA
TTACAGCAAGAAGGTTATTCCATCTTCTTAGAAATTGGACCCAAACCAACTTTGTTAGGCATGGAAGACA
GTGCTTGCCAGAAGATGTGGGAGTTTGGTTGCCTTCTTTGAGACCAGGTCAAGAAGACTGGCAGCAAATGC
TACAAAGTTTGGCTGAACTATATGTGCATGGAGTTAAAGTTGATTGGTTAGGGTTTGATAAAGATTATTCT
CGTAGCAAGGTAGTATTGCCGACTTATCCCTTTCAACGGCAACGTTATTGGATCGAGGCTTCCCAGGGATA
TACGAAACAACTGAATCAACAAATGTATCCACTATTGGGAATTAAGGTAGAACTACCATCCACCGAGCAGA
TAATTTACCACCAGCATATCAATCTAACCAGTCATCCCTGGATTAGAGACCACAAACTCTACGAGACGGAT
GTAATTCCCGGTGTGAGCTATATTGCCATGACATTTGCAGCTGTGGGTACACCAGTAGCGGTGGAGGAGGT
TAACTTTATACAACCTCTAATTTTGGCAACCGCCAATACTACCCGTGAAACAGAACTGTTGATTCACCCTG
CTGATACTACCCAGACTAAACAAAAAGTACAAGTTTTAGCCGAGATACTACCTCCAAAGACCAATGGGAG
CAGCATGCTGAAATGACTTTAGTGAAGACCCCCCGTCTTGCCAGTTTTAAACCTAGACATCAAAGCTCT
CAAGCAAAAGTTGAGAGCAATTGATAATGATAATTTAAAAGAAATTTACAACCAAATGTATGTGAACACAG
GCTTCTGGATCGGTCCGATGCTGGATGCAATGCGTCAGGTTTGGGTAGGCGAAGGAACTTACCTTGGGGAA
ATCGAAGTGCCACAAGCCTTGGAATCCCAACTTGCTGGGGAACCAATCCATCCAGCTCTTCTTGATGCCTG
TGCTCGCGCAACTCCTGAGATTTTAGATTCTCGTCTTGATGAACCAGGAGTATTTTGGACTCCATGGAAGG
TGCAGGGGATGACCCTGAGTCGTCCAGCTCCGCGCCGTTTCTATGCCTATGTTAATCAACCCACTCGATTC
AATGAACAATTGCAGACCCGTACTTTTGATATGCATCTACTAGATGAAAAGGGTCAGTCCTTTGGTCGCAT
TGACGGTTTTACCCTTCGACGTGCTCCCCGTGAAAAATTTTTGAGGAGTTTGCAACTTACACAAACGGAAT
CAATTACAGATTGGTTGTATTCTGTGGAATGGAGAAGCAAAGGTCTTTTGGGTAGGCTGCCAGCCCCTGAT
TTCCTGTTAACACCAGTAGAAATAGAGCAAAAACTGACGAAGGACCTTACAGAATTAGTTACTCAGATAGA
TGACAATAGTACTTTGCTTTTCGCAAGAAGCTTAGAGGAATTAAGCGTAGATTATATAGTGCAAGGACTGC
TGTCAATGGGTTGGTCATACAAACTGGGAGAGACTTTTGACTCCGATACAGCAGCCCAACGCTTAGGAGTA
GTTCCAACTCAGCAGCGATTATTCAAGCGTTTATTACAAATATTATCAGAAGCGGGCATTCTTGAGTGCAA
ACAACAACAGTGGAAGGTTGGACAAACCTTGGAAAAAGTCAACCCCACGGGAAAAAACCAGAATTTACTTC
GCCAAGCTCCAGATGAAGCTGCAACATTGACATTATTAGACCGTTGTGGTACTCAACTGTATGGGGTACTG
CGAGGAGCAGTAGACCCAGTGCAACTGGTTTTCCCCAAGGAGATTTAACTACAGCAACCCAACTGTATGA
AGATTCAAGTGCAGCCAAGGTGATGAACACTATTGTGCAAAAAGTCATCACCCAAGGCACCGAGAAACTAC
CTCCGACAAGAGGAATACGGTTATTGGAAATTGGAGCTGGAACAGGAGGAACCACTAGTTATGTTCTACCC
AATCTAAATCCAAGCCAGGCACAATATCTGTTCACAGATATTGGAGCATTATTCACTGGTAAAGCCCAAGA
AAAATTCCGTGATTATAAATTTTTAAAATATCAAACCTTAGATATTGAAGAAGACCCAGCAACCCAAGGAT
TTGAATATTATCAATATGATGTAATTATTGCAGCCAATGTCCTCCATGCAACAACTAATATCAAGCAAACA
CTATCCAATGTGAAGCAATTGTTAGCACCAGGGGGAATGTTAGTTTTGTATGAAGCAACAACTCGCACAAG
TTGGGTGGATTTAGTCTTTGGATTGTTAGAAGGATGGTGGAAGTTCCAAGATTATCAATTAAGACCAGACT
ATCCTCTGCTAAGTCGTAGTAATTGGAAGAAAGTGTTAGAGGATACAGGTTTTACTCAGGTAGTTACCTTG
CCAGAAGTTCAAGGAATGCCAGAAATATTGTCTCAACAAGCAGTAATTATAGCTCAAGCACCTCAAACAAT
TGAGTGCACTGGATCAACAGCGAAGAGTTGGTTGCTATTCGCAGATGATAAAGGAGTTGCTCAACAACTAG
CAAGACAACTAAATTCTCATGGAGATGTTTGTACCTTAGTATTTGCTGGGGACAAATATGAACAAATTGCC
CCAACAGAGTTTACTATTAACCCCAATAACCTATCAGAATATGAGCTACTCATAAGGGAACTAGCAACATC
TTCACCATCATTAAACGGAGTAGTGCAATGTTGGAGTATCTCTTCAGGAGTAAGTAAAACTATCAATTCTG
ACGAATTAGAAAAGTTATCTTTCAATGGGTGTGGCACCACCTTATTTTGCTACAGGCATTAGTCAAAGGG
GGGTTATCTCAACCACCCTGGTTATGGTTAGTAACTTCTGGTTCTCAACCAGTACCGACGAATCACCCAGT
CATACCAGGAGTTGCCCAATCTTCACTATGGGGAATGGGTAAAGTGATTAACTTAGAACACCCAGAACTCA
ACTGTGTACGCATAGATTTAGACCCACTGCAGGCCATAGAAGATCAAGTAAATGCACTATTTAATGAAATC
```

FIG. 14-3

TGGTCTCTGGATAAGGAAGACCAGGTAGCATGGCGTGGTAATTCTCGTTATGTAGCTAGGTTGGTGCCCAG
TTCTTATAGGCAAACCTTGATCGAAGGACGACAGTCATCATCAGATAATGTAAATACTCAAAAGCCTTTAA
GTTTCCGCTCCGATGCTACCTACTTAATTACCGGAGGTATGGGAGGTTTGGGCTTACTAGTAGCCCATTGG
ATGGTATCCAAGGGAGCCAAGAATTTAGTCTTGGTAGGGCGCAGTTCACCGGATGAAGCCGCCAAGAAAAA
ACTCACGGAGTTGGAAATGGCCGGAGCGGCAGTGGTAGTAGAAAAGGCAGATGTGTCTGATATTACAGCTA
TTACAAGAGTGCTGCATAACATTGAGAACTCCAAGATACCATTAGCGGGGATAATTCATTCTGCGGAATG
TTATCTGATCGGGTATTGGCAAATCAAACTTGGTCAAGCTTTGAGAAAGTGATGGCTGCCAAAGTCCAGGG
AGCTTGGCATCTGCATCAATTAACTCAAAATCAGTCATTGGACTTTTTTGTGTTGTTTTCTTCTGTTGCAT
CCCTGTTGGGTTCTTCTGGTCAAGGAAATTATTCTGCAGCCAATGGGTTTCTTGATGGTTTAGCCCATTAT
CGTCAAGCTATGGGACTACCAGGATTGAGCTTGCATTGGGGGGCAGTTTCTCAAGTGGGAGAGGCTGCAGA
ACGAGGTGTCGAAACTAGGATTCATCAACAGGGTATGGGTGTGATATCTCCGAACCAGATGTTAGAATGCC
TAGAATTACTAATGAGTGGTAATGCTAGACCGGAAGGTAAGCTATCAGACGCTGAAGTAGGGATTGTGCCA
ATTGAGTGGTCAGCATGGCAAGAGAAAGTAGCCAATTGGACATTTTTGTCAGATTGGCAAAAAATTATCCA
AACAACTTATGGTGTAACTGGCTCGGAATTTCTGTCTAAGTTGGAAGCTGCAGCGACCGAGGAGCGTCGTT
CCCTATTAGTGGCTCATATCCGTCGTCAATTATCCTTAGTCGTGGGAATCAATAATCCCGAATCTATTTCA
TTAGAAACTGGCTTTTTTGACCTGGGTATGGATTCTTTAACTTCTGTGGAGTTGAGGAATAAGTTGCAAAC
TAGTTTGAGTTGTTCGGTACCATCTACTTTGGCTTTTGATTATCCTACAGTTGGTAAGCTAGTAGATTATC
TAGTATCAAATGTTCTTTCTATGGAATTTGTAATTTATCTGATGATTTGGAGTTGCAAAACGAGAATGAA
ACTGAATTAACAATTCCTGCAGAGCTAGAAGAACTTTCGGAATCAGACGCTGAAGTTTTGCTTCTTGAGAA
ACTTAGAAATATTAGTTACTGA (SEQ ID NO:42)

CrpA
MITPSHENLGANVQALSNSGYLGMPADAPKSLSEVLQRAVKKHSGRGLTYINLDGSEYNQSYQDLLEEAQK
ILGGLRKLGLKPQDKVIFQLERNQDFIAGFWGCILGGFIPIPVPVPINYEEGSNSTNKLHHIWQLLEQCLI
LTDIKSVSKIRPLSKLFQSEQFETIAIDELRECEPDKNLYVSQPEDLALLMLTSGSTSIPKAVKISHQNLL
SMTAGTIVMNGFNRQDVTLNWMPMDHVGALVFLSIMAVDLGCQQVHIPTEYILQNPLNWLDLITRHQGTIS
WAPNFAFTLLCDRAEEISRKHWNLSSMRFLVNAGEPVIAKTARNFLKLLGQHGLPSTALHPAFGMCETCSG
ITWSNSFSLETTSDEDTFVSVGGPIPGASVRIVDENQQVVEEGTIGQLQLQGNSVTIGYYQNEEANQEAFT
KDGWFNTGDLGFLKGGCLTITGRQKDVIIVNGVNYYSHEIEAVVEELGEVEVSYTAACAIWNENRSTDRLA
IFFNTEKTIDNGLVELIKSIRTHVVKSIGINPNYLIPLEKTTIPKTSIGKIQRKQLKERFENGEFKEIVAQ
ISTALAELKAQNFVSGNELERDVAEIWQGVLQIPEVGIHDNFFELGGHSVMLAQVHSKLQELFDTTLSVVD
LFKYPTIHTIVEYLTKKDSLEGSSQDGIARAKLRTSAVNQRDVAIIGMACRFPGAENISQFWQNLCDGVES
ISFFSKEEVLNEGIHKQRLENKNYVKAAPIIKNIEEFDANFFGYSTREAMIIDPQQRLFLECAWEALEDAG
YDGNTYEGAIGMYAGAGMNTYFMHNLFPNRNQFNAEDGPNLMMLDSMGGFQIQIANDKDYLPTRVSYKLNL
KGPSLNVQTACSTSLVAIHTAYQSVVSGECDMALAGGVSVSVPQKAGHLYEDGMILSPDGHCRAFDAKAQG
TIFGNGSGIVLLKRLNEAIADGDHIYCVIKGSAINNDGAMKVGYSATSQEGQATGVTESIALAGINAETIT
YFETHGTGTSMGDPIEVAAMTQAFRSTTNKLGFCAIGSVKTNVGHLQIASGVAGFIKTALALKYKKIPPIL
HFDQPNPLIDFANSPFYVNKKLQDWKTDGIPRRAGVKSLGIGGTNACLILEEPPNQVKTGRGEGSKNNDYQ
ERSLHLLTLSAKTPKALEELVSRYEHHLESNVELEIADICYTANTGRSHFDHRLAIIAPDTQVLTDELVKI
SAKEEINGVFTGKPSSNNQSSLIAFLFTGQGSQYINMGRQLYKTQPVFRQTLEQCEQILQPYLKKSILDII
YPEDNQKLNSSIIDQTAYTQVALFAIEYALYKLWESWGIKPDVVMGHSAGEYVAATVAGIFSLEDGLKLIA
HRGRLMQQLSSGGEMLSVMASIEKVNQLIAPYSQKVAIASINGPQSIVISGEAEAIGAVQNSLEAEDIKTK
RLQVSHAFHSHLMEPMLADFEAVASEITYNQPNIPLVSNVTGARAENSIATASYWVNHVRQPVKFAQSMDA
LQQEGYSIFLEIGPKPTLLGMRQCLPEDVGVWLPSLRPGQEDWQQMLQSLAELYVHGVKVDWLGFDKDYS
RSKVVLPTYPFQRQRYWIEASQGYTKQLNQQMYPLLGIKVELPSTEQIIYHQHINLTSHPWIRDHKLYETD
VIPGVSYIAMTFAAVGTPVAVEEVNFIQPLILATANTTRETELLIHPADTTQTKQKVQVFSRDTTSKDQWE
QHAEMTLVKTPPSLPVLNLDIKALKQKLRAIDNDNLKEIYNQMYVNTGFWIGPMLDAMRQVWVGEGTYLGE
IEVPQALESQLAGEPIHPALLDACARATPEILDSRLDEPGVFWTPWKVQGMTLSRPAPRRFYAYVNQPTRF
NEQLQTRTFDMHLLDEKGQSFGRIDGFTLRRAPREKFLRSLQLTQTESITDWLYSVEWRSKGLLGRLPAPD
FLLTPVEIEQKLTKDLTELVTQIDDNSTLLFARSLEELSVDYIVQGLLSMGWSYKLGETFDSDTAAQRLGV
VPTQQRLFKRLLQILSEAGILECKQQQWKVGQTLEKVNPTGKNQNLLRQAPDEAATLTLLDRCGTQLYGVL
RGAVDPVQLVFPQGDLTTATQLYEDSSAAKVMNTIVQKVITQGTEKLPPTRGIRLLEIGAGTGGTTSYVLP
NLNPSQAQYLFTDIGALFTGKAQEKFRDYKFLKYQTLDIEEDPATQGFEYYQYDVIIAANVLHATTNIKQT

FIG. 14-4

```
LSNVKQLLAPGGMLVLYEATTRTSWVDLVFGLLEGWWKFQDYQLRPDYPLLSRSNWKKVLEDTGFTQVVTL
PEVQGMPEILSQQAVIIAQAPQTIECTGSTAKSWLLFADDKGVAQQLARQLNSHGDVCTLVFAGDKYEQIA
PTEFTINPNNLSEYELLIRELATSSPSLNGVVQCWSISSGVSKTINSDELEKLSFNGCGTTLFLLQALVKG
GLSQPPWLWLVTSGSQPVPTNHPVIPGVAQSSLWGMGKVINLEHPELNCVRIDLDPLQAIEDQVNALFNEI
WSLDKEDQVAWRGNSRYVARLVPSSYRQTLIEGRQSSSDNVNTQKPLSFRSDATYLITGGMGGLGLLVAHW
MVSKGAKNLVLVGRSSPDEAAKKKLTELEMAGAAVVVEKADVSDITAITRVLHNIENSKIPLAGIIHSAGM
LSDRVLANQTWSSFEKVMAAKVQGAWHLHQLTQNQSLDFFVLFSSVASLLGSSGQGNYSAANGFLDGLAHY
RQAMGLPGLSLHWGAVSQVGEAAERGVETRIHQQGMGVISPNQMLECLELLMSGNARPEGKLSDAEVGIVP
IEWSAWQEKVANWTFLSDWQKIIQTTYGVTGSEFLSKLEAAATEERRSLLVAHIRRQLSLVVGINNPESIS
LETGFFDLGMDSLTSVELRNKLQTSLSCSVPSTLAFDYPTVGKLVDYLVSNVLSMEFCNLSDDLELQNENE
TELTIPAELEELSESDAEVLLLEKLRNISY (SEQ ID NO:43)
```

FIG. 15-1

```
crpB
ATGGACATGAATATTAATAGGCGTAATACTTCTAACTCAAAACAAGCTGACTCTCTATCGCCAACTAAACA
AGCGCTACTTGCCTTAGAGAGGATGCAATCCAAACTGGACGCTTTAGAATATGCCAAGACTGAACCAATAG
CAATCATTGGAATGGGCTGCCGCTTCCCCGGAGGTGCATCTACTCCGAAAGGGTTTTGGGAAGTTTTAAAA
AACGGAGTAGATGCCATCACTCAAGTACCCCCAAATCGATGGAATCTTGATAATTACTATGACCCAAACCC
AGAATCTCCTGGTAAAATTTATACTCCTTATGGGGGATTCATTGAGCTTCTAGATCAGTTTGATGCTAATT
TGTTCGGTATTTCTCCTAGAGAAGCGATTCATTTAGACCCTCAACAGCGATTACTATTAGAAGTTACTTGG
GAAGCCATAGAGAATGCTCTAATAAATCCGACTGAACTTAACGGAAGCCAAACAAGTGTTTTACTGGCAT
TTGTGGCAATGATTATTACCAACGCGTAATTGCTCAAGACTCAGAACAAATTGATGCTTATGTTGTATCAG
GTAATGCTCATAGTACGGCATCGGGGCGAATTTCCTATATTTAGGGTTACTCGGACCTTCTTTAGCAGTA
GACACAGCCTGCTCCTCTTCTTTGGTAAGTGTGCATTTAGCTTGCTCCAGTTTAAGAAGAGGAGAATCTAA
CCTAGCATTGGCAGGAGGAGTGAATAGAATAATTTCTCCAGAGGTGAGTATAGCTTTTTCTAAAGCCCGTA
TGTTGTCCTTTAATGGGCGATGTAAGACTTTTGACGCTAGTGCAGATGGTTTTGTTCGTGGTGAAGGATGC
CGTGTTGTTGTACTCAAACGTTTATCAGATGCATTAACTGATAAAGACAATATCTTGGCTGTGATTCGGCG
AAGCGCCATTAACCAAGATGGTCACACCAGTGGTTTAACGGTTCCTAACGGTCCTTCTCAACAAGCAGTAA
TTCGCCAAGCTTTGGAAAATGGGGGAGTAGAACCGGCAAATATTAGTTATTTTGAAGCTCATGGTACAGGG
ACATCCTTGGGAGATCCGATTGAAGTTGGAGCCCTAGGGACTGTATTTGGCACAAGCCACTCTAAAGAGCA
ACCTTTAATAGTTGGCTCAGTAAAAACTAACATTGGACACTTAGAGGCAGCAGCAGGAGTTGCTGGTTTGA
TCAAAATAGTCCTACAACTGCAAAATCAACAAATAGTACCATCACTGCATTTTAACCAGCCTAATCCTTAT
ATTAATTGGTCGGAATTACCAGTAAAAATTCCGACGCAGATTAGCCCTTGGCCAACAAATGGAAAAAGCCG
TATAGCTGGAGTTAGTTCTTTTGGGTTTAGTGGAACTAATGCTCATGTAATTTAGAAGAAGCTCCGACTC
AACAGTCCCAGGTTAAGGATTCTGATTTGGGTAAGCATCCTTGGCACATACTAACCTTATCTGCCAAATGT
GAAAAAGCACTGCAAGAAATGATCCAAAGCTATGAAGAATTTTAAGTAATGATAATACAGCAACAATTGC
TGATATATGTTTTAGTGCTCATATAAGTCGCAGCCATTTTGACTATCGCCTTGCTTTAATAGCTCCATCAA
CCGAGAAATTGCGCCAAAAATTAAAGGTTTTTCAAAAAAACCCGGAAGATACTCTAGGAGTGGTGAGGGGT
CAAGTTGACAGTAAAAAGTTAGCGAAAATAGTATTTTTATTCACTGGTCAGGGCTCCCAATATATCAATAT
GGGAAGACAACTATATGAAACACAACCTGTCTTCCGTCAAACCTTAGAGCAGTGCGAACAAATTCTACAAC
CATATTTAAAAAAATCGATTTTAGATATTATTTACCCAGAAGATAATCAAAAATTAAACAGTAGTATTATT
GACCAAACCGCCTATACCCAAGTAGCTTTATTTGCAATAGAATATGCTCTTTATAAACTATGGGAATCCTG
GGGAATAAAACCGGATGTGGTGATGGGGCATAGTGTTGGGGAATATGTGGCAGCCACAGTAGCAGGAATAT
TTAGTTTAGAAGATGGTTTAAAACTGATTGCTCATAGAGGAAGACTAATGCAACAGTTATCCTCTGGGGGT
GAAATGTTATCTGTAATGGCTTCAATTGAAAAGGTAAATCAACTAATTGCACCATACTCTCAAAAACTAGC
GATCGCATCGATTAACGGACCCCAAAGCATTGTCATTTCTGGTGAGGCAGAAGCAATTGGAGCGGTTCAAA
ATAGCTTAGAAGCAGAAGACATTAAGACAAAACGACTGCAAGTATCCCACGCATTCCATTCACATTTGATG
GAACCAATGTTGGCCGACTTTGAAGCAGTAGCATCAGAAATAACCTACAATCAACCAAATATTCCATTAGT
ATCAAATGTAACGGGAGCTAGGGCAGAGAATAGTATTGCCACAGCAAGCTATTGGGTAAATCATGTCCGGC
AACCGGTAAAATTTGCCCAAAGTATGGACACATTACAGCAAGAAGGTTATTCCATCTTCTTAGAAATTGGA
CCCAAACCAACTTTGTTAGGCATGGAAGACAGTGCTTGCCAGAAGATGTGGGAGTTTGGTTGCCTTCTTT
GAGACCAGGTCAAGAAGACTGGCAGCAAATGCTACAAAGTTTGGCTGAACTATATGTGCATGGAGTTAAAG
TTGATTGGTTAGGGTTTGATAAAGATTATTCTCGTAGCAAGGTAGTATTGCCGACTTATCCCTTTCAACGG
CAACGTTATTGGATTGAGAGCACGGAAAGTCAAAGCCAAAAAGCAGCTTATTCCTCTTGTGAAACAAAGAG
TACTCCAATTTTCGATTTGCTAATCCATGGGAATATCCAACAGTTGGCTCAACAAATAGAAAAAATTGGTA
AATTTTCTCCAGAACAAGTCAATCTCCTGCCAGAATTTCTAGAAGTATTAGTAAAACAGCACCAGAAACAA
CTAATTATAGAAACTACCAAAGATTTCTTGTACCAAGTACAGTGGAAACCTTTAGTTGATACCCAACCCAA
GACAAGCATTAAACCTAGCCATTGGTTAATTTTTGCAGACACCACCGCAGTAGGGGAAAAATTAGTTCAGC
AATTGCAATCGCACCATTGTGAATGTAGTTTAGTTTATCGAAGTGATTGCTACCGAAAACTAGACGAAGGT
ACTTATCAACTCAATCCCACAGAGGCTCAAGAGTTTGAACAACTAATTCAAGCTATCGGGGAAAATAGCAA
ATTACCCTTACTCCATGTGATTAATTTGTGGAGTTTAGATATTCAAGGAACGCAAGACTTAACAACCACAA
CTTTAAAACAAGCACAACTTTGGGGATGTGGCACGGTGCTACAACTAGTGAAAGTGCTAACTAAAACCAAA
ACTGTAGCCAAACTGTGGTTAGTGACTCGAGGTGCTCAATTAGTCAAATCCCAAACCGAATCAGTCTGTGT
GGCTGCATCACCCTTGTGGGAATGGGGCGAGTAATATCTCTGGAGCATCCCCAACTGTGGGTGGAATGG
TAGATTTAGACCCAATTTCTCCAGAATCAGAAGCATACACACTACTACAACTTCAGTAAATTCTAACCAA
TTAGAAGACCATCTAGCTTTACGGGCAGATAATTTATACTTTGCTCGTTTAGTCAAGCAATCTCTCAAACC
```

FIG. 15-2

```
ATATGATTCTGTGTCACTCAAGGATAATGCGACATATTTAATAACAGGAGGATTGGGAGCTTTAGGATTAC
ACACAGCGCGGTGGATGGTTCAACAAGCAGCAAGACATTTAGTACTCACCGGACGTAAGCAGCCTAACCTT
GAAGCTCAACAAATCATTGAAGAACTGCAAAAGCTAGGGGCACAAATATTAGTCTTATGTGGGGATATCTC
CGATGAAGTTGATGCGACTACAATTTTTTCAGAAATTGAAGCATCTTTACCGACCCTAAAAGGTGTAATTA
ATGCTGCTGGGGTATTAGATGATGCCTTGCTCCACTCTATGAGTTGGGAACAATTTACACAGGTGATGGCA
CCGAAAGTACAAGGGGCTTGGCATCTTCATAATTTAACTCAGAATAAAGCTTTGGACTTTTTGTTTGTTT
CTCCTCGATGGCTTCATTGGTAGGTTCACCCGGTCAAGGAAATTATGCCGCAGCTAATGCTTTTATGGATG
CTTTAGCCCATCATCGACGGGAATGGGTTTACCAGGTTTAAGTATTAACTGGGGACCTTGGGCACAAGCA
GGAATGGCAGCAAGCTTAGATAATCGTAATAGAGATCGAATGGTTGCCTCTGGAATCACTCCTTTGACTCC
AGAGCAGGGATTGCAGGTTCTAGGACAACTACTCGAACAGTCCTTACCACAGGTAGGAGTTTTATCGGTTC
AATGGTCAGTGTTCCAAGAGAAATTTAGTTTTGGTAATCAAATACCATTACTTTTGGAATTGCTAGGAGAA
ACCGAATCACAACAAAAAGCCTTTAGAACAAAGACAAAGCAAAATGAGCTTTTAAAACGATTGGAATCTTT
GCCTTGTAAAGAGCGCTACTATGTATTGAGAACTGAAATTCAGAGTGAAGTAGCCAAAGTATTGGCGCTCA
ATGATTCCCAACTACCTGGTTTTGAGCAAGGATTCTTTGACTTGGGTATGGACTCATTAATGGCAGTGGAA
TTACGTAACCGCATCACCCAATTACTAAAGGTGACATTACCCTCAACCCTAAGCTTTGACTTTCCCAATAT
TGAACAACTAACTAAGTATATAAGCTCTCAAATACTAGACCTGAGTACCTCGAATGATGGTCAGCAGCCAG
AACAAAAAGTAAAAGCTGCAGAACATGAACCCATAGCGATTATAGGTATGGGATGTTCCTTACCTGGTGGA
GCAAACACCCCAGAAAAATTCTGGGAATTATTGCATTCAGGTACTAGTGCCCGTGAAGAAATTCCAGCACA
GCGATGGGACGTCAATAGCTACTATGACCCAGACCGAGAAGCCGCAGGTAAAATGGTCACCCGTTACGGTC
ACTTTATTAGTGGAGTAGATCAATTTGACCCAGAATTTTTGGCATCTCTCCGAGGGAAGCAACAGCCATG
GATCCCCAACATCGGTTGCTACTGGAAGTAAGTTGGCAAGCCTTAGAGCGAGCCGGACAAAAGGTGGAACG
TCTATCATCCGAACCCGTTGGGGTATTTGTGGGTAACGATGGACATGACTACGAACAACTGATGCAAAGC
ATTTAGAGCAAGAGCCCAACAGTACCTTTGGCACCTATACATGCACTGGTAACAGTCCTTCGAGTGCGTCA
GGACGTTTGGCTTATACATTTGGGTTCACGGGACCAACAGTAACCATTGATACCGCCTGTTCTTCTTCCTT
AGTGGCGATTCATCAAGCTTGCAACAGCATACGCCTGGGAGAATGTCAGATGGCAATTGCTGGGGAGTGA
AACTCCATCTAACTCCTAGTAGCTATATTTTACTTCCCGAGCCGGAATGATTTCCCCAGACGGATTGTGC
AAAACCTTTCATATATCAGCGGATGGTTATGGTCGGGGAGAAGGCTGTGGTATGGTGGTGCTCAAGTCTTT
GAGTCAAGCCCAAGCAGACGGTGACCCAATTTTAGCCTTGATTCTGGGCAGTGCGGTGAACCAAGATGGAC
CCAGTAGTGGCTTAACAGTGCCTAATGGCCAGTCCCAACAAAAATTGATTTTACAAGCACTCAAACAAGCT
CGGGTAGAACCGGCAGATATTAGCTACTTAGAAGCCCATGGTACGGGTACATCTTTGGGAGACCCCATAGA
GGTAAATGCAGCAGCAGCAGTACTAGGGCTCCAACGTTCACCAAGTCAGCCCTTGTGGATAGGTACGGTAA
AGACAAATATTGGGCATTTGGAGTCGGCAGCGGGGGTATCGGGACTAATTAAGGTAGTACTATCTCTACAG
CATCAGCAAATACCTGCCAATTTACATCTGCAAGAGCCTAACCCCAAGATTGACTGGCAACCTTGGTTACA
GGTACCTCAAGCTTTGACCCCTTGGGTTGGGTCGAAAGGTAGGTTGGCGGGGGTAAGTTCTTTTGGGTTTA
CGGGTACTAATGCCCATGTGGTGCTATCGGAAACCCCTGCTGCCATTGCCAGTTCTACAGTAGAGTATGAG
CGTCCACTACATCTGTTGCAGTTGTCAGCCAAAAATGACTTGGCTTTGGCACAGCTAGCCCAACGCTATAG
TGACCATTTAAAAACGCACCTAGAGCAGGACTTAAGGGATATCTGCTTTACTGCCAATAGTAGTAGGTTGG
CTCACAAGCATCGTCTGGCGGTGGTCGCGAGCAATCGAAAAGAGTTGCAACAAAAGCTGGGTAACTTTGGT
ACAGATTCAGAAAGGATGGATTTGGTAACTGGACAAGTCAGTAGTAGTCAGTTGACCAAAGTTGCAATGCT
TTTCACTGGTCAAGGGTCTCAATATGTGGGTATGGGTCGCCAGCTTTACCAAACCCAACCGACCTTCAAAC
AATTTGTGGATCAATGTGCCCAAATATTAGAAAACTACTTAGACAAACCTTTATTAGAAATACTTGATGTC
GCTCAAGTACAGGAAAATGTCCTAGCTCAAACCGCCTATACCCAAGTAGCTTTATTTGCAATAGAATATGC
TCTTTATAAACTATGGGAATCCTGGGGAATAAAACCGGATGTGGTTATGGGCATAGTGCTGGGAATATG
TGGCAGCCACAGTAGCAGGAATATTTAGTTTAGAAGATGGTTTAAAACTGATTGCTCATAGAGGAAGACTA
ATGCAACAGTTACCCTCTGGGGGTGAAATGTTATCTGTAATGGCTTCAATTGAAAAGGTAAATCAACTAAT
TGCACCATACTCTCAAAAAGTAGCGATCGCATCGATTAACGGACCCCAAAGCATTGTCATTTCTGGTGAGG
CAGAAGCAATTGGAGCGGTTCAAAATAGCTTAGAAGCAGAAGACATTAAGACAAAACGACTGCAAGTATCC
CACGCATTCCATTCACATTTGATGGAACCAATGTTGGCGGACTTTGAAGCAGTAGCATCAGAAATAACCTA
CAATCAACCAAATATTCCATTAGTATCAAATGTAACGGGAGCTAGGGCAGAGAATAGTATTGCCACAGCAA
GCTATTGGGTAAATCATGTCCGGCAACCGGTGAAATTTGCCCAAAGTATGGACACATTACAGCAAGAAGGT
TATTCCATCTTCTTAGAAATTGGACCCAAACCAACTTTGTTAGGCATGGGAAGACAGTGCTTGCCAGAAGA
TGTGGGAGTTTGGTTGCCTTCTTTGAAACCAGGTCAAGAAGACTGGCAGCAAATGCTACAAAGTTTGGCTG
AACTATATGTGCATGGAGTTAAAGTTGATTGGTTAGGGTTTGATAAAGATTATTCTCGTAGCAAGGTAGTA
```

FIG. 15-3

```
TTGCCGACTTATCCCTTTCAACGGCAACGTTATTGGATTGAGACAAATAATAATCTAATACATCAAAAACA
GTTTTTATCAAATCATAAAAATCTTCACCCTCTACTCGGTCAAAGATTACATTTAGCAGCCTTAGAACAGC
AAATTCGTTTTGAATGTCAAATTAGTGCTTCTCAACCAACTTACCTGCAACACCACTGTGTTTTTTCTCAA
CCTGTTTTCCCAGCAGCAGCTTACTTGGAAATAGCCTTAGCAGCAGGTTCAATTTTATTCAATTCAGATGA
TTTAATCCTAGAAGATATAGCAATCCAAAAGTATTAATTTTATCAAAGGATGAAATTAATACAATTCAGA
TAGTTTTAAATTTACAGTTAGTACAAAGCTATAAATTCCAAATTTTCAGTTTGGATATAAACACTAATTCT
TCAGAACCTAAATGGATTCTACATATTGAAGGAAAAATATTAGTAGGTAATAAAGACCCCCAATTAGAAAC
AACAAACTTAAAAGCGATTAAAGACGAGTATAACCAACAGATATTACCTACTGAATTCTACCAAAAATTTG
AAGAATGGGGTCTTAATTACGGTTCTTCTTTCCAAGCCGTTAAACAACTGTGGCACAGCGAAGGAAAAGCA
CTAGGTGAAATTCAGTTACCAGAAACTGAGGTGAATGTTGCAACTTTATACCAACTGCACCCAATTCTTTT
AGATGCTAGCTTCCAGGTGTTAGCAGCAGTTATGGGTAAAACGGACAACCAAGAAACTTATTTGCCATTGG
AAATAAAACGACTACAAATTTATCGGAGTGGTAGTAATAGTTTGTGGACTCAAGTAGAGATAGGTGCAACA
GAAACTAATAAACAAACTTTGAGCGGTAAAGTTTGTTTATTGGATGAACAAGGAATAGTAGTAGCAAGAGT
TGAAGGTTTAACTTTATTACGTACTTCTCGCGAGGCTTTGTTGCGTAATATTGAACCAAAATTTAATAATT
GGTTATATCAAATCCATTGGCAAACCCAATCAATTTCACCCCATAACCAATCAATTGACTTAACAAAATCA
GGTAGCTGGTTATTGTTTTCCCCACCCACAGGTATAGGCAAACATCTGGTAGAATCCTTAGAACAACAAGG
TTGGCATTGTATATTAGTAACACCAGGGGAAAATTACCAGCAGTTAGAATCTCAACATTATCAAATCAACC
CCAACCATCCTGAGGAATTCCTGCACCTATTGCAATCAAGCTTGGAGCAGCAACCCCCATTACGAGGAATT
ATTCACCTGTGGAGTTTGGACTCAACAATAGCACTAAGGACTGGGGCACAGGAGTTGCAAAAATCCCAAGA
ACTGGGCTGTGGCAGCGTACTTCATTTAGTCCAAGCCTTAGTAAAAAATCAAGATATGGAAAGTGCCCCAT
TATGGTTAGTGACTCAAGGCTCACAATCTGTGGGTAATGAGTCCCTTCCTATACAATTCCAACAAACACCT
TTATGGGGGTTAGGTCGAGTAATTGCCCAGGAACATAGGGAATTACAATGCCGGTGTTTAGACTTAGATCC
AACTATGGAAGATTCCCAAACAGTAGCTGCTTTGTTAGAGGAACTATTATCTCCTGGTGATGAAACCAAA
TTGCTTACTGTCAAGGGGTACGTCACGTTGCCCGGTTAGAGCGGCAACAAAAAATGAGTACATCTACACAG
TCCGGATTACAAATTTCCTCGCAACAACCATTTCAACTGAAGCTATCAGAATATAAGTCTTTAGACAACCT
AATCCAAGCCGAAGCCAGTTACTTAATTACCGGAGGTCTGGGAGCACTGGGGTTAAAAACCGCTGAGTGGA
TGGTACAACAAGGGGTCAAATATTTAGTACTTACCGGACGTAGGCAGCCATCAGCAAAAGCTCAACAAACC
ATTGAACAATTACAGAAGGCAGGAGCGCAAGTATTAGTCCTGTGTGGAGATATTTCCCAACAAGAAAATGT
GGCAAGAATTATAGAGTCAATCAAAGTATCTTTGCCAGCATTACGAGGAATAATTCATGCTGCTGGGATAT
TGGATGATGGTTTGCTGTTAAACATGAATTGGGAAAAATTTACACAGGTGATGGCACCAAAAGTACAAGGG
GCTTGGCATTTGCATAATTTGACTCAGAATCTACCTTTGGACTTTTTGTTTGTTTTCCTCTATGGCTTC
AATATTGGGTTCGCCTGGTCAAGGGAATTATGCTGCTGCTAATGCTTTCATGGATGGTTTAGCCCATCATC
GACGGGGTATGGGTTTACCTGGCTTGAGCATTAACTGGGGACCATGGGCACAAGAGGGAATGGCAGCAAAT
TTGGATAGTCCTCATCAAGATAGAATGGTGTCCAAGGGAATGACTTTTTTGTCTTCAGAACAGGGATTGCA
GGTTCTAGGACAATTACTCGAACAATCCATACCACAAGTAGGAGTCCTACCAATTCAATGGTCAGTGTTCC
AAGAGCAATTTAGTTTTGGTAATCAAATACCATTGCTGTCCCAATTGGTAAAAGAAAGCAAATCACAGCAA
AAAGCCCTCAAAACAAAGACAAAGCACAATGAATTTTTAGAACAGCTAAAAGCTGCTTTACCAAGAGAAAG
AGAAAAGCTTTTGATAATTTACATTAAAGATGAAATTTCTCAAGTACTTTCTTTGAGCACTTCTCAAATTG
ATATGCAACAGCCCCTGAACACTATGGGGCTTGATTCTCTAATGGCTGTGGAATTGCACAATAGGCTTCAA
ACTGACTTGCTCGTGGATATATCTATAGTCAAATTTATAGAAGATATCAGTATCGTTGATTTAGCCACTGA
AGTGAATGAGCAACTGAGCCAAGTTGCTCAGAATCAAGGAGTTGAGTCAGAAAATAATGGGCAACTCACC
AAAGCAATAGGAAAGAAAACGAGCGGATAAGAGGTGAATTATGA (SEQ ID NO:44)
```

CrpB

```
MDMNINRRNTSNSKQADSLSPTKQALLALERMQSKLDALEYAKTEPIAIIGMGCRFPGGASTPKGFWEVLK
NGVDAITQVPPNRWNLDNYYDPNPESPGKIYTPYGGFIELLDQFDANLFGISPREAIHLDPQQRLLLEVTW
EAIENALINPTELNGSQTSVFTGICGNDYYQRVIAQDSEQIDAYVVSGNAHSTASGRISYILGLLGPSLAV
DTACSSSLVSVHLACSSLRRGESNLALAGGVNRIISPEVSIAFSKARMLSFNGRCKTFDASADGFVRGEGC
GVVVLKRLSDALTDKDNILAVIRGSAINQDGHTSGLTVPNGPSQQAVIRQALENGGVEPANISYFEAHGTG
TSLGDPIEVGALGTVFGTSHSKEQPLIVGSVKTNIGHLEAAAGVAGLIKIVLQLQNQQIVPSLHFNQPNPY
INWSELPVKIPTQISPWPTNGKSRIAGVSSFGFSGTNAHVILEEAPTQQSQVKDSDLGKHPWHILTLSAKC
EKALQEMIQSYEEFLSNDNTATIADICFSAHISRSHFDYRLALIAPSTEKLRQKLKVFQKNPEDTLGVVRG
```

FIG. 15-4

```
QVDSKKLAKIVFLFTGQGSQYINMGRQLYETQPVFRQTLEQCEQILQPYLKKSILDIIYPEDNQKLNSSII
DQTAYTQVALFAIEYALYKLWESWGIKPDVVMGHSVGEYVAATVAGIFSLEDGLKLIAHRGRLMQQLSSGG
EMLSVMASIEKVNQLIAPYSQKVAIASINGPQSIVTSGEAEAIGAVQNSLEAEDIKTKRLQVSHAFHSHLM
EPMLADFEAVASEITYNQPNIPLVSNVTGARAENSIATASYWVNHVRQPVKFAQSMDTLQQEGYSIFLEIG
PKPTLLGMGRQCLPEDVGVWLPSLRPGQEDWQQMLQSLAELYVHGVKVDWLGFDKDYSRSKVVLPTYPFQR
QRYWIESTESQSQKAAYSSCETKSTPIFDLLIHGNIQQLAQQIEKIGKFSPEQVNLLPEFLEVLVKQHQKQ
LIIETTKDFLYQVQWKPLVDTQPKTSIKPSHWLIFADTTAVGEKLVQQLQSHHCECSLVYRSDCYRKLDEG
TYQLNPTEAQEFEQLIQAIGENSKLPLLHVINLWSLDIQGTQDLTTTILKQAQLWGCGTVLQLVKVLTKTK
SVAKLWLVTRGAQLVKSQTESVCVAASPLWGMGRVISLEHPQLWGGMVDLDPISPESEAYTLLQLLVNSNQ
LEDHLALRADNLYFARLVKQSLKPYDSVSLKDNATYLITGGLGALGLHTARWMVQQGARHLVLTGRKQPNL
EAQQIIEELQKLGAQILVLCGDISDEVDATTIFSEIEASLPTLKGVINAAGVLDDALLHSMSWEQFTQVMA
PKVQGAWHLHNLTQNKALDFFVCFSSMASLVGSPGQGNYAAANAFMDALAHHRRGMGLPGLSINWGPWAQA
GMAASLDNRNRDRMVASGITPLTPEQGLQVLGQLLEQSLPQVGVLSVQWSVFQEKFSFGNQIPLLLELLGE
TESQQKAFRTKTKQNELLKRLESLPCKERYYVLRTEIQSEVAKVLALNDSQLPGFEQGFFDLGMDSLMAVE
LRNRITQLLKVTLPSTLSFDFPNIEQLTKYISSQILDLSTSNDGQQPEQKVKAAEHEPIAIIGMGCSLPGG
ANTPEKFWELLHSGTSAREEIPAQRWDVNSYYDPDREAAGKMVTRYGHFISGVDQFDPEFFGISPREATAM
DPQHRLLLEVSWQALERAGQKVERLSSEPVGVFVGNDGHDYEQLMQKHLEQEPNSTFGTYTCTGNSPSSAS
GRLAYTFGFTGPTVTIDTACSSSLVAIHQACNSIRLGECQMAIAGGVKLHLTPSSYIFTSRAGMISPDGLC
KTFDISADGYGRGEGCGMVVLKSLSQAQADGDPILALILGSAVNQDGPSSGLTVPNGQSQQKLILQALKQA
RVEPADISYLEAHGTGTSLGDPIEVNAAAAVLGLQRSPSQPLWIGTVKTNIGHLESAAGVSGLIKVVLSLQ
HQQIPANLHLQEPNPKIDWQPWLQVPQALTPWVGSKGRLAGVSSFGFTGTNAHVVLSETPAAIASSTVEYE
RPLHLLQLSAKNDLALAQLAQRYSDHLKTHLEQDLRDICFTANSSRLAHKHRLAVVASNRKELQQKLGNFG
TDSERMDLVTGQVSSSQLTKVAMLFTGQGSQYVGMGRQLYQTQPTFKQFVDQCAQILENYLDKPLLEILDV
AQVQENVLAQTAYTQVALFAIEYALYKLWESWGIKPDVVMGHSAGEYVAATVAGIFSLEDGLKLIAHRGRL
MQQLPSGGEMLSVMASIEKVNQLIAPYSQKVAIASINGPQSIVISGEAEAIGAVQNSLEAEDIKTKRLQVS
HAFHSHLMEPMLADFEAVASEITYNQPNIPLVSNVTGARAENSIATASYWVNHVRQPVKFAQSMDTLQQEG
YSIFLEIGPKPTLLGMGRQCLPEDVGVWLPSLKPGQEDWQQMLQSLAELYVHGVKVDWLGFDKDYSRSKVV
LPTYPFQRQRYWIETNNNLIHQKQFLSNHKNLHPLLGQRLHLAALEQQIRFECQISASQPTYLQHHCVFSQ
PVFPAAAYLEIALAAGSILFNSDDLILEDIAIQKVLILSKDEINTIQIVLNLQLVQSYKFQIFSLDINTNS
SEPKWILHIEGKILVGNKDPQLETTNLKAIKDEYNQQTILPTEFYQKFEEWGLNYGSSFQAVKQLWHSEGKA
LGEIQLPETEVNVATLYQLHPILLDASFQVLAAVMGKTDNQETYLPLEIKRLQIYRSGSNSLWTQVEIGAT
ETNKQTLSGKVCLLDEQGIVVARVEGLTLLRTSREALLRNIEPKFNNWLYQIHWQTQSISPHNQSIDLTKS
GSWLLFSPPTGIGKHLVESLEQQGWHCILVTPGENYQQLESQHYQINPNHPEEFLHLLQSSLEQQPPLRGI
IHLWSLDSTIALRTGAQELQKSQELGCGSVLHLVQALVKNQDMESAPLWLVTQGSQSVGNESLPIQFQQTP
LWGLGRVIAQEHRELQCRCLDLDPTMEDSQTVAALLEEELLSPGDENQIAYCQGVRHVARLERQQKMSTSTQ
SGLQISSQQPFQLKLSEYKSLDNLIQAEASYLITGGLGALGLKTAEWMVQQGVKYLVLTGRRQPSAKAQQT
IEQLQKAGAQVLVLCGDISQQENVARIIESIKVSLPALRGIIHAAGILDDGLLLNMNWEKFTQVMAPKVQG
AWHLHNLTQNLPLDFFVCFSSMASILGSPGQGNYAAANAFMDGLAHHRRGMGLPGLSINWGPWAQEGMAAN
LDSPHQDRMVSKGMTFLSSEQGLQVLGQLLEQSIPQVGVLPIQWSVFQEQFSFGNQIPLLSQLVKESKSQQ
KALKTKTKHNEFLEQLKAALPREREKLLIIYIKDEISQVLSLSTSQIDMQQPLNTMGLDSLMAVELHNRLQ
TDLLVDISIVKFIEDISIVDLATEVNEQLSQVAQNQGVESENNGQLYQSNRKENERIRGEL
(SEQ ID NO:45)
```

US 7,566,558 B2

NUCLEIC ACIDS AND POLYPEPTIDES INVOLVED IN THE PRODUCTION OF CRYPTOPHYCIN

CROSS REFERENCE TO RELATED APPLICATIONS

This application claims priority under 35 U.S.C. §119(e) of U.S. Application No. 60/820,715, filed Jul. 28, 2006.

FEDERALLY SPONSORED RESEARCH OR DEVELOPMENT

The U.S. Government has certain rights in this invention pursuant to Grant Nos. CA083155 and CA009676 awarded by the National Institutes of Health.

TECHNICAL FIELD

This invention relates to production of cryptophycin, and more particularly to the polypeptides involved in the biosynthesis of cryptophycin and the nucleic acids encoding such polypeptides.

BACKGROUND

Cryptophycins are novel macrolides first isolated from blue-green algae (*Nostoc* sp. GSV22 and *Nostoc* sp. ATCC 53789) and are potent tumor selective cytotoxins in vivo. Many syntheses of the major natural products, cryptophycins 1-4, and a wide range of analogs have been published. For example, cryptophycins have been synthesized by a convergent method in which four components, Unit A, Unit B, Unit C, and Unit D (Golakati et al., 1995, *J. Am. Chem. Soc.*, 117(49):12031), are coupled together to form the final product (see, for example, U.S. Pat. No. 6,013,626). In other methods, novel semi-synthetic compounds are generated, for example, by converting the epoxide of a natural cryptophycin to a carbon-carbon double bond (see, for example, U.S. Pat. Nos. 4,845,085 and 4,845,086). Stereo-selective addition of functional groups is often problematic during chemical synthesis of cryptophycins, however. Therefore, few of the methodologies for cryptophycin syntheses are considered viable or practical on a commercial scale.

SUMMARY

The present invention provides polypeptides involved in cryptophycin biosynthesis and the nucleic acid molecules that encode such polypeptides. The nucleic acid molecules and polypeptides of the invention or variants thereof can be used in the methods of the invention to produce cryptophycins.

In one aspect, the invention provides an isolated nucleic acid molecule that includes a nucleic acid sequence having at least 85% (e.g., 85%, 90%, 95%, 99%, or 100%) sequence identity to the sequence shown in SEQ ID NO:1 or to a fragment thereof. Such a sequence encodes at least one enzyme involved in biosynthesizing cryptophycin.

The invention further provides for a vector containing such a nucleic acid molecule, and host cells containing such vectors. The invention also provides for cryptophycin or cryptophycin analogues made by such host cells.

In another aspect, the invention provides methods of producing cryptophycin. Such a method generally includes the step of culturing the above-described host cells in the presence of an appropriate substrate and under conditions appropriate for the production of cryptophycin. Such a method can further include the step of purifying the cryptophycin.

In another aspect, the invention provides an isolated nucleic acid molecule comprising a nucleic acid sequence having at least 85% (e.g., 85%, 90%, 95%, 99%, or 100%) sequence identity to SEQ ID NOs: 2, 4, 6, 8, 10, 12, 14, 16, 18, 20, 22, 24, 26, 28, 30, 42 or 44, or to a fragment thereof, wherein the nucleic acid sequence encodes a polypeptide that exhibits functional activity.

The invention further provides for vectors containing such nucleic acid molecules, and host cells containing such vectors. The invention also provides for intermediates in cryptophycin biosynthesis made by such host cells.

The invention further provides a polypeptide encoded by the nucleic acid sequence having at least 85% (e.g., 85%, 90%, 95%, 99%, or 100%) sequence identity to SEQ ID NOs: 2, 4, 6, 8, 10, 12, 14, 16, 18, 20, 22, 24, 26, 28, 30, 42 or 44, or to a fragment thereof. Such polypeptides can have the sequence shown in 3, 5, 7, 9, 11, 13, 15, 17, 19, 21, 23, 25, 27, 29, 31, 43 or 45, respectively.

In still another aspect, the invention provides an isolated nucleic acid molecule comprising a nucleic acid sequence having at least 85% (e.g., 85%, 90%, 95%, 99%, or 100%) sequence identity to nucleotides 9,199 to 10,032 of SEQ ID NO:6, or to a fragment thereof, wherein the nucleic acid sequence encodes a polypeptide that exhibits thioesterase activity under appropriate conditions.

In yet another aspect, the invention provides an isolated nucleic acid molecule comprising a nucleic acid sequence having at least 85% (e.g., 85%, 90%, 95%, 99%, or 100%) sequence identity to the sequence shown in SEQ ID NO:8, or to a fragment thereof, wherein the nucleic acid sequence encodes a polypeptide that exhibits epoxidase activity under appropriate conditions.

In another aspect, the invention provides an isolated nucleic acid molecule comprising a nucleic acid sequence having at least 85% (e.g., 85%, 90%, 95%, 99%, or 100%) sequence identity to the sequence shown in SEQ ID NO:14, or to a fragment thereof, wherein the nucleic acid sequence encodes a polypeptide that exhibits halogenase activity under appropriate conditions.

In another aspect, the invention provides an isolated nucleic acid molecule comprising a nucleic acid sequence having at least 85% (e.g., 85%, 90%, 95%, 99%, or 100%) sequence identity to SEQ ID NO:42 or 44, or to a fragment thereof, wherein the nucleic acid sequence encodes a polypeptide that exhibits polyketide synthetase activity under appropriate conditions.

In another aspect, the invention provides for methods of producing an intermediate in cryptophycin biosynthesis. Such a method includes culturing one or more host cells that contain one or more vectors comprising one or more of the nucleic acid sequences shown in SEQ ID NOs:2, 4, 6, 8, 10, 12, 14, 16, 18, 20, 22, 24, 26, 28, 30, 42 or 44 in the presence of one or more appropriate substrates under conditions appropriate for production of an intermediate in cryptophycin biosynthesis.

Representative appropriate conditions include pH, media, temperature, and/or the presence or absence of co-factors. Representative substrates and intermediates in cryptophycin biosynthesis include Cryptophycin 2, 3, 4, 5, 16, and 17 (see FIG. 1B).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

DESCRIPTION OF DRAWINGS

FIG. 1 shows cryptophycin structures.

FIG. 5 is the nucleotide sequence of the cloned insert of pDAM163 (SEQ ID NO:1).

FIG. 6 is the nucleotide and amino acid sequences of the genes and polypeptides involved in cryptophycin biosynthesis (SEQ ID NOs:2-31).

FIG. 7 shows SEQ ID NOs: 32-37, which have 75%, 80%, 85%, 90%, 95%, and 99% sequence identity, respectively, to SEQ ID NO:2.

FIG. 14 is a nucleotide (SEQ ID NO:42) and encoded amino acid sequence (SEQ ID NO:43) of crpA.

FIG. 15 is a nucleotide (SEQ ID NO:44) and encoded amino acid sequence (SEQ ID NO:45) of crpB.

DESCRIPTION OF SEQUENCES

Figure 1A:
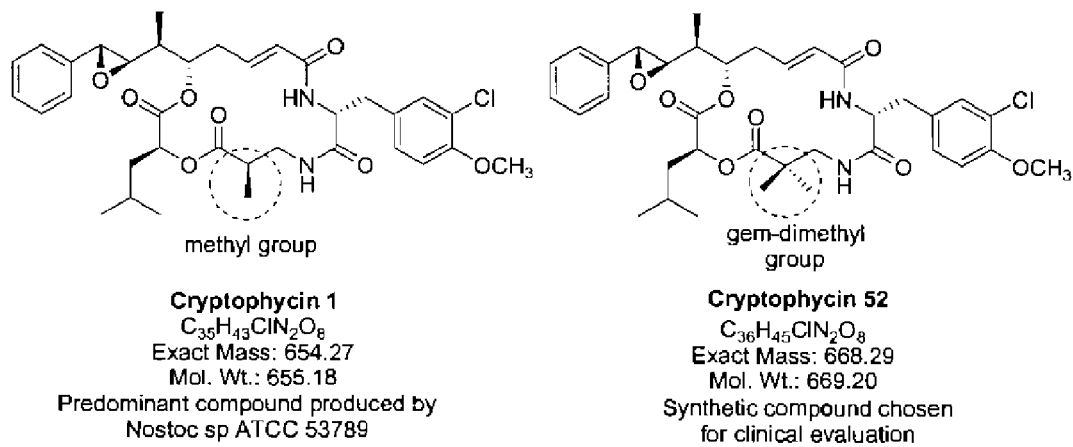
FIG. 1A is a natural cryptophycin, Cryptophycin 1, and a synthetic cryptophycin, Cryptophycin 52.

SEQ ID NO:1 is the nucleotide sequence of the cloned insert of pDAM163.
SEQ ID NO:2 is a nucleotide sequence having homology to crpA.
SEQ ID NO:3 is an amino acid sequence having homology to CrpA.
SEQ ID NO:4 is the nucleotide sequence of crpC.
SEQ ID NO:5 is the amino acid sequence of CrpC.
SEQ ID NO:6 is the nucleotide sequence of crpD.
SEQ ID NO:7 is the amino acid sequence of CrpD.
SEQ ID NO:8 is the nucleotide sequence of crpE.
SEQ ID NO:9 is the amino acid sequence of CrpE.
SEQ ID NO:10 is the nucleotide sequence of crpF.
SEQ ID NO:11 is the amino acid sequence of CrpF.
SEQ ID NO:12 is the nucleotide sequence of crpG.
SEQ ID NO:13 is the amino acid sequence of CrpG.
SEQ ID NO:14 is the nucleotide sequence of crpH.
SEQ ID NO:15 is the amino acid sequence of CrpH.
SEQ ID NO:16 is the nucleotide sequence of crpM.
SEQ ID NO:17 is the amino acid sequence of CrpM.
SEQ ID NO:18 is the nucleotide sequence of crpN.
SEQ ID NO:19 is the amino acid sequence of CrpN.
SEQ ID NO:20 is the nucleotide sequence of crpP.
SEQ ID NO:21 is the amino acid sequence of CrpP.
SEQ ID NO:22 is the nucleotide sequence of crpU.
SEQ ID NO:23 is the amino acid sequence of CrpU.
SEQ ID NO:24 is the nucleotide sequence of crpV.
SEQ ID NO:25 is the amino acid sequence of CrpV.
SEQ ID NO:26 is the nucleotide sequence of crpX.
SEQ ID NO:27 is the amino acid sequence of CrpX.
SEQ ID NO:28 is the nucleotide sequence of crpY.
SEQ ID NO:29 is the amino acid sequence of CrpY.
SEQ ID NO:30 is the nucleotide sequence of crpZ.
SEQ ID NO:31 is the amino acid sequence of CrpZ.
SEQ ID NO:32 is a nucleotide sequence having 75% sequence identity to SEQ ID NO:2.
SEQ ID NO:33 is a nucleotide sequence having 80% sequence identity to SEQ ID NO:2.
SEQ ID NO:34 is a nucleotide sequence having 85% sequence identity to SEQ ID NO:2.
SEQ ID NO:35 is a nucleotide sequence having 90% sequence identity to SEQ ID NO:2.
SEQ ID NO:36 is a nucleotide sequence having 95% sequence identity to SEQ ID NO:2.
SEQ ID NO:37 is a nucleotide sequence having 99% sequence identity to SEQ ID NO:2.
SEQ ID NO:38 is the sequence of an oligonucleotide.
SEQ ID NO:39 is the sequence of an oligonucleotide.
SEQ ID NO:40 is the sequence of an oligonucleotide.
SEQ ID NO:41 is the sequence of an oligonucleotide.
SEQ ID NO:42 is the nucleotide sequence of crpA.
SEQ ID NO:43 is the amino acid sequence of CrpA.
SEQ ID NO:44 is the nucleotide sequence of crpB.
SEQ ID NO:45 is the amino acid sequence of CrpB.

DETAILED DESCRIPTION

Cryptophycin biosynthesis is accomplished via a mixed Type I PKS/NRPS system. Manipulation of polyketide synthetases (PKSs) and non-ribosomal peptide synthetases (NRPSs) through mutasynthesis, combinatorial biosynthesis, and directed biosynthesis feeding (chemoenzymatic synthesis) has been described for many PKS and NRPS polypeptides. The identification of the corresponding genes allows for these types of approaches with the cryptophycin system. It is possible that altering the PKS enzyme for Unit A formation or the NRPS for Unit B, C, and D formation could generate a wide variety of new cryptophycins. With this invention, it is also possible to incorporate these enzymes in "total synthesis" of cryptophycins to lower the cost and increase the overall yields. For example, the ability of biosynthetic enzymes to exhibit high levels of stereo-chemical control and relaxed substrate specificity, and the sensitivity of the biological and chemical assays for identifying cryptophycins, allow for production of rational "biologically" derived cryptophycins that have superior properties.

Cryptophycins

Figure 1B:
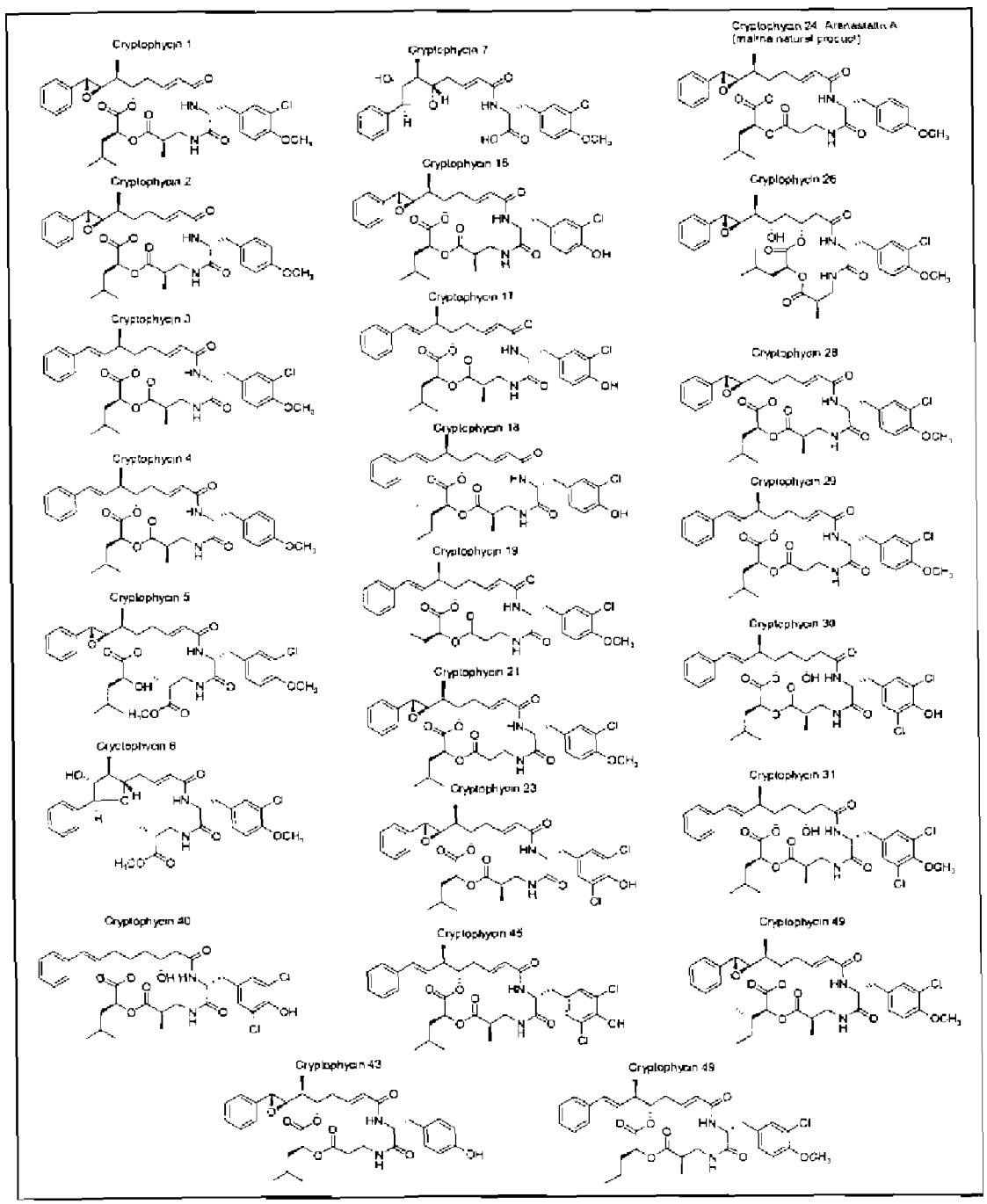
FIG. 1B illustrates the diversity of natural cryptophycins isolated from *Nostoc* spp.
Figure 2:
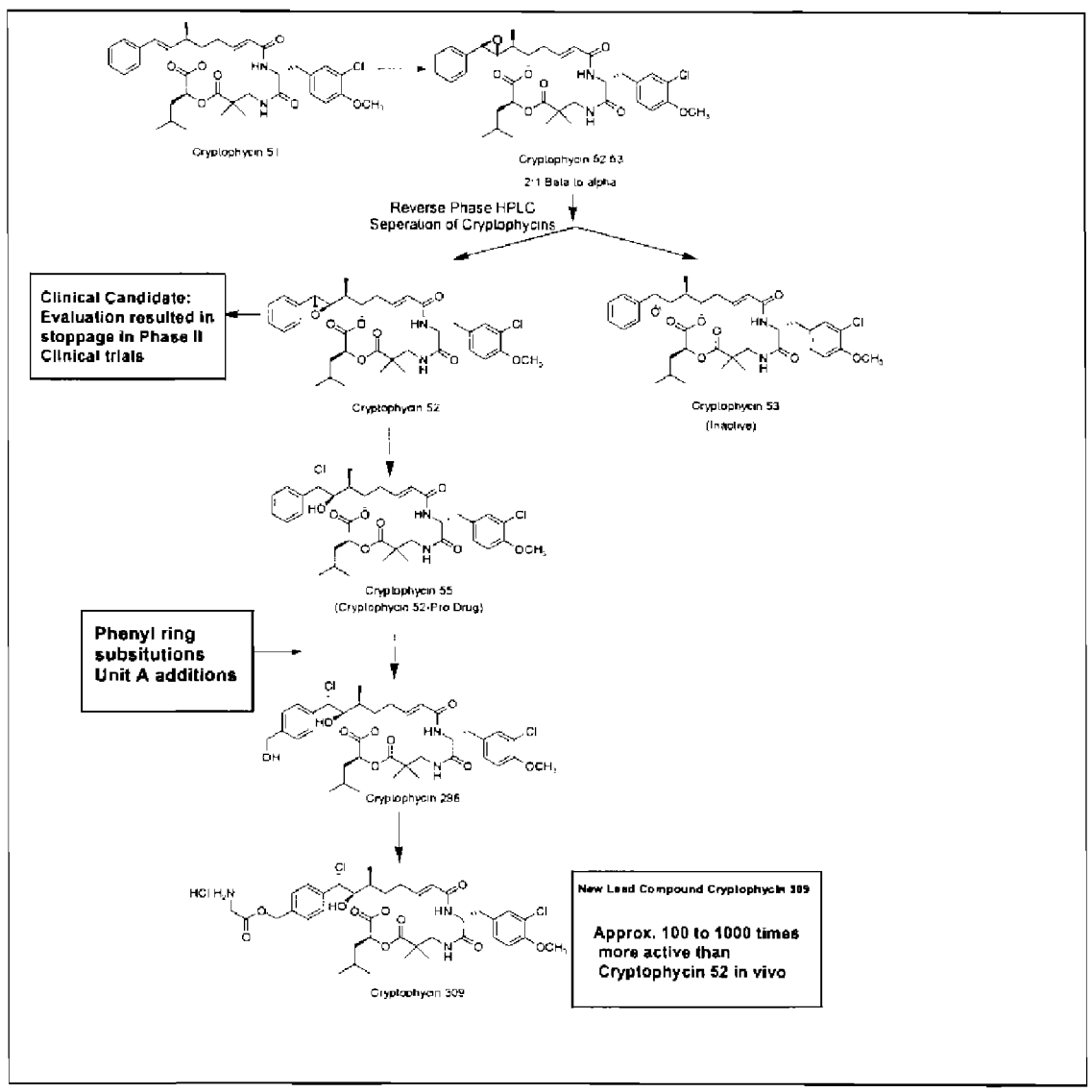
FIG. 2 is a schematic of the lineage of biologically active cryptophycins.

FIG. 1A shows Cryptophycin 1 and Cryptophycin 52. Cryptophycin 52 is nearly identical to Cryptophycin 1, the most active natural compound, except for the presence of gem-dimethyl on the β-alanine unit of Cryptophycin 52 instead of the methyl group on Cryptophycin 1. FIG. 1B shows numerous other natural cryptophycins that have been isolated from *Nostoc* spp. A chlorohydrin analog (Cryptophycin 309; see U.S. Publication No. 20020065261 and FIG. 2 of the instant application) has been identified and has been shown to be much more active than the current clinical candidate, Cryptophycin 52.

Purification

Routine chromatographic techniques such as high-performance liquid chromatography (HPLC) or thin-layer chromatography (TLC) can be used to purify cryptophycins. See, for example, U.S. Pat. No. 5,952,298, which describes specific HPLC conditions for purifying different cryptophycins.

Structure Identification

The structures of cryptophycins can be determined using methodology that is well known to those of skill in the art. Mass spectral analysis can be used, for example. Proton and carbon NMR data obtained from COSY, HMQC, HMBC, and NOESY spectra allows determination of the gross structures of the depsipeptide-type compounds. The presence of the various hydroxy and amino acid units in each compound can be detected by gas chromatographic mass spectral analysis. Total structures, including absolute stereochemistries, can be determined using a combination of chemical degradative and analytical techniques on cryptophycin compounds.

Anti-Fungal Activity

Cryptophycin compounds can be tested against fungal organisms known to be sensitive to such compounds using, for example, a disk-diffusion assay such as a Corbett assay (see, for example, Kemp, 1980, Organic Chemistry, Worth Publishers Inc.). The anti-fungal activity of a cryptophycin is usually correlated with the size of the zone of inhibition (i.e., an area of no microbial growth around an antimicrobial agent in a disk-diffusion test). An organism that can be used to evaluate the anti-fungal activity of a cryptophycin is *Candida albicans*.

Anti-Cancer Activity

The anti-cancer activity of a cryptophycin can be examined using a number of different assays such as cell proliferation assays and cell cycle arrest assays. In addition, cytoskeletal structures such as tubulin can be examined using, for example, immunofluorescence assays. See, for example, U.S. Pat. No. 5,945,315.

Cryptophycins can be evaluated for anti-cancer activity against a number of different cell types. For example, murine leukemia cells (e.g., L1210 or P388), murine solid tumor cells (e.g., colon adenocarcinoma 38, pancreatic ductal adenocarcinoma 03, mammary adenocarcinoma M16/M17), human solid tumor cells (e.g., colon CX-1, HCT8, H116, lung H125, mammary MX-1, MCF-7), low malignancy fibroblast cells (e.g., LML), human nasopharyngeal carcinoma cells (e.g., KB), human colon carcinoma cells (e.g., LoVo), and human ovarian carcinoma cells (e.g., SKOV3) can be used to evaluate the anti-cancer activity of a cryptophycin. For example, a disk diffusion assay much like the Corbett assay (Kemp, supra) commonly used in antifungal and antibacterial testing can be used to evaluate the anti-cancer activity of a cryptophycin. A zone of inhibition can be correlated with the anti-cancer activity of a cryptophycin.

Nucleic Acids and Polypeptides Involved in Cryptophycin Biosynthesis

Figure 4:
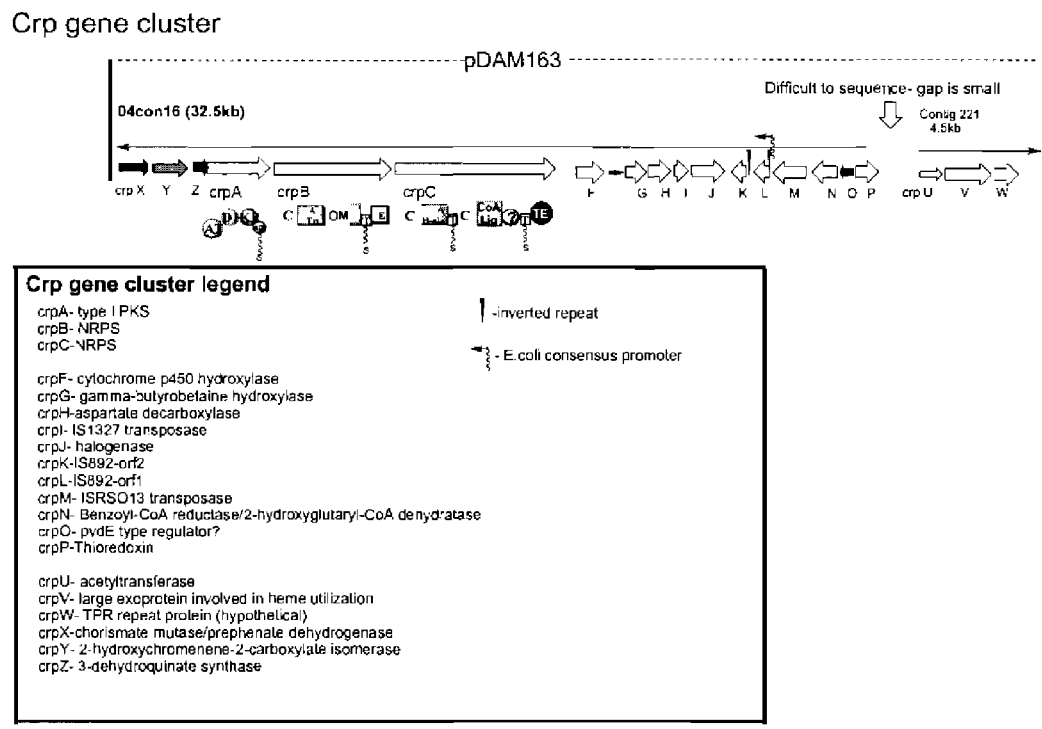
FIG. 4 is a schematic of cosmid pDAM163 and genes identified with relationships to cryptophycin biosynthesis.

Approximately 45 kb of DNA corresponding to the genes predicted to be involved in cryptophycin biosynthesis were cloned into a cosmid designated pDAM163 and sequenced. FIG. 4 shows a schematic of pDAM163, while FIG. 5 shows the nucleotide sequence of the cloned insert of pDAM163 (SEQ ID NO:1). This cosmid replicated efficiently and stably in well-developed fermentation strains such as *E. coli* B (*E. coli* BL21pLys) and *E. coli* K (DH5α) derivatives. Expressing the coding regions contained within pDAM163 can result in the production of cryptophycin in the *E. coli* strains. A variety of microorganisms such as bacteria (e.g., *Escherichia coli*), yeast (e.g., *Pichia pastoris* or *Saccharomyces cerevisiae*), or fungi (e.g., *Neurospora crassa*) that include expression constructs such as pDAM163 or variants thereof can be used to generate cryptophycins.

The components of the biosynthetic pathway are summarized in Table 1, which provides information related to the putative function of each polypeptide.

TABLE 1

Nucleic Acids and Polypeptides Involved in Cryptophycin Biosynthesis

| Designation (SEQ ID NO: Nucleic Acid/Polypeptide) | Length (amino acids) | Putative Function |
|---|---|---|
| crpA (SEQ ID NO: 42/43) | 2942 | Polyketide synthetase (PKS) |
| crpB (SEQ ID NO: 44/45) | 3470 | Polyketide synthetase (PKS) |
| crpC (SEQ ID NO: 4/5) | 1944 | Nonribosomal Peptide Synthetase (NRPS) |
| crpD (SEQ ID NO: 6/7) | 3344 | NRPS |
| crpE (SEQ ID: NO: 8/9) | 451 | Cytochrome p450 (epoxidase) |
| crpF (SEQ ID NO: 10/11) | 295 | Iron-dependent non-heme hydroxylase |
| crpG (SEQ ID NO: 12/13) | 114 | Aspartate decarboxylase |
| crpH (SEQ ID NO: 14/15) | 492 | Non-heme halogenase |
| crpI | $a$ | IS1327 Transposase |
| crpK | $a$ | IS892-orf2 |
| crpL | $a$ | IS892-orf1 |
| crpM (SEQ ID NO: 16/17) | 461 | ISRSO13 Transposase |
| crpN (SEQ ID NO: 18/19) | 314 | Benzoyl-CoA reductase/ 2-Hydroxyglutaryl-CoA dehydratase |
| crpO | $b$ | pvdE type regulator |
| crpP (SEQ ID NO: 20/21) | 210 | Thioredoxin |
| crpU (SEQ ID NO: 22/23) | 155 | N-acetyltransferase |
| crpV (SEQ ID NO: 24/25) | 784 | Large exoprotein involved in heme utilization |
| crpW | $a$ | TPR repeat protein |
| crpX (SEQ ID NO: 26/27) | 132 | Chorismate mutase/Prephenate dehydrogenase |
| crpY (SEQ ID NO: 28/29) | 214 | 2-Hydroxychromenene-2-carboxylate isomerase |
| crpZ (SEQ ID NO: 30/31) | 90 | 3-Dehydroquinate synthase |

$a$, no open reading frame identified;
$b$, multiple open reading frames identified.

Nucleic Acid Molecules

The present invention is based, in part, on the identification of nucleic acid molecules that encode polypeptides involved in cryptophycin synthesis. Particular nucleic acid molecules of the invention include the sequences shown in SEQ ID NOs:1, 2, 4, 6, 8, 10, 12, 14, 16, 18, 20, 22, 24, 26, 28, 30, 42 and 44. As used herein, the term "nucleic acid molecule" can include DNA molecules and RNA molecules and analogs of the DNA or RNA molecule generated using nucleotide analogs. A nucleic acid molecule of the invention can be single-stranded or double-stranded, and the strandedness will depend upon its intended use.

The invention further encompasses nucleic acid molecules that differ from the nucleotide sequence of SEQ ID NOs: 1, 2, 4, 6, 8, 10, 12, 14, 16, 18, 20, 22, 24, 26, 28, 30, 42 and 44. Nucleic acid molecules of the invention include molecules that are at least 10 nucleotides in length and that have at least 75% sequence identity (e.g., at least 80%, 85%, 90%/, 95%/, or 99% sequence identity) to any of SEQ ID NOs: 1, 2, 4, 6, 8, 10, 12, 14, 16, 18, 20, 22, 24, 26, 28, 30, 42 and 44. Nucleic acid molecules that differ in sequence from the nucleic acid sequences shown in SEQ ID NOs: 1, 2, 4, 6, 8, 10, 12, 14, 16, 18, 20, 22, 24, 26, 28, 30, 42 and 44 can be generated by standard techniques, such as site-directed mutagenesis or PCR-mediated mutagenesis. In addition, nucleotide changes can be introduced randomly along all or part of a nucleic acid molecule of the invention, such as by saturation mutagenesis. Alternatively, nucleotide changes can be introduced into a sequence by chemically synthesizing a nucleic acid molecule having such changes.

In calculating percent sequence identity, two sequences are aligned and the number of identical matches of nucleotides or amino acid residues between the two sequences is determined. The number of identical matches is divided by the length of the aligned region (i.e., the number of aligned nucleotides or amino acid residues) and multiplied by 100 to arrive at a percent sequence identity value. It will be appreciated that the length of the aligned region can be a portion of one or both sequences up to the full-length size of the shortest sequence. It also will be appreciated that a single sequence can align with more than one other sequence and hence, can have different percent sequence identity values over each aligned region. It is noted that the percent identity value is usually rounded to the nearest integer. For example, 78.1%, 78.2%, 78.3%, and 78.4% are rounded down to 78%, while 78.5%, 78.6%, 78.7%, 78.8%, and 78.9% are rounded up to 79%. It is also noted that the length of the aligned region is always an integer.

The alignment of two or more sequences to determine percent sequence identity is performed using the algorithm described by Altschul et al. (1997, *Nucleic Acids Res.*, 25:3389-3402) as incorporated into BLAST (basic local alignment search tool) programs, available at ncbi.nlm.nih.gov on the World Wide Web. BLAST searches can be performed to determine percent sequence identity between a nucleic acid molecule of the invention and any other sequence or portion thereof aligned using the Altschul et al. algorithm. BLASTN is the program used to align and compare the identity between nucleic acid sequences, while BLASTP is the program used to align and compare the identity between amino acid sequences. When utilizing BLAST programs to calculate the percent identity between a sequence of the invention and another sequence, the default parameters of the respective programs are used. Sequence analysis of the nucleic acid sequences as performed herein used BLAST version 2.2.8 (updated on Feb. 10, 2004).

The sequences of representative nucleic acids of the invention having 75%, 80%, 85%, 90%, 95%, and 99% sequence identity to SEQ ID NO:2 are shown in FIG. 7 (SEQ ID NOs:32-37, respectively). Such sequences can be generated using a computer or by hand. The nucleic acid sequences shown in SEQ ID NOs:32-37 were generated by hand by randomly changing 25 nucleotides out of every 100 nucleotides of SEQ ID NO:2, 2 out of every 10, 15 out of every 100, 1 out of every 10, 5 out of every 100, or 1 nucleotide out of every 100 nucleotides of SEQ ID NO:2, respectively. By "changing," it is meant that the nucleotide at a particular position is replaced randomly with one of the other three nucleotides. It is apparent to those of ordinary skill in the art that any nucleic acid molecule within the scope of the invention can be generated using the same method described herein (i.e., by similarly changing nucleotides within the sequence of SEQ ID NOs: 1, 2, 4, 6, 8, 10, 12, 14, 16, 18, 20, 22, 24, 26, 28, 30, 42 or 44).

Nucleic acid fragments are included in the invention. Nucleic acid fragments suitable for use in the invention are those fragments that encode a polypeptide having functional activity. These fragments can be called "functional fragments," although it is understood that it is not the nucleic acid that possesses functionality.

For example, nucleic acid fragments of crpA (SEQ ID NO:42) can be at least 50 nucleotides in length (e.g., 100, 246, 298, 356, 387, 455, 578, 621, 780, 881, 972, 1040, 1128, 1287, 1344, 1468, 1579, 1622, 1734, 1849, 1931, 2006, 2143, 2267, 2389, 2467, 2590, 2671, 2742, 2862, 2944, 3050, 3133, 3266, 3378, 3496, 3577, 3658, 3792, 3846, 3930, 4002, 4127, 4239, 4347, 4437, 4569, 4672, 4722, 4892, 4956, 5012, 5168, 5234, 5378, 5499, 5546, 5623, 5749, 5832, 5911, 6049, 6128, 6226, 6359, 6439, 6533, 6677, 6788, 6873, 6912, 7019, 7128, 7246, 7359, 7456, 7599, 7688, 7744, 7834, 7926, 8022, 8156, 8277, 8359, 8466, 8523, 8611, 8752, 8801, or 8820); nucleic acid fragments of crpB (SEQ ID NO:44) can be at least can be at least 50 nucleotides in length (e.g., 100, 233, 256, 389, 363, 443, 560, 622, 789, 832, 976, 1056, 1158, 1264, 1322, 1489, 1552, 1619, 1729, 1838, 1974, 2077, 2129, 2202, 2376, 2433, 2511, 2683, 2794, 2805, 2905, 3078, 3124, 3285, 3385, 3424, 3536, 3615, 3728, 3894, 3973, 4084, 4121, 4290, 4357, 4483, 4549, 4614, 4799, 4843, 4983, 5003, 5177, 5245, 5308, 5446, 5577, 5636, 5763, 5878, 5939, 6049, 6177, 6275, 6393, 6429, 6504, 6648, 6793, 6847, 6914, 7028, 7148, 7258, 7324, 7427, 7558, 7677, 7742, 7812, 7978, 8093, 8178, 8262, 8393, 8455, 8522, 8644, 8775, 8848, 8954, 9032, 9168, 9256, 9356, 9419, 9521, 9628, 9720, 9811, 9920, 10025, 10257, 10368, or 10400); nucleic acid fragments of crpC (SEQ ID NO:4) can be at least 292 nucleotides in length (e.g., 292, 306, 382, 461, 592, 715, 825, 947, 1059, 1172, 1236, 1358, 1496, 1590, 1671, 1774, 1889, 1923, 2047, 2135, 2265, 2346, 2477, 2588, 2667, 2754, 2863, 2954, 3084, 3126, 3278, 3345, 3412, 3551, 3670, 3781, 3890, 3910, 4044, 4123, 4266, 4378, 4423, 4513, 4622, 4783, 4822, 4989, 5002, 5156, 5237, 5368, 5486, 5572, 5691, 5765, or 5831); nucleic acid fragments of crpD (SEQ ID NO:6) can be at least 502 nucleotides in length (e.g., 502, 624, 738, 829, 914, 1026, 1138, 1257, 1318, 1452, 1525, 1637, 1768, 1828, 1987, 2074, 2183, 2294, 2338, 2444, 2557, 2637, 2789, 2816, 2942, 3067, 3178, 3227, 3348, 3459, 3504, 3684, 3759, 3812, 3943, 4005, 4276, 4495, 4658, 4827, 5048, 5276, 5424, 5608, 5877, 6034, 6269, 6447, 6632, 6874, 7006, 7284, 7472, 7647, 7814, 8038, 8246, 8459, 8644, 8888, 9053, 9298, 9436, 9666, 9878, or 10,032); nucleic acid fragments of crpE (SEQ ID NO:8) can be at least 68 nucleotides in length (e.g., 68, 74, 82, 88, 95, 105, 168, 235, 367, 489, 524, 665, 784, 863, 925, 1064, 1138, 1279, or 1352); nucleic acid fragments of crpF (SEQ ID NO:10) can be at least 44 nucleotides in length (e.g., 44, 54, 58, 67, 74, 83, 97, 107, 189, 267, 345, 457, 536, 679, 772, or 884); nucleic acid fragments of crpG (SEQ ID NO:12) can be at least 33 nucleotides in length (e.g., 33, 45, 52, 68, 73, 84, 93, 108, 168, 216, 248, 293, 312, or 332); nucleic acid fragments of crpH (SEQ ID NO:14) can be at least 74 nucleotides in length (e.g., 74, 106, 187, 254, 304, 379, 467, 522, 592, 667, 714, 781, 859, 911, 978, 1049, 1138, 1273, 1347, 1405, or 1475); nucleic acid fragments of crpM (SEQ ID NO:16) can be at least 69 nucleotides in length (e.g., 69, 136, 216, 362, 486, 592, 647, 781, 844, 919, 1049, 1138, 1274, or 1382); nucleic acid fragments of crpN (SEQ ID NO:18) can be at least 94 nucleotides in length (e.g., 94, 182, 261, 358, 442, 580, 625, 740, 862, or 941); nucleic acid fragments of crpP (SEQ ID NO:20) can be at least 32 nucleotides in length (e.g., 32, 85, 120, 175, 232, 286, 310, 379, 433, 561, or 632); nucleic acid fragments of crpU (SEQ ID NO:22) can be at least 23 nucleotides in length (e.g., 23, 74, 112, 178, 215, 280, 315, 369, 402, or 467); nucleic acid fragments of crpV (SEQ ID NO:24) can be at least 118 nucleotides in length (e.g., 118, 235, 366, 440, 521, 636, 783, 852, 918, 1044, 1168, 1238, 1350, 1448, 1569, 1722, 1838, 1924, 2052, 2167, 2288, or 2354); nucleic acid fragments of crpX (SEQ ID NO:26) can be at least 60 nucleotides in length (e.g., 60, 98, 137, 182, 214, 278, 308, 357, or 398); nucleic acid fragments of crpY (SEQ ID NO:28) can be at least 32 nucleotides in length (e.g., 32, 74, 121, 169, 204, 263, 298, 355, 391, 426, 484, 523, 577, 624, or 644); and nucleic acid fragments of crpZ (SEQ ID NO:30) can be at least 27 nucleotides in length (e.g., 27, 68, 103, 158, 193, 243, or 272). Based on contemporaneous public database searches, such fragments appear not to have more than 85% sequence identify to sequences in the public databases.

As used herein, an "isolated" nucleic acid molecule is a nucleic acid molecule that is separated from other nucleic acid molecules that are usually associated with the reference nucleic acid molecule in the genome. Thus, an "isolated" nucleic acid molecule includes, without limitation, a nucleic acid molecule that is free of sequences that naturally flank one or both ends of the nucleic acid in the genome of the organism from which the isolated nucleic acid molecule is derived (e.g., a cDNA or genomic DNA fragment produced by PCR or restriction endonuclease digestion). Such an isolated nucleic acid molecule is generally introduced into a vector (e.g., a cloning vector, or an expression vector) for convenience of manipulation or to generate a fusion nucleic acid molecule. In addition, an isolated nucleic acid molecule can include an engineered nucleic acid molecule such as a recombinant or a synthetic nucleic acid molecule. A nucleic acid molecule existing among hundreds to millions of other nucleic acid molecules within, for example, a nucleic acid library (e.g., a cDNA, or genomic library) or a portion of a gel (e.g., agarose, or polyacrylamine) containing restriction-digested genomic DNA is not to be considered an isolated nucleic acid.

Isolated nucleic acid molecules of the invention can be obtained using techniques routine in the art. For example, isolated nucleic acids within the scope of the invention can be obtained using any method including, without limitation, recombinant nucleic acid technology, and/or the polymerase chain reaction (PCR). General PCR techniques are described, for example in *PCR Primer: A Laboratory Manual*, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid molecule of the invention. Isolated nucleic acids of the invention also can be chemically synthesized, either as a single nucleic acid molecule or as a series of oligonucleotides. In addition, isolated nucleic acid molecules of the invention also can be obtained by mutagenesis. For example, an isolated nucleic acid that shares identity with an art known sequence can be mutated using common molecular cloning techniques (e.g., site-directed mutagenesis). Possible mutations include, without limitation, deletions, insertions, substitutions, and combinations thereof.

Vectors containing nucleic acid molecules that encode polypeptides involved in cryptophycin synthesis also are provided by the invention. Vectors, including expression vectors, suitable for use in the present invention are commercially available and/or produced by recombinant DNA technology methods routine in the art. A vector containing a nucleic acid molecule of the invention can have elements necessary for expression operably linked to such a nucleic acid molecule, and further can include sequences such as those encoding a selectable marker (e.g., an antibiotic resistance gene), and/or those that can be used in purification of a polypeptide involved in cryptophycin synthesis (e.g., 6×His tag).

Elements necessary for expression include nucleic acid sequences that direct and regulate expression of nucleic acid coding sequences. One example of an element necessary for expression is a promoter sequence. Elements necessary for expression also can include introns, enhancer sequences, response elements, or inducible elements that modulate expression of a nucleic acid molecule of the invention. Elements necessary for expression can be of bacterial, yeast, insect, mammalian, or viral origin and vectors can contain a combination of elements from different origins. Elements necessary for expression are described, for example, in Goeddel, 1990, *Gene Expression Technology: Methods in Enzymology*, 185, Academic Press, San Diego, Calif. As used herein, operably linked means that a promoter and/or other regulatory element(s) are positioned in a vector relative to a nucleic acid molecule of the invention in such a way as to direct or regulate expression of the nucleic acid molecule. Many methods for introducing nucleic acids into host cells, both in vivo and in vitro, are well known to those skilled in the art and include, without limitation, calcium phosphate precipitation, electroporation, heat shock, lipofection, microinjection, and viral-mediated nucleic acid transfer.

Another aspect of the invention pertains to host cells into which a vector of the invention, e.g., an expression vector, or an isolated nucleic acid molecule of the invention has been introduced. The term "host cell" refers not only to the particular cell but also to the progeny or potential progeny of such a cell. A host cell can be any prokaryotic or eukaryotic cell. For example, nucleic acid molecules of the invention can be expressed in bacterial cells such as *E. coli*, or in insect cells, yeast or mammalian cells (such as Chinese hamster ovary cells (CHO) or COS cells). Other suitable host cells are known to those skilled in the art.

Conditions for amplification of a nucleic acid and detection of an amplification product are known to those of skill in the art (see, e.g., *PCR Primer: A Laboratory Manual*, 1995, Dieffenbach & Dveksler, Eds., Cold Spring Harbor Laboratory Press, Cold Spring Harbor, N.Y.; and U.S. Pat. Nos. 4,683,195; 4,683,202; 4,800,159; and 4,965,188). Modifications to the original PCR also have been developed. For example, anchor PCR, RACE PCR, or ligation chain reaction (LCR) are additional PCR methods known in the art (see, e.g., Landegran et al., 1988, Science, 241:1077-1080; and Nakazawa et al., 1994, *Proc. Natl. Acad. Sci. USA*, 91:360-364).

Hybridization between nucleic acid molecules is discussed in detail in Sambrook et al. (1989, *Molecular Cloning: A Laboratory Manual*, $2^{nd}$ Ed., Cold Spring Harbor Laboratory Press, Cold Spring Harbor, N.Y.; Sections 7.37-7.57, 9.47-9.57, 11.7-11.8, and 11.45-11.57). For oligonucleotide probes less than about 100 nucleotides, Sambrook et al. discloses suitable Southern blot conditions in Sections 11.45-11.46. The Tm between a sequence that is less than 100 nucleotides in length and a second sequence can be calculated using the formula provided in Section 11.46. Sambrook et al. additionally discloses prehybridization and hybridization conditions for a Southern blot that uses oligonucleotide probes greater than about 100 nucleotides (see Sections 9.47-9.52). Hybridizations with an oligonucleotide greater than 100 nucleotides generally are performed 15-25° C. below the $T_m$. The $T_m$ between a sequence greater than 100 nucleotides in length and a second sequence can be calculated using the formula provided in Sections 9.50-9.51 of Sambrook et al. Additionally, Sambrook et al. recommends the conditions indicated in Section 9.54 for washing a Southern blot that has been probed with an oligonucleotide greater than about 100 nucleotides.

The conditions under which membranes containing nucleic acids are prehybridized and hybridized, as well as the conditions under which membranes containing nucleic acids are washed to remove excess and non-specifically bound probe can play a significant role in the stringency of the hybridization. Such hybridizations and washes can be performed, where appropriate, under moderate or high stringency conditions. Such conditions are described, for example, in Sambrook et al. section 11.45-11.46. For example, washing conditions can be made more stringent by decreasing the salt concentration in the wash solutions and/or by increasing the temperature at which the washes are performed. In addition, interpreting the amount of hybridization can be affected, for example, by the specific activity of the labeled oligonucleotide probe, by the number of probe-binding sites on the template nucleic acid to which the probe has hybridized, and by the amount of exposure of an autoradiograph or other detection medium.

It will be readily appreciated by those of ordinary skill in the art that although any number of hybridization and washing conditions can be used to examine hybridization of a probe nucleic acid molecule to immobilized target nucleic acids, it is more important to examine hybridization of a probe to target nucleic acids under identical hybridization, washing, and exposure conditions. Preferably, the target nucleic acids are on the same membrane.

A nucleic acid molecule is deemed to hybridize to a nucleic acid of the invention but not to another nucleic acid if hybridization to a nucleic acid of the invention is at least 5-fold (e.g., at least 6-fold, 7-fold, 8-fold, 9-fold, 10-fold, 20-fold, 50-fold, or 100-fold) greater than hybridization to another nucleic acid. The amount of hybridization can be quantitated directly on a membrane or from an autoradiograph using, for example, a PhosphorImager or a Densitometer (Molecular Dynamics, Sunnyvale, Calif.).

Detection of an amplification product or a hybridization complex is usually accomplished using detectable labels. The term "labeled" with regard to an agent (e.g., an oligonucleotide or a polypeptide) is intended to encompass direct labeling of the agent by coupling (i.e., physically linking) a detectable substance to the agent, as well as indirect labeling of the agent by reactivity with another reagent that is directly labeled with a detectable substance. Detectable substances include various enzymes, prosthetic groups, fluorescent materials, luminescent materials, bioluminescent materials, and radioactive materials.

Polypeptides

One aspect of the invention pertains to purified polypeptides involved in cryptophycin synthesis as well as polypeptide fragments, particularly those that possess enzymatic activity (i.e., functional fragments). Predicted amino acid sequences of polypeptides involved in cryptophycin synthesis are shown in SEQ ID NOs:3, 5, 7, 9, 11, 13, 15, 17, 19, 21, 23, 25, 27, 29, 31, 43 and 45.

The term "purified" polypeptide as used herein refers to a polypeptide that has been separated or purified from cellular components that naturally accompany it. Typically, the polypeptide is considered "purified" when it is at least 70% (e.g., at least 75%, 80%, 85%, 90%, 95%, or 99%) by dry weight, free from the proteins and naturally occurring molecules with which it is naturally associated. Since a polypeptide that is chemically synthesized is, by nature, separated from the components that naturally accompany it, a synthetic polypeptide is "purified."

Polypeptides involved in cryptophycin synthesis can be purified from natural sources (e.g., a biological sample) by known methods such as DEAE ion exchange, gel filtration, and hydroxyapatite chromatography. A purified polypeptide also can be obtained, for example, by expressing a nucleic acid molecule of the invention in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis.

In addition to the naturally-occurring polypeptides involved in cryptophycin biosynthesis, the skilled artisan will further appreciate that changes can be introduced into a nucleic acid molecule (e.g., those having the sequence shown in SEQ ID NOs: 1, 2, 4, 6, 8, 10, 12, 14, 16, 18, 20, 22, 234, 26, 28, 30, 42 and 44) as discussed herein, thereby leading to changes in the amino acid sequence of the encoded polypeptide. For example, changes can be introduced into nucleic acid coding sequences leading to conservative and/or non-conservative amino acid substitutions at one or more amino acid residues. A "conservative amino acid substitution" is one in which one amino acid residue is replaced with a different amino acid residue having a similar side chain. Similarity between amino acid residues has been assessed in the art. For example, Dayhoff et al. (1978, in *Atlas of Protein Sequence and Structure,* 5(Suppl. 3):345-352) provides frequency tables for amino acid substitutions that can be employed as a measure of amino acid similarity. A non-conservative substitution is one in which an amino acid residue is replaced with an amino acid residue that does not have a similar side chain.

The invention also provides for chimeric or fusion polypeptides. As used herein, a "chimeric" or "fusion" polypeptide includes a polypeptide involved in cryptophycin synthesis operatively linked to a heterologous polypeptide. A heterologous polypeptide can be at either the N-terminus or C-terminus of a polypeptide involved in cryptophycin synthesis. Within a chimeric or fusion polypeptide, the term "operatively linked" is intended to indicate that the two polypeptides are encoded in-frame relative to one another. In a fusion polypeptide, the heterologous polypeptide generally has a desired property such as the ability to purify the fusion polypeptide (e.g., by affinity purification). A chimeric or fusion polypeptide of the invention can be produced by standard recombinant DNA techniques, and can use commercially available vectors.

A polypeptide commonly used in a fusion polypeptide for purification is glutathione S-transferase (GST), although numerous other polypeptides are available and can be used. In addition, a proteolytic cleavage site can be introduced at the junction between a polypeptide and a heterologous polypeptide to enable separation of the two polypeptides subsequent to purification of the fusion polypeptide. Enzymes that cleave such proteolytic sites include Factor Xa, thrombin, or enterokinase. Representative expression vectors encoding a heterologous polypeptide that can be used in affinity purification of a polypeptide involved in cryptophycin synthesis include pGEX (Pharmacia Biotech Inc; Smith & Johnson, 1988, *Gene,* 67:31-40), pMAL (New England Biolabs, Beverly, Mass.) and pRIT5 (Pharmacia, Piscataway, N.J.).

Antibodies can be used to detect the presence or absence of polypeptides involved in cryptophycin synthesis. Techniques for detecting polypeptides using antibodies include enzyme linked immunosorbent assays (ELISAs), Western blots, immunoprecipitations and immunofluorescence. An antibody can be polyclonal or monoclonal, and usually is detectably labeled. An antibody having specific binding affinity for a polypeptide involved in cryptophycin synthesis can be generated using methods well known in the art. The antibody can be attached to a solid support such as a microtiter plate using methods known in the art (see, for example, Leahy et al., 1992, *BioTechniques*, 13:738-743). In the presence of a polypeptide involved in cryptophycin synthesis, an antibody-polypeptide complex is formed.

Detection of a polypeptide-antibody complex is usually accomplished by detectably labeling the antibody. The term "labeled" with regard to an antibody is intended to encompass direct labeling of the antibody by coupling (i.e., physically linking) a detectable substance to the antibody, as well as indirect labeling of the antibody by reactivity with another reagent that is directly labeled with a detectable substance. Detectable substances are described above.

Biosynthesis of Cryptophycin

Figure 3:
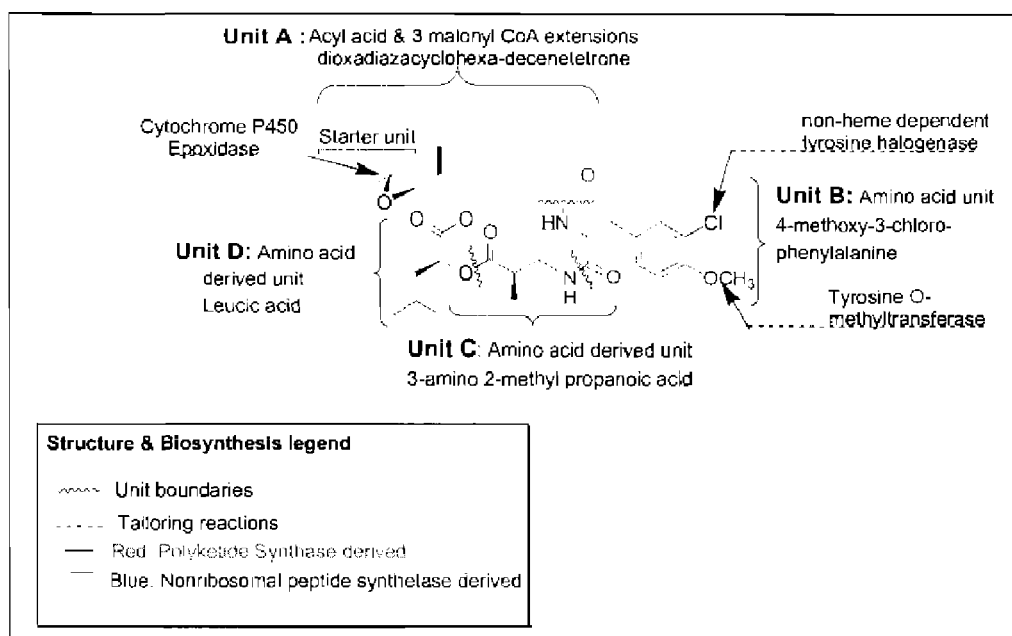
FIG. 3 is a schematic of the modular structure of the cryptophycins and retro-biosynthesis assembly.

FIG. 3 shows the modular structure of cryptophycins. Cryptophycin biosynthesis is a result of a mixed Type I PKS/NRPS system.

Figure 8:
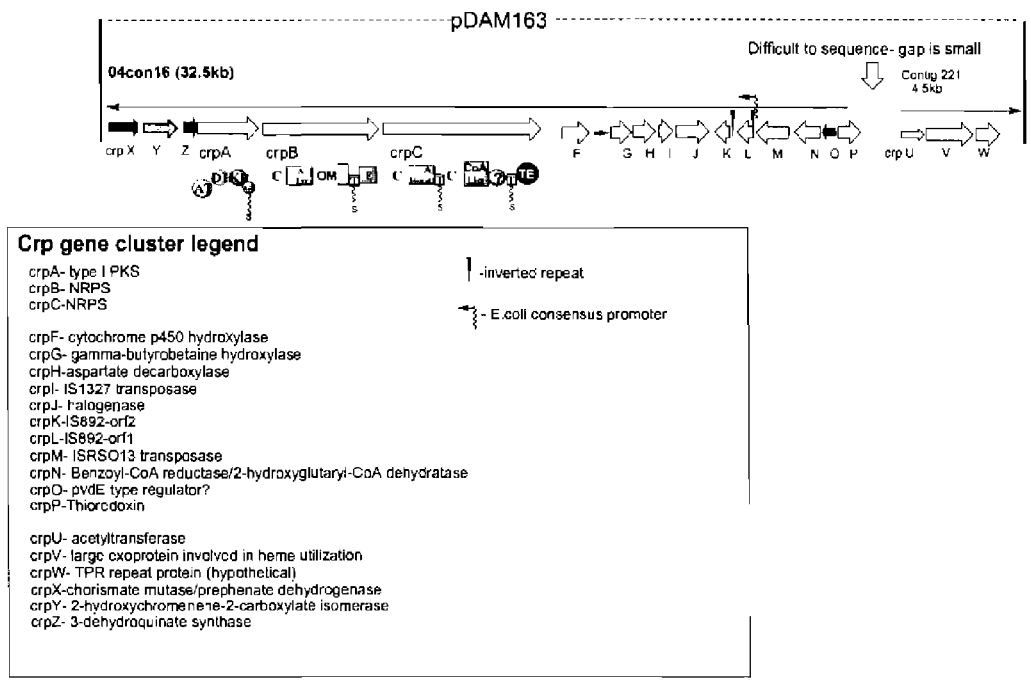
FIG. 8 is a schematic depicting the predicted cryptophycin assembly line.

Unit A is a polyketide synthetase derived unit. Incorporation and linkage of unnatural amino acids such as chlorinated methoxy D-tyrosine amino acid (Unit B) and β-methyl β-alanine (Unit C) are consistent with activities of non-ribosomal peptide synthetase domains. The final terminating unit, the rare carboxylic acid of leucine, leucic acid, could be the result of a NRPS system. However, the ester linkage between Unit C and D is not consistent with a peptide bond forming condensation domain of such a system. It is possible that incorporation of this ester occurs by a novel domain as part of a larger NRPS system. Alternatively, incorporation of the ester may be directed by an enzyme that previously has not been described. The generation of the macrocycle to form the core cryptophycin chemical skeleton involves a chain-terminating cyclization step, likely completed by a member of the hydrolase superfamily of enzymes or domains. The lactone formed between Unit A (the hydroxyl group) and Unit D points to a classic thioesterase dependent mechanism. Additional enzymes such as a cytochrome p450-dependent hydroxylase (likely a cryptophycin epoxidase), a non-heme dependent halogenase, o-methyltransferase, and enzymes involved in activation and methylation of the β-carbon of 3-amino propanoic acid are involved in Unit A, B, C, or D synthesis or in final structural components of cryptophycin. Many of these types of enzymes have been previously described from other polyketide and nonribosomal peptide synthetases. For an overview of the predicted pathway of cryptophycin biosynthesis, see FIG. 8. See also, FIG. 2.

Polyketide Synthetase

Based on homology searches of the GenBank database, the nucleotide sequences designated crpA (SEQ ID NO:42) and crpB (SEQ ID NO:44) appear to encode PKSs (CrpA, SEQ ID NO:43; CrpB, SEQ ID NO:45). With respect to SEQ ID NO:2, a portion of which has homology to SEQ ID NO:42, sequence analysis indicated that SEQ ID NO:2 contains a PKS domain (positioned at approximately nucleotides 1-450 of SEQ ID NO:2), an acyltransferase domain (positioned at approximately nucleotides 1-220 of SEQ ID NO:2), a dehydrogenase domain (positioned at approximately nucleotides 760-1000 or 860-1000 of SEQ ID NO:2), a ketoreductase domain (positioned at approximately nucleotides 850-1000 of SEQ ID NO:2), and an acyl carrier protein domain.

Polyketides are diverse biologically active molecules with a wide variety of structures. Polyketides are synthesized from 2-carbon units through a series of condensations and subsequent modifications, and occur in many types of organisms including fungi and mycelial bacteria. Polyketide synthetases (PKSs) catalyze the biosynthesis of polyketides through repeated, decarboxylative Claisen condensations between acylthioester building blocks. The building blocks used to form complex polyketides are typically acylthioesters such as acetyl, butyryl, propionyl, malonyl, hydroxymalonyl, methylmalonyl, and ethylmalonyl CoA.

The sequencing of several genes encoding enzymes that produce type 1 modular PKSs has revealed a linear organization of modules, each of which contains the activities needed for one cycle of polyketide chain elongation. The minimal module contains a ketosynthase (KS), an acyltransferase (AT), and an acyl carrier protein (ACP) that together catalyze a 2-carbon extension of the chain similar to the condensation of 2-carbon units in the biosynthesis of fatty acids. In PKS polypeptides, the regions that encode enzymatic activities are separated by linker regions, also called scaffold regions. These scaffold regions encode amino acid sequences that space the enzymatic activities at the appropriate distances and in the correct order.

PKS is likely responsible for synthesis of the Unit A region, which is one of the most challenging aspects in the chemical synthesis of cryptophycins. The Unit A portion of the molecule is a dioxadiazacyclo, hexadecenetetrone moiety and represents the beginning polyketide unit (FIG. 3).

Non-Ribosomal Peptide Synthetase

Based on homology searches of the GenBank database, the nucleotide sequence designated crpC (SEQ ID NO:4) appears to encode a non-ribosomal peptide synthetase (NRPS) (CrpC; SEQ ID NO:5) involved in production of the Unit B peptide portion of cryptophycin. Sequence analysis indicated that CrpC may contain one or more NRPS domains (positioned at approximately nucleotides 300-950 and 1290-1425 of SEQ ID NO:4), one or more condensation domains (positioned at approximately nucleotides 50-350 and 1475-1780 of SEQ ID NO:4), an adenylation domain, an o-methyltransferase domain (positioned at approximately nucleotides 1000-1200 of SEQ ID NO:4), one or more peptidyl carrier protein domains, an epimerase domain, and one or more acyl CoA synthetase (positioned at approximately nucleotides 525-1000 of SEQ ID NO:4).

Based on homology searches of the GenBank database, the nucleotide sequence designated crpD (SEQ ID NO:6) appears to encode a NRPS (Crp D; SEQ ID NO:7) involved in production of the Units C and D peptide portions of cryptophycin. CrpD also apparently generates a 16-membered peptolide ring during cryptophycin biosynthesis. Sequence analysis indicated that CrpD contains one or more NRPS domains (positioned at approximately nucleotides 250-975, 1350-1600, 1850-2300, and 2950-3100 of SEQ ID NO:6), one or more condensation domains (positioned at approximately nucleotides 1-300 and 1150-1450 of SEQ ID NO:6), an adenylation domain, one or more peptidyl carrier protein domains, one or more acyl CoA ligase domains (positioned at approximately nucleotides 500-1000 and 1900-2400 of SEQ ID NO:6), one or more acyl CoA synthetase domains (positioned at approximately nucleotides 475-1000 and 1900-2400 of SEQ ID NO:6), and a thioesterase domain.

NRPSs are modular in nature, where a module is usually defined as a segment of the NRPS necessary to catalyze the activation of a specific amino acid and result in the incorporation of that amino acid into a non-ribosomal peptide. A minimal module typically contains three domains: (1) an adenylation domain (about 60 kDa) responsible for selecting and activating an amino acid and transferring the aminoacyl adenylate to a peptidyl carrying center; (2) a thiolation domain, also referred to as a peptidyl carrier protein (8-10 kDa), containing a serine residue that is post-translationally modified with a 4-phosphopantetheine group (Ppant) and acts as an acceptor for the aminoacyl adenylate; and (3) a condensation domain (50-60 kDa), which catalyzes peptide bond-forming chain-translocating steps between an upstream peptidyl-s-Ppant and the downstream aminoacyl-Ppant of the adjacent module. This minimal module for chain extension is typically repeated within a NRPS. A co-linear relationship exists between the number of modules present and the number of amino acids in the final product, with the order of the modules in the synthetase determining the order of the amino acids in the peptide.

Thioesterase Domain

Based on homology searches of the GenBank database, a thioesterase domain is positioned at approximately nucleotide 9,199 to nucleotide 10,032 of CrpD (SEQ ID NO:6).

The cryptophycin thioesterase is likely responsible for the cyclization and release of the cryptophycins from the phosphopantethienyl group of the C-terminal phosphopantethienyl carrier protein (PCP) of a NRPS. The synthetic methods used for ring closure of cryptophycin thus far limit the scope and ease of derivatization of cyptophycins.

The utility of thioesterase domains as semi-synthetic tools for cyclization of synthetic molecules has been demonstrated for gramicidin, epothilone C, and tyrocidine semi-synthesis. See, for example, Wu et al., 2003, *Org. Lett.*, 5:1749; Kohli et al. 2003, *J. Am. Chem. Soc.*, 125:7160; Kohli et al., 2002, *Nature*, 418:658; and Boddy et al., 2003, *J. Am. Chem. Soc.*, 125:3428. Use of the cryptophycin thioesterase for semi-synthesis of cryptophycin provides a new route to synthesis of cryptophycin and its analogues that allows for rapid generation in diversity throughout the entire cryptophycin molecule. Use of a thioesterase domain of the invention to cyclize a cryptophycin chain elongation intermediate (e.g., a seco-SNAC-cryptophycin thioester) provides an approach for generating novel cryptophycins.

Cytochrome p450

Based on homology searches of the GenBank database, the crpE nucleic acid sequence (SEQ ID NO:8) appears to encode a cytochrome p450 (CrpE; SEQ ID NO:9), which is likely an epoxidase involved in cryptophycin biosynthesis.

A survey of the structure-activity relationship of cryptophycins has demonstrated the necessity of the epoxide for high-level tubulin depolymerization and anti-proliferative activities toward tumor cells. Opening of the epoxide, however, is one of the major problems encountered in clinical uses of cryptophycins. A new generation of compounds has been synthesized containing a chlorohydrin. Chlorohydrin analogs are generated from cryptophycins containing an epoxide, and act as pro-drugs. Once chlorohydrins are injected into the serum, the compounds are rapidly converted back to the corresponding epoxides.

High-level tubulin depolymerization and anti-proliferative activities toward tumor cells also requires proper stereochemistry of the epoxide group (β epoxide). Synthesis of cryptophycins containing an epoxide often results in a mixture of two diastereomers. One of the diastereomers is usually inactive, thereby requiring reverse-phase HPLC to separate the two compounds. See, for example, FIG. 2. In addition to the extra expense and time required for separation, separation of the diastereomers results in a significant loss of starting material.

Figure 9:
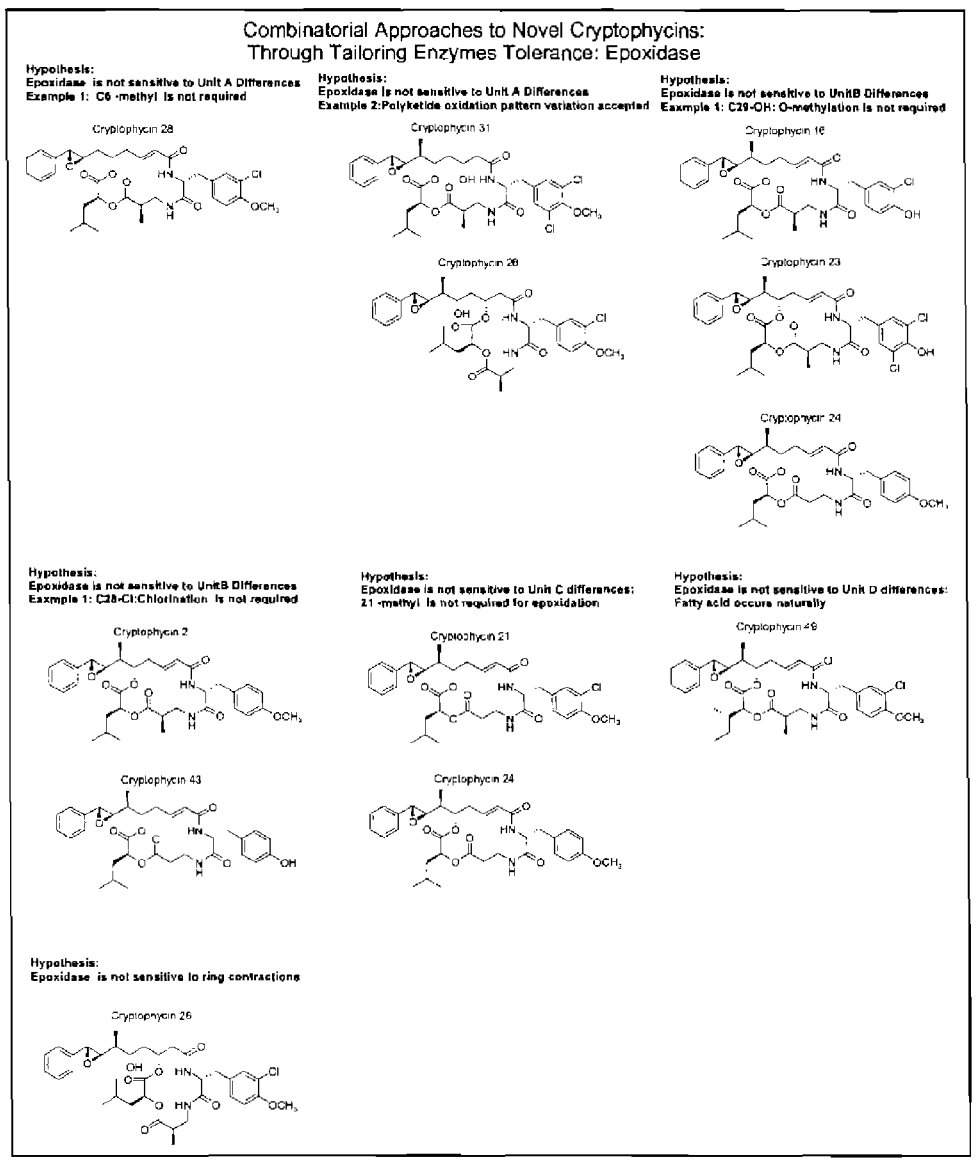
FIG. 9 is a schematic demonstrating that the cryptophycin epoxidase (CrpE) has substrate flexibility but a high degree of stereoselectivity.

Using a recombinant cell line expressing an epoxidase or a purified form of an epoxidase could dramatically increase overall yields, eliminate a separation step (e.g., HPLC), and allow more flexibility in synthetic strategies. Since no known natural cryptophycin contains the α-epoxide, the native epoxidase enzyme seems to be highly efficient at generating the desired epoxide diastereomer (see FIG. 9). Further, the cryptophycin epoxidase apparently exhibits a high degree of flexibility since it is able to use various substrates (e.g., those having different ring sizes).

Additional Enzymes

Additional enzymes having a variety of functions are involved in cryptophycin biosynthesis. In addition to the PKS, the NRPS, and the epoxidase discussed above, sequence analysis indicated that the following types of enzymes are likely involved in cryptophycin biosynthesis.

Based on homology searches of the GenBank database, crpF (SEQ ID NO:10) appears to encode an iron-dependent non-heme hydroxylase (CrpF; SEQ ID NO:11), which is a member of the γ-butyrobetaine hydroxylase group. Non-heme iron-dependent enzymes generally catalyze a wide variety of $O_2$ reactions. An iron-dependent non-heme hydroxylase is likely involved in hydroxylation of cryptophycins.

Based on homology searches of the GenBank database, crpG (SEQ ID NO:12) appears to encode an aspartate decarboxylase (CrpG; SEQ ID NO:13). An aspartate decarboxylase (EC 4.1.1.1.1) is likely involved in production of β-alanine or methyl-β-alanine, which is a precursor for NRPS. See, for example, Williamson & Brown, 1979, *J. Biol. Chem.*, 254:8074-82; and Ramjee et al., 1997, *Biochem. J*, 323:661-9.

Based on homology searches of the GenBank database, crpI appears to be the remnants of an IS1327 transposition event. The sequences identified as having homology to IS1327 are positioned at approximately nucleotides 9154-8514 of SEQ ID NO:1 (pDAM163). No open reading frame or coding sequences, however, were identified.

Based on homology searches of the GenBank database, crpH (SEQ ID NO:14) appears to encode a non-heme-dependent, flavin-dependent halogenase (CrpH; SEQ ID NO:15). See, for example, van Pee & Unversucht, 2003, *Chemosphere*, 52:299-312; and Littlechild, 1999, *Curr. Opin. Chem. Biol.*, 3:28-34. A halogenase is likely involved in chlorination of the Unit B amino acid, o-methyl tyrosine.

Based on homology searches of the GenBank database, crpK appears to be the remnants of an IS892-orf2 transposition event. The sequences identified as having homology to IS892-orf2 are positioned at approximately nucleotides 4730-7039 of SEQ ID NO:1 (pDAM163). No open reading frame or coding sequences, however, were identified.

Based on homology searches of the GenBank database, crpL appears to be the remnants of an IS892-orf1 transposition event. The sequences identified as having homology to IS892-orf2 are positioned at approximately nucleotides 4730-7039 of SEQ ID NO:1 (pDAM163). No open reading frame or coding sequences, however, were identified.

Based on homology searches of the GenBank database, crpM appears to be an ISRSO13 transposase sequence. The identified coding sequence (crpM; SEQ ID NO:16) encodes a polypeptide designated CrpM (SEQ ID NO:17) with unknown function.

Based on homology searches of the GenBank database, crpN (SEQ ID NO:18) appears to encode a non-heme-dependent, iron-dependent hydroxylase (CrpN, SEQ ID NO:19). See, for example, Solomon et al., 2003, *PNAS USA*, 100: 3589-94; and Ryle et al., *PNAS USA*, 100:3790-5.

Based on homology searches of the GenBank database, crpO appears to encode a pvdE-type regulator (CrpO). The sequences identified as having homology to a pvdE-type regulator are positioned at approximately nucleotides 786-1768 of SEQ ID NO:1 (pDAM163). A pvdE-type regulator is likely involved in regulating cryptophycin biosynthesis. See, for example, Wilson et al., 2001, *J. Bacteriol.*, 183:2151-5.

Based on homology searches of the GenBank database, crpP (SEQ ID NO:20) appears to encode a thioredoxin (CrpP, SEQ ID NO:21). Thioredoxins are generally reduction/oxidation (redox)-regulatory proteins thought to have anti-apoptotic effects. Thioredoxin is likely involved in redox reactions (e.g., cytochrome p450-dependent hydroxylations) associated with cryptophycin biosynthesis.

Based on homology searches of the GenBank database, crpU (SEQ ID NO:22) appears to encode an N-acetyltransferase (EC 2.3.1.5) (CrpU, SEQ ID NO:23). N-acetyltransferases usually catalyze the transfer of acetyl groups from acetyl-CoA to arylamines.

Based on homology searches of the GenBank database, crpV (SEQ ID NO:24) appears to encode a large exoprotein involved in heme utilization (CrpV, SEQ ID NO:25). A large exoprotein involved in heme utilization may be involved in redox reactions associated with cryptophycin formation (i.e., cytochrome p450-dependent hydroxylations).

Based on homology searches of the GenBank database, crpW appears to encode a tetratricopeptide repeat (TPR) protein (CrpW). A TPR is a 34 amino acid repeated sequence motif found in a number of diverse proteins that may be involved in transcriptional repression, mitochondrial and/or peroxisomal protein transport, cell cycle regulation, protein kinase inhibition, heat shock response, and/or mediating protein-protein interactions. See, for example, Sikorski et al., 1991, *Cold Spring Harbor Symp. Quant. Biol.*, 56:663-73; and Lamb et al., 1995, *Trends Biosci.*, 20:257-9.

Based on homology searches of the GenBank database, crpX (SEQ ID NO:26) appears to encode a chorismate mutase-prephenate dehydrogenase (CrpX, SEQ ID NO:27). A chorismate mutase-prephenate dehydrogenase (EC 1.3.1.12) usually catalyzes the first two steps in the biosynthesis of tyrosine (the chorismate mutase activity) and the conversion of prephenate to p-hydroxyphenylpyruvate in the presence of NAD (the prephenate dehydrogenase activity). A chorismate mutase-prephenate dehydrogenase is likely involved in the production of shikimate-derived PKS starter units in cryptophycin biosynthesis.

Based on homology searches of the GenBank database, crpY (SEQ ID NO:28) appears to encode a 2-hydroxychromene-2-carboxylate isomerase (CrpY, SEQ ID NO:29). A 2-hydroxychromene-2-carboxylate isomerase is involved in the naphthalene catabolic pathway and catalyzes the reaction of 2-hydroxychromene-2-carboxylate into trans-o-hydroxybenzylidenepyruvate. See, for example, Eaton, 1994, *J. Bacteriol.*, 176:7757-62; and Zylstra et al., 1997, *FEMS Microbiol. Lett.*, 153:479-84. A 2-hydroxychromene-2-carboxylate isomerase is likely involved in the production of shikimate-derived PKS starter units in cryptophycin biosynthesis.

Based on homology searches of the GenBank database, crpZ (SEQ ID NO:30) appears to encode a 3-dehydroquinate synthase (CrpZ, SEQ ID NO:31). A 3-dehydroquinate synthase (EC 4.2.3.4) usually catalyzes the cyclization of 3-deoxy-D-arabino-heptulosonic acid 7-phosphate (DAHP) to dehydroquinate. A 3-dehydroquinate synthase may be involved in the production of shikimate-derived PKS starter units.

Combinatorial Techniques and Domain Swapping

It will be apparent to one of skill in the art that any number and/or combination of nucleic acid molecules of the invention (e.g., SEQ ID NOs:2, 4, 6, 8, 10, 12, 14, 16, 18, 20, 22, 24, 26, 28, 30, 42 and/or 44) can be joined together to generate a longer nucleic acid molecule (e.g., pDAM163; shown in FIGS. 4 and 5 and SEQ ID NO:1). In addition, the nucleic acid molecules (SEQ ID NOs:2, 4, 6, 8, 10, 12, 14, 16, 18, 20, 22, 24, 26, 28, 30, 42 and 44) can be manipulated using standard techniques to delete or inactivate activity encoding regions, insert regions from different molecules encoding corresponding activities from the same or different biosynthesis systems, or be otherwise mutated using standard procedures for obtaining genetic alterations. Mutations can be made to the native sequences using conventional techniques such as those described above.

Chemical approaches have lead to highly informative structure-activity relationships. Therefore, the regions suggested for modifications are well defined, particularly in view of the modular-type structure of the PKSs and NRPSs. In addition to approaches that provide mutated polypeptides, it is possible to manipulate entire domains or portions of domains. For example, a domain having a particular activity from one biosynthetic pathway can be exchanged or replaced with a domain having a corresponding activity from a different biosynthetic pathway. Alternatively, a domain having a particular activity from a biosynthetic pathway can be exchanged or replaced with a domain having an unrelated activity from the same or a different biosynthetic pathway.

If replacement of a particular nucleic acid region encoding a host enzyme is to be made, this replacement can be conducted in vitro using suitable restriction enzymes and cloning techniques or can be effected in vivo using recombinant techniques involving homologous sequences framing the replacement region in a donor plasmid and a receptor region in a recipient plasmid. A representative exchange system that involves plasmids that have different temperature sensitivities is described in PCT Publication No. WO 96/40968.

The various nucleic acid molecules involved in cryptophycin biosynthesis, individually or as a cocktail of such molecules, can be cloned into one or more recombinant vectors. When more than one molecule is cloned together, such elements can be under the control of a single element for expression (e.g., a promoter) or each molecule can be under the control of an element for expression. The nucleotide sequences encoding an enzymatic subunit or a cocktail of such molecules can include flanking restriction sites to allow for the easy deletion and insertion of other molecules or regions of a molecule. In this manner, nucleotide sequences encoding hybrid or chimeric enzymes can be generated. The design of such unique restriction sites is known to those of skill in the art and can be accomplished using the techniques described above such as site-directed mutagenesis and PCR.

Expression vectors containing nucleotide sequences encoding a variety of enzymatic activities can be transformed into an appropriate host cell to construct a library. In one approach, a mixture of such vectors is transformed into host cells and the resulting cells plated into individual colonies and selected for successful transformants. Each individual colony represents a colony expressing an enzyme having a particular activity and, ultimately, the ability to produce a particular product. Alternatively, expression vectors can be used individually to transform host cells, which are then assembled into a library. Methods are known for screening a library or isolates from a library for substrate-specificity and/or production of a particular product. Another strategy for preparing a variety of products is by random digestion-religation leading to chimeric domains or modules. A similar such method has been described as a "DNA shuffling method" (see Patten et al., 1997, *Curr Op. Biotechnol.*, 8: 724-733).

As one non-limiting example, the creation of novel macrolides can be achieved through genetic manipulation of polyketide synthetases. The module nature of polyketide synthetases allows for domain exchange between different polyketide synthetase genes, resulting in hybrid genes that produce polyketide synthetases with altered properties that, in turn, produce modified macrolide structures. Thus, it is possible to control chain length, choice of chain extender unit, degree of β-carbon oxidation level, and stereochemistry. See, for example, PCT publication Nos. WO 93/13663; WO 95/08548; WO 97/02358; WO 98/27203; and WO 98/49315; U.S. Pat. Nos. 4,874,748; 5,063,155; 5,098,837; 5,149,639; 5,672,491; 5,712,146; 5,830,750; and 5,843,718; and Fu et al., 1994, *Biochemistry*, 33:9321-9326; McDaniel et al., 1993, *Science*, 262:1546-1550; and Rohr, 1995, *Angew. Chem. Int. Ed. Engl.*, 34(8):881-888.

The application of innovative combinatorial techniques to this type of genetic organization has prompted the generation of novel natural products, by adding, deleting, or exchanging domains or entire modules. See, for example, U.S. Pat. Nos. 5,672,491; 5,712,146; 5,830,750; 5,843,718; 5,962,290; and 6,022,731; and Tang et al., 2000, *Science*, 287:640-2). The invention allows for combinatorial biosynthesis technology to produce a diversity of cryptophycin analogues in addition to those cryptophycin analogues produced to date.

The invention will be further described in the following examples, which do not limit the scope of the invention described in the claims.

EXAMPLES

Example 1

Cloning and Sequencing the crp Gene Cluster Contained within pDAM163

Primer synthesis and cosmid sequencing was preformed at the University of Minnesota Advanced Genetic Sequencing and Analysis Center-AGAC (St. Paul, Minn.). Degenerate PCR primers specific for conserved core motifs of peptide synthetase adenylation domains A2 and A8 (Marahiel et al., 1997, *Chem. Rev.*, 97:2651-74) were used and consisted of the following sequences: MTF2' forward primer (5'-GCNGG (ct) GG (ct) GCNTA (ct) GTNCC-3' (SEQ ID NO:38)) and MTR reverse primer (5'-CCNGG (agt) AT (tc) TTNAC (tc) TG-3' (SEQ ID NO:39)) (Neilan et al., 1999, *J. Bacteriol.*, 181.4089-97). Adenylation domain containing DNA fragments of approximately 1100 bp in length were synthesized by PCR using a Hybaid Express PCR thermocycler (30 cycles: 95° C. for 1 min, 55° C. for 1 min, 72° C. for 1 min) with *Nostoc* sp ATCC 53789 genomic DNA as a template. End sequencing of one fragment, pNAM124, using an Applied Biosystems, Inc. ABI3700 sequencer (Foster City, Calif.) confirmed that the fragment contained an adenylation domain. Prediction of its substrate specificity (aromatic amino acid activating) was determined using methods described previously (Challis et al., 2000, *Chem. Biol.*, 7:211-24). The fragment was radiolabeled using the RadPrime labeling kit (Pharmacia) with [α-$^{32}$P] dCTP (Amersham) according to the manufacturer's directions. The radiolabeled fragment was used to probe the genomic library using standard colony hybridization protocols (Sambrook & Russell, 2000, *Molecular Cloning: A Laboratory Manual*, Cold Spring Harbor Laboratory Press). One cosmid, pDAM163, was selected because it hybridized to the adenylation domain encoding DNA probe contained within pNAM124. The DNA sequence of pDAM163 was obtained by creating a shotgun library of the cosmid within the sequencing vector, pUC18. Sequences obtained were assembled using SeqMan version 5.06 (DNAStar, Madison, Wis.) and Frameplot 2.3.2 (Ishikawa & Hotta, 1999, *FEMS Microbiol Lett.*, 174:251-3) used to identify individual open reading frames. The putative functions of the crp biosynthesis genes were assessed by using the open reading frames and their putative protein products versus genes/proteins contained within the GenBank database using BlastN and BlastP.

Example 2

Cloning Genes Involved in Cryptophycin Biosynthesis

DNA encoding a putative cryptophycin biosynthetic gene cluster was contained on a cosmid designated pDAM163. pDAM163 DNA was prepared using a Qiagen large construct DNA extraction kit from a 500 mL culture grown overnight at 25° C. in LB media containing 50 μg/mL ampicillin.

Example 3

Cryptophycin Production

The cosmid, pDAM163, or sub-vectors such as cosmid, plasmids, yeast artificial chromosomes, bacterial artificial chromosomes, or phage vectors containing pDAM163 sequences can be used to biosynthetically prepare cryptophycins in a non-*Nostoc* spp. host. pDAM163 is introduced into an *Escherichia coli* strain that harbors a phosphopantetheinyl transferase gene required for expressing active polyketide synthase and nonribosomal peptide synthetase enzymes. Fermentation of the resulting strain on a large scale, and extracting and detecting cryptophycins are performed as described previously (Subbaraju et al., 1997, *J. Nat. Prod.*, 60:302-5; and Golakoti et al., 1994, *J. Am. Chem. Soc.*, 116:4729-37).

Example 4

Cloning Strategy of the Thioesterase Domain

DNA encoding the cryptophycin thioesterase domain is contained at the 3'-end of the 3'-terminal open reading frame of CrpC, which also codes for domains necessary for incorporation of units C and D of cryptophycin. Therefore, truncation of the DNA in the final ORF was necessary in order to isolate the cryptophycin thioesterase. Identification of the DNA encoding the cryptophycin thioesterase was elucidated through use of the NCBI "CDART" program for identification of conserved domains. The "nnpredict" secondary structure prediction program (Kneller et al., 1990, *J. Mol. Biol.*, 214:171) was used to determine the putative secondary structure of the gene product of the putative thioesterase domain and a domain capable of being phosphopantetheinlyated. The forward primer, 5'-ATT TAT CAT ATG GGT TCC GAT TCC GGA GCC GA-3' (SEQ ID NO:40), was designed to a position immediately 3' of a nucleic acid sequence predicted to encode a protein capable of being phosphopantethienylated in a region appearing to lack secondary structure based on the "nnpredict" program results and contained an NdeI restriction site. The reverse primer, 5'-AAA TAA GAA TCC TCA TCA TTT TTC CAA TTG ATG GGT-3' (SEQ ID NO:41), was constructed to anneal to the 3' end of the open reading frame and contained a BamHI restriction site.

PCR reactions were performed with 0.1 μL of pDAM163 DNA from the extraction, 1 μM forward primer, 1 μM reverse primer, 1×ExTaq buffer (Takara), 1 μL ExTaq polymerase (Takara), and 1 μM dNTP (Takara) to a final volume of 50 μL with water. The PCR program consisted of 30 cycles of the following amplification conditions: denaturation 1 min at 95° C., 1 min annealing at 50° C., 1.5 min extension at 72° C. PCR fragments corresponding to the desired length were separated on a 1% agarose gel and purified from the gel using a Qiagen gel extraction kit. The PCR fragment was cloned into a pGEM T-Easy vector (Promega) using T-overhang cloning with the pGEM T-Easy kit (Promega).

Clones were transformed into XL-1 Blue competent cells using heat shock protocols as described in the pGEM T-Easy kit. Constructs containing inserts were identified using blue/white screening according to the pGEM T-Easy kit protocol. Five clones containing insert were re-plated and half of the colony was subjected to PCR to verify insert of the desired DNA size using the same PCR condition listed above, with the exception of a 5 min incubation of each clone at 96° C. prior to the amplification cycles.

One clone containing the desired size insert was grown in a 2 mL culture overnight in LB media containing ampicillin (50 μg/mL; Research Products International Corp). DNA was purified using a Qiagen mini-prep kit. DNA was submitted for sequencing to the University of Michigan DNA Sequencing Core Lab and sequenced 3 times from the 5' end using the T7 primer binding site and 3 times from the 3' end using the SP6 primer-binding site. DNA from the sequenced clone was ligated into the NdeI and BamHI sites in pET28b (Novagen) and transformed into BL21 competent cells using electroporation. All cells were plated on LB plates containing kanamycin (50 μg/mL; Research Products International Corp) and incubated overnight at 37° C. Ten colonies were subjected to PCR verification of the desired DNA insert using the primers and protocols listed above.

Example 5

Expression and Purification of the Cryptophycin Thioesterase Domain

A clone containing the desired insert size, as visualized by agarose gel electrophoresis, was grown overnight in 25 mL of 2YT broth (16 g tryptone, 10 g yeast extract, 10 g NaCl) containing 50 μg/mL kanamycin at 37° C. 5 mL of the overnight culture were used to inoculate 1 L of 2YT media containing 50 μg/mL kanamycin, which was grown at 37° C. The culture was induced at an $OD_{595}$ of 0.7 with 0.2 mM IPTG and grown overnight at 30° C. Cells were harvested at 5000 g for 30 min. The pellet was resuspended in 20 mL 0.1 M sodium phosphate buffer (pH 8) containing 20 mM imidazole and 300 mM NaCl. 4 mg of lysozyme and 2 g sucrose were added to the cell suspension and incubated at room temperature for 30 min until the viscosity of the solution increased. The solution was put on ice and subjected to sonication (5 times for 20 sec) at a level of 6 on the sonicator until the solution became less viscous. The suspension was centrifuged at 17,000 g for 1 hour at 4° C.

The supernatant was collected and incubated with 7 mL of Qiagen Ni-Agarose overnight at 4° C. The agarose was then loaded into a column and washed with 10 column volumes of 0.1 M sodium phosphate buffer (pH 8) containing 20 mM imidazole and 300 mM NaCl. The column was washed with 10-column volumes wash buffer containing 50 mM imidazole. Protein was eluted with wash buffer containing 100 mM imidazole. The eluted sample contained 50 mg of protein as determined using a BioRad Bradford assay kit. Samples were run on a 4-20% SDS-PAGE gel to check for purity. A band corresponding the expected molecular weight was observed at >95% purity. Protein was subjected to a PD-10 column prior to kinetic assays for buffer exchange to 100 mM sodium phosphate buffer (pH 8).

Example 6

Preparation of Substrates

Figure 10:
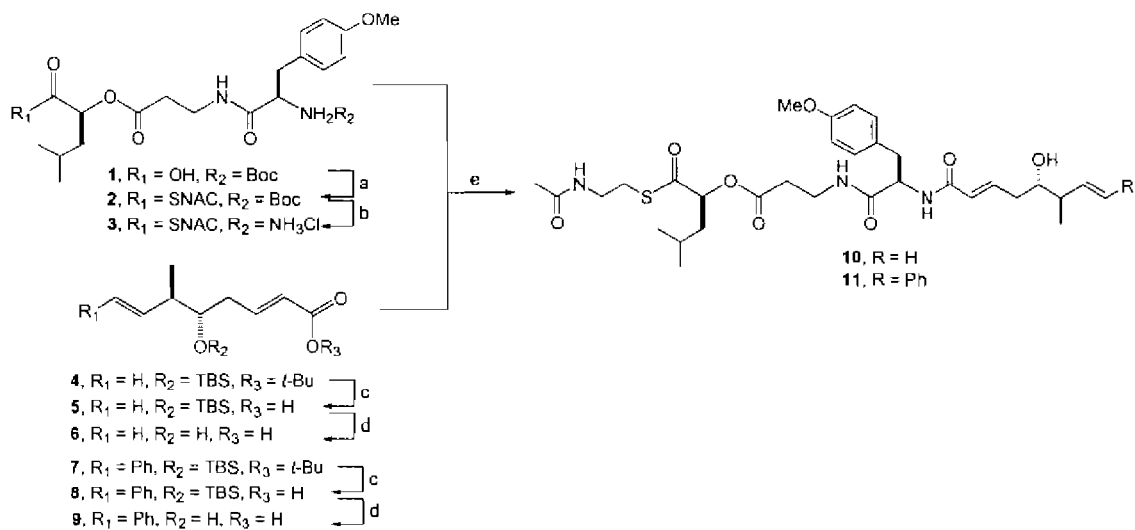
FIG. 10 is a schematic of the synthesis of SNAC substrates.

Referring to FIG. 10, substrate 3 represents the tri-depsipeptide sector of cryptophycin except that the methyl β-alanine residue has been replaced by β-alanine. The remaining functionality has been preserved. The halogenation of the tyrosine residue likely is a tailoring modification, which is performed after thioesterase-mediated cyclization. Therefore, a simple tyrosine methyl ether was employed. The SNAC thioester substrate 3 was prepared from known tri-depsipeptide 1 (Georg et al., *J. Org. Chem.*, 2000, 65:7792-7799) by PyBOP coupling of N-acetylcysteamine followed by Boc deprotection with 4 N HCl in 1,4-dioxane to provide 3 as the hydrochloride salt (FIG. 10).

Similarly, the Unit A analogs 6 and 9 were prepared by stepwise deprotection of the t-butyl ester with TFA containing 1% triethylsilane followed by TBS cleavage with 5% hydrofluoric acid in acetonitrile from known Unit A fragments 4 and 7 (Georg et al., supra). PyBOP mediated coupling of subunit 3 with fragments 6 and 9 afforded the seco-SNAC-cryptophycin thioester substrates 10 and 11 respectively, which were purified by reverse-phase semi-preparative HPLC (C18, Alltech Econosil 10×250 mm, 5 mL/min, 10-100% AcCN/$H_2O$+0.1% TFA, 30 minutes).

Example 7

Kinetic Characterization of Cryptophycin Thioesterase Activity with a Substrate

A standard curve of the cleaved product was determined on a 10-67% acetonitrile/water (0.1% TFA) gradient over 30 min. Cleavage reactions were run for 15 min at 30° C. with 1.4 μM cryptophycin thioesterase with substrate concentrations of 0.3125, 0.625, 1.25, 2.5, and 5 mM substrate containing 4% DMSO in 0.1 M $NaH_2PO_4$ buffer at pH 7, 8, and 8.75. The hydrolyzed version of substrate 3 was monitored in order to determine the rate of hydrolysis for the reactions. All reactions were run in triplicate.

Example 8

Cyclization of Cryptophycin Substrates

A 1 mL solution containing 100 μM substrate 10 or substrate 11, with 7 μM cryptophycin thioesterase, 0.095 M $NaH_2PO_4$ buffer (pH 7), and 5% DMSO was incubated for 1 hour at 30° C. Negative control reactions containing all reagents except for the cryptophycin thioesterase were run in parallel. The total contents of each reaction were separated using reverse phase chromatography with a 10-100% gradient (acetonitrile+0.1% TFA/water+0.1% TFA) over 37 min on an Alltech Econosil 10 U C18 column with dimensions 250 mm×4.6 mm. The products were analyzed by electrospray mass spectrometry (ES+). The relative concentration of the products was determined by comparing absorption at 245 nM, which corresponds to the enone functionality contained within each molecule examined.

Example 9

Results

Immediately 5' of the nucleotide sequences encoding the cryptophycin thioesterase are sequences that putatively encode a phosphopantetheinylation domain. The thioesterase domain was, therefore, constructed to begin immediately following the 3' end of DNA predicted to encode the phosphopantetheinylation domain.

The molecular weight of cryptophycin TE was determined to be 35,424 Da by ES+mass spectrometry and 35,410 by MALDI-TOF mass spectrometry. The calculated average mass for the cryptophycin TE was 35,550.08, and the monoisoptopic mass was determined to be 35527.66. The mass spectrometry determined that the molecular weight of cryptophycin thioesterase corresponds to a thioesterase that is missing its N-terminal methionine. Processing of the N-terminal methionine commonly occurs when proteins are expressed small amino acids adjacent to the N-terminal methionine, such as the glycine that is located adjacent to the N-terminal methionine in the engineered construct.

The cyclized cryptophycins are fairly insoluble in water and, therefore, kinetic characterization of hydrolytic rate of the cryptophycin thioesterase was determined using a substrate modeled after the depsipeptide fragment corresponding to Units B, C and D of Cryptophycin 1.

Figure 11:
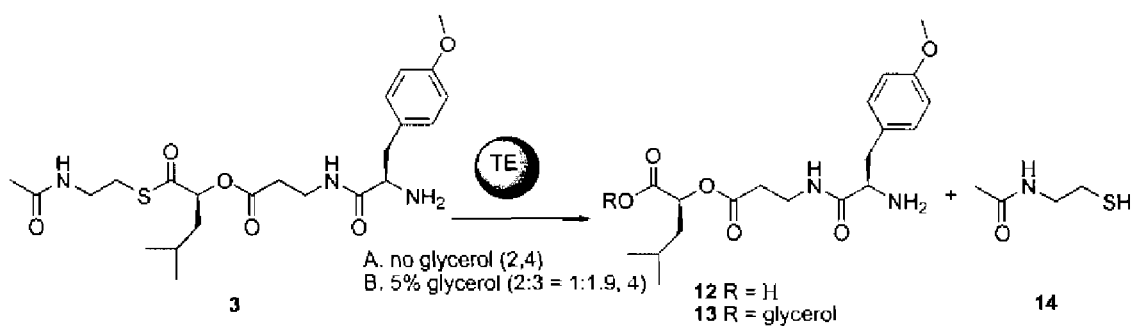
FIG. 11 is a schematic of cryptophycin thioesterase-catalyzed conversion of substrate 1 to products 2, 3, and 4 in 0.1 M NaPi buffer (pH 8.0) containing 4% DMSO.

Characterization of the cryptophycin thioesterase-catalyzed hydrolysis of the substrate 3 was monitored by HPLC. The two hydrolysis products produced by the reaction were determined using ES+ mass spectrometry to be N-acetyl cystamine and molecule 12 (FIG. 11).

Initially, the cryptophycin thioesterase was stored in 5% glycerol containing buffer. However, analysis by HPLC/MS of hydrolysis of the substrate 3 with cryptophycin thioesterase containing 5% glycerol revealed that the glycerol adduct was the major product of the reaction with a minor product of the hydrolyzed substrate. Therefore, the expression strain containing cryptophycin thioesterase was recultured and the cryptophycin thioesterase was purified in the absence of glycerol. Subsequent analysis of the cryptophycin thioesterase-catalyzed hydrolysis of the substrate 3 did not reveal a glycerol adduct peak. The generation of the glycerol adduct (molecule 13, FIG. 11) warrants caution when determining kinetics using buffers containing glycerol (especially using indirect methods).

Figure 12:
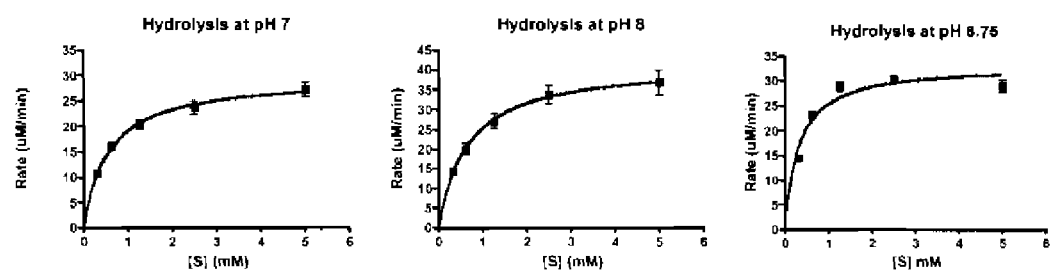
FIG. 12 are graphs of cryptophycin thioesterase-catalyzed hydrolysis of substrate 1 using 1.4 µM thioesterase in 50 µL reactions containing 0.1 M $NaH_2PO_4$ and 4% DMSO.

The hydrolytic activity of cryptophycin thioesterase was determined for the substrate 3 using steady state kinetic analysis utilizing HPLC analytical methods. FIG. 12 outlines the catalytic rate constants for hydrolysis of the substrate 3 with cryptophycin thioesterase at pH 7, pH 8, and pH 8.75.

Figure 13:
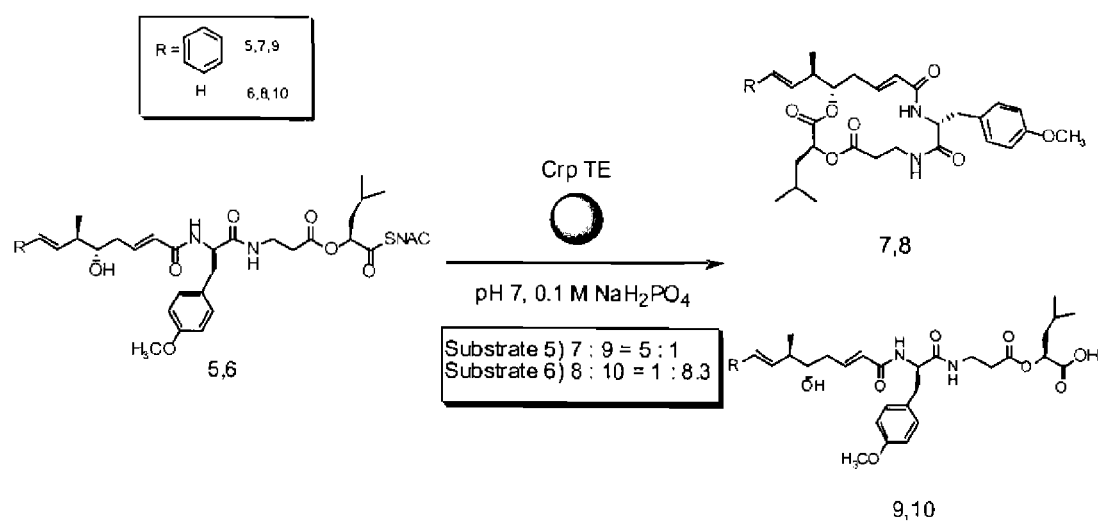
FIG. 13 is a schematic of cryptophycin thioesterase-catalyzed cyclization and hydrolysis of the seco-SNAC-ester of arenastatin and the seco-SNAC-ester of the vinyl derivative of arenastatin.

The ability of the cryptophycin thioesterase to cyclize substrates was examined using seco-SNAC-des-epoxy-arenastatin 11 and the des-benzyl derivative of seco-SNAC-des-epoxy-arenastatin 10 as substrates (FIG. 13).

The partition ratio of cyclization to hydrolysis for the cryptophycin catalyzed reaction with seco-SNAC-des-epoxy arenastatin 11 was 5:1, while the partition ratio of cyclization to hydrolysis with the seco-SNAC-des-benzyl-des-epoxy-arenastatin 10 was 1:8.3, as determined by HPLC/MS with quantitation of the quantity of enone functionality at 245 nM. Therefore, the cryptophycin thioesterase preferentially cyclized the SNAC thioester of seco-des-epoxy-arenastatin over the SNAC thioester of seco-des-benzyl-des-epoxy-arenastatin.

The specificity constant ($k_{cat}/K_M$) for the cryptophycin thioesterase catalyzed hydrolysis of the substrate 3 increased over the pH range from 7 to 8.75 (FIG. 12). The increase in the specificity constant was due to an increase in the $k_{cat}$ from pH 7 to pH 8, and a decrease in $k_{cat}$ from pH 8 to pH 8.75. The $K_M$ for the hydrolysis of the substrate 3 decreased slightly from pH 8 to pH 8.75, although the $k_{cat}$ for hydrolysis also decreased, resulting in an overall increase in the specificity constant.

Interestingly, although substrate 3 contains both a thioester bond and an ester bond, hydrolysis occurred specifically at the thioester, even after complete hydrolysis of the thioester, indicating a selective preference for that site.

Example 10

Identification of Coding Sequences within the Polyketide Portion of a Biosynthetic Operon Two additional coding sequences designated crpA and crpB were identified in the polyketide portion of the operon. crpA (SEQ ID NO:42) and the encoded amino acid sequence (SEQ ID NO:43) are shown in FIG. 14, while crpB (SEQ ID NO:44) and the encoded amino acid sequence (SEQ ID NO:45) are shown in FIG. 15.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. An isolated nucleic acid molecule comprising a nucleic acid sequence having at least 95% sequence identity to the sequence shown in SEQ ID NO:42, wherein said nucleic acid sequence encodes a polypeptide that exhibits polyketide synthetase activity in the biosynthesis of cryptophycin under appropriate conditions.

2. The nucleic acid molecule of claim 1, wherein said nucleic acid sequence has at least 99% sequence identity to the sequence shown in SEQ ID NO:42.

3. The nucleic acid molecule of claim 1, wherein said nucleic acid sequence is SEQ ID NO:42.

4. A vector comprising the nucleic acid molecule of claim 1.

5. An isolated host cell comprising the vector of claim 4.

* * * * *

UNITED STATES PATENT AND TRADEMARK OFFICE
CERTIFICATE OF CORRECTION

PATENT NO. : 7,566,558 B2
APPLICATION NO. : 11/830656
DATED : July 28, 2009
INVENTOR(S) : David H. Sherman Page 1 of 1

It is certified that error appears in the above-identified patent and that said Letters Patent is hereby corrected as shown below:

Title Page item 56, References Cited, Other Publications, Witkowski et al. reference, please delete "replacemnt" and insert --replacement-- therefor;

Title Page item 56, References Cited, Other Publications, "NiceZyme View of Enzyme" reference, please delete "niceyme.pl?" and insert --nicezyme.pl?-- therefor.

Signed and Sealed this

Sixth Day of October, 2009

David J. Kappos
*Director of the United States Patent and Trademark Office*

SEQUENCE LISTING

```
<160> NUMBER OF SEQ ID NOS: 45

<210> SEQ ID NO 1
<211> LENGTH: 33260
<212> TYPE: DNA
<213> ORGANISM: Nostoc species

<400> SEQUENCE: 1
tgatattaga tgtttaatat cttaggaaat tttgataaac aggaaagctt atgactgtca      60
gttgcgagaa cggtaaattt ttaaacatat ttgctcaact ttctcaacca ccaaatactt     120
tgccttcagc ttaaaaagca aatatacttc ttattcgctt tggatataac gaaagttcat     180
```

-continued

```
atcccccttg tagccagaag ctttcgcaag atccttaaag ttttgcacgc cggtatactg      240
atgtccattg ataacccaag ttggtacacc tgggactttc gccgcattgc acaagtctgg      300
gtggggattg atacctctct tatcgcactc aactttaata ctgtcgttga ttatttggta      360
ggcttgcttc ccaaagatta acttttgttc gtgacagtga ggacaccacc aagaaacata      420
ttcttttgcc ccgatataca ccaaatgctt cgccaaggct agttctgcct tccctgaagt      480
ggtagtgatt tcccaaccga ctccggtctg aggtcgttct ttgggcagga agaaaataat      540
cgatggggac ttttggttgt ctgtttgttg agcaatatct gtcagtagtg cagagccaga      600
actcgtacca acacaaataa tggagagcgt taacagtgca aataaaaaag ggtgtttgat      660
agccatatta aatatatact ttgattgaat agttgtcgaa gctaacaatt gtatgtttaa      720
gattgtagta ttttgtataa ctgataatac gaagccagak ratccccatc ttatcttcgt      780
cataatcgaa attatcatca ccatgttctt cataccactt tctttcttcc tccaaagcga      840
tttctctctc gatgattttt ctttctagaa tttcactttc tagaatttca ctttcaagct      900
tttctctttc aaatctttct ctttctattc tttctcttct ctgcctttct ttctcttctc      960
tttctctctc aagttgaatt aatcgctgct ccactctctc acagtaaaaa tccaaggctt     1020
taccagtggc tgctccggta attgcaccac cagccaaaaa tattattaca gttttccagc     1080
cttgaatggg attaccgctc cactccaaac taccctcatt gagccacact agtaggaagt     1140
aaacgagaat tccaataaca gtattgatcg gtgcaaaaac tctcggtgtc atctgggttt     1200
gacgaagtat cagccattgc gccagggtga gaatcacacc aaagattgcc gcagcaattc     1260
ctgagagaat cagattacct gggaaactaa acggatctac tgtaaatcta atgattagcg     1320
tgataataat cggggcagag agcaaaaagc tcagaagtaa gctagcgcta atcgcaagaa     1380
accagtagcg accgagataa cccaggcgaa attctaacaa cgactcttgt acttccaaac     1440
aaagtcatcc aaaatgcaat actcgcggtc aaataatcaa gcattagccg ttgttttacc     1500
cgtgtgttga agagggtatt ttctagaata cgcccaaaca gtattttgtt gttgtggtgg     1560
ctctggtgtg gtgttttttt ttttgataat tgctctatga gattttttcaa tgagttttat     1620 atttggtagt gctttaaggc tgcaaaatat aaaaagcaac gaaaaacccc atccttcata     1680
caggttgggg ggatagataa aaaacatata ttccatgatg acacaattca atatttgttc     1740
gactgctgtc agcctagagg tggggcaatg aacaaaccac catccagacg caagaaaatt     1800 accccctgcga catctgagga accaaagcta gcaactgacc ctgctcagga aaatacttct     1860
ttgcacgaaa atccagggg agcaactatc acggtgacgg ctgttgaagt aacagatttg     1920
acccaggaag aacaaagctt acgcctgcat ttagaacacc gtgtggagag agcattttg     1980 gaggcgggtc aagcgttgat ggagttgcgg gacagacggc tgtaccgttc cacgcaccgg     2040
acttttgaag aatactgccg cgaacgcttc aattatagtc gtgacgcggc ttacttgaag     2100
atttcggcta ctgtggttta tgagaatctt caaaagtttt tgccgaccat ggtcggcaa     2160 attccaatgc cgaccaacga acgacaattg cgttttttgg cgaaagccga gttggaaccg     2220
gctgtgcaag cggatgtatg gcggcaggca gtggagcaag ctggcaataa gattccatcc     2280
ggtcgcatag tgaaagatgt tgtagatagg atacgcgaaa ggacgaaagt acccaatcct     2340
taccacgttg gggagatatg cgttcttcta cccaaagata atgcagactt gagaggtaaa     2400
gcgggttatt ggggcgtggt cagccatgtt ggagaataca gttgtacact ccagatatgg     2460
gacggtgact ataccgtaaa aatcgaacac ctgaaatcac tggaattact tgatgaagat     2520
tgccaattca tgcagcagtt atgtgtgagg ttacggcagt tgcatcaagt ggacaggcgt     2580
```

```
gacgaggctg tggattggct gttgcagtgg ttggggaaac aggccaaacc ttatctgtca    2640
tccttgcagt caaagctgct ggcgtttgtt gagagagagt acaacctggt ttggaagcag    2700
cagaagtgat gagatagcta gtaaacaata ggttaatcca acaaatacac aatgcaacaa    2760
ttaactcatt gcatgaaagc ggtaagcgat cgcggagggt ctggtagagt tgccatgctg    2820
gaaggcttat cggttcaaga agaaatctga gtaggtcatg gggagtgtcc ttttatagcc    2880
gccataaccg gacagttacc attttccct catgacatag cactaaatct taccagcact     2940
tcaaattaaa ggtaaagcag tgctagtcat cagtcacgat gataaatatt tccatttagc    3000
atctcgcatt gtaaggctgg attacggaca tcttaagtat gagtcatgaa aattatgtat    3060
tccaaacccg acaacttact gcatccactg tacccaatca ggcgcagatg tcatcaattg    3120
actaaactta tcagtgtaag tatcgtcaaa ctctagcatc actccccatc gctcatcact    3180
cgtgaatcgg aaaattggaa ctgaagccga tgcagaggaa cataaccgcc acaaagctga    3240
agtaagcgca gcagatgatt agctctacga tccagccctc tcaatattga caaatagtac    3300
actatgtgag ttttctaaga aggtaagact aaaactgcac ttaagcgctt atgttatctc    3360
ccctatttga tgcttttgta gaggcaagcc ccgtcagtgt aatgatgcga gtcctaatgg    3420
aaaacatttt taattcctcg cgaatgaatc aaatatttga tacatcaagc gttcgccaat    3480
actctcaaga gctactgttt tcgactcagg tggatttgat gagtctagta gtgtgtggga    3540
tgtatccctc ggttcatgca gcctatcaga agaaggcagt ggaggtaagt gtcagcgcca    3600
cagcgttata caacaaactg caacggattg aactgcctgt aagtcgggca ttagtgcatg    3660
agacagcatc tgacctccag cagttgctgt tgatgttgaa tgtggaacgc cccagtcctc    3720
taggaaaaca atatcggttg cggattgtag atggcagttg tttagccgga accgaacgca    3780
gactagcagc gctgcgcccc catgcagcca aaccattacc cggaaaaaca atcgccattc    3840
tcgacccagg gacaaaactg gtggttgatg tgattccttg tgaagacggt cattcccaag    3900
aacgctccaa gtttcatcag gttttggcac aagtgcaacc ccaacaggta tggattgcag    3960
accgtaactt ttgtaccgca ggatttctcc atactattgc caaacttgga gcgttttttg    4020
tgattcgtca acacgggggt ttaggatacg agccttttgg tgagttacaa gctgttgggt    4080
tgtgccaaac aggaactgtg tttgaacaac aggtggaaat tgtccatgag ggagggactt    4140
ttcggtgtcg ccgtatcgta gttaagttga ctcgtcccac ccgtgaccaa gagtgggaaa    4200
ttgccatttt taccaactta ccacccactg acgcagacgg cattctggtg gcacaactct    4260
atcaagggcg gtggagtgtg gaaactttat tccaaactgt gacccaaaac tttcatggag    4320
aaattgaaac cctagcttat cctaaagctg ccttattctc ctactgcatg gcactgtcag    4380
cctacaacct tttagcgaca cttaaagcag ttcttggcag tgtacatggg gtagacaaaa    4440
tcgatattgg gctatccgat ttttacctag tagatgatat ccattccatc tatcggggca    4500
tgatgattgc tattcctccg gttcattggc aattctttga ggagtttacc aacattcaga    4560
tggtagacgt tctccagcat ctagcaacca agtacatct caaatctttt cgcaaacacc     4620
ccagaagtcc caaaaagaaa cgaccaccac tctctgttga tggcaaacat tcccactgtt    4680
ccactactcg aaagctcaag caatacaaag cagctcttga tgctatcccg tgaagcaatt    4740
tcataaaata tgttatttgt caatattgag agggctggct ctacgatcct aacgtggcaa    4800
aacttactag agaagagtaa aaatcctgta atcttgacct tgtagcgaaa taatggtgcg    4860
aaaacttggc atgaaattgt ctaaaaccag aggcaacatc gtttgaagta ctcgattgtg    4920
ttcaaaaaaa atgcccttcg tgcggtcaag caatgtggaa tgaatacaat aatcctcgac    4980
```

```
atataagaac gttaaacggg gtagtagaac tacaactaaa aattcgtcga tgtcaaaata   5040
attcatgtct gcggtacaaa aaagcatatc gaccagagca agaagggtca ctcgctctac   5100
cacaaaacga atttggtttg gatgtgattt tataaggagc attacgctac caggaacata   5160
gaagtgttcc ccaaatacac gctcacctcg aattaaaagg tatatgtata agtcaacgaa   5220
cggtcacgca cctaattgac agatatgacg agttactttc tttatggcta aaagaccata   5280
aaaggttaaa agcaatagtg gctaatcaag gacgggttat attagcgatc gatggaatgc   5340
agccagaaat tggacatgag gtattatgta tgctttgaat cataatgtga gaaaaatttt   5400
gatccataaa ttagaaaaaa gttaacgaaa attcaggctt tcgtgctaat caaaaattaa   5460
aactttgaat caaattatga gtgagagttg aaattctgaa tcataactag agaatgagtt   5520
gaaaaaacac aattggacaa aacttgcaca aaaaatccct gacaaaattt ctctaactta   5580
aactttcaat tcagaatatg gttcaaatac caatgttatg gttcaaaact tttacacaag   5640
ctgttagggt agcattactt agtattgctc atggtttatg tcattatcat tacctgaagg   5700
aagcaattaa acccatatat gaggcggatc gacatgcaaa aaaggaataa aaaaaaaggt   5760
tagaggatta cgagacattg aatgtagtgt tgtcaatgaa gatcagaaaa tggcgactat   5820
tattgaagat tattgctcgg cagtacgtag ttctataacc aatgatggtc aaaccaattc   5880
gcaattgaca attcgcaatt cgcagttgaa ttcaaagtta gctctgaacc cacccctgaa   5940
ttgagtctac tgatttagag aatcagagtt agctctgaga cccattaatt aacaattcaa   6000
caattaagta atttcttgtc tttaattgcg aattgcgaat tgacaattgt ttcggtcatc   6060
caccgttaga ggcatctgga ttaaagttac aagaaaattt gacgttgata gaacaaagct   6120
tagaacggat ggaaaaaaag tgctwtacca ccacctttag tcaacctaaa atactgatag   6180
ccaagggatt atctgcgact gtatctttat tttcacttgt tagggttgca tatcagtggg   6240
ttgataaagc tagttatatt ctcaacaata aaatagcttt tgatgctgct ggagtcaaac   6300
aaagttatca acaactgtta acagaaatgt cccaacaaaa atagaaagct ggtacactga   6360
ataccgcaat cgataacttt ataaaaacca cccataacta ctggtctaga cttttcatt    6420 gttacgaaat tgaagatttt tccagaacta ataatgactt agaacatgct tttggtatgt   6480
tacgtcatca tcaacgtcgt tgtactggtc gtaaggttgc tccctcatcc ctcgttattc   6540
gtggctctgt caaacttgcc tgtgcgtagg cgtagcccgt cgtagacatc gctactaagc   6600
ttcactcttt taccgcatct gatttagcac aagttgatat tcatacttgg ctcgaattac   6660
gatctcaact gcaaaacac cacaaagcca gaattgaaca atatcgattt ctcagagacc    6720
ccaagggtta cttggctaat ttagagagtc gtcttctcta gtaagtttta ccatactagg   6780 ttttcttgt tctcaaatcc tgttgccatg actcggatct tgcagctaga tggtaagaat    6840
tataccctag ctcgcatagt gccactttca acccgacgtt gcagttcagg taagtccgct   6900
tgtcaatagg gtttgagacg cgctaaccct ggggtatgaa gacttaaacg atcatgaaca   6960
attacgtcat gacaagatgt tcgtcttggc gagcagcatc gcataaattt ttaccatttt   7020
tagtatttcc aggctctaag tgtggagcaa agagtttctt tggagaggga ttacctgtac   7080
caatcctaat tttggctgag ttgtaacata tagaccatca actgccccaa ctgccgatag   7140
tatggaaaat ccctcgactg cattgaaaaa ctgggcattt gtcttcatta cctcgttacc   7200
ttttcccctt tcgattgcca acgcctgctt gtcttgccta atgctgtggc ttgactgaat   7260
ccgctgagac atctctgcca taacaaaatc ggcaatcccc tccttagcgt cctccaagtc   7320
ctcgacgccg gacaccagat tcaagaatgc tagctttagg ttagaactgc cgaagtcacg   7380
```

```
gcgactaagc cgttgtgcct cccagaaata ggaatccttg ccacggtttt gatcgtagaa    7440
ggctgatacg aacactaaga aacgcaaata agcctgccga tagctctgat cgtagaaaga    7500
agcagcttgt gactcagtca cctcgccacg tataacactt gtgatactgg ctgcggctaa    7560
caaagcgcta taagtagcaa gatgcacccc actcgatagt aggggtcta ggaagcaagc     7620
agcgtctccc gatatgaagt aggctggtcc tgaaaaggag tcggaagtgt aagagtaatc    7680
ttgctcaact ttcacgtctg agactagctc ccctagtgca accagatccg ctatcaaggg    7740
acactctgca atcgcctcca cgtagatatc cttcaagttc ttagtcagtc tctccttgta    7800
ggttgactta tgcatcacta caccaacgct cataatttcc tcatccaaag gaattcccca    7860
cacccaacca tctggaatgg agcccaaggc aatcgcaccc gactgacctt taggtagtct    7920
caaggcgttt ttccagtacc cccagatgcc aacattctgg aatacgtcgt gtagacggcg    7980
gtttttcaga tactccgtcg ccatgatccc agcacgacct gaagcgtcaa tcataaagtc    8040
aaaagaaatc tccccggtag tatcatttga ttgtgaccaa gtagcgctgc gcgggcgatc    8100
gccatcaaaa gacaactggc gaatttagt ccccttcaaaa accttcacac cctggctctt     8160
tgaatgctct aaaagcaagt ggtcgaattc gtcacggcga acttggaagc tgtaggtgtt    8220
gtcccccgta agttccccaa aattgaggct ccacttttcc gttccccatt ctatgtacgc    8280
tccaggttta cgctgaaagc cataagcttc aatttttctcg cgtacgccaa gcaggtcaaa   8340
aatttctaaa gcagagggca aaagagattc cccaacgtgg taacgcggga atacctctcg    8400
ttctaacagc gttacatcaa agccctcacg agccaatagg gtagcagcag tagatccaga    8460
aggtccccct ccgataatta gaatctgtgt ggaattaggc agtgtagaca ttgcaggttt    8520
cttctccaaa agatacagta ttttcgcaac aatggcggtt gtgtcgccta gggacaaaca    8580
atctgtctta ctcgtgtggc attaagcgac aactccaaag atttctttga taaacttggc    8640
ttgagctaca ctgttccccg gccgataaag atacttccac tcccctttaa cttggatgta    8700
agtttcgtct acccgccatg aatcattcgt ctgcttcaaa taaatgagga cgaatccgaa    8760
atccagttcc aagccgcatt tcaacaccca tcaattcagg gtggaatgat ccacgtctat    8820
gcctcgctcc tacatcatct cctccaagtc ccaatagaac aacgagcggc agtaccaacg    8880
cacattaagc aggatgattt ctggcaaaag gtgacgccat ttgaacaggg agcgagtgga    8940
aatggaaagc taagagcctg tcaagaaaca acttttacaa tttattatct agaaagctta    9000
ctgagaaagc atttctagct caaaagaggc aaggttgtta catgacaagc tctaagcatt    9060
aacgacaagg atttcctacc ctgcactatc tcactcagct ttttgcgaca caaccttttaa   9120
aagcacactt ttaaaatgcg atgggcttac gccttacagg tacttgagaa acttgttgtt    9180
ttcatccacg ataattttttt tcggttcctt gatttcgtca gttacctcga atgctagcaa   9240
tgtgataagg tctcctgaat tgactaggtg ggcggagcca ccgttcatac agattacccc    9300
ggaattttcc tcaccttcta ggacataggt ttctagacga ttaccattag tgttgtccac    9360
caccataacc ttttcacccg gtagtatgtc tgccttttcc atcagaactt tgtctactgt    9420
aatacttccg atgtagttaa cgttggcttc cgtcaccgtc gctctgtgaa ttttcgactt    9480
caacataata cgcatcgttt ctttcctcat gtggctttaa atttcaattg agttgactga    9540
gaaatatctg agcctatatc tatttgagat ggctgatact ttttagcaaa taaactcaag    9600
ttttttgggg ctatagaaat accaaacttt aaatttataa tatcagattg tccatcaaac    9660
caaagtcgat ttagtagcct atactcttgt ttggaaaatg cagttcttcc atgcaaaact    9720
ctagtattat ctacaataat tatttggttt tgtgcaagtt taaaaattac ttgattgtca    9780
```

-continued

```
ggattattta caaagttttc aaatgattta aatgccgcaa aacttttcga ttcaaccgaa    9840
acatgagctg cattatctgc tctaaacctt acaataagcc cagcatgatg ttcttcaaaa    9900
ataggtttag ttgctttttt attatctctt ttgactgtaa tcgcatcagg attaaacaaa    9960
gttaacaatc caactgggtt tgtccgcttt agatgttcat ataccagctt gccatcaata   10020
agcttggtga acccgccatt tgcagcagca atctggcact gcattgccat tactttggt    10080
ggagtaattg tgaacgctcc atccgtatgt aacgataaat ctgtagttgt agtatttaca   10140
tattctggat aactatcaac aggactgatg ggaacaattc cctgtgaatc agaatgttcg   10200
tgctgaataa ttgttccaaa ataatcagac aattttaata agttattctt aggtgttgct   10260
gaaggttcgt gttctagtat tacgaatcca aactcattaa atttatttgc catctcagct   10320
tctttagaaa ctggcatttc taatacactt ttcactctaa ttattagatt ttcaattttt   10380
attgaataca ttttaattt tctcctggat gtcactgctc tgctacaact agcttaattt   10440
ttttagaatt ctcatgttta caataaatac gttttcaaaa aaaatactat aagtcttgct   10500
gatataggtt gtaaatccct cgatatagct aggtaataat caaacataaa attaaatgcc   10560
tctattgcat gtttatttag agcatgataa gtatgtttaa acagaattat ttacattcag   10620
tagaccaaaa agctttccaa aagacttacc agctattgat tttccttggg aatgcaataa   10680
tccgccgata taagctttta agaggatgtt taaaaattg ggagttgagt aaaaaatatt   10740
ttaaacatcc tctaatagtt taaaattcag ttttttacaa tacaaccatt tttaatccac   10800
cttgaggata aattgagaaa atatctcgta ctggttttaa aggaggtttg cctaccaatt   10860
ccaattgcca attccgcaaa atattagcca atactaactt cattttaaac tgagcaaatg   10920
ccataccaat gcaagttcgg ttaccgccac cgaaagggaa atactcataa tttaaaaatt   10980
tattatctag aaaacgttct ggcttaaact gtttagagtt aggatatagt tcttcccggt   11040
ggtgaattag ataaatacat ggataaagac aagttcctac ctcaaattga tgacctccaa   11100
tttctattgg cgattttaca attcgaggaa aagtagttag accaactgga tatattctca   11160
aggtttcagc acaaactgca ttgagataag gtaatttgct tatttccgtt gggtctggat   11220
tatctcctaa ctcatctaat tcttgcaata acttggctct tatctctggt aagtaatgaa   11280
tccaataata tgcccatgtt attgctgcag atgtagtttc atatccagaa aagataagtg   11340
tcattaactc atcttgcaac tcctcatctg tcatttttcc tccattttca tctcgtgctg   11400
ccatcagcat actgaggata tcattgttgt aattgttaca attttctcta cgttctttga   11460
tttctgcaga aatgatattt gcaatctgac gttggcaacg taaagatta ccccaggcac   11520
tccaagaacc ccagtctctt ctaaacacat tgaagaaaag agagctagaa gcaaagggat   11580
tagttatagt ggatactatt tgattaacta tcaatttgag ttgttgataa cgttccgttt   11640
tatctgaacc cagtaaaacc gttaacatcg ctcgcagcgt aatttctttg acttccttgt   11700
aaataatcaa tctttgacca ggttgccaat tagaagtaac ctgcttcgtt gcatggcata   11760
ttagttctcc atagttagat atattttgac catgaaaagc aggcatcagt agtttacgct   11820
gtcgtttatg actacttcca tcaagcaagg tgacggaatt gttgcctaaa aaaaatcctg   11880
ctaaatcgtt agcttttagct tttccactgt caaaatactt gtgtttatca aaatttctt    11940
ttatatcctt aggattacta ataagtacta aaggttcaaa accaatagct ttgaaggtaa   12000
aagtgtctcc atagcgtgct cgacactctt ccaaaaattc acaaggatta ttaagccatt   12060
gcaataagtt ccaccaagat ggtgtagtgg gaccaggaag taatgaggat ttagcagtat   12120
taatcatttt agttatgctg gatttggcgt aaatttacta attagacttt ggacactatt   12180
```

```
gaatttcatt tttccaattg atgggttttc tgtgcttgtt caagagatat ttgcatttgt    12240
tgagccaata ccttgacatg aggctcactc agcattgaaa catgattacc cggaactata    12300
tggatttcca cttctccatc agaaaactga ttccaacccc atgttggctc ttggaaaatg    12360
tgagaataac tttcttgctc tggatttatc tccctcgcac aaaacaaagt gattggagtt    12420
ttataagtct tttccggttc atacttaatt tgacattgag tttggaaaac ttgtaataaa    12480
ccacgaacaa ttttgatatc tgtttgagca ggcaaaaaac caactatttc taacttttgc    12540
ttgaaataat ttaattgttg ctcccaagtt agagaagtta gagtttcata agataaaaat    12600
agattttctc caacaatatc ttcaataacc tcagccattc gacatatcca ctttgcatta    12660
tcccagttag aaaaatcatt ctgatgatta gcttgagaag ttggtgcagg agtatctaaa    12720
attccaacat aagcaacaga cttttccaata agttgtagtt gattcgccat ttcaaatact    12780
acatgactgc caaaggaatg accagccaag aagtaaggac caactggttg aactgtttga    12840
attgctttaa tgtgttggga ggctatttct tcaacacttt tatgaggttc ggtttcacca    12900
tcaagacctt gtgcttgtaa accgtataac ggttgattat ttccaagata ttgtgctaag    12960
tggtggaagt agagaacatt tccacctgct cctggtacac agaacaaagg tggtaatgaa    13020
ccgttttgtt gaattggtac taatggagac caaagttcgg ctccggaatc ggaaccaaca    13080
agaagtgcta gtcgttcaat ggtgggattt tgaaaaagag tggctaaagg taaattttc     13140 tggaattgtt gttgaatctc ggacattaga cggacagcta aagggaatg tcctcctaag     13200 ctaaagaagt tgtcatgaat accaatagag ggtagattga gaacttcttg gaaaatctca    13260
actaactgac gttctgtttg attccgtggt tttgtctgct cagaagtatt caaacctcca    13320
tatatagcag caatttgttc ccgattaatt tctcctcttt gagtaagggg tatttgttca    13380
agttggacaa agttaatttg attgggtatc ccaaagcgat cgtgtagttg taactcttgt    13440
aaggagagtg cagcaagttc tggtgtggga gaggtgaagt aagcagttaa tttctgcttg    13500
ggctgacaat cacgaatcaa atgttcaaca tttgttttag ttccatccaa tccgattaat    13560
agattatgtt ccgaaccaga taaagctgct aaaaatgagt aaaatccttg ttgaggagta    13620
ataataaaat agcccttagc acgactgagt tcttggaatt gatagccatg acttattccg    13680
gtttcattcc acatactcca agagcagcaa tagctttgga aaccgttttg ttgttgataa    13740
tcgctccatg ctgactgaaa actatttgct gcactataag ctgcaacatt ggttcctcca    13800
aagaaaccat ttacagaaca aaagtggaca aataaagcat tttctttatc cttgagcaat    13860
tgatgcaata cccaagtacc gctaacttta ggacgtaaaa cagcagcgat atttcctggg    13920
gtttctttct cgattggcgt ttcctgaata atcccagcca tatgaaatac cccatcaagt    13980
tgagtcctcc attcttgtgt tgcttttttct actacctgtt gtaaacctac taaatcacaa    14040
atatctacag tttgataaat tattgaacct ggtagttttt ctaattcttg atacctctgc    14100
aattttgtgc tagcttcctc attattatct tcaatttgag ttctaccaac taatattaaa    14160
tttgcttgat aatgttctaa taagtacttt gcaataacag tcccaattcc tccaagccct    14220
cctgtaagta gatacgttcc tcctggtaga atcggaattt tttgttttc cttagcagtc     14280 atatctactg gttccagacc agacacaaaa cgttctctat gcgtatagc aacttccaat     14340 tctttatcag cagaatacag ttcttgccaa atataactat tgttgagttc tggtgctaat    14400
ggtaaatcta aatgacgagt agttaaccaa ggcatttctt gactaacagt tttaagtaag    14460
cctaaaacag tggattttc gggttgaatt ttatctgtgg gatgaactaa ttggctttga     14520
ttagcaatcc ataataattt gactgcttgc tgtttgcctt gaatttcttc taaagcttgt    14580
```

```
actaaaaata gtaaactgta aattccttgt tgttgagtgg actctaaatt ttccaagcta   14640 gaaattttt  cagtctgctc gttgtagttc caaagatgaa gaatttgact aattacttgg   14700
ctattttgcc tcaaagaatc aattaacaag cgatagtgtt gtggatttcc aggaacaaca   14760
gaataatgat ttgggctaat ttgagcaaaa tttgaaccaa tagtaacttg agcatatggt   14820
tgaacagttt gggacattcc tcggttatct tgttgccaac ccaaattatc tgtaaatatt   14880
agggttaaag ttttctgaga agaataattg agtaaagtat ttttactttc tttaatttgc   14940
catactttac ggtaaaacca gttgggaata gtattagtat tatcaagcaa caagtctaca   15000
cgctgtctga gagatttaaa ctcaccacat tcaaaacgtt gcttaaggag gaacgttga    15060 attttaccga tggaagtttt gggaatcagt tctttatcta tgggtattaa ataacttgga   15120
tttatcccgc agtattttat aacttgttcc ctaacctttt tcaaaagctc taataattga   15180
ttcttctcag atacatacgg agtgaaaaag attactaatt cttcggtatt attgctagca   15240
acgcagactc cacaggctgc ggtataagaa acttcaacct ctcctaattc ttcaacaaca   15300
gcttctattt catgactata ataattaact ccattaataa taatgatatc ttttttgtcgt  15360 cctgtaatcg ttaagcatcc atcttttata aatcctaaat cacctgtatt aaaccaacca   15420
tcttcggtaa atgcttcctt atttgctttt ggattttgat aataaccaga agtaacggtt   15480
aatcctttga cctgaagtaa accaatttca ccttctgata atacttccat gtcttgattg   15540
actattctca gacaagtacc cctaatcggt tttccaagat ttacaaagga attatcatct   15600
gaacttgata gagtgaaaaa attgtcagaa taagtaatac cagaggaaac ctcagccatt   15660
ccccaagatg gagtcatagc atccccaggt aagccaaagg gagcaagtaa tttcaaaaaa   15720
cgtcttgctg ttgctgcaac aatttgttcc gcaccattta acatcaagcg aatagaagat   15780
aaattccaat tctgcttttc tatttcttga acaaaatcat taattaaact ataagcaaag   15840
ttaggagcaa aagtaacagt gacaccaaaa gtatcaatcc aatccaacca tcttaaaggt   15900
ttttcaatca ctaattgact agtagcatga atttgtttac atcctaaata aatatcccgg   15960
atatgaaaat atattaaacc tgcaacatgg tctaagggca tccaatttaa ggttatatct   16020
tctggggtaa aattattcat ttgtattgaa ccaatagtcc tactcagtag atttaaatgg   16080
ctcaactgta ccaccttaga catacctgta ctaccggaag taagcatgaa cagtgctaaa   16140
tcttctggtt gggcattata gtaatctttat tctgttgaga acttttgtaa actttcaata  16200
gtttctaact taaagttgtc gtcatttaga ttttgagacc atttctttag ttctgacaat   16260 gatttttat  ctgttaaaat caaaggtctt tctaacatct gccaactatt ttgtaattta   16320
tttagattga cattgggctg gtcatagctt acaggaatta caacgggtac gggaataaag   16380
cctcccaaca cacaacccca aaaagcacta ataaaatctt tatttctttt taattgcaaa   16440
ataactttat cttgtggctt aattcccagt tttctgaagc cacctagaat tctttgagca   16500
tcttctaata actgggcata tgattgaact tgttcggaac catcagagtt aatataagtg   16560 attccttgt  gaggaaattt cccagcagtt ttttgcagca tctcccctaa agtttctgga   16620
gatgattctg gaaagattaa tacttcttcg tggctgatgg caggtgattt tatttctaat   16680
agggaactac tctcttttcc cctagcagtt ctgggagttt caactggagt agaaccttga   16740
ttgaaaatag cttggattga tggtaaaagt tcttctaaat gtatcggaga aatcgttttt   16800
acatttggct caataaaaac agcaacttta tcaatttccg cctgagaacc tatttgttct   16860
tcccaagtgt taattaactc agaatcaatt atgctaatag aagctaaacc tacttcatca   16920
acttctccaa aacttgtcaa tggtaaagca gatactggta catgagatgca gggtaatggg   16980
```

```
tatccaggta actgagattt taaataatgg tgtaaaaact ccctagccca agaaccatct    17040
ttgactacgt aagcgactaa tttttgattg cgtaccatta catagcaatc ttctacccct    17100
ttcgctgttt gtaaagcttg ttcaatacgt tgtaggttaa ttcgttgtcc attaactgtg    17160
acaattcgat gctctttttcc tagcaattcc agagaaccat cgactcgacg acaacccat    17220
tcccctgttt ttaataactt acccagttgg gtatgttcta tgaaacttat aaattttct    17280
ggttctggat gtaacttgtc tgggagtaaa tcgcaattcc ccaaataaat ttctccttct    17340
acactcaaag gaactaattg ttgatggtta tctaaaatgt aaatttgtaa attatttgaa    17400
ctcaggaaat gaacatattt atccagcagg taagttgtag cgatgttatt gtaactgtgc    17460
agtacctgct cttgctcaga atctgtgaat aatggtaatt cacttatctt ttgttgggga    17520
ttttctacaa tcgcgctaca cagattctgg aaatgagcag tcatgcgctc aatagttgac    17580
ccatcaaata agtcagtgtt gtattcccat gaacccacta gtgcttcgga agtttgctgc    17640
attgatactg ttaaatcaaa ccgggctgtt tctgtttgag aactcaataa attaagggtc    17700
acaccaggta attctaattc acccatgggt gcattctgca acacaaacat tacctggaat    17760
aagggtgcat aactcaaaga gcgttgtggt tgtagtactt caactacctg ttcaaaaggc    17820
acatcctgat gttcataagc ttcaagtgta gtttccctaa cttgtgccag caaattctca    17880
aaactgggat tatcttcaaa acgggttttc aataccaaag tattggcaaa aaagccaatc    17940
aaagactcaa tttcactgca gttgcgattg gcaatgggtg aaccaattaa aatatctaat    18000
tgaccgctgt agcgatagag taaagtggca aacgctgcgt gcagggtcat aaataaggta    18060
gtacccgagt tccgagacag ggtttgcaac ttctctttta aatcagtatt taaactaaaa    18120
ctttgagtag tacccggaa agtttgcacg gttggacgag gacggtcagt aggtaattgt    18180
aacaattctg gtgcaccctc taactgagaa agccagtaat tgagttgagt ttctagtacc    18240
tttccactta accattgtct ttgccaaact gcaaagtctg catactggat tggtaattct    18300
gccaaggggg atggttttcc tgcactaaaa gcttgatata aagtagatag ttcttggctg    18360
aatatcccca ttgaccaacc atcagagaca atgtggtgca tcgtcagtaa taacacatat    18420
tctctggcat ctaactgcaa taaactacac ctgattagtg gtgcagtttc taagtcaaag    18480
ggggtaattg ctgcaagttg tgcttgttgg tgaaggacac tttcccgttc tgttgcttct    18540
agttgctgta agtccgccac actgatgttc atggtggctt ctgggtgaat tacctgtatt    18600
ggtgtgccat tcacagttcg gaagctggtg cgtagtactt catgacggcg gactatttct    18660
gataatgctt gttgcaaggc attaatatcc aactttccag tgacacgaat tgctcctggc    18720
atgttataag tggcacttga cccttcaagt tggttgagga accacaaccg gtcttgtgca    18780
aaagataggg gtaattgttg gttctgtgtt cttggctgaa tgggggggaag acttaatgcg    18840
ctattagtag tacgtaattg ggttaatgtt tgctctaatt gagctacagt gggagaggaa    18900
aagactcac ttagttctat ttctacttca aaggcaactc tgagtcggga aattaatcgg    18960
gttgctagta gggaatgtcc tcccaattca aagaagttgt catggattcc aacattttgc    19020
acacctagaa tagaagcgaa gatgttggct attatttctt cacccgatgt acgtggtggg    19080
acatattcat gttctcggct aatttctcca tcaggtgctg gaagggcttt acggtctatt    19140
ttaccgctgg gtgtcaacgg taaggtgtct aagatgacaa aggcactggg catcatgtat    19200
tctggtagct tttgtttgag gaattcacgc aggtgatagg tacttagtga ttcatcctca    19260
cagactatgt aggctactaa acgtttgcta cctggaaata cttctatggc aatgacaacg    19320
acttgttgga tttggggggtg ggtactgagg actgcttcga tttctccaag ttcaatgcgg    19380
```

```
aagcccccgca ccttcacttg gtgatcgata cgccctacaa attcgatatt accatccggc   19440
agccagcggg ctaggtctcc agtcctaaac aatctttctg cttgtgcctt tttacttttc   19500
cccctgtcct tcacaaacgg gttggggata aacttttccc gcgttaactc gggcagattt   19560
aaataccctt ttgcaagccc atctccgccg acgtatagct cacccgtaac accaggtggc   19620
aaaagatcgc catacttgtc gaggatgtaa atttgtgtgt ttgaaatcgg ttttccaatc   19680
ggaatcgtat ttcttttcag atattcttct agagcttctc ctaaatctgc tcttcgctcg   19740
tctgccaact gcaaatgtat tatttcttta tgcaggacag cagtttccct atcccctgag   19800
ccactaggaa gattttttaa agcatcaagt ttctctttac tttttgcttc aatttgattt   19860
gcgattctca gtttgacttc aaagcatgta acatcagcgg caacttctga agagccgtag   19920
agattgaaca atctggcaga gctgattttc tggtgaaatt ccttagccaa ggttagcggt   19980
aagacttcac cgctgcaaaa gacatatttg agatatcgaa gttttgtcag ttgttggggc   20040
gcattttcca gtatcgcttt taatagcgat ggaacgagaa caattctagt taccttttcga  20100 tcgctcaaca ggctcattag cctgggaata ttgccccgta tatcatctgg aacgatcaca   20160
aggggaattc ctttgagaag gggagaaaat atttccgcaa catgatcgcc aaaattgatg   20220
gatgttttct gagagcaaat ctcatctgcc ccaaatggta gcatttccca gatccaatgc   20280
aagcgattga caatgccgcg aagcgtgccg agaacggctt tgggttttcc agtagaacca   20340
gacgtataga ttgcgtatgc aaggtcatcc agtgttgttt gccgatccag attttcaacg   20400
ccttccctag caatgacatc cctatccctg tccaggcaaa cgatatgggc attttgaggg   20460
gaaatctttt cgagcagagg ctgctgggtc aatatgatat gcacattgga atcttcctgc   20520
atgaacgcca gtcgttcttg cggatagttc ggatctaacg gcacatatac accaccagct   20580
ttaagtatcc ccaacagtcc tacaatcata tcaatggagt attctatgca aatacccacc   20640
agcacttctg gtttcactcc cagagtttgt agataatgtg ctaattggtt cgcttttga    20700 tttaattgtt ggtaggttga ttgttcttct tcaaacacca ctgctatgga gttggggttt   20760
ttttctacct gttgctcaaa taactgatga atacatttat cagatgggta atccgttgca   20820
gtgttattcc actcaaccaa taactgatga cgttctactt cacttaataa aggtaattga   20880
gctaccttat gtgaaggatt ttccacaatt gcaattgctg ataaaacagt ttgcagatat   20940
cctaaaatcc actcaatagt atttgaagag aaacgagcag tatcgtaact aatcctaact   21000
gacaacttat ccccaggaac tgcaactaaa gttagtggat aattagtttg ttcaaaaacc   21060
tctatatcac ctaagtgtaa tgaaccttct tcattcaaca aagaattatc aattggataa   21120
ttctcaaaca ccacaatgct ctcaaacaaa ggtattccac ctggtatctc agaagtagct   21180
tgaatatcaa caagaggagt ataaaaatac tcttgtaatt caaccattga ctgttgtatt   21240
ttttgcaacc aaggtatgag ttgctcctgg gtggatactt gtactcgtaa gggaagggtg   21300
ttaataaaca gtcctaccat attttctatc tcagagaggc taggaggacg accagaaaca   21360
gtcacaccaa atactacatc tttctcacca ctataacgac tcaatagtaa agcccaagca   21420
gcttgtacta cagttgataa agtcacatga tgttgttgtg ctatatgaag taacttctga   21480
gtgcattcag gggataaact acttgttctc tcctgataat ccgcagtttt atactgttgc   21540
tctttcagaa attgagtttt atccattacc aatggagtgg gagcactaaa accttgtaaa   21600
gtttgttgcc aaaactcaat tgctgctgat ttgtcttgag aattcaacca agcaatataa   21660
tcctggtaag gacgtggttt tggcaattgg caattttcac caagcagatg tgctttatag   21720
aaaattaaaa tttctttaaa aataattgat aaacaccatc catccataag gatgtggtga   21780
```

```
tgactccaga taaatttgta attatcttcg cctagcctga ctaacgtaca ccgcattaat   21840
ggtgcttggg ataagttaaa accttgttct ctttgtgttt gcaataattg ttttaattgt   21900
tgttgttgat cattagaaga aagttctcgc caatcaagag tattccaagg aacattaacc   21960
tgttttagta ctacttgtaa tggagtttgg cgattttccc aaacaaaaaa tgtacgtaga   22020
attgaatgtc tatctaaaac ttttttgcca agctctttcaa aagcagcaac attgatattc   22080
cccttcaaac cccaggtcat ctgttcaaga tataccccac tataaggtgc ataaagactg   22140
tggaacagca tcccttgttg catgggagaa agtggataaa ttgaagagat atttcttcta   22200
atttcttcgt tgctcattgt tctctctttt tttatctata ttttttatat ttacactatt   22260
tgcccaagtt ttttaataac tcatcaagtt ctaattgatt taactgtgca tctgggaaat   22320
cactagctgt atatccaaaa ccattttctg actggcaatg ttctattatt gacttaattg   22380
cttgaatata gcttgtgtc aaattttta ctgtatcatg agtatgaaaa ttactactat   22440
aagtccaatc aatttgtaat tcaccttcta ccaccagact attaatctct aatagatggt   22500
gacgagtttg ctttgaacta tgattatctc cagtagattc tggcgcaaat ttccaacccg   22560
tttccgattg tatttggtca aattgtccta ggtagtaaaa actaatttct ggagtaggaa   22620
ttgtctgtag tttttgggtt acagtagtat cttcacacaa gtaacgcaat ataccaaagc   22680
caataccacg atggggaatc tctcgtaatt gttctttaat tgacttgata acttctgctg   22740
gttgtttatc gtctggtaat cgcaataata ctgggaataa actggtaaac caacctattg   22800
ttcttgataa gtctacatct gaaatagtt cttctctgcc atgtccttct aggtcaatta   22860
gtacttttga atctcccgtc cactctgcca aggaaactac taatgcactg aggaggatat   22920
cgttaatttg tgtgttataa gctgagttta ctgaccccag caaagcgcgg gtttcttctg   22980
gactcaattt cactctataa ttaatcgcac tatcaactgt tttttctgct tgagtgtgag   23040
cagaatctaa tggtagtggt gttgtttctg accaaggttg gttgagccaa tagtctaact   23100
cttgtttgat ttttctgat tgtgcataat ttttcaattt ctctgcccaa tcaataaatg   23160
ctgttgtttt cgcatttagc tgtattgatt gttgagcgat tagttgttga tagattgttt   23220
ctaagtctga tagtaaaatt cgccaactca caccatctac tgctaggtga tgaataataa   23280
tcagtaaacg ggcatcaact tcactaccta agttaaacat caccacttgc attaaaggtc   23340
cctctgagag gtttaaactt gcttgatatt ccgtggcgat ctgtgataaa gcttgtggtt   23400
gttcaatgac aggagttgat gataaatcaa ctacagtaaa tgctacggga tcatcaaagc   23460
catggtttat ttgtttgtac tcagatgcaa ctgatgtgaa tcgtaaacgc agagcatcgt   23520
gatgctctaa taattttttc aaggctgttt cgattaattc agtttgcaga tgattgggaa   23580
tctgcaataa aactgattgg ttgtaatggt gtgcttcttg gctattttgt gcaaagaacc   23640
actgttgaat tggtgttagg ggtgcaactc cagtaactat accttggtta gcactgacag   23700
taactgttgt attggctact aatgctagtt tggcgatggt ttgattttgg aatatttgtt   23760
tgggagtgat ttgtattcct aagttttggg cacgagaaac tacttgaata ccaaggatgg   23820
agtcgccacc aatttcaaag aagttgtcat ggatgctgac ttgttcttta aggagcagtt   23880
cwtgccaaat gttggttaag atttgttcta tttctgtgcg tggtgcgaca tattcatcct   23940
ctcggctaac ttccccatca ggtgcactta gggctttgcg gtctacttta ccgttgggtg   24000
tcaacggtag ggtgtctaag atgacaaagc tagaggggag catatattct ggcaatttag   24060
actttaggta ggagcgcaat tcattgctac tcagtacctt acgttcaggc tttgacttat   24120
taattgtgta atcttctaga ttatttcag caaacaatcg ttgataaaaa gggttttgct   24180
```

```
taaacaattg tttccaatga tatgagatgt attcaaactc aatctctttt ccagtttttt   24240
ttaaaagacg acctcgaaga gtataatctg gattcaaatt attttcacaa agcgttctcg   24300
tacaaacagc ttcgatgata tctccttcat ttacataaat tcctggttca aacactggaa   24360
gataaactgg taaccagcaa tgttcatttt ctaaaatatc tatacattct ccttcaattg   24420
tgtgtaagtt taatcccact gaaaaaccat ctaatcttcc tgattttca atagttaatt    24480 taatttggtg agtagattct gtgctaacaa gcttgctaaa gtctaaatcc tcaaaaactc   24540
ctcgattgga caaccagttt acttgattta atcctttaat acatactcgt aaatcaaaag   24600
gatatccaac ttgctcaaat atcttctggg tataataacc tgaaactttt gtaaattggg   24660
gttgatttag taattcatca ggaagagtta ctgcaataat ttgagtcaca cttctttggg   24720
gaatcattac accatctgat ttgagaaatc ttctggcgtt gttgataatt actgctgctc   24780
cttcagatcc accaatgggt cccacaattt cagaaacaca tacatcaact tcttctggta   24840
agttggctgt agtagcgtct ccatgtatga tttgaatttg ttctgataac cccaactctt   24900
gcacgcaagc tgaagctaac ttactggttt gctcgtctct ctcaattgcg tagactttct   24960
tagcacctgc ttctgcacaa aatctggcta taattgcatc cttgcccgtg ccaatttcaa   25020
caactacttt atctttaacc atttgattaa ttgcgacttg gtaactctgg tttcgacgat   25080
gatcattggt catcgcatag tacaagagct catcataaac gtagaattct gctactgagg   25140
gccaaagttc aattcctgtc tggggctggg gatctttttc ttttgactga agaggaacta   25200
aatatgctac caaccgtttg tgacccggag tatcttccct ttcggtgact gcgacttgct   25260
gtacttgagg atgggtactc agaactgatt ctatttctcc tagttctatg cggaaaccac   25320
gtattttcac ctggttatca agacgaccaa gaaactcaat attaccatct ggtaagtatc   25380
gagctaaatc tccagtttta tatagttttg atctgctatt gaaggggtta gggatgaatt   25440
tctctaaagt taattccggt cggttgaggt aacctctggc taagccataa cctccgatgt   25500
ataattctcc ggatacactt atgggtactg gttctaagtg cttatctaag atatagattt   25560
gggtgtttgc aatggggcga ccgatagtaa ctttctcgct accatggctg atttgagcca   25620
ctgcagcacc aatagtagac tcagtaggcc cataaccatt aaacaaacga cgaccaacag   25680
accactgatt ggccaattck amwytasaag swtcccctgc cacaattatc tgacccaagg   25740
ctggaaattc atcagtagct agtactgcca gggcagaggg aggtaacgta acatgagtta   25800
cacatctttc ttgtaaaatt tgctttaaat ccgaacccgg gattaactca gaagctatag   25860
ccaaaattag cattgctcca gaagtcaaag cgataaatat ttccgaaact gaagcatcaa   25920
aacttataga agcaaattga agaacacgac tatttggttc tagataaaat aaatttttct   25980
gtgcttgaat aaggttgcac aaagaaaaat gttcaatccc aacccccttg ggaactccag   26040
tagaaccaga agtataaatc acataagcca aattatctga acataccca acatcaagat    26100 tctcctgact gtgttgctca atcactcccc aatcactatc caaacaaacc acctgtgcag   26160
tatgtgacgg caaagattcc agtagggact tttgagccaa caacacctca acacctgaat   26220
ccgccaacat ataactcaac cgttcttggg gataattggg gtcaaggggt cataagccc    26280 caccagcctt gagtatcccc aagagcccta ccaccatttc aaaagaacgc tccacgtaaa   26340
tccctaccag cacctctggt tcgactcgca aggaaagcag gtgatgtgct agttggttgg   26400 cttttttgatt taattgttgg taggttaact gctgattctc aaataccacc gcgactgcat   26460
ccggtgttct ctctacctgc tcttcaaaca attgatggaa acatttactg ggatattccc   26520
ttgctgtatc attccactcc accaacaact gatgccgttc tacttcactc aatagggtg    26580
```

```
attcacttac cttttgttga ggattttcca caatcgctga caataaattc tggaaatgac   26640
cagccatgcg ctcaatggtt gactcatcaa acaagtcagt gttgtactta aaaccccaa    26700 aaacagatga actcccctcc accatttcta aacctaaatc taactgacct tcctgttgag   26760
gtatttcata aggttttatc ttcaattctc cccaatcaac ataggtttct atttgattta   26820
caaacaactt ctgtatatct tgagattttt ggaactgcag tagagaaaaa gaagcctgaa   26880
aaatcggcga acgactgggg tcgcggtgtg gctgtagctt ttctaccaat agagcaaatg   26940
ggtaatcttg atgagcaagt gcttccaata cggtttggcg tacttgggcg aggaaatctt   27000
tgaaactggg atttcccgat aaatttgctc gcataacaac aggatcaaca aagtagccca   27060
agatcgaagc aaacttagct tgactcctac ctgaggtggg agaaccgact aaaatatcct   27120
cctggcctgt gtaacgatac aaaaacacct gaaaagttgc taagagcatc atgtaaagtg   27180
ttgctcccga gtttaaagcc agctccttga gttgcttagt gagcttgtca gataatttga   27240
agtgatggga agcaccatta taagttttta tcggtggtcg ctgtcttgag gttgctaggt   27300
ttagtgctgg caaatcgcct gtcagttttt gctgccagta gttccagagt cttccccctt   27360
cagtctcctg caaaatattc ctctgccaac gaacgtaatc ttggtaagaa tgctttagag   27420
gagaaagggg tgtcttaaaa tcagcccatt gtacttggta gagttgtggc aactcctgta   27480
ttaacatatc taaagaccag gcatcgcaag caatgtggtg tatggttagc aacaggacat   27540
gttcttcctt ggaacgagta accaccgaa ctcgcataac aggccctcgt tcgaggtcaa    27600
aatattgttg atggctctca atcactttcc ctttcagttc atcttcactc caagcagaag   27660
catcaatttg caagaaattt aattcctgaa aattatttac ctgttggatt gactcagatc   27720
cgagtttggg ataatttgta cgcaatatcg gatgccgttc tattagtttc tcaaatgcct   27780
tttgcattgc tgtaatatct actgttgagc aaatacgagc gacaaatgat acgttataag   27840
catgactttc tggtgctaat tgccacaaaa accaaagtgc ccgttgaccg taagaaaggg   27900
gatagacgtt taaaatatct gggcgatcgc gcagcaattg taatatttcg gttttgtatt   27960
gtttcagttg agctaatact aaagcagttg attcttcttg aggagcatcg taacaaagcc   28020
gttcgccctc actccacact tgccaacctt ttattgaaat atcttgtaaa aattcgatta   28080
aattcataat tcacctctta tccgctcgtt ttctttccta ttgctttggt agagttgccc   28140
attattttct gactcaactc cttgattctg agcaacttgg ctcagttgct cattcacttc   28200
agtggctaaa tcaacgatac tgatatcttc tataaatttg actatagata tatccacgag   28260
caagtcagtt tgaagcctat tgtgcaattc cacagccatt agagaatcaa gccccatagt   28320
gttcaggggc tgttgcatat caatttgaga agtgctcaaa gaaagtactt gagaaatttc   28380
atctttaatg taaattatca aaagcttttc tctttctctt ggtaaagcag cttttagctg   28440
ttctaaaaat tcattgtgct ttgtctttgt tttgagggct ttttgctgtg atttgctttc   28500
ttttaccaat tgggacagca atggtatttg attaccaaaa ctaaattgct cttggaacac   28560
tgaccattga attggtagga ctcctacttg tggtatggat tgttcgagta attgtcctag   28620
aacctgcaat ccctgttctg aagacaaaaa agtcattccc ttggacacca ttctatcttg   28680
atgaggacta tccaaatttg ctgccattcc ctcttgtgcc catggtcccc agttaatgct   28740
caagccaggt aaacccatac cccgtcgatg atgggctaaa ccatccatga aagcattagc   28800
agcagcataa ttcccttgac caggcgaacc caatattgaa gccatagagg aaaaacaaac   28860 aaaaagtcc aaaggtagat tctgagtcaa attatgcaaa tgccaagccc cttgtacttt    28920
tggtgccatc acctgtgtaa attttcccca attcatgttt aacagcaaac catcatccaa   28980
```

```
tatcccagca gcatgaatta ttcctcgtaa tgctggcaaa gatactttga ttgactctat    29040
aattcttgcc acattttctt gttgggaaat atctccacac aggactaata cttgcgctcc    29100
tgccttctgt aattgttcaa tggttttgttg agcttttgct gatggctgcc tacgtccggt    29160
aagtactaaa tatttgaccc cttgttgtac catccactca gcggttttta accccagtgc    29220
tcccagacct ccggtaatta agtaactggc ttcggcttgg attaggttgt ctaaagactt    29280
atattctgat agcttcagtt gaaatggttg ttgcgaggaa atttgtaatc cggactgtgt    29340
agatgtactc attttttgtt gccgctctaa ccgggcaacg tgacgtaccc cttgacagta    29400
agcaatttgg ttttcatcac caggagataa tagttcctct aacaaagcag ctactgtttg    29460
ggaatcttcc atagttggat ctaagtctaa acaccggcat tgtaattccc tatgttcctg    29520
ggcaattact cgacctaacc cccataaagg tgtttgttgg aattgtatag aagggactc    29580 attacccaca gattgtgagc cttgagtcac taaccataat ggggcacttt ccatatcttg    29640 atttttact aaggcttgga ctaaatgaag tacgctgcca cagcccagtt cttgggattt    29700
ttgcaactcc tgtgccccag tccttagtgc tattgttgag tccaaactcc acaggtgaat    29760
aattcctcgt aatgggggtt gctgctccaa gcttgattgc aataggtgca ggaattcctc    29820
aggatggttg gggttgattt gataatgttg agattctaac tgctggtaat tttcccctgg    29880
tgttactaat atacaatgcc aaccttgttg ttctaaggat tctaccagat gtttgcctat    29940
acctgtgggt ggggaaaaca ataaccagct acctgatttt gttaagtcaa ttgattggtt    30000
atggggtgaa attgattggg tttgccaatg gatttgatat aaccaattat taaattttgg    30060
ttcaatatta cgcaacaaag cctcgcgaga agtacgtaat aaagttaaac cttcaactct    30120
tgctactact attccttgtt catccaataa acaaacttta ccgctcaaag tttgtttatt    30180
agtttctgtt gcacctatct ctacttgagt ccacaaacta ttactaccac tccgataaat    30240
ttgtagtcgt tttatttcca atggcaaata agtttcttgg ttgtccgttt tacccataac    30300
tgctgctaac acctggaagc tagcatctaa aagaattggg tgcagttggt ataaagttgc    30360
aacattcacc tcagtttctg gtaactgaat ttcacctagt gcttttcctt cgctgtgcca    30420
cagttgttta acggcttgga aagaagaacc gtaattaaga ccccattctt caaatttttg    30480
gtagaattca gtaggtaata tctgttggtt atactcgtct ttaatcgctt ttaagtttgt    30540
tgtttctaat tgggggtctt tattacctac taatattttt ccttcaatat gtagaatcca    30600
tttaggttct gaagaattag tgtttatatc caaactgaaa atttggaatt tatagctttg    30660
tactaactgt aaatttaaaa ctatctgaat tgtattaatt tcatcctttg ataaaattaa    30720
tactttttgg attgctatat cttctaggat taaatcatct gaattgaata aaattgaacc    30780
tgctgctaag gctatttcca agtaagctgc tgctgggaaa acaggttgag aaaaaacaca    30840
gtggtgttgc aggtaagttg gttgagaagc actaatttga cattcaaaac gaatttgctg    30900
ttctaaggct gctaaatgta atctttgacc gagtagaggg tgaagatttt tatgatttga    30960
taaaaactgt ttttgatgta ttagattatt atttgtctca atccaataac gttgccgttg    31020
aaagggataa gtcggcaata ctaccttgct acgagaataa tctttatcaa accctaacca    31080 atcaactttta actccatgca catatagttc agccaaactt tgtagcattt gctgccagtc    31140
ttcttgacct ggtttcaaag aaggcaacca aactcccaca tcttctggca agcactgtct    31200
tcccatgcct aacaaagttg gtttgggtcc aatttctaag aagatggaat aaccttcttg    31260
ctgtaatgtg tccatacttt gggcaaattt caccggttgc cggacatgat ttacccaata    31320
gcttgctgtg gcaatactat tctctgccct agctcccgtt acatttgata ctaatggaat    31380
```

-continued

```
atttggttga ttgtaggtta tttctgatgc tactgcttca aagtccgcca acattggttc   31440
catcaaatgt gaatggaatg cgtgggatac ttgcagtcgt tttgtcttaa tgtcttctgc   31500
ttctaagcta ttttgaaccg ctccaattgc ttctgcctca ccagaaatga caatgctttg   31560
gggtccgtta atcgatgcga tcgctacttt ttgagagtat ggtgcaatta gttgatttac   31620
cttttcaatt gaagccatta cagataacat ttcacccccca gagggtaact gttgcattag   31680
tcttcctcta tgagcaatca gttttaaacc atcttctaaa ctaaatattc ctgctactgt   31740
ggctgccaca tattccccag cactatgccc cataaccaca tccggtttta ttccccagga   31800
ttcccatagt ttataaagag catattctat tgcaaataaa gctacttggg tataggcggt   31860
ttgagctagg acattttcct gtacttgagc gacatcaagt atttctaata aggtttgtc   31920 taagtagttt tctaatattt gggcacattg atcgctagta cctctccata aaacttggta   31980
tacgcaacta attgcttcac caattccggt tgatacttta atattcctgc gtctaccacc   32040
gcaactattt tcttcggctt tgtctcctca tctgccgaaa ttacttgcgc tagcgtcggg   32100
tttttcaact caaataaatt ttgggtgaag taaatctcat agttaaaagt aaccgaaaca   32160
cgttgatgaa ttaatctatt tttttgcttg atgtcaacta tcatattttt gcaggtatat   32220
ctaaaagtgc agtactattc aaagcttcaa ggaaaacctc aaccgagtga gaaccattta   32280
ccttgacttg attattcatg atgaaaaacg gcacgctgtt gatgccattt aagcgagcaa   32340
atgccgattc agcaacaact gtatcaacga catcgcgatc gtttaattgc aactttaatt   32400
cggtagcatc catctggtat gctgtaccga tggcaacaat aacgttaata tctccaatat   32460
tcaaaccctc ttcaaagtaa gctctataaa tagcttcaac gacatcattt tttatgtttg   32520
tcggtgctaa tgcaatcagt tggtgagcaa gcttagtatt gacagccaaa cggattttt   32580 caaaatctag cttaaccccca gccgcctccc ctgcgcgttg cgtataatca acatctgtt   32640 gcatttctgg cgctttaatg ccttttctat tttgcataaa gctactaaat tcgtaccct   32700 cagcaggaac agtatcatcc agaagaaagg gatgccatcg gatatttact tcttgttctt   32760
gccattgtgc cagtgcatca aatagatgtt ttttcccaat tctgcaccaa gggcaaacgg   32820
tatcatgaaa gatatctatc agcatagttt ttgtcactca aatgctaata tttgtgtgca   32880
tctggggttt aaaatctcgt tgcagagccg ttgtatttaa aggctggaga aaactattaa   32940
ttttctcttc aaaaaaactt tgagtatttt caaactcttt aattaatgcc tctctatcct   33000
tcctagccac cagtctagcc aatcggctgt aagttttagc taaaaagcta atagcattac   33060 accttttcttc agtcgctagc ataatatcaa cgcataaatt aggattttgc gaaaataaac   33120
gttttacaat atcaatctct tgacgatagt taggagttga cattgttaaa ctctgctcta   33180
tctctactct tgattgtgct aagaaaacac caagactaaa tctacagaaa tgctgcgtgg   33240
cttgaataat caccatcatt                                              33260
```

<210> SEQ ID NO 2
<211> LENGTH: 3690
<212> TYPE: DNA
<213> ORGANISM: Nostoc species

<400> SEQUENCE: 2

```
atggggcata gtgctgggga atatgtggca gccacagtag caggaatatt tagtttagaa    60
gatggtttaa aactgattgc tcatagagga agactaatgc aacagttacc ctctgggggt   120
gaaatgttat ctgtaatggc ttcaattgaa aaggtaaatc aactaattgc accatactct   180
caaaaagtag cgatcgcatc gattaacgga ccccaaagca ttgtcatttc tggtgaggca   240
```

```
gaagcaattg gagcggttca aaatagctta gaagcagaag acattaagac aaaacgactg      300
caagtatccc acgcattcca ttcacatttg atggaaccaa tgttggcgga ctttgaagca      360
gtagcatcag aaataaccta caatcaacca aatattccat tagtatcaaa tgtaacggga      420
gctagggcag agaatagtat tgccacagca agctattggg taaatcatgt ccggcaaccg      480
gtgaaatttg cccaaagtat ggacacatta cagcaagaag ttattccat cttcttagaa       540 attggaccca aaccaacttt gttaggcatg gaagacagt gcttgccaga agatgtggga       600
gtttggttgc cttctttgaa accaggtcaa gaagactggc agcaaatgct acaaagtttg      660
gctgaactat atgtgcatgg agttaaagtt gattggttag ggtttgataa agattattct      720
cgtagcaagg tagtattgcc gacttatccc tttcaacggc aacgttattg gattgagaca      780
aataataatc taatacatca aaaacagttt ttatcaaatc ataaaaatct tcaccctcta      840
ctcggtcaaa gattacattt agcagcctta gaacagcaaa ttcgttttga atgtcaaatt      900
agtgcttctc aaccaactta cctgcaacac cactgtgttt tttctcaacc tgttttccca      960
gcagcagctt acttggaaat agccttagca gcaggttcaa ttttattcaa ttcagatgat      1020
ttaatcctag aagatatagc aatccaaaaa gtattaattt tatcaaagga tgaaattaat      1080
acaattcaga tagttttaaa tttacagtta gtacaaagct ataaattcca aattttcagt      1140
ttggatataa acactaattc ttcagaacct aaatggattc tacatattga aggaaaaata      1200
ttagtaggta ataaagaccc ccaattagaa acaacaaact aaaagcgat taaagacgag       1260 tataaccaac agatattacc tactgaattc taccaaaaat ttgaagaatg gggtcttaat      1320
tacggttctt cttttccaag ccgttaaaca actgtggcaca gcgaaggaaa agcactaggt     1380
gaaattcagt taccagaaac tgaggtgaat gttgcaactt taccaact gcacccaatt       1440 cttttagatg ctagcttcca ggtgttagca gcagttatgg gtaaaacgga caaccaagaa     1500
acttatttgc cattggaaat aaaacgacta caaatttatc ggagtggtag taatagtttg     1560
tggactcaag tagagatagg tgcaacagaa actaataaac aaactttgag cggtaaagtt      1620
tgtttattgg atgaacaagg aatagtagta gcaagagttg aaggtttaac tttattacgt      1680
acttctcgcg aggctttgtt gcgtaatatt gaaccaaaat ttaataattg gttatatcaa      1740
atccattggc aaacccaatc aatttcaccc cataaccaat caattgactt aacaaaatca      1800
ggtagctggt tattgttttc cccacccaca ggtataggca aacatctggt agaatcctta     1860
gaacaacaag gttggcattg tatattagta acaccagggg aaaattacca gcagttagaa      1920
tctcaacatt atcaaatcaa ccccaaccat cctgaggaat tcctgcacct attgcaatca      1980
agcttggagc agcaacccc attacgagga attattcacc tgtggagttt ggactcaaca       2040
atagcactaa ggactggggc acaggagttg caaaaatccc aagaactggg ctgtggcagc      2100
gtacttcatt tagtccaagc cttagtaaaa aatcaagata tggaaagtgc cccattatgg      2160
ttagtgactc aaggctcaca atctgtgggt aatgagtccc ttcctataca attccaacaa      2220 acaccttat gggggttagg tcgagtaatt gcccaggaac atagggaatt acaatgccgg       2280
tgtttagact tagatccaac tatggaagat tcccaaacag tagctgcttt gttagaggaa      2340
ctattatctc ctggtgatga aaaccaaatt gcttactgtc aaggggtacg tcacgttgcc      2400
cggttagagc ggcaacaaaa aatgagtaca tctacacagt ccggattaca aatttcctcg      2460
caacaaccat ttcaactgaa gctatcagaa tataagtctt tagacaacct aatccaagcc      2520
gaagccagtt acttaattac cggaggtctg gagcactgg ggttaaaaac cgctgagtgg       2580
atggtacaac aaggggtcaa atatttagta cttaccggac gtaggcagcc atcagcaaaa      2640
```

-continued

```
gctcaacaaa ccattgaaca attacagaag gcaggagcgc aagtattagt cctgtgtgga   2700
gatatttccc aacaagaaaa tgtggcaaga attatagagt caatcaaagt atctttgcca   2760
gcattacgag gaataattca tgctgctggg atattggatg atggtttgct gttaaacatg   2820
aatgggaaaa aatttacaca ggtgatggca ccaaaagtac aaggggcttg gcatttgcat   2880
aatttgactc agaatctacc tttggacttt tttgtttgtt tttcctctat ggcttcaata   2940
ttgggttcgc ctggtcaagg gaattatgct gctgctaatg ctttcatgga tggtttagcc   3000
catcatcgac ggggtatggg tttacctggc ttgagcatta actggggacc atgggcacaa   3060
gagggaatgg cagcaaattt ggatagtcct catcaagata aatggtgtc caagggaatg   3120
acttttttgt cttcagaaca gggattgcag gttctaggac aattactcga caatccata   3180
ccacaagtag gagtcctacc aattcaatgg tcagtgttcc aagagcaatt tagttttggt   3240
aatcaaatac cattgctgtc ccaattggta aagaaagca atcacagca aaaagccctc    3300
aaaacaaaga caaagcacaa tgaattttta gaacagctaa aagctgcttt accaagagaa   3360
agagaaaagc ttttgataat ttacattaaa gatgaaattt ctcaagtact ttctttgagc   3420
acttctcaaa ttgatatgca acagcccctg aacactatgg ggcttgattc tctaatggct   3480
gtggaattgc acaataggct tcaaactgac ttgctcgtgg atatatctat agtcaaattt   3540
atagaagata tcagtatcgt tgatttagcc actgaagtga atgagcaact gagccaagtt   3600
gctcagaatc aaggagttga gtcagaaaat aatgggcaac tctaccaaag caataggaaa   3660
gaaaacgagc ggataagagg tgaattatga                                    3690
```

<210> SEQ ID NO 3
<211> LENGTH: 1229
<212> TYPE: PRT
<213> ORGANISM: Nostoc species

<400> SEQUENCE: 3

```
Met Gly His Ser Ala Gly Glu Tyr Val Ala Ala Thr Val Ala Gly Ile
  1               5                  10                  15

Phe Ser Leu Glu Asp Gly Leu Lys Leu Ile Ala His Arg Gly Arg Leu
                 20                  25                  30

Met Gln Gln Leu Pro Ser Gly Gly Glu Met Leu Ser Val Met Ala Ser
             35                  40                  45

Ile Glu Lys Val Asn Gln Leu Ile Ala Pro Tyr Ser Gln Lys Val Ala
         50                  55                  60

Ile Ala Ser Ile Asn Gly Pro Gln Ser Ile Val Ile Ser Gly Glu Ala
 65                  70                  75                  80

Glu Ala Ile Gly Ala Val Gln Asn Ser Leu Glu Ala Glu Asp Ile Lys
                 85                  90                  95

Thr Lys Arg Leu Gln Val Ser His Ala Phe His Ser His Leu Met Glu
                100                 105                 110

Pro Met Leu Ala Asp Phe Glu Ala Val Ala Ser Glu Ile Thr Tyr Asn
            115                 120                 125

Gln Pro Asn Ile Pro Leu Val Ser Asn Val Thr Gly Ala Arg Ala Glu
        130                 135                 140

Asn Ser Ile Ala Thr Ala Ser Tyr Trp Val Asn His Val Arg Gln Pro
145                 150                 155                 160

Val Lys Phe Ala Gln Ser Met Asp Thr Leu Gln Gln Glu Gly Tyr Ser
                165                 170                 175

Ile Phe Leu Glu Ile Gly Pro Lys Pro Thr Leu Leu Gly Met Gly Arg
            180                 185                 190
```

-continued

```
Gln Cys Leu Pro Glu Asp Val Gly Val Trp Leu Pro Ser Leu Lys Pro
        195                 200                 205

Gly Gln Glu Asp Trp Gln Gln Met Leu Gln Ser Leu Ala Glu Leu Tyr
    210                 215                 220

Val His Gly Val Lys Val Asp Trp Leu Gly Phe Asp Lys Asp Tyr Ser
225                 230                 235                 240

Arg Ser Lys Val Val Leu Pro Thr Tyr Pro Phe Gln Arg Gln Arg Tyr
                245                 250                 255

Trp Ile Glu Thr Asn Asn Leu Ile His Gln Lys Gln Phe Leu Ser
        260                 265                 270

Asn His Lys Asn Leu His Pro Leu Gly Gln Arg Leu His Leu Ala
        275                 280                 285

Ala Leu Glu Gln Gln Ile Arg Phe Glu Cys Gln Ile Ser Ala Ser Gln
    290                 295                 300

Pro Thr Tyr Leu Gln His His Cys Val Phe Ser Gln Pro Val Phe Pro
305                 310                 315                 320

Ala Ala Ala Tyr Leu Glu Ile Ala Leu Ala Ala Gly Ser Ile Leu Phe
                325                 330                 335

Asn Ser Asp Asp Leu Ile Leu Glu Asp Ile Ala Ile Gln Lys Val Leu
            340                 345                 350

Ile Leu Ser Lys Asp Glu Ile Asn Thr Ile Gln Ile Val Leu Asn Leu
        355                 360                 365

Gln Leu Val Gln Ser Tyr Lys Phe Gln Ile Phe Ser Leu Asp Ile Asn
    370                 375                 380

Thr Asn Ser Ser Glu Pro Lys Trp Ile Leu His Ile Glu Gly Lys Ile
385                 390                 395                 400

Leu Val Gly Asn Lys Asp Pro Gln Leu Glu Thr Thr Asn Leu Lys Ala
                405                 410                 415

Ile Lys Asp Glu Tyr Asn Gln Gln Ile Leu Pro Thr Glu Phe Tyr Gln
            420                 425                 430

Lys Phe Glu Glu Trp Gly Leu Asn Tyr Gly Ser Ser Phe Gln Ala Val
        435                 440                 445

Lys Gln Leu Trp His Ser Glu Gly Lys Ala Leu Gly Glu Ile Gln Leu
    450                 455                 460

Pro Glu Thr Glu Val Asn Val Ala Thr Leu Tyr Gln Leu His Pro Ile
465                 470                 475                 480

Leu Leu Asp Ala Ser Phe Gln Val Leu Ala Ala Val Met Gly Lys Thr
                485                 490                 495

Asp Asn Gln Glu Thr Tyr Leu Pro Leu Glu Ile Lys Arg Leu Gln Ile
            500                 505                 510

Tyr Arg Ser Gly Ser Asn Ser Leu Trp Thr Gln Val Glu Ile Gly Ala
        515                 520                 525

Thr Glu Thr Asn Lys Gln Thr Leu Ser Gly Lys Val Cys Leu Leu Asp
    530                 535                 540

Glu Gln Gly Ile Val Val Ala Arg Val Glu Gly Leu Thr Leu Leu Arg
545                 550                 555                 560

Thr Ser Arg Glu Ala Leu Leu Arg Asn Ile Glu Pro Lys Phe Asn Asn
                565                 570                 575

Trp Leu Tyr Gln Ile His Trp Gln Thr Gln Ser Ile Ser Pro His Asn
            580                 585                 590

Gln Ser Ile Asp Leu Thr Lys Ser Gly Ser Trp Leu Leu Phe Ser Pro
        595                 600                 605
```

-continued

```
Pro Thr Gly Ile Gly Lys His Leu Val Glu Ser Leu Glu Gln Gln Gly
    610                 615                 620

Trp His Cys Ile Leu Val Thr Pro Gly Glu Asn Tyr Gln Gln Leu Glu
625                 630                 635                 640

Ser Gln His Tyr Gln Ile Asn Pro Asn His Pro Glu Glu Phe Leu His
                645                 650                 655

Leu Leu Gln Ser Ser Leu Glu Gln Gln Pro Pro Leu Arg Gly Ile Ile
                660                 665                 670

His Leu Trp Ser Leu Asp Ser Thr Ile Ala Leu Arg Thr Gly Ala Gln
            675                 680                 685

Glu Leu Gln Lys Ser Gln Glu Leu Gly Cys Gly Ser Val Leu His Leu
    690                 695                 700

Val Gln Ala Leu Val Lys Asn Gln Asp Met Glu Ser Ala Pro Leu Trp
705                 710                 715                 720

Leu Val Thr Gln Gly Ser Gln Ser Val Gly Asn Glu Ser Leu Pro Ile
                725                 730                 735

Gln Phe Gln Gln Thr Pro Leu Trp Gly Leu Gly Arg Val Ile Ala Gln
                740                 745                 750

Glu His Arg Glu Leu Gln Cys Arg Cys Leu Asp Leu Asp Pro Thr Met
            755                 760                 765

Glu Asp Ser Gln Thr Val Ala Ala Leu Leu Glu Glu Leu Leu Ser Pro
    770                 775                 780

Gly Asp Glu Asn Gln Ile Ala Tyr Cys Gln Gly Val Arg His Val Ala
785                 790                 795                 800

Arg Leu Glu Arg Gln Gln Lys Met Ser Thr Ser Thr Gln Ser Gly Leu
                805                 810                 815

Gln Ile Ser Ser Gln Gln Pro Phe Gln Leu Lys Leu Ser Glu Tyr Lys
                820                 825                 830

Ser Leu Asp Asn Leu Ile Gln Ala Glu Ala Ser Tyr Leu Ile Thr Gly
            835                 840                 845

Gly Leu Gly Ala Leu Gly Leu Lys Thr Ala Glu Trp Met Val Gln Gln
    850                 855                 860

Gly Val Lys Tyr Leu Val Leu Thr Gly Arg Arg Gln Pro Ser Ala Lys
865                 870                 875                 880

Ala Gln Gln Thr Ile Glu Gln Leu Gln Lys Ala Gly Ala Gln Val Leu
                885                 890                 895

Val Leu Cys Gly Asp Ile Ser Gln Gln Glu Asn Val Ala Arg Ile Ile
                900                 905                 910

Glu Ser Ile Lys Val Ser Leu Pro Ala Leu Arg Gly Ile Ile His Ala
            915                 920                 925

Ala Gly Ile Leu Asp Asp Gly Leu Leu Leu Asn Met Asn Trp Glu Lys
    930                 935                 940

Phe Thr Gln Val Met Ala Pro Lys Val Gln Gly Ala Trp His Leu His
945                 950                 955                 960

Asn Leu Thr Gln Asn Leu Pro Leu Asp Phe Phe Val Cys Phe Ser Ser
                965                 970                 975

Met Ala Ser Ile Leu Gly Ser Pro Gly Gln Gly Asn Tyr Ala Ala Ala
                980                 985                 990

Asn Ala Phe Met Asp Gly Leu Ala His His Arg Arg Gly Met Gly Leu
            995                1000                1005

Pro Gly Leu Ser Ile Asn Trp Gly Pro Trp Ala Gln Glu Gly Met Ala
    1010                1015                1020
```

```
Ala Asn Leu Asp Ser Pro His Gln Asp Arg Met Val Ser Lys Gly Met
1025                1030                1035                1040

Thr Phe Leu Ser Ser Glu Gln Gly Leu Gln Val Gly Gln Leu Leu
        1045                1050                1055

Glu Gln Ser Ile Pro Gln Val Gly Val Leu Pro Ile Gln Trp Ser Val
            1060                1065                1070

Phe Gln Glu Gln Phe Ser Phe Gly Asn Gln Ile Pro Leu Leu Ser Gln
        1075                1080                1085

Leu Val Lys Glu Ser Lys Ser Gln Gln Lys Ala Leu Lys Thr Lys Thr
    1090                1095                1100

Lys His Asn Glu Phe Leu Glu Gln Leu Lys Ala Ala Leu Pro Arg Glu
1105                1110                1115                1120

Arg Glu Lys Leu Leu Ile Ile Tyr Ile Lys Asp Glu Ile Ser Gln Val
            1125                1130                1135

Leu Ser Leu Ser Thr Ser Gln Ile Asp Met Gln Gln Pro Leu Asn Thr
        1140                1145                1150

Met Gly Leu Asp Ser Leu Met Ala Val Glu Leu His Asn Arg Leu Gln
    1155                1160                1165

Thr Asp Leu Leu Val Asp Ile Ser Ile Val Lys Phe Ile Glu Asp Ile
    1170                1175                1180

Ser Ile Val Asp Leu Ala Thr Glu Val Asn Glu Gln Leu Ser Gln Val
1185                1190                1195                1200

Ala Gln Asn Gln Gly Val Glu Ser Glu Asn Asn Gly Gln Leu Tyr Gln
            1205                1210                1215

Ser Asn Arg Lys Glu Asn Glu Arg Ile Arg Gly Glu Leu
            1220                1225

<210> SEQ ID NO 4
<211> LENGTH: 5832
<212> TYPE: DNA
<213> ORGANISM: Nostoc species

<400> SEQUENCE: 4
atgaatttaa tcgaattttt acaagatatt tcaataaaag gttggcaagt gtggagtgag      60
ggcgaacggc tttgttacga tgctcctcaa gaagaatcaa ctgctttagt attagctcaa     120
ctgaaacaat acaaaaccga atattacaa ttgctgcgcg atcgcccaga tattttaaac     180
gtctatcccc tttcttacgg tcaacgggca ctttggtttt tgtggcaatt agcaccagaa     240
agtcatgctt ataacgtatc atttgtcgct cgtatttgct caacagtaga tattacagca     300
atgcaaaagg catttgagaa actaatagaa cggcatccga tattgcgtac aaattatccc     360
aaactcggat ctgagtcaat ccaacaggta ataattttc aggaattaaa tttcttgcaa     420
attgatgctt ctgcttggag tgaagatgaa ctgaaaggga agtgattga gagccatcaa     480 caatattttg acctcgaacg agggcctgtt atgcgagttc ggtggtttac tcgttccaag     540
aaagaacatg tcctgttgct aaccatacac acattgctt gcgatgcctg gtctttagat     600
atgttaatac aggagttgcc acaactctac caagtacaat gggctgattt aagacaccc      660 ctttctcctc taaagcattc ttaccaagat tacgttcgtt ggcagaggaa tattttgcag     720
gagactgaag gggaaagact ctggaactac tggcagcaaa aactgacagg cgatttgcca     780
gcactaaacc tagcaacctc aagacagcga ccaccgataa aaacttataa tggtgcttcc     840
catcacttca aattatctga caagctcact aagcaactca aggagctggc tttaaactcg     900
ggagcaacac tttacatgat gctcttagca acttttcagg tgttttgta tcgttacaca     960
```

-continued

```
ggccaggagg atattttagt cggttctccc acctcaggta ggagtcaagc taagtttgct    1020
tcgatcttgg gctactttgt tgatcctgtt gttatgcgag caaatttatc gggaaatccc    1080
agtttcaaag atttcctcgc ccaagtacgc caaaccgtat tggaagcact tgctcatcaa    1140
gattacccat ttgctctatt ggtagaaaag ctacagccac accgcgaccc cagtcgttcg    1200 ccgattttc aggcttcttt ttctctactg cagttccaaa aatctcaaga tatacagaag    1260
ttgtttgtaa atcaaataga aacctatgtt gattggggaa aattgaagat aaaaccttat    1320
gaaatacctc aacaggaagg tcagttagat ttaggtttag aaatggtgga ggggagttca    1380
tctgtttttg gggtttttaa gtacaacact gacttgtttg atgagtcaac cattgagcgc    1440
atggctggtc atttccagaa tttattgtca gcgattgtgg aaaatcctca acaaaaggta    1500
agtgaatcac ccctattgag tgaagtagaa cggcatcagt tgttggtgga gtggaatgat    1560
acagcaaggg aatatcccag taaatgtatc catcaattgt ttgaagagca ggtagagaga    1620
acaccggatg cagtcgcggt ggtatttgag aatcagcagt taacctacca acaattaaat    1680
caaaaagcca accaactagc acatcacctg cttttccttgc gagtcgaacc agaggtgctg    1740
gtagggattt acgtggagcg ttcttttgaa atggtggtag ggctcttggg gatactcaag    1800
gctggtgggg cttatgtacc ccttgacccc aattatcccc aagaacggtt gagttatatg    1860
ttggcggatt caggtgttga ggtgttgttg gctcaaaagt ccctactgga atctttgccg    1920
tcacatactg cacaggtggt ttgtttggat agtgattggg gagtgattga gcaacacagt    1980
caggagaatc ttgatgttgg ggtatgttca gataatttgg cttatgtgat ttatacttct    2040
ggttctactg gagttcccaa gggggttggg attgaacatt tttctttgtg caaccttatt    2100
caagcacaga aaaatttatt ttatctagaa ccaaatagtc gtgttcttca atttgcttct    2160
ataagttttg atgcttcagt ttcggaaata tttatcgctt tgacttctgg agcaatgcta    2220
attttggcta tagcttctga gttaatcccg ggttcggatt taaagcaaat tttacaagaa    2280
agatgtgtaa ctcatgttac gttacctccc tctgccctgg cagtactagc tactgatgaa    2340
tttccagcct tgggtcagat aattgtggca ggggawsctt staywmtkga attggccaat    2400
cagtggtctg ttggtcgtcg tttgtttaat ggttatgggc ctactgagtc tactattggt    2460
gctgcagtgg ctcaaatcag ccatggtagc gagaaagtta ctatcggtcg ccccattgca    2520
aacacccaaa tctatatctt agataagcac ttagaaccag tacccataag tgtatccgga    2580
gaattataca tcggaggtta tggcttagcc agaggttacc tcaaccgacc ggaattaact    2640
ttagagaaat tcatccctaa ccccttcaat agcagatcaa aactatataa aactggagat    2700
ttagctcgat acttaccaga tggtaatatt gagtttcttg gtcgtcttga taaccaggtg    2760
aaaatacgtg gtttccgcat agaactagga gaaatagaat cagttctgag tacccatcct    2820
caagtacagc aagtcgcagt caccgaaagg gaagatactc cgggtcacaa acggttggta    2880
gcatatttag ttcctcttca gtcaaaagaa aaagatcccc agcccagac aggaattgaa    2940 ctttggccct cagtagcaga attctacgtt tatgatgagc tcttgtacta tgcgatgacc    3000
aatgatcatc gtcgaaacca gagttaccaa gtcgcaatta atcaaatggt taagataaa    3060 gtagttgttg aaattggcac gggcaaggat gcaattatag ccagatttg tgcagaagca    3120 ggtgctaaga agtctacgc aattgagaga gacgagcaaa ccagtaagtt agcttcagct    3180
tgcgtgcaag agttgggggtt atcagaacaa attcaaatca tacatggaga cgctactaca    3240
gccaacttac cagaagaagt tgatgtatgt gtttctgaaa ttgtgggacc cattggtgga    3300
tctgaaggag cagcagtaat tatcaacaac gccagaagat ttctcaaatc agatggtgta    3360
```

```
atgattcccc aaagaagtgt gactcaaatt attgcagtaa ctcttcctga tgaattacta    3420
aatcaacccc aatttacaaa agtttcaggt tattataccc agaagatatt tgagcaagtt    3480
ggatatcctt ttgatttacg agtatgtatt aaaggattaa atcaagtaaa ctggttgtcc    3540
aatcgaggag tttttgagga tttagacttt agcaagcttg ttagcacaga atctactcac    3600
caaattaaat taactattga aaaatcagga agattagatg ttttttcagt gggattaaac    3660
ttacacacaa ttgaaggaga atgtatagat attttagaaa atgaacattg ctggttacca    3720
gtttatcttc cagtgtttga accaggaatt tatgtaaatg aaggagatat catcgaagct    3780
gtttgtacga gaacgctttg tgaaaataat ttgaatccag attatactct tcgaggtcgt    3840
cttttaaaaa aaactggaaa agagattgag tttgaataca tctcatatca ttggaaacaa    3900
ttgtttaagc aaaacccttt ttatcaacga ttgtttgctg aaaataatct agaagattac    3960
acaattaata agtcaaagcc tgaacgtaag gtactgagta gcaatgaatt gcgctcctac    4020
ctaaagtcta aattgccaga atatatgctc ccctctagct ttgtcatctt agacacccta    4080
ccgttgacac ccaacggtaa agtagaccgc aaagccctaa gtgcacctga tggggaagtt    4140
agccgagagg atgaatatgt cgcaccacgc acagaaatag aacaaatctt aaccaacatt    4200
tggcawgaac tgctccttaa agaacaagtc agcatccatg acaacttctt tgaaattggt    4260
ggcgactcca tccttggtat tcaagtagtt tctcgtgcca aaaacttagg aatacaaatc    4320
actcccaaac aaatattcca aaatcaaacc atcgccaaac tagcattagt agccaataca    4380
acagttactg tcagtgctaa ccaaggtata gttactggag ttgcacccct aacaccaatt    4440
caacagtggt tcttttgcaca aaatagccaa gaagcacacc attacaacca atcagtttta    4500
ttgcagattc ccaatcatct gcaaactgaa ttaatcgaaa cagccttgaa aaaattatta    4560
gagcatcacg atgctctgcg tttacgattc acatcagttg catctgagta caaacaaata    4620
aaccatggct ttgatgatcc cgtagcattt actgtagttg atttatcatc aactcctgtc    4680
attgaacaac cacaagcttt atcacagatc gccacggaat atcaagcaag tttaaacctc    4740
tcagagggac ctttaatgca agtggtgatg tttaacttag gtagtgaagt tgatgcccgt    4800
ttactgatta ttattcatca cctagcagta gatggtgtga gttggcgaat tttactatca    4860
gacttagaaa caatctatca acaactaatc gctcaacaat caatacagct aaatgcgaaa    4920
acaacagcat ttattgattg ggcagagaaa ttgaaaaatt atgcacaatc agaaaaaatc    4980
aaacaagagt tagactattg gctcaaccaa ccttggtcag aaacaacacc actaccatta    5040
gattctgctc acactcaagc agaaaaaaca gttgatagtg cgattaatta tagagtgaaa    5100
ttgagtccag aagaacccg cgctttgctg gggtcagtaa actcagctta taacacacaa    5160
attaacgata tcctcctcag tgcattagta gttttccttgg cagagtggac gggagattca    5220
aaagtactaa ttgacctaga aggacatggc agagaagaac tattttcaga tgtagactta    5280
tcaagaacaa taggttggtt taccagttta ttcccagtat tattgcgatt accagacgat    5340
aaacaaccag cagaagttat caagtcaatt aaagaacaat tacgagagat tccccatcgt    5400
ggtattggct ttggtatatt gcgttacttg tgtgaagata ctactgtaac ccaaaaacta    5460
cagacaattc ctactccaga aattagtttt aactacctag acaatttga ccaaatacaa    5520
tcggaaacgg gttggaaatt tgcgccagaa tctactggag ataatcatag ttcaaagcaa    5580
actcgtcacc atctattaga gattaatagt ctggtggtag aaggtgaatt acaaattgat    5640
tggacttata gtagtaattt tcatactcat gatacagtaa aaaatttgac acaaagctat    5700
attcaagcaa ttaagtcaat aatagaacat tgccagtcag aaaatggttt tggatataca    5760
```

```
gctagtgatt tcccagatgc acagttaaat caattagaac ttgatgagtt attaaaaaac    5820
ttgggcaaat ag                                                        5832
```

<210> SEQ ID NO 5
<211> LENGTH: 1943
<212> TYPE: PRT
<213> ORGANISM: Nostoc species
<220> FEATURE:
<221> NAME/KEY: VARIANT
<222> LOCATION: 792-796, 1402
<223> OTHER INFORMATION: Xaa= Unknown

<400> SEQUENCE: 5

```
Met Asn Leu Ile Glu Phe Leu Gln Asp Ile Ser Ile Lys Gly Trp Gln
 1               5                  10                  15

Val Trp Ser Glu Gly Glu Arg Leu Cys Tyr Asp Ala Pro Gln Glu Glu
             20                  25                  30

Ser Thr Ala Leu Val Leu Ala Gln Leu Lys Gln Tyr Lys Thr Glu Ile
         35                  40                  45

Leu Gln Leu Leu Arg Asp Arg Pro Asp Ile Leu Asn Val Tyr Pro Leu
     50                  55                  60

Ser Tyr Gly Gln Arg Ala Leu Trp Phe Leu Trp Gln Leu Ala Pro Glu
 65                  70                  75                  80

Ser His Ala Tyr Asn Val Ser Phe Val Ala Arg Ile Cys Ser Thr Val
                 85                  90                  95

Asp Ile Thr Ala Met Gln Lys Ala Phe Glu Lys Leu Ile Glu Arg His
            100                 105                 110

Pro Ile Leu Arg Thr Asn Tyr Pro Lys Leu Gly Ser Glu Ser Ile Gln
        115                 120                 125

Gln Val Asn Asn Phe Gln Glu Leu Asn Phe Leu Gln Ile Asp Ala Ser
    130                 135                 140

Ala Trp Ser Glu Asp Glu Leu Lys Gly Lys Val Ile Glu Ser His Gln
145                 150                 155                 160

Gln Tyr Phe Asp Leu Glu Arg Gly Pro Val Met Arg Val Arg Trp Phe
                165                 170                 175

Thr Arg Ser Lys Lys Glu His Val Leu Leu Thr Ile His His Ile
            180                 185                 190

Ala Cys Asp Ala Trp Ser Leu Asp Met Leu Ile Gln Glu Leu Pro Gln
        195                 200                 205

Leu Tyr Gln Val Gln Trp Ala Asp Phe Lys Thr Pro Leu Ser Pro Leu
    210                 215                 220

Lys His Ser Tyr Gln Asp Tyr Val Arg Trp Gln Arg Asn Ile Leu Gln
225                 230                 235                 240

Glu Thr Glu Gly Glu Arg Leu Trp Asn Tyr Trp Gln Gln Lys Leu Thr
                245                 250                 255

Gly Asp Leu Pro Ala Leu Asn Leu Ala Thr Ser Arg Gln Arg Pro Pro
            260                 265                 270

Ile Lys Thr Tyr Asn Gly Ala Ser His His Phe Lys Leu Ser Asp Lys
        275                 280                 285

Leu Thr Lys Gln Leu Lys Glu Leu Ala Leu Asn Ser Gly Ala Thr Leu
    290                 295                 300

Tyr Met Met Leu Leu Ala Thr Phe Gln Val Phe Leu Tyr Arg Tyr Thr
305                 310                 315                 320

Gly Gln Glu Asp Ile Leu Val Gly Ser Pro Thr Ser Gly Arg Ser Gln
                325                 330                 335
```

```
Ala Lys Phe Ala Ser Ile Leu Gly Tyr Phe Val Asp Pro Val Val Met
            340                 345                 350
Arg Ala Asn Leu Ser Gly Asn Pro Ser Phe Lys Asp Phe Leu Ala Gln
            355                 360                 365
Val Arg Gln Thr Val Leu Glu Ala Leu Ala His Gln Asp Tyr Pro Phe
            370                 375                 380
Ala Leu Leu Val Glu Lys Leu Gln Pro His Arg Asp Pro Ser Arg Ser
385                 390                 395                 400
Pro Ile Phe Gln Ala Ser Phe Ser Leu Leu Gln Phe Gln Lys Ser Gln
                405                 410                 415
Asp Ile Gln Lys Leu Phe Val Asn Gln Ile Glu Thr Tyr Val Asp Trp
                420                 425                 430
Gly Glu Leu Lys Ile Lys Pro Tyr Glu Ile Pro Gln Gln Glu Gly Gln
            435                 440                 445
Leu Asp Leu Gly Leu Glu Met Val Glu Gly Ser Ser Val Phe Gly
            450                 455                 460
Val Phe Lys Tyr Asn Thr Asp Leu Phe Asp Glu Ser Thr Ile Glu Arg
465                 470                 475                 480
Met Ala Gly His Phe Gln Asn Leu Leu Ser Ala Ile Val Glu Asn Pro
                485                 490                 495
Gln Gln Lys Val Ser Glu Ser Pro Leu Leu Ser Glu Val Glu Arg His
                500                 505                 510
Gln Leu Leu Val Glu Trp Asn Asp Thr Ala Arg Glu Tyr Pro Ser Lys
            515                 520                 525
Cys Ile His Gln Leu Phe Glu Gln Val Glu Arg Thr Pro Asp Ala
            530                 535                 540
Val Ala Val Val Phe Glu Asn Gln Gln Leu Thr Tyr Gln Gln Leu Asn
545                 550                 555                 560
Gln Lys Ala Asn Gln Leu Ala His His Leu Leu Ser Leu Arg Val Glu
                565                 570                 575
Pro Glu Val Leu Val Gly Ile Tyr Val Glu Arg Ser Phe Glu Met Val
            580                 585                 590
Val Gly Leu Leu Gly Ile Leu Lys Ala Gly Ala Tyr Val Pro Leu
            595                 600                 605
Asp Pro Asn Tyr Pro Gln Glu Arg Leu Ser Tyr Met Leu Ala Asp Ser
            610                 615                 620
Gly Val Glu Val Leu Leu Ala Gln Lys Ser Leu Leu Glu Ser Leu Pro
625                 630                 635                 640
Ser His Thr Ala Gln Val Val Cys Leu Asp Ser Asp Trp Gly Val Ile
                645                 650                 655
Glu Gln His Ser Gln Glu Asn Leu Asp Val Gly Val Cys Ser Asp Asn
                660                 665                 670
Leu Ala Tyr Val Ile Tyr Thr Ser Gly Ser Thr Gly Val Pro Lys Gly
            675                 680                 685
Val Gly Ile Glu His Phe Ser Leu Cys Asn Leu Ile Gln Ala Gln Lys
            690                 695                 700
Asn Leu Phe Tyr Leu Glu Pro Asn Ser Arg Val Leu Gln Phe Ala Ser
705                 710                 715                 720
Ile Ser Phe Asp Ala Ser Val Ser Glu Ile Phe Ile Ala Leu Thr Ser
                725                 730                 735
Gly Ala Met Leu Ile Leu Ala Ile Ala Ser Glu Leu Ile Pro Gly Ser
            740                 745                 750
```

-continued

Asp Leu Lys Gln Ile Leu Gln Glu Arg Cys Val Thr His Val Thr Leu
            755                 760                 765

Pro Pro Ser Ala Leu Ala Val Leu Ala Thr Asp Glu Phe Pro Ala Leu
    770                 775                 780

Gly Gln Ile Ile Val Ala Gly Xaa Xaa Xaa Xaa Glu Leu Ala Asn
785                 790                 795                 800

Gln Trp Ser Val Gly Arg Arg Leu Phe Asn Gly Tyr Gly Pro Thr Glu
                805                 810                 815

Ser Thr Ile Gly Ala Ala Val Ala Gln Ile Ser His Gly Ser Glu Lys
                820                 825                 830

Val Thr Ile Gly Arg Pro Ile Ala Asn Thr Gln Ile Tyr Ile Leu Asp
                835                 840                 845

Lys His Leu Glu Pro Val Pro Ile Ser Val Ser Gly Glu Leu Tyr Ile
    850                 855                 860

Gly Gly Tyr Gly Leu Ala Arg Gly Tyr Leu Asn Arg Pro Glu Leu Thr
865                 870                 875                 880

Leu Glu Lys Phe Ile Pro Asn Pro Phe Asn Ser Arg Ser Lys Leu Tyr
                885                 890                 895

Lys Thr Gly Asp Leu Ala Arg Tyr Leu Pro Asp Gly Asn Ile Glu Phe
                900                 905                 910

Leu Gly Arg Leu Asp Asn Gln Val Lys Ile Arg Gly Phe Arg Ile Glu
            915                 920                 925

Leu Gly Glu Ile Glu Ser Val Leu Ser Thr His Pro Gln Val Gln Gln
        930                 935                 940

Val Ala Val Thr Glu Arg Glu Asp Thr Pro Gly His Lys Arg Leu Val
945                 950                 955                 960

Ala Tyr Leu Val Pro Leu Gln Ser Lys Glu Lys Asp Pro Gln Pro Gln
                965                 970                 975

Thr Gly Ile Glu Leu Trp Pro Ser Val Ala Glu Phe Tyr Val Tyr Asp
            980                 985                 990

Glu Leu Leu Tyr Tyr Ala Met Thr Asn Asp His Arg Arg Asn Gln Ser
    995                 1000                1005

Tyr Gln Val Ala Ile Asn Gln Met Val Lys Asp Lys Val Val Glu
    1010                1015                1020

Ile Gly Thr Gly Lys Asp Ala Ile Ile Ala Arg Phe Cys Ala Glu Ala
1025                1030                1035                1040

Gly Ala Lys Lys Val Tyr Ala Ile Glu Arg Asp Glu Gln Thr Ser Lys
                1045                1050                1055

Leu Ala Ser Ala Cys Val Gln Glu Leu Gly Leu Ser Glu Gln Ile Gln
                1060                1065                1070

Ile Ile His Gly Asp Ala Thr Thr Ala Asn Leu Pro Glu Glu Val Asp
        1075                1080                1085

Val Cys Val Ser Glu Ile Val Gly Pro Ile Gly Gly Ser Glu Gly Ala
        1090                1095                1100

Ala Val Ile Ile Asn Asn Ala Arg Arg Phe Leu Lys Ser Asp Gly Val
1105                1110                1115                1120

Met Ile Pro Gln Arg Ser Val Thr Gln Ile Ile Ala Val Thr Leu Pro
                1125                1130                1135

Asp Glu Leu Leu Asn Gln Pro Gln Phe Thr Lys Val Ser Gly Tyr Tyr
            1140                1145                1150

Thr Gln Lys Ile Phe Glu Gln Val Gly Tyr Pro Phe Asp Leu Arg Val
            1155                1160                1165

-continued

Cys Ile Lys Gly Leu Asn Gln Val Asn Trp Leu Ser Asn Arg Gly Val
            1170                1175                1180

Phe Glu Asp Leu Asp Phe Ser Lys Leu Val Ser Thr Glu Ser Thr His
1185                1190                1195                1200

Gln Ile Lys Leu Thr Ile Glu Lys Ser Gly Arg Leu Asp Gly Phe Ser
                1205                1210                1215

Val Gly Leu Asn Leu His Thr Ile Glu Gly Glu Cys Ile Asp Ile Leu
            1220                1225                1230

Glu Asn Glu His Cys Trp Leu Pro Val Tyr Leu Pro Val Phe Glu Pro
        1235                1240                1245

Gly Ile Tyr Val Asn Glu Gly Asp Ile Ile Glu Ala Val Cys Thr Arg
    1250                1255                1260

Thr Leu Cys Glu Asn Asn Leu Asn Pro Asp Tyr Thr Leu Arg Gly Arg
1265                1270                1275                1280

Leu Leu Lys Lys Thr Gly Lys Glu Ile Glu Phe Glu Tyr Ile Ser Tyr
                1285                1290                1295

His Trp Lys Gln Leu Phe Lys Gln Asn Pro Phe Tyr Gln Arg Leu Phe
            1300                1305                1310

Ala Glu Asn Asn Leu Glu Asp Tyr Thr Ile Asn Lys Ser Lys Pro Glu
        1315                1320                1325

Arg Lys Val Leu Ser Ser Asn Glu Leu Arg Ser Tyr Leu Lys Ser Lys
    1330                1335                1340

Leu Pro Glu Tyr Met Leu Pro Ser Ser Phe Val Ile Leu Asp Thr Leu
1345                1350                1355                1360

Pro Leu Thr Pro Asn Gly Lys Val Asp Arg Lys Ala Leu Ser Ala Pro
                1365                1370                1375

Asp Gly Glu Val Ser Arg Glu Asp Glu Tyr Val Ala Pro Arg Thr Glu
            1380                1385                1390

Ile Glu Gln Ile Leu Thr Asn Ile Trp Xaa Glu Leu Leu Lys Glu
        1395                1400                1405

Gln Val Ser Ile His Asp Asn Phe Phe Glu Ile Gly Gly Asp Ser Ile
    1410                1415                1420

Leu Gly Ile Gln Val Val Ser Arg Ala Lys Asn Leu Gly Ile Gln Ile
1425                1430                1435                1440

Thr Pro Lys Gln Ile Phe Gln Asn Gln Thr Ile Ala Lys Leu Ala Leu
                1445                1450                1455

Val Ala Asn Thr Thr Val Thr Val Ser Ala Asn Gln Gly Ile Val Thr
            1460                1465                1470

Gly Val Ala Pro Leu Thr Pro Ile Gln Gln Trp Phe Phe Ala Gln Asn
        1475                1480                1485

Ser Gln Glu Ala His His Tyr Asn Gln Ser Val Leu Leu Gln Ile Pro
    1490                1495                1500

Asn His Leu Gln Thr Glu Leu Ile Glu Thr Ala Leu Lys Lys Leu Leu
1505                1510                1515                1520

Glu His His Asp Ala Leu Arg Leu Arg Phe Thr Ser Val Ala Ser Glu
                1525                1530                1535

Tyr Lys Gln Ile Asn His Gly Phe Asp Asp Pro Val Ala Phe Thr Val
            1540                1545                1550

Val Asp Leu Ser Ser Thr Pro Val Ile Glu Gln Pro Gln Ala Leu Ser
        1555                1560                1565

Gln Ile Ala Thr Glu Tyr Gln Ala Ser Leu Asn Leu Ser Glu Gly Pro
    1570                1575                1580

```
Leu Met Gln Val Val Met Phe Asn Leu Gly Ser Glu Val Asp Ala Arg
1585                1590                1595                1600

Leu Leu Ile Ile Ile His His Leu Ala Val Asp Gly Val Ser Trp Arg
            1605                1610                1615

Ile Leu Leu Ser Asp Leu Glu Thr Ile Tyr Gln Gln Leu Ile Ala Gln
            1620                1625                1630

Gln Ser Ile Gln Leu Asn Ala Lys Thr Thr Ala Phe Ile Asp Trp Ala
            1635                1640                1645

Glu Lys Leu Lys Asn Tyr Ala Gln Ser Glu Lys Ile Lys Gln Glu Leu
            1650                1655                1660

Asp Tyr Trp Leu Asn Gln Pro Trp Ser Glu Thr Thr Pro Leu Pro Leu
1665                1670                1675                1680

Asp Ser Ala His Thr Gln Ala Glu Lys Thr Val Asp Ser Ala Ile Asn
            1685                1690                1695

Tyr Arg Val Lys Leu Ser Pro Glu Glu Thr Arg Ala Leu Leu Gly Ser
            1700                1705                1710

Val Asn Ser Ala Tyr Asn Thr Gln Ile Asn Asp Ile Leu Leu Ser Ala
            1715                1720                1725

Leu Val Val Ser Leu Ala Glu Trp Thr Gly Asp Ser Lys Val Leu Ile
            1730                1735                1740

Asp Leu Glu Gly His Gly Arg Glu Glu Leu Phe Ser Asp Val Asp Leu
1745                1750                1755                1760

Ser Arg Thr Ile Gly Trp Phe Thr Ser Leu Phe Pro Val Leu Leu Arg
            1765                1770                1775

Leu Pro Asp Asp Lys Gln Pro Ala Glu Val Ile Lys Ser Ile Lys Glu
            1780                1785                1790

Gln Leu Arg Glu Ile Pro His Arg Gly Ile Gly Phe Gly Ile Leu Arg
            1795                1800                1805

Tyr Leu Cys Glu Asp Thr Thr Val Thr Gln Lys Leu Gln Thr Ile Pro
            1810                1815                1820

Thr Pro Glu Ile Ser Phe Asn Tyr Leu Gly Gln Phe Asp Gln Ile Gln
1825                1830                1835                1840

Ser Glu Thr Gly Trp Lys Phe Ala Pro Glu Ser Thr Gly Asp Asn His
            1845                1850                1855

Ser Ser Lys Gln Thr Arg His His Leu Leu Glu Ile Asn Ser Leu Val
            1860                1865                1870

Val Glu Gly Glu Leu Gln Ile Asp Trp Thr Tyr Ser Ser Asn Phe His
            1875                1880                1885

Thr His Asp Thr Val Lys Asn Leu Thr Gln Ser Tyr Ile Gln Ala Ile
            1890                1895                1900

Lys Ser Ile Ile Glu His Cys Gln Ser Glu Asn Gly Phe Gly Tyr Thr
1905                1910                1915                1920

Ala Ser Asp Phe Pro Asp Ala Gln Leu Asn Gln Leu Glu Leu Asp Glu
            1925                1930                1935

Leu Leu Lys Asn Leu Gly Lys
            1940

<210> SEQ ID NO 6
<211> LENGTH: 10032
<212> TYPE: DNA
<213> ORGANISM: Nostoc species
```

```
<400> SEQUENCE: 6
atgagcaacg aagaaattag aagaaatatc tcttcaatttt atccactttc tcccatgcaa    60
caagggatgc tgttccacag tctttatgca ccttatagtg gggtatatct tgaacagatg   120
acctggggtt tgaagggaa tatcaatgtt gctgcttttg aaagagcttg gcaaaaagtt    180
ttagatagac attcaattct acgtacattt tttgtttggg aaaatcgcca aactccatta   240
caagtagtac taaaacaggt taatgttcct tggaatactc ttgattggcg agaactttct   300
tctaatgatc aacaacaaca attaaaacaa ttattgcaaa cacaaagaga caaggtttt    360
aacttatccc aagcaccatt aatgcggtgt acgttagtca ggctaggcga agataattac   420
aaatttatct ggagtcatca ccacatcctt atggatggat ggtgtttatc aattattttt   480
aaagaaattt taattttcta taagcacat  ctgcttggtg aaaattgcca attgccaaaa   540
ccacgtcctt accaggatta tattgcttgg ttgaattctc aagacaaatc agcagcaatt   600
gagttttggc aacaaacttt acaaggtttt agtgctccca ctccattggt aatggataaa   660
actcaattc  tgaaagagca acagtataaa actgcggatt atcaggagag aacaagtagt   720
ttatcccctg aatgcactca gaagttactt catatagcac aacaacatca tgtgacttta   780
tcaactgtag tacaagctgc ttgggcttta ctattgagtc gttatagtgg tgagaaagat   840
gtagtatttg gtgtgactgt ttctggtcgt cctcctagcc tctctgagat agaaaatatg   900
gtaggactgt ttattaacac ccttccctta cgagtacaag tatccaccca ggagcaactc   960
ataccttggt tgcaaaaaat acaacagtca atggttgaat tacaagagta ttttttatact  1020
cctcttgttg atattcaagc tacttctgag ataccaggtg gaatacccttt gtttgagagc  1080
attgtggtgt ttgagaatta tccaattgat aattctttgt tgaatgaaga aggttcatta  1140
cacttaggtg atatagaggt ttttgaacaa actaattatc cactaacttt agttgcagtt  1200
cctggggata agttgtcagt taggattagt tacgatactg ctcgtttctc ttcaaatact  1260
attgagtgga ttttaggata tctgcaaact gttttatcag caattgcaat tgtggaaaat  1320
ccttcacata aggtagctca attaccttta ttaagtgaag tagaacgtca tcagttattg  1380
gttgagtgga ataacactgc aacggattac ccatctgata aatgtattca tcagttatttt 1440
gagcaacagg tagaaaaaaa cccccaactcc atagcagtgg tgtttgaaga agaacaatca  1500
acctaccaac aattaaatca aaaagcgaac caattagcac attatctaca aactctggga  1560
gtgaaaccag aagtgctggt gggtatttgc atagaatact ccattgatat gattgtagga  1620
ctgttgggga tacttaaagc tggtggtgta tatgtgccgt tagatccgaa ctatccgcaa  1680
gaacgactgg cgttcatgca ggaagattcc aatgtgcata tcatattgac ccagcagcct  1740
ctgctcgaaa agatttcccc tcaaaatgcc catatcgttt gcctggacag ggatagggat  1800
gtcattgcta gggaaggcgt tgaaaatctg gatcggcaaa caacactgga tgaccttgca  1860
tacgcaatct atacgtctgg ttctactgga aaacccaaag ccgttctcgg cacgcttcgc  1920
ggcattgtca atcgcttgca ttggatctgg gaaatgctac catttggggc agatgagatt  1980
tgctctcaga aaacatccat caatttttggc gatcatgttg cggaaatatt ttctccccctt 2040
ctcaaaggaa ttccccttgt gatcgttcca gatgatatac ggggcaatat tcccaggcta  2100
atgagcctgt tgagcgatcg aaaggtaact agaattgttc tcgttccatc gctattaaaa  2160
gcgatactgg aaaatgcgcc ccaacaactg acaaaacttc gatatctcaa atatgtctttt 2220
tgcagcggtc aagtcttacc gctaaccttg gctaaggaat tcaccagaa  aatcagctct  2280
gccagattgt tcaatctcta cggctcttca gaagttgccg ctgatgttac atgctttgaa  2340
```

```
gtcaaactga gaatcgcaaa tcaaattgaa gcaaaaagta aagagaaact tgatgcttta    2400
aaaaatcttc ctagtggctc aggggatagg gaaactgctg tcctgcataa agaaataata    2460
catttgcagt tggcagacga gcgaagagca gatttaggag aagctctaga agaatatctg    2520
aaaagaaata cgattccgat tggaaaaccg atttcaaaca cacaaattta catcctcgac    2580
aagtatggcg atcttttgcc acctggtgtt acgggtgagc tatacgtcgg cggagatggg    2640
cttgcaaaag ggtatttaaa tctgcccgag ttaacgcggg aaaagtttat ccccaacccg    2700
tttgtgaagg acaggggaa aagtaaaaag gcacaagcag aaagattgtt taggactgga    2760
gacctagccc gctggctgcc ggatggtaat atcgaatttg tagggcgtat cgatcaccaa    2820
gtgaaggtgc ggggcttccg cattgaactt ggagaaatcg aagcagtcct cagtacccac    2880
ccccaaatcc aacaagtcgt tgtcattgcc atagaagata ttccaggtag caaacgttta    2940
gtagcctaca tagtctgtga ggatgaatca ctaagtacct atcacctgcg tgaattcctc    3000
aaacaaaagc taccagaata catgatgccc agtgcctttg tcatcttaga caccttaccg    3060
ttgacaccca gcggtaaaat agaccgtaaa gcccttccag cacctgatgg agaaattagc    3120
cgagaacatg aatatgtccc accacgtaca tcgggtgaag aaataatagc caacatcttc    3180
gcttctattc taggtgtgca aaatgttgga atccatgaca acttctttga attgggagga    3240
cattccctac tagcaacccg attaatttcc cgactcagag ttgcctttga agtagaaata    3300
gaactaagtg cagtcttttc ctctcccact gtagctcaat tagagcaaac attaacccaa    3360
ttacgtacta ctaatagcgc attaagtctt cccccccattc agccaagaac acagaaccaa    3420
caattacccc tatcttttgc acaagaccgg ttgtggttcc tcaaccaact tgaagggtca    3480
agtgccactt ataacatgcc aggagcaatt cgtgtcactg gaaagttgga tattaatgcc    3540
ttgcaacaag cattatcaga aatagtccgc cgtcatgaag tactacgcac cagcttccga    3600
actgtgaatg gcacaccaat acaggtaatt cacccagaag ccaccatgaa catcagtgtg    3660
gcggacttac agcaactaga agcaacagaa cgggaaagtg tccttcacca acaagcacaa    3720
cttgcagcaa ttaccccctt tgacttagaa actgcaccac taatcaggtg tagtttattg    3780
cagttagatg ccagagaata tgtgttatta ctgacgatgc accacattgt ctctgatggt    3840
tggtcaatgg ggatattcag ccaagaacta tctactttat atcaagcttt tagtgcagga    3900
aaaccatccc ccttggcaga attaccaatc cagtatgcag actttgcagt ttggcaaaga    3960
caatggttaa gtggaaaggt actagaaact caactcaatt actggctttc tcagttagag    4020
ggtgcaccag aattgttaca attacctact gaccgtcctc gtccaaccgt gcaaactttc    4080
cggggtacta ctcaaagttt tagttttaaat actgatttaa aagagaagtt gcaaaccctg    4140
tctcggaact cgggtactac cttatttatg accctgcacg cagcgtttgc cactttactc    4200
tatcgctaca gcggtcaatt agatatttta attggttcac ccattgccaa tcgcaactgc    4260
agtgaaattg agtctttgat tggctttttt gccaatactt tggtattgaa acccgttttt    4320
gaagataatc ccagttttga gaatttgctg gcacaagtta gggaaactac acttgaagct    4380
tatgaacatc aggatgtgcc ttttgaacag gtagttgaag tactacaacc acaacgctct    4440
ttgagttatg caccttatt ccaggtaatg tttgtgttgc agaatgcacc catgggtgaa    4500
ttagaattac ctggtgtgac ccttaattta ttgagttctc aaacagaaac agcccggttt    4560
gatttaacag tatcaatgca gcaaacttcc gaagcactag tgggttcatg gaatacaac    4620 actgacttat tgatgggtc aactattgag cgcatgactg ctcatttcca gaatctgtgt    4680
agcgcgattg tagaaaatcc ccaacaaaag ataagtgaat taccattatt cacagattct    4740
```

```
gagcaagagc aggtactgca cagttacaat aacatcgcta caacttacct gctggataaa   4800
tatgttcatt tcctgagttc aaataattta caaatttaca ttttagataa ccatcaacaa   4860
ttagttcctt tgagtgtaga aggagaaatt tatttgggga attgcgattt actcccagac   4920
aagttacatc cagaaccaga aaaatttata agtttcatag aacataccca actgggtaag   4980
ttattaaaaa caggggaatg gggttgtcgt cgagtcgatg gttctctgga attgctagga   5040
aaagagcatc gaattgtcac agttaatgga caacgaatta acctacaacg tattgaacaa   5100
gctttacaaa cagcgaaagg ggtagaagat tgctatgtaa tggtacgcaa tcaaaaatta   5160
gtcgcttacg tagtcaaaga tggttcttgg gctaggagt ttttacacca ttatttaaaa   5220
tctcagttac ctggataccc attaccctgc atctatgtac cagtatctgc tttaccattg   5280
acaagttttg gagaagttga tgaagtaggt ttagcttcta ttagcataat tgattctgag   5340
ttaattaaca cttgggaaga acaaataggt tctcaggcgg aaattgataa agttgctgtt   5400
tttattgagc caaatgtaaa aacgattct ccgatacatt tagaagaact tttaccatca   5460
atccaagcta ttttcaatca aggttctact ccagttgaaa ctcccagaac tgctagggga   5520
aaagagagta gttccctatt agaaataaaa tcacctgcca tcagccacga agaagtatta   5580
atctttccag aatcatctcc agaaacttta ggggagatgc tgcaaaaaac tgctgggaaa   5640
tttcctcaca aaggaatcac ttatattaac tctgatggtt ccgaacaagt tcaatcatat   5700
gcccagttat tagaagatgc tcaaagaatt ctaggtggct tcagaaaact gggaattaag   5760
ccacaagata aagttatttt gcaattaaaa gaaaataaag attttattag tgcttttttgg   5820 ggttgtgtgt tgggaggctt tattcccgta cccgttgtaa ttcctgtaag ctatgaccag   5880
cccaatgtca atctaaataa attacaaaat agttggcaga tgttagaaag acctttgatt   5940
ttaacagata aaaaatcatt gtcagaacta agaaatggt ctcaaaatct aaatgacgac   6000
aactttaagt tagaaactat tgaaagttta caaaagttct caacagataa agattactat   6060
aatgcccaac cagaagattt agcactgttc atgcttactt ccggtagtac aggtatgtct   6120
aaggtggtac agttgagcca tttaaatcta ctgagtagga ctattggttc aatacaaatg   6180
aataatttta ccccagaaga tataaaccta aattggatgc ccttagacca tgttgcaggt   6240
ttaatatatt ttcatatccg ggatatttat ttaggatgta aacaaattca tgctactagt   6300
caattagtga ttgaaaaacc tttaagatgg ttggattgga ttgatacttt tggtgtcact   6360 gttactttg ctcctaactt tgcttatagt ttaattaatg attttgttca agaaatagaa   6420
aagcagaatt ggaatttatc ttctattcgc ttgatgttaa atggtgcgga acaaattgtt   6480
gcagcaacag caagacgttt tttgaaatta cttgctccct ttggcttacc tgggatgct   6540 atgactccat cttggggaat ggctgaggtt tcctctggta ttacttattc tgacaatttt   6600
tcactcttat caagttcaga tgataattcc tttgtaaatc ttggaaaacc gattagggt   6660 acttgtctga aatagtcaa tcaagacatg gaagtattat cagaaggtga aattggttta   6720
cttcaggtca aggattaac cgttacttct ggttattatc aaaatccaaa agcaaataag   6780
gaagcattta ccgaagatgg ttggtttaat acaggtgatt taggatttat aaaagatgga   6840
tgcttaacga ttacaggacg acaaaaagat atcattatta ttaatggagt taattattat   6900
agtcatgaaa tagaagctgt tgttgaagaa ttaggagagg ttgaagtttc ttataccgca   6960
gcctgtggag tctgcgttgc tagcaataat accgaagaat tagtaatctt tttcactccg   7020
tatgtatctg agaagaatca attattagag cttttgaaaa aggttaggga acaagttata   7080
aaatactgcg ggataaatcc aagttattta ataccccatag ataaagaact gattcccaaa   7140
```

```
acttccatcg gtaaaattca acgttccctc cttaagcaac gttttgaatg tggtgagttt    7200
aaatctctca gacagcgtgt agacttgttg cttgataata ctaatactat tcccaactgg    7260
ttttaccgta aagtatggca aattaaagaa agtaaaaata ctttactcaa ttattcttct    7320
cagaaaactt taaccctaat atttacagat aatttgggtt ggcaacaaga taaccgagga    7380
atgtcccaaa ctgttcaacc atatgctcaa gttactattg gttcaaattt tgctcaaatt    7440
agcccaaatc attattctgt tgttcctgga atccacaac actatcgctt gttaattgat     7500
tctttgaggc aaaatagcca agtaattagt caaattcttc atctttggaa ctacaacgag    7560
cagactgaaa aaatttctag cttggaaaat ttagagtcca ctcaacaaca aggaatttac    7620
agtttactat ttttagtaca agctttagaa gaaattcaag gcaaacagca agcagtcaaa    7680
ttattatgga ttgctaatca aagccaatta gttcatccca cagataaaat tcaacccgaa    7740
aaatccactg ttttaggctt acttaaaact gttagtcaag aaatgccttg gttaactact    7800
cgtcatttag atttaccatt agcaccagaa ctcaacaata gttatatttg gcaagaactg    7860
tattctgctg ataaagaatt ggaagttgct atacgcaata gagaacgttt tgtgtctggt    7920
ctggaaccag tagatatgac tgctaaggaa aaacaaaaaa ttccgattct accaggagga    7980
acgtatctac ttacaggagg gcttggagga attgggactg ttattgcaaa gtacttatta    8040
gaacattatc aagcaaattt aatattagtt ggtagaactc aaattgaaga taataatgag    8100
gaagctagca caaaattgca gaggtatcaa gaattagaaa aactaccagg ttcaataatt    8160
tatcaaactg tagatatttg tgatttagta ggtttacaac aggtagtaga aaaagcaaca    8220
caagaatgga ggactcaact tgatggggta tttcatatgg ctgggattat tcaggaaacg    8280
ccaatcgaga aagaaacccc aggaaatatc gctgctgttt tacgtcctaa agttagcggt    8340
acttgggtat tgcatcaatt gctcaaggat aaagaaaatg ctttatttgt ccacttttgt    8400
tctgtaaatg gtttctttgg aggaaccaat gttgcagctt atagtgcagc aaatagtttt    8460
cagtcagcat ggagcgatta tcaacaacaa aacggtttcc aaagctattg ctgctcttgg    8520
agtatgtgga atgaaccgg aataagtcat ggctatcaat tccaagaact cagtcgtgct    8580
aagggctatt ttattattac tcctcaacaa ggatttact cattttttagc agctttatct    8640 ggttcggaac ataatctatt aatcggattg gatggaacta aaacaaatgt tgaacatttg    8700
attcgtgatt gtcagcccaa gcagaaatta actgcttact tcacctctcc cacaccagaa    8760
cttgctgcac tctccttaca agagttacaa ctacacgatc gctttgggat acccaatcaa    8820
attaactttg tccaacttga acaaatacc cttactcaaa gaggagaaat taatcggaa     8880 caaattgctg ctatatatgg aggtttgaat acttctgagc agacaaaacc acggaatcaa    8940
acagaacgtc agttagttga gattttccaa gaagttctca atctaccctc tattggtatt    9000
catgacaact tctttagctt aggaggacat tcccttctag ctgtccgtct aatgtccgag    9060
attcaacaac aattccagaa aaatttacct ttagccactc tttttcaaaa tcccaccatt    9120
gaacgactag cacttcttgt tggttccgat tccggagccg aactttggtc tccattagta    9180
ccaattcaac aaaacggttc attaccacct tgttctgtg taccaggagc aggtggaaat     9240
gttctctact tccaccactt agcacaatat cttggaaata tcaaccgtt atacggttta     9300 caagcacaag gtcttgatgg tgaaaccgaa cctcataaaa gtgttgaaga aatagcctcc    9360
caacacatta aagcaattca aacagttcaa ccagttggtc cttacttctt ggctggtcat    9420
tcctttggca gtcatgtagt atttgaaatg gcgaatcaac tacaacttat tggaaagtct    9480
gttgcttatg ttggaatttt agatactcct gcaccaactt ctcaagctaa tcatcagaat    9540
```

```
gatttttcta actgggataa tgcaaagtgg atatgtcgaa tggctgaggt tattgaagat    9600
attgttggag aaaatctatt tttatcttat gaaactctaa cttctctaac ttgggagcaa    9660
caattaaatt atttcaagca aaagttagaa atagttggtt ttttgcctgc tcaaacagat    9720
atcaaaattg ttcgtggttt attacaagtt ttccaaactc aatgtcaaat taagtatgaa    9780
ccggaaaaga cttataaaac tccaatcact ttgttttgtg cgagggagat aaatccagag    9840
caagaaagtt attctcacat tttccaagag ccaacatggg gttggaatca gttttctgat    9900
ggagaagtgg aaatccatat agttccgggt aatcatgttt caatgctgag tgagcctcat    9960
gtcaaggtat tggctcaaca aatgcaaata tctcttgaac aagcacagaa aacccatcaa   10020
ttggaaaaat ga                                                       10032
```

<210> SEQ ID NO 7
<211> LENGTH: 3343
<212> TYPE: PRT
<213> ORGANISM: Nostoc species

<400> SEQUENCE: 7

```
Met Ser Asn Glu Glu Ile Arg Arg Asn Ile Ser Ser Ile Tyr Pro Leu
  1               5                  10                  15

Ser Pro Met Gln Gln Gly Met Leu Phe His Ser Leu Tyr Ala Pro Tyr
                 20                  25                  30

Ser Gly Val Tyr Leu Glu Gln Met Thr Trp Gly Leu Lys Gly Asn Ile
             35                  40                  45

Asn Val Ala Ala Phe Glu Arg Ala Trp Gln Lys Val Leu Asp Arg His
         50                  55                  60

Ser Ile Leu Arg Thr Phe Phe Val Trp Glu Asn Arg Gln Thr Pro Leu
 65                  70                  75                  80

Gln Val Val Leu Lys Gln Val Asn Val Pro Trp Asn Thr Leu Asp Trp
                 85                  90                  95

Arg Glu Leu Ser Ser Asn Asp Gln Gln Gln Leu Lys Gln Leu Leu
                100                 105                 110

Gln Thr Gln Arg Glu Gln Gly Phe Asn Leu Ser Gln Ala Pro Leu Met
            115                 120                 125

Arg Cys Thr Leu Val Arg Leu Gly Glu Asp Asn Tyr Lys Phe Ile Trp
        130                 135                 140

Ser His His His Ile Leu Met Asp Gly Trp Cys Leu Ser Ile Ile Phe
145                 150                 155                 160

Lys Glu Ile Leu Ile Phe Tyr Lys Ala His Leu Leu Gly Glu Asn Cys
                165                 170                 175

Gln Leu Pro Lys Pro Arg Pro Tyr Gln Asp Tyr Ile Ala Trp Leu Asn
            180                 185                 190

Ser Gln Asp Lys Ser Ala Ala Ile Glu Phe Trp Gln Gln Thr Leu Gln
        195                 200                 205

Gly Phe Ser Ala Pro Thr Pro Leu Val Met Asp Lys Thr Gln Phe Leu
    210                 215                 220

Lys Glu Gln Gln Tyr Lys Thr Ala Asp Tyr Gln Glu Arg Thr Ser Ser
225                 230                 235                 240

Leu Ser Pro Glu Cys Thr Gln Lys Leu Leu His Ile Ala Gln Gln His
                245                 250                 255

His Val Thr Leu Ser Thr Val Val Gln Ala Ala Trp Ala Leu Leu Leu
            260                 265                 270

Ser Arg Tyr Ser Gly Glu Lys Asp Val Val Phe Gly Val Thr Val Ser
        275                 280                 285
```

```
Gly Arg Pro Ser Leu Ser Glu Ile Glu Asn Met Val Gly Leu Phe
290                 295                 300

Ile Asn Thr Leu Pro Leu Arg Val Gln Val Ser Thr Gln Glu Gln Leu
305                 310                 315                 320

Ile Pro Trp Leu Gln Lys Ile Gln Gln Ser Met Val Glu Leu Gln Glu
                325                 330                 335

Tyr Phe Tyr Thr Pro Leu Val Asp Ile Gln Ala Thr Ser Glu Ile Pro
                340                 345                 350

Gly Gly Ile Pro Leu Phe Glu Ser Ile Val Val Phe Glu Asn Tyr Pro
                355                 360                 365

Ile Asp Asn Ser Leu Leu Asn Glu Glu Gly Ser Leu His Leu Gly Asp
370                 375                 380

Ile Glu Val Phe Glu Gln Thr Asn Tyr Pro Leu Thr Leu Val Ala Val
385                 390                 395                 400

Pro Gly Asp Lys Leu Ser Val Arg Ile Ser Tyr Asp Thr Ala Arg Phe
                405                 410                 415

Ser Ser Asn Thr Ile Glu Trp Ile Leu Gly Tyr Leu Gln Thr Val Leu
                420                 425                 430

Ser Ala Ile Ala Ile Val Glu Asn Pro Ser His Lys Val Ala Gln Leu
                435                 440                 445

Pro Leu Leu Ser Glu Val Glu Arg His Gln Leu Leu Val Glu Trp Asn
450                 455                 460

Asn Thr Ala Thr Asp Tyr Pro Ser Asp Lys Cys Ile His Gln Leu Phe
465                 470                 475                 480

Glu Gln Gln Val Glu Lys Asn Pro Asn Ser Ile Ala Val Val Phe Glu
                485                 490                 495

Glu Glu Gln Ser Thr Tyr Gln Gln Leu Asn Gln Lys Ala Asn Gln Leu
                500                 505                 510

Ala His Tyr Leu Gln Thr Leu Gly Val Lys Pro Glu Val Leu Val Gly
                515                 520                 525

Ile Cys Ile Glu Tyr Ser Ile Asp Met Ile Val Gly Leu Leu Gly Ile
530                 535                 540

Leu Lys Ala Gly Gly Val Tyr Val Pro Leu Asp Pro Asn Tyr Pro Gln
545                 550                 555                 560

Glu Arg Leu Ala Phe Met Gln Glu Asp Ser Asn Val His Ile Ile Leu
                565                 570                 575

Thr Gln Gln Pro Leu Leu Glu Lys Ile Ser Pro Gln Asn Ala His Ile
                580                 585                 590

Val Cys Leu Asp Arg Asp Arg Asp Val Ile Ala Arg Glu Gly Val Glu
                595                 600                 605

Asn Leu Asp Arg Gln Thr Thr Leu Asp Asp Leu Ala Tyr Ala Ile Tyr
                610                 615                 620

Thr Ser Gly Ser Thr Gly Lys Pro Lys Ala Val Leu Gly Thr Leu Arg
625                 630                 635                 640

Gly Ile Val Asn Arg Leu His Trp Ile Trp Glu Met Leu Pro Phe Gly
                645                 650                 655

Ala Asp Glu Ile Cys Ser Gln Lys Thr Ser Ile Asn Phe Gly Asp His
                660                 665                 670

Val Ala Glu Ile Phe Ser Pro Leu Leu Lys Gly Ile Pro Leu Val Ile
                675                 680                 685

Val Pro Asp Asp Ile Arg Gly Asn Ile Pro Arg Leu Met Ser Leu Leu
690                 695                 700
```

```
Ser Asp Arg Lys Val Thr Arg Ile Val Leu Val Pro Ser Leu Leu Lys
705                 710                 715                 720

Ala Ile Leu Glu Asn Ala Pro Gln Gln Leu Thr Lys Leu Arg Tyr Leu
                725                 730                 735

Lys Tyr Val Phe Cys Ser Gly Val Leu Pro Leu Thr Leu Ala Lys
                740                 745                 750

Glu Phe His Gln Lys Ile Ser Ser Ala Arg Leu Phe Asn Leu Tyr Gly
                755                 760                 765

Ser Ser Glu Val Ala Ala Asp Val Thr Cys Phe Glu Val Lys Leu Arg
                770                 775                 780

Ile Ala Asn Gln Ile Glu Ala Lys Ser Lys Glu Lys Leu Asp Ala Leu
785                 790                 795                 800

Lys Asn Leu Pro Ser Gly Ser Gly Asp Arg Glu Thr Ala Val Leu His
                805                 810                 815

Lys Glu Ile Ile His Leu Gln Leu Ala Asp Glu Arg Arg Ala Asp Leu
                820                 825                 830

Gly Glu Ala Leu Glu Glu Tyr Leu Lys Arg Asn Thr Ile Pro Ile Gly
                835                 840                 845

Lys Pro Ile Ser Asn Thr Gln Ile Tyr Ile Leu Asp Lys Tyr Gly Asp
                850                 855                 860

Leu Leu Pro Pro Gly Val Thr Gly Glu Leu Tyr Val Gly Gly Asp Gly
865                 870                 875                 880

Leu Ala Lys Gly Tyr Leu Asn Leu Pro Glu Leu Thr Arg Glu Lys Phe
                885                 890                 895

Ile Pro Asn Pro Phe Val Lys Asp Arg Gly Lys Ser Lys Lys Ala Gln
                900                 905                 910

Ala Glu Arg Leu Phe Arg Thr Gly Asp Leu Ala Arg Trp Leu Pro Asp
                915                 920                 925

Gly Asn Ile Glu Phe Val Gly Arg Ile Asp His Gln Val Lys Val Arg
930                 935                 940

Gly Phe Arg Ile Glu Leu Gly Glu Ile Glu Ala Val Leu Ser Thr His
945                 950                 955                 960

Pro Gln Ile Gln Gln Val Val Ile Ala Ile Glu Asp Ile Pro Gly
                965                 970                 975

Ser Lys Arg Leu Val Ala Tyr Ile Val Cys Glu Asp Glu Ser Leu Ser
                980                 985                 990

Thr Tyr His Leu Arg Glu Phe Leu Lys Gln Lys Leu Pro Glu Tyr Met
                995                 1000                1005

Met Pro Ser Ala Phe Val Ile Leu Asp Thr Leu Pro Leu Thr Pro Ser
1010                1015                1020

Gly Lys Ile Asp Arg Lys Ala Leu Pro Ala Pro Asp Gly Glu Ile Ser
1025                1030                1035                1040

Arg Glu His Glu Tyr Val Pro Pro Arg Thr Ser Gly Glu Glu Ile Ile
                1045                1050                1055

Ala Asn Ile Phe Ala Ser Ile Leu Gly Val Gln Asn Val Gly Ile His
                1060                1065                1070

Asp Asn Phe Phe Glu Leu Gly Gly His Ser Leu Leu Ala Thr Arg Leu
                1075                1080                1085

Ile Ser Arg Leu Arg Val Ala Phe Glu Val Glu Ile Glu Leu Ser Ala
                1090                1095                1100

Val Phe Ser Ser Pro Thr Val Ala Gln Leu Glu Gln Thr Leu Thr Gln
1105                1110                1115                1120
```

```
Leu Arg Thr Thr Asn Ser Ala Leu Ser Leu Pro Pro Ile Gln Pro Arg
            1125                1130                1135

Thr Gln Asn Gln Gln Leu Pro Leu Ser Phe Ala Gln Asp Arg Leu Trp
        1140                1145                1150

Phe Leu Asn Gln Leu Glu Gly Ser Ser Ala Thr Tyr Asn Met Pro Gly
        1155                1160                1165

Ala Ile Arg Val Thr Gly Lys Leu Asp Ile Asn Ala Leu Gln Gln Ala
        1170                1175                1180

Leu Ser Glu Ile Val Arg Arg His Glu Val Leu Arg Thr Ser Phe Arg
1185                1190                1195                1200

Thr Val Asn Gly Thr Pro Ile Gln Val Ile His Pro Glu Ala Thr Met
            1205                1210                1215

Asn Ile Ser Val Ala Asp Leu Gln Gln Leu Glu Ala Thr Glu Arg Glu
        1220                1225                1230

Ser Val Leu His Gln Gln Ala Gln Leu Ala Ala Ile Thr Pro Phe Asp
        1235                1240                1245

Leu Glu Thr Ala Pro Leu Ile Arg Cys Ser Leu Leu Gln Leu Asp Ala
        1250                1255                1260

Arg Glu Tyr Val Leu Leu Leu Thr Met His His Ile Val Ser Asp Gly
1265                1270                1275                1280

Trp Ser Met Gly Ile Phe Ser Gln Glu Leu Ser Thr Leu Tyr Gln Ala
            1285                1290                1295

Phe Ser Ala Gly Lys Pro Ser Pro Leu Ala Glu Leu Pro Ile Gln Tyr
        1300                1305                1310

Ala Asp Phe Ala Val Trp Gln Arg Gln Trp Leu Ser Gly Lys Val Leu
        1315                1320                1325

Glu Thr Gln Leu Asn Tyr Trp Leu Ser Gln Leu Glu Gly Ala Pro Glu
        1330                1335                1340

Leu Leu Gln Leu Pro Thr Asp Arg Pro Arg Pro Thr Val Gln Thr Phe
1345                1350                1355                1360

Arg Gly Thr Thr Gln Ser Phe Ser Leu Asn Thr Asp Leu Lys Glu Lys
            1365                1370                1375

Leu Gln Thr Leu Ser Arg Asn Ser Gly Thr Thr Leu Phe Met Thr Leu
        1380                1385                1390

His Ala Ala Phe Ala Thr Leu Leu Tyr Arg Tyr Ser Gly Gln Leu Asp
        1395                1400                1405

Ile Leu Ile Gly Ser Pro Ile Ala Asn Arg Asn Cys Ser Glu Ile Glu
        1410                1415                1420

Ser Leu Ile Gly Phe Phe Ala Asn Thr Leu Val Leu Lys Thr Arg Phe
1425                1430                1435                1440

Glu Asp Asn Pro Ser Phe Glu Asn Leu Leu Ala Gln Val Arg Glu Thr
            1445                1450                1455

Thr Leu Glu Ala Tyr Glu His Gln Asp Val Pro Phe Glu Gln Val Val
        1460                1465                1470

Glu Val Leu Gln Pro Gln Arg Ser Leu Ser Tyr Ala Pro Leu Phe Gln
        1475                1480                1485

Val Met Phe Val Leu Gln Asn Ala Pro Met Gly Glu Leu Glu Leu Pro
        1490                1495                1500

Gly Val Thr Leu Asn Leu Leu Ser Ser Gln Thr Glu Thr Ala Arg Phe
1505                1510                1515                1520

Asp Leu Thr Val Ser Met Gln Gln Thr Ser Glu Ala Leu Val Gly Ser
            1525                1530                1535
```

```
Trp Glu Tyr Asn Thr Asp Leu Phe Asp Gly Ser Thr Ile Glu Arg Met
            1540                1545                1550

Thr Ala His Phe Gln Asn Leu Cys Ser Ala Ile Val Glu Asn Pro Gln
        1555                1560                1565

Gln Lys Ile Ser Glu Leu Pro Leu Phe Thr Asp Ser Glu Gln Glu Gln
    1570                1575                1580

Val Leu His Ser Tyr Asn Asn Ile Ala Thr Thr Tyr Leu Leu Asp Lys
1585                1590                1595                1600

Tyr Val His Phe Leu Ser Ser Asn Asn Leu Gln Ile Tyr Ile Leu Asp
            1605                1610                1615

Asn His Gln Gln Leu Val Pro Leu Ser Val Glu Gly Glu Ile Tyr Leu
        1620                1625                1630

Gly Asn Cys Asp Leu Leu Pro Asp Lys Leu His Pro Glu Pro Glu Lys
    1635                1640                1645

Phe Ile Ser Phe Ile Glu His Thr Gln Leu Gly Lys Leu Leu Lys Thr
1650                1655                1660

Gly Glu Trp Gly Cys Arg Arg Val Asp Gly Ser Leu Glu Leu Leu Gly
1665                1670                1675                1680

Lys Glu His Arg Ile Val Thr Val Asn Gly Gln Arg Ile Asn Leu Gln
            1685                1690                1695

Arg Ile Glu Gln Ala Leu Gln Thr Ala Lys Gly Val Glu Asp Cys Tyr
        1700                1705                1710

Val Met Val Arg Asn Gln Lys Leu Val Ala Tyr Val Lys Asp Gly
    1715                1720                1725

Ser Trp Ala Arg Glu Phe Leu His His Tyr Leu Lys Ser Gln Leu Pro
    1730                1735                1740

Gly Tyr Pro Leu Pro Cys Ile Tyr Val Pro Val Ser Ala Leu Pro Leu
1745                1750                1755                1760

Thr Ser Phe Gly Glu Val Asp Glu Val Gly Leu Ala Ser Ile Ser Ile
            1765                1770                1775

Ile Asp Ser Glu Leu Ile Asn Thr Trp Glu Glu Gln Ile Gly Ser Gln
        1780                1785                1790

Ala Glu Ile Asp Lys Val Ala Val Phe Ile Glu Pro Asn Val Lys Thr
    1795                1800                1805

Ile Ser Pro Ile His Leu Glu Glu Leu Leu Pro Ser Ile Gln Ala Ile
    1810                1815                1820

Phe Asn Gln Gly Ser Thr Pro Val Glu Thr Pro Arg Thr Ala Arg Gly
1825                1830                1835                1840

Lys Glu Ser Ser Ser Leu Leu Glu Ile Lys Ser Pro Ala Ile Ser His
            1845                1850                1855

Glu Glu Val Leu Ile Phe Pro Glu Ser Ser Pro Glu Thr Leu Gly Glu
        1860                1865                1870

Met Leu Gln Lys Thr Ala Gly Lys Phe Pro His Lys Gly Ile Thr Tyr
    1875                1880                1885

Ile Asn Ser Asp Gly Ser Glu Gln Val Gln Ser Tyr Ala Gln Leu Leu
    1890                1895                1900

Glu Asp Ala Gln Arg Ile Leu Gly Gly Phe Arg Lys Leu Gly Ile Lys
1905                1910                1915                1920

Pro Gln Asp Lys Val Ile Leu Gln Leu Lys Glu Asn Lys Asp Phe Ile
            1925                1930                1935

Ser Ala Phe Trp Gly Cys Val Leu Gly Gly Phe Ile Pro Val Pro Val
        1940                1945                1950
```

-continued

Val Ile Pro Val Ser Tyr Asp Gln Pro Asn Val Asn Leu Asn Lys Leu
    1955                1960                1965

Gln Asn Ser Trp Gln Met Leu Glu Arg Pro Leu Ile Leu Thr Asp Lys
    1970                1975                1980

Lys Ser Leu Ser Glu Leu Lys Lys Trp Ser Gln Asn Leu Asn Asp Asp
1985                1990                1995                2000

Asn Phe Lys Leu Glu Thr Ile Glu Ser Leu Gln Lys Phe Ser Thr Asp
                2005                2010                2015

Lys Asp Tyr Tyr Asn Ala Gln Pro Glu Asp Leu Ala Leu Phe Met Leu
            2020                2025                2030

Thr Ser Gly Ser Thr Gly Met Ser Lys Val Val Gln Leu Ser His Leu
        2035                2040                2045

Asn Leu Leu Ser Arg Thr Ile Gly Ser Ile Gln Met Asn Asn Phe Thr
    2050                2055                2060

Pro Glu Asp Ile Thr Leu Asn Trp Met Pro Leu Asp His Val Ala Gly
2065                2070                2075                2080

Leu Ile Tyr Phe His Ile Arg Asp Ile Tyr Leu Gly Cys Lys Gln Ile
                2085                2090                2095

His Ala Thr Ser Gln Leu Val Ile Glu Lys Pro Leu Arg Trp Leu Asp
            2100                2105                2110

Trp Ile Asp Thr Phe Gly Val Thr Val Thr Phe Ala Pro Asn Phe Ala
        2115                2120                2125

Tyr Ser Leu Ile Asn Asp Phe Val Gln Glu Ile Glu Lys Gln Asn Trp
    2130                2135                2140

Asn Leu Ser Ser Ile Arg Leu Met Leu Asn Gly Ala Glu Gln Ile Val
2145                2150                2155                2160

Ala Ala Thr Ala Arg Arg Phe Leu Lys Leu Leu Ala Pro Phe Gly Leu
                2165                2170                2175

Pro Gly Asp Ala Met Thr Pro Ser Trp Gly Met Ala Glu Val Ser Ser
            2180                2185                2190

Gly Ile Thr Tyr Ser Asp Asn Phe Ser Leu Leu Ser Ser Ser Asp Asp
        2195                2200                2205

Asn Ser Phe Val Asn Leu Gly Lys Pro Ile Arg Gly Thr Cys Leu Arg
    2210                2215                2220

Ile Val Asn Gln Asp Met Glu Val Leu Ser Glu Gly Glu Ile Gly Leu
2225                2230                2235                2240

Leu Gln Val Lys Gly Leu Thr Val Thr Ser Gly Tyr Tyr Gln Asn Pro
                2245                2250                2255

Lys Ala Asn Lys Glu Ala Phe Thr Glu Asp Gly Trp Phe Asn Thr Gly
            2260                2265                2270

Asp Leu Gly Phe Ile Lys Asp Gly Cys Leu Thr Ile Thr Gly Arg Gln
        2275                2280                2285

Lys Asp Ile Ile Ile Ile Asn Gly Val Asn Tyr Tyr Ser His Glu Ile
    2290                2295                2300

Glu Ala Val Val Glu Glu Leu Gly Glu Val Glu Val Ser Tyr Thr Ala
2305                2310                2315                2320

Ala Cys Gly Val Cys Val Ala Ser Asn Asn Thr Glu Glu Leu Val Ile
                2325                2330                2335

Phe Phe Thr Pro Tyr Val Ser Glu Lys Asn Gln Leu Leu Glu Leu Leu
            2340                2345                2350

Lys Lys Val Arg Glu Gln Val Ile Lys Tyr Cys Gly Ile Asn Pro Ser
        2355                2360                2365

-continued

```
Tyr Leu Ile Pro Ile Asp Lys Glu Leu Ile Pro Lys Thr Ser Ile Gly
        2370            2375            2380

Lys Ile Gln Arg Ser Leu Leu Lys Gln Arg Phe Glu Cys Gly Glu Phe
2385            2390            2395            2400

Lys Ser Leu Arg Gln Arg Val Asp Leu Leu Asp Asn Thr Asn Thr
            2405            2410            2415

Ile Pro Asn Trp Phe Tyr Arg Lys Val Trp Gln Ile Lys Glu Ser Lys
            2420            2425            2430

Asn Thr Leu Leu Asn Tyr Ser Ser Gln Lys Thr Leu Thr Leu Ile Phe
            2435            2440            2445

Thr Asp Asn Leu Gly Trp Gln Gln Asp Asn Arg Gly Met Ser Gln Thr
            2450            2455            2460

Val Gln Pro Tyr Ala Gln Val Thr Ile Gly Ser Asn Phe Ala Gln Ile
2465            2470            2475            2480

Ser Pro Asn His Tyr Ser Val Val Pro Gly Asn Pro Gln His Tyr Arg
            2485            2490            2495

Leu Leu Ile Asp Ser Leu Arg Gln Asn Ser Gln Val Ile Ser Gln Ile
            2500            2505            2510

Leu His Leu Trp Asn Tyr Asn Glu Gln Thr Glu Lys Ile Ser Ser Leu
            2515            2520            2525

Glu Asn Leu Glu Ser Thr Gln Gln Gln Gly Ile Tyr Ser Leu Leu Phe
            2530            2535            2540

Leu Val Gln Ala Leu Glu Glu Ile Gly Lys Gln Gln Ala Val Lys
2545            2550            2555            2560

Leu Leu Trp Ile Ala Asn Gln Ser Gln Leu Val His Pro Thr Asp Lys
            2565            2570            2575

Ile Gln Pro Glu Lys Ser Thr Val Leu Gly Leu Leu Lys Thr Val Ser
            2580            2585            2590

Gln Glu Met Pro Trp Leu Thr Thr Arg His Leu Asp Leu Pro Leu Ala
            2595            2600            2605

Pro Glu Leu Asn Asn Ser Tyr Ile Trp Gln Glu Leu Tyr Ser Ala Asp
            2610            2615            2620

Lys Glu Leu Glu Val Ala Ile Arg Asn Arg Glu Arg Phe Val Ser Gly
2625            2630            2635            2640

Leu Glu Pro Val Asp Met Thr Ala Lys Glu Lys Gln Lys Ile Pro Ile
            2645            2650            2655

Leu Pro Gly Gly Thr Tyr Leu Leu Thr Gly Gly Leu Gly Gly Ile Gly
            2660            2665            2670

Thr Val Ile Ala Lys Tyr Leu Leu Glu His Tyr Gln Ala Asn Leu Ile
            2675            2680            2685

Leu Val Gly Arg Thr Gln Ile Glu Asp Asn Asn Glu Glu Ala Ser Thr
            2690            2695            2700

Lys Leu Gln Arg Tyr Gln Glu Leu Glu Lys Leu Pro Gly Ser Ile Ile
2705            2710            2715            2720

Tyr Gln Thr Val Asp Ile Cys Asp Leu Val Gly Leu Gln Gln Val Val
                2725            2730            2735

Glu Lys Ala Thr Gln Glu Trp Arg Thr Gln Leu Asp Gly Val Phe His
            2740            2745            2750

Met Ala Gly Ile Ile Gln Glu Thr Pro Ile Glu Lys Glu Thr Pro Gly
            2755            2760            2765

Asn Ile Ala Ala Val Leu Arg Pro Lys Val Ser Gly Thr Trp Val Leu
            2770            2775            2780
```

```
His Gln Leu Leu Lys Asp Lys Glu Asn Ala Leu Phe Val His Phe Cys
2785                2790                2795                2800

Ser Val Asn Gly Phe Phe Gly Thr Asn Val Ala Ala Tyr Ser Ala
            2805                2810                2815

Ala Asn Ser Phe Gln Ser Ala Trp Ser Asp Tyr Gln Gln Asn Gly
        2820                2825                2830

Phe Gln Ser Tyr Cys Cys Ser Trp Ser Met Trp Asn Glu Thr Gly Ile
    2835                2840                2845

Ser His Gly Tyr Gln Phe Gln Glu Leu Ser Arg Ala Lys Gly Tyr Phe
2850                2855                2860

Ile Ile Thr Pro Gln Gln Gly Phe Tyr Ser Phe Leu Ala Ala Leu Ser
2865                2870                2875                2880

Gly Ser Glu His Asn Leu Leu Ile Gly Leu Asp Gly Thr Lys Thr Asn
            2885                2890                2895

Val Glu His Leu Ile Arg Asp Cys Gln Pro Lys Gln Lys Leu Thr Ala
        2900                2905                2910

Tyr Phe Thr Ser Pro Thr Pro Glu Leu Ala Ala Leu Ser Leu Gln Glu
            2915                2920                2925

Leu Gln Leu His Asp Arg Phe Gly Ile Pro Asn Gln Ile Asn Phe Val
2930                2935                2940

Gln Leu Glu Gln Ile Pro Leu Thr Gln Arg Gly Glu Ile Asn Arg Glu
2945                2950                2955                2960

Gln Ile Ala Ala Ile Tyr Gly Gly Leu Asn Thr Ser Glu Gln Thr Lys
        2965                2970                2975

Pro Arg Asn Gln Thr Glu Arg Gln Leu Val Glu Ile Phe Gln Glu Val
            2980                2985                2990

Leu Asn Leu Pro Ser Ile Gly Ile His Asp Asn Phe Phe Ser Leu Gly
            2995                3000                3005

Gly His Ser Leu Leu Ala Val Arg Leu Met Ser Glu Ile Gln Gln Gln
        3010                3015                3020

Phe Gln Lys Asn Leu Pro Leu Ala Thr Leu Phe Gln Asn Pro Thr Ile
3025                3030                3035                3040

Glu Arg Leu Ala Leu Leu Val Gly Ser Asp Ser Gly Ala Glu Leu Trp
            3045                3050                3055

Ser Pro Leu Val Pro Ile Gln Gln Asn Gly Ser Leu Pro Pro Leu Phe
            3060                3065                3070

Cys Val Pro Gly Ala Gly Gly Asn Val Leu Tyr Phe His His Leu Ala
            3075                3080                3085

Gln Tyr Leu Gly Asn Asn Gln Pro Leu Tyr Gly Leu Gln Ala Gln Gly
        3090                3095                3100

Leu Asp Gly Glu Thr Glu Pro His Lys Ser Val Glu Ile Ala Ser
3105                3110                3115                3120

Gln His Ile Lys Ala Ile Gln Thr Val Gln Pro Val Gly Pro Tyr Phe
        3125                3130                3135

Leu Ala Gly His Ser Phe Gly Ser His Val Val Phe Glu Met Ala Asn
            3140                3145                3150

Gln Leu Gln Leu Ile Gly Lys Ser Val Ala Tyr Val Gly Ile Leu Asp
        3155                3160                3165

Thr Pro Ala Pro Thr Ser Gln Ala Asn His Gln Asn Asp Phe Ser Asn
        3170                3175                3180

Trp Asp Asn Ala Lys Trp Ile Cys Arg Met Ala Glu Val Ile Glu Asp
3185                3190                3195                3200
```

Ile Val Gly Glu Asn Leu Phe Leu Ser Tyr Glu Thr Leu Thr Ser Leu
                3205                3210                3215

Thr Trp Glu Gln Gln Leu Asn Tyr Phe Lys Gln Lys Leu Glu Ile Val
                3220                3225                3230

Gly Phe Leu Pro Ala Gln Thr Asp Ile Lys Ile Val Arg Gly Leu Leu
                3235                3240                3245

Gln Val Phe Gln Thr Gln Cys Gln Ile Lys Tyr Glu Pro Glu Lys Thr
                3250                3255                3260

Tyr Lys Thr Pro Ile Thr Leu Phe Cys Ala Arg Glu Ile Asn Pro Glu
3265                3270                3275                3280

Gln Glu Ser Tyr Ser His Ile Phe Gln Glu Pro Thr Trp Gly Trp Asn
                3285                3290                3295

Gln Phe Ser Asp Gly Glu Val Glu Ile His Ile Val Pro Gly Asn His
                3300                3305                3310

Val Ser Met Leu Ser Glu Pro His Val Lys Val Leu Ala Gln Gln Met
                3315                3320                3325

Gln Ile Ser Leu Glu Gln Ala Gln Lys Thr His Gln Leu Glu Lys
                3330                3335                3340

<210> SEQ ID NO 8
<211> LENGTH: 1353
<212> TYPE: DNA
<213> ORGANISM: Nostoc species

<400> SEQUENCE: 8

| | | | | | |
|---|---|---|---|---|---|
| atgattaata | ctgctaaatc | ctcattactt | cctggtccca | ctacaccatc | ttggtggaac | 60 |
| ttattgcaat | ggcttaataa | tccttgtgaa | tttttggaag | agtgtcgagc | acgctatgga | 120 |
| gacactttta | ccttcaaagc | tattggtttt | gaacctttag | tacttattag | taatcctaag | 180 |
| gatataaaag | aaattttga | taaacacaag | tattttgaca | gtggaaaagc | taaagctaac | 240 |
| gatttagcag | gatttttttt | aggcaacaat | tccgtcacct | tgcttgatgg | aagtagtcat | 300 |
| aaacgacagc | gtaaactact | gatgcctgct | tttcatggtc | aaaatatatc | taactatgga | 360 |
| gaactaatat | gccatgcaac | gaagcaggtt | acttctaatt | ggcaacctgg | tcaaagattg | 420 |
| attatttaca | aggaagtcaa | agaaattacg | ctgcgagcga | tgttaacggt | ttactgggt | 480 |
| tcagataaaa | cggaacgtta | tcaacaactc | aaattgatag | ttaatcaaat | agtatccact | 540 |
| ataactaatc | cctttgcttc | tagctctctt | ttcttcaatg | tgtttagaag | agactggggt | 600 |
| tcttggagtg | cctggggtaa | tcttttacgt | tgccaacgtc | agattgcaaa | tatcatttct | 660 |
| gcagaaatca | agaacgtag | agaaaattgt | aacaattaca | acaatgatat | cctcagtatg | 720 |
| ctgatggcag | cacgagatga | aaatggagga | aaaatgacag | atgaggagtt | gcaagatgag | 780 |
| ttaatgacac | ttatctttc | tggatatgaa | actacatctg | cagcaataac | atgggcatat | 840 |
| tattggattc | attacttacc | agagataaga | gccaagttat | tgcaagaatt | agatgagtta | 900 |
| ggagataatc | cagacccaac | ggaaataagc | aaattacctt | atctcaatgc | agtttgtgct | 960 |
| gaaaccttga | atatatcc | agttggtcta | actactttc | ctcgaattgt | aaaatcgcca | 1020 |
| atagaaattg | gaggtcatca | atttgaggta | ggaacttgtc | tttatccatg | tatttatcta | 1080 |
| attcaccacc | gggaagaact | atatcctaac | tctaaacagt | ttaagccaga | acgttttcta | 1140 |
| gataataaat | ttttaaatta | tgagtatttc | cctttcggtg | gcggtaaccg | aacttgcatt | 1200 |
| ggtatggcat | tgctcagtt | taaaatgaag | ttagtattgg | ctaatatttt | gcggaattgg | 1260 |

```
caattggaat tggtaggcaa acctccttta aaaccagtac gagatatttt ctcaatttat   1320
cctcaaggtg gattaaaaat ggttgtattg taa                                1353
```

<210> SEQ ID NO 9
<211> LENGTH: 450
<212> TYPE: PRT
<213> ORGANISM: Nostoc species

<400> SEQUENCE: 9

```
Met Ile Asn Thr Ala Lys Ser Ser Leu Leu Pro Gly Pro Thr Thr Pro
  1               5                  10                  15

Ser Trp Trp Asn Leu Leu Gln Trp Leu Asn Asn Pro Cys Glu Phe Leu
             20                  25                  30

Glu Glu Cys Arg Ala Arg Tyr Gly Asp Thr Phe Thr Phe Lys Ala Ile
         35                  40                  45

Gly Phe Glu Pro Leu Val Leu Ile Ser Asn Pro Lys Asp Ile Lys Glu
     50                  55                  60

Ile Phe Asp Lys His Lys Tyr Phe Asp Ser Gly Lys Ala Lys Ala Asn
 65                  70                  75                  80

Asp Leu Ala Gly Phe Phe Leu Gly Asn Asn Ser Val Thr Leu Leu Asp
                 85                  90                  95

Gly Ser Ser His Lys Arg Gln Arg Lys Leu Leu Met Pro Ala Phe His
            100                 105                 110

Gly Gln Asn Ile Ser Asn Tyr Gly Glu Leu Ile Cys His Ala Thr Lys
        115                 120                 125

Gln Val Thr Ser Asn Trp Gln Pro Gly Gln Arg Leu Ile Ile Tyr Lys
    130                 135                 140

Glu Val Lys Glu Ile Thr Leu Arg Ala Met Leu Thr Val Leu Leu Gly
145                 150                 155                 160

Ser Asp Lys Thr Glu Arg Tyr Gln Gln Leu Lys Leu Ile Val Asn Gln
                165                 170                 175

Ile Val Ser Thr Ile Thr Asn Pro Phe Ala Ser Ser Ser Leu Phe Phe
            180                 185                 190

Asn Val Phe Arg Arg Asp Trp Gly Ser Trp Ala Trp Gly Asn Leu
        195                 200                 205

Leu Arg Cys Gln Arg Gln Ile Ala Asn Ile Ile Ser Ala Glu Ile Lys
    210                 215                 220

Glu Arg Arg Glu Asn Cys Asn Asn Tyr Asn Asn Asp Ile Leu Ser Met
225                 230                 235                 240

Leu Met Ala Ala Arg Asp Glu Asn Gly Gly Lys Met Thr Asp Glu Glu
                245                 250                 255

Leu Gln Asp Glu Leu Met Thr Leu Ile Phe Ser Gly Tyr Glu Thr Thr
            260                 265                 270

Ser Ala Ala Ile Thr Trp Ala Tyr Tyr Trp Ile His Tyr Leu Pro Glu
        275                 280                 285

Ile Arg Ala Lys Leu Leu Gln Glu Leu Asp Glu Leu Gly Asp Asn Pro
    290                 295                 300

Asp Pro Thr Glu Ile Ser Lys Leu Pro Tyr Leu Asn Ala Val Cys Ala
305                 310                 315                 320

Glu Thr Leu Arg Ile Tyr Pro Val Gly Leu Thr Thr Phe Pro Arg Ile
                325                 330                 335

Val Lys Ser Pro Ile Glu Ile Gly Gly His Gln Phe Glu Val Gly Thr
            340                 345                 350
```

Cys Leu Tyr Pro Cys Ile Tyr Leu Ile His His Arg Glu Glu Leu Tyr
            355                 360                 365

Pro Asn Ser Lys Gln Phe Lys Pro Glu Arg Phe Leu Asp Asn Lys Phe
        370                 375                 380

Leu Asn Tyr Glu Tyr Phe Pro Phe Gly Gly Asn Arg Thr Cys Ile
385                 390                 395                 400

Gly Met Ala Phe Ala Gln Phe Lys Met Lys Leu Val Leu Ala Asn Ile
                405                 410                 415

Leu Arg Asn Trp Gln Leu Glu Leu Val Gly Lys Pro Pro Leu Lys Pro
            420                 425                 430

Val Arg Asp Ile Phe Ser Ile Tyr Pro Gln Gly Gly Leu Lys Met Val
        435                 440                 445

Val Leu
    450

<210> SEQ ID NO 10
<211> LENGTH: 885
<212> TYPE: DNA
<213> ORGANISM: Nostoc species

<400> SEQUENCE: 10
atgtattcaa taaaaattga aaatctaata attagagtga aaagtgtatt agaaatgcca      60
gtttctaaag aagctgagat ggcaaataaa tttaatgagt ttggattcgt aatactagaa     120
cacgaacctt cagcaacacc taagaataac ttattaaaat tgtctgatta ttttggaaca     180
attattcagc acgaacattc tgattcacag ggaattgttc ccatcagtcc tgttgatagt     240
tatccagaat atgtaaatac tacaactaca gatttatcgt tacatacgga tggagcgttc     300
acaattactc caccaaaagt aatggcaatg cagtgccaga tgctgctgc aaatggcggg      360 ttcaccaagc ttattgatgg caagctggta tatgaacatc taaagcggac aaacccagtt     420
ggattgttaa ctttgtttaa tcctgatgcg attacagtca aaagagataa taaaaaagca     480
actaaaccta ttttgaaga acatcatgct gggcttattg taaggtttag agcagataat     540
gcagctcatg tttcggttga atcgaaaagt tttgcggcat ttaaatcatt tgaaaacttt     600
gtaaataatc ctgacaatca agtaattttt aaacttgcac aaaaccaaat aattattgta     660
gataatacta gagttttgca tggaagaact gcatttttcca acaagagta taggctacta     720 aatcgacttt ggtttgatgg acaatctgat attataaatt taagtttgg tatttctata     780 gccccaaaaa acttgagttt atttgctaaa aagtatcagc catctcaaat agatataggc     840
tcagatattt ctcagtcaac tcaattgaaa tttaaagcca catga                     885

<210> SEQ ID NO 11
<211> LENGTH: 294
<212> TYPE: PRT
<213> ORGANISM: Nostoc species

<400> SEQUENCE: 11

Met Tyr Ser Ile Lys Ile Glu Asn Leu Ile Ile Arg Val Lys Ser Val
1               5                   10                  15

Leu Glu Met Pro Val Ser Lys Glu Ala Glu Met Ala Asn Lys Phe Asn
            20                  25                  30

Glu Phe Gly Phe Val Ile Leu Glu His Glu Pro Ser Ala Thr Pro Lys
        35                  40                  45

Asn Asn Leu Leu Lys Leu Ser Asp Tyr Phe Gly Thr Ile Ile Gln His
    50                  55                  60

```
Glu His Ser Asp Ser Gln Gly Ile Val Pro Ile Ser Pro Val Asp Ser
 65                  70                  75                  80

Tyr Pro Glu Tyr Val Asn Thr Thr Thr Asp Leu Ser Leu His Thr
             85                  90                  95

Asp Gly Ala Phe Thr Ile Thr Pro Pro Lys Val Met Ala Met Gln Cys
            100                 105                 110

Gln Ile Ala Ala Ala Asn Gly Gly Phe Thr Lys Leu Ile Asp Gly Lys
            115                 120                 125

Leu Val Tyr Glu His Leu Lys Arg Thr Asn Pro Val Gly Leu Leu Thr
130                 135                 140

Leu Phe Asn Pro Asp Ala Ile Thr Val Lys Arg Asp Asn Lys Lys Ala
145                 150                 155                 160

Thr Lys Pro Ile Phe Glu Glu His His Ala Gly Leu Ile Val Arg Phe
                165                 170                 175

Arg Ala Asp Asn Ala Ala His Val Ser Val Glu Ser Lys Ser Phe Ala
            180                 185                 190

Ala Phe Lys Ser Phe Glu Asn Phe Val Asn Asn Pro Asp Asn Gln Val
        195                 200                 205

Ile Phe Lys Leu Ala Gln Asn Gln Ile Ile Val Asp Asn Thr Arg
    210                 215                 220

Val Leu His Gly Arg Thr Ala Phe Ser Lys Gln Glu Tyr Arg Leu Leu
225                 230                 235                 240

Asn Arg Leu Trp Phe Asp Gly Gln Ser Asp Ile Ile Asn Leu Lys Phe
                245                 250                 255

Gly Ile Ser Ile Ala Pro Lys Asn Leu Ser Leu Phe Ala Lys Lys Tyr
            260                 265                 270

Gln Pro Ser Gln Ile Asp Ile Gly Ser Asp Ile Ser Gln Ser Thr Gln
        275                 280                 285

Leu Lys Phe Lys Ala Thr
    290

<210> SEQ ID NO 12
<211> LENGTH: 333
<212> TYPE: DNA
<213> ORGANISM: Nostoc species

<400> SEQUENCE: 12
atgttgaagt cgaaaattca cagagcgacg gtgacggaag ccaacgttaa ctacatcgga     60
agtattacag tagacaaagt tctgatggaa aaggcagaca tactaccggg tgaaaaggtt    120
atggtggtgg acaacactaa tggtaatcgt ctagaaacct atgtcctaga aggtgaggaa    180
aattccgggg taatctgtat gaacggtggc tccgcccacc tagtcaattc aggagacctt    240
atcacattgc tagcattcga ggtaactgac gaaatcaagg aaccgaaaaa aattatcgtg    300
gatgaaaaca acaagtttct caagtacctg taa                                 333

<210> SEQ ID NO 13
<211> LENGTH: 110
<212> TYPE: PRT
<213> ORGANISM: Nostoc species

<400> SEQUENCE: 13

Met Leu Lys Ser Lys Ile His Arg Ala Thr Val Thr Glu Ala Asn Val
  1               5                  10                  15

Asn Tyr Ile Gly Ser Ile Thr Val Asp Lys Val Leu Met Glu Lys Ala
             20                  25                  30
```

```
Asp Ile Leu Pro Gly Glu Lys Val Met Val Val Asp Asn Thr Asn Gly
        35                  40                  45

Asn Arg Leu Glu Thr Tyr Val Leu Glu Gly Glu Asn Ser Gly Val
    50                  55                  60

Ile Cys Met Asn Gly Gly Ser Ala His Leu Val Asn Ser Gly Asp Leu
65                  70                  75                  80

Ile Thr Leu Leu Ala Phe Glu Val Thr Asp Glu Ile Lys Glu Pro Lys
                85                  90                  95

Lys Ile Ile Val Asp Glu Asn Asn Lys Phe Leu Lys Tyr Leu
            100                 105                 110
```

<210> SEQ ID NO 14
<211> LENGTH: 1476
<212> TYPE: DNA
<213> ORGANISM: Nostoc species

<400> SEQUENCE: 14

```
atgtctacac tgcctaattc cacacagatt ctaattatcg agggggacc ttctggatct      60
actgctgcta ccctattggc tcgtgagggc tttgatgtaa cgctgttaga acgagaggta    120
ttcccgcgtt accacgttgg ggaatctctt ttgccctctg ctttagaaat ttttgacctg    180
cttggcgtac gcgagaaaat tgaagcttat ggctttcagc gtaaacctgg agcgtacata    240
gaatggggaa cggaaaagtg gagcctcaat tttggggaac ttacggggga caacacctac    300
agcttccaag ttcgccgtga cgaattcgac cacttgcttt tagagcattc aaagagccag    360
ggtgtgaagg ttttgaagg actaaaaatt cgccagttgt cttttgatgg cgatcgcccg    420
cgcagcgcta cttggtcaca atcaaatgat actaccgggg agatttcttt tgactttatg    480
attgacgctt caggtcgtgc tgggatcatg gcgacggagt atctgaaaaa ccgccgtcta    540
cacgacgtat tccagaatgt tggcatctgg gggtactgga aaaacgcctt gagactacct    600
aaaggtcagt cgggtgcgat tgccttgggc tccattccag atggttgggt gtggggaatt    660
cctttggatg aggaaattat gagcgttggt gtagtgatgc ataagtcaac ctacaaggag    720
agactgacta gaacttgaa ggatatctac gtggaggcga ttgcagagtg tcccttgata    780
gcggatctgg ttgcactagg ggagctagtc tcagacgtga agttgagca agattactct    840
tacacttccg actccttttc aggaccagcc tacttcatat cgggagacgc tgcttgcttc    900
ctagaccccc tactatcgag tggggtgcat cttgctactt atagcgcttt gttagccgca    960
gccagtatca aagtgttat acgtggcgag gtgactgagt cacaagctgc ttcttttctac   1020
gatcagagct atcggcaggc ttatttgcgt ttcttagtgt tcgtatcagc cttctacgat   1080
caaaaccgtg gcaaggattc ctatttctgg gaggcacaac ggcttagtcg ccgtgacttc   1140
ggcagttcta acctaaagct agcattcttg aatctggtgt ccggcgtcga ggacttggag   1200
gacgctaagg aggggattgc cgattttgtt atggcagaga tgtctcagcg gattcagtca   1260
agccacagca ttaggcaaga caagcaggcg ttggcaatcg aaagggaaaa aggtaacgag   1320
gtaatgaaga caaatgccca gttttcaat gcagtcgagg attttccat actatcggca    1380
gttggggcag ttgatggtct atatgttaca actcagccaa aattaggatt ggtacaggta   1440
atccctctcc aaagaaactc tttgctccac acttag                             1476
```

<210> SEQ ID NO 15
<211> LENGTH: 491
<212> TYPE: PRT
<213> ORGANISM: Nostoc species

```
<400> SEQUENCE: 15

Met Ser Thr Leu Pro Asn Ser Thr Gln Ile Leu Ile Ile Gly Gly Gly
  1               5                  10                  15

Pro Ser Gly Ser Thr Ala Ala Thr Leu Leu Ala Arg Glu Gly Phe Asp
             20                  25                  30

Val Thr Leu Leu Glu Arg Glu Val Phe Pro Arg Tyr His Val Gly Glu
         35                  40                  45

Ser Leu Leu Pro Ser Ala Leu Glu Ile Phe Asp Leu Leu Gly Val Arg
     50                  55                  60

Glu Lys Ile Glu Ala Tyr Gly Phe Gln Arg Lys Pro Gly Ala Tyr Ile
 65                  70                  75                  80

Glu Trp Gly Thr Glu Lys Trp Ser Leu Asn Phe Gly Glu Leu Thr Gly
                 85                  90                  95

Asp Asn Thr Tyr Ser Phe Gln Val Arg Arg Asp Glu Phe Asp His Leu
            100                 105                 110

Leu Leu Glu His Ser Lys Ser Gln Gly Val Lys Val Phe Glu Gly Thr
        115                 120                 125

Lys Ile Arg Gln Leu Ser Phe Asp Gly Asp Arg Pro Arg Ser Ala Thr
130                 135                 140

Trp Ser Gln Ser Asn Asp Thr Thr Gly Glu Ile Ser Phe Asp Phe Met
145                 150                 155                 160

Ile Asp Ala Ser Gly Arg Ala Gly Ile Met Ala Thr Glu Tyr Leu Lys
                165                 170                 175

Asn Arg Arg Leu His Asp Val Phe Gln Asn Val Gly Ile Trp Gly Tyr
            180                 185                 190

Trp Lys Asn Ala Leu Arg Leu Pro Lys Gly Gln Ser Gly Ala Ile Ala
        195                 200                 205

Leu Gly Ser Ile Pro Asp Gly Trp Val Trp Gly Ile Pro Leu Asp Glu
    210                 215                 220

Glu Ile Met Ser Val Gly Val Val Met His Lys Ser Thr Tyr Lys Glu
225                 230                 235                 240

Arg Leu Thr Lys Asn Leu Lys Asp Ile Tyr Val Glu Ala Ile Ala Glu
                245                 250                 255

Cys Pro Leu Ile Ala Asp Leu Val Ala Leu Gly Glu Leu Val Ser Asp
            260                 265                 270

Val Lys Val Glu Gln Asp Tyr Ser Tyr Thr Ser Asp Ser Phe Ser Gly
        275                 280                 285

Pro Ala Tyr Phe Ile Ser Gly Asp Ala Ala Cys Phe Leu Asp Pro Leu
    290                 295                 300

Leu Ser Ser Gly Val His Leu Ala Thr Tyr Ser Ala Leu Leu Ala Ala
305                 310                 315                 320

Ala Ser Ile Thr Ser Val Ile Arg Gly Glu Val Thr Glu Ser Gln Ala
                325                 330                 335

Ala Ser Phe Tyr Asp Gln Ser Tyr Arg Gln Ala Tyr Leu Arg Phe Leu
            340                 345                 350

Val Phe Val Ser Ala Phe Tyr Asp Gln Asn Arg Gly Lys Asp Ser Tyr
        355                 360                 365

Phe Trp Glu Ala Gln Arg Leu Ser Arg Arg Asp Phe Gly Ser Ser Asn
    370                 375                 380

Leu Lys Leu Ala Phe Leu Asn Leu Val Ser Val Glu Asp Leu Glu
385                 390                 395                 400

Asp Ala Lys Glu Gly Ile Ala Asp Phe Val Met Ala Glu Met Ser Gln
                405                 410                 415
```

```
Arg Ile Gln Ser Ser His Ser Ile Arg Gln Asp Lys Gln Ala Leu Ala
            420                 425                 430

Ile Glu Arg Glu Lys Gly Asn Glu Val Met Lys Thr Asn Ala Gln Phe
        435                 440                 445

Phe Asn Ala Val Glu Gly Phe Ser Ile Leu Ser Ala Val Gly Ala Val
    450                 455                 460

Asp Gly Leu Tyr Val Thr Thr Gln Pro Lys Leu Gly Leu Val Gln Val
465                 470                 475                 480

Ile Pro Leu Gln Arg Asn Ser Leu Leu His Thr
                485                 490

<210> SEQ ID NO 16
<211> LENGTH: 1383
<212> TYPE: DNA
<213> ORGANISM: Nostoc species

<400> SEQUENCE: 16
atgttatctc cctatttga tgcttttgta gaggcaagcc cgtcagtgt aatgatgcga      60 gtcctaatgg aaaacatttt taattcctcg cgaatgaatc aaatatttga tacatcaagc   120
gttcgccaat actctcaaga gctactgttt tcgactcagg tggatttgat gagtctagta   180
gtgtgtggga tgtatccctc ggttcatgca gcctatcaga agaaggcagt ggaggtaagt   240
gtcagcgcca cagcgttata caacaaactg aacggattg aactgcctgt aagtcgggca   300
ttagtgcatg agacagcatc tgacctccag cagttgctgt tgatgttgaa tgtggaacgc   360
cccagtcctc taggaaaaca atatcggttg cggattgtag atggcagttg tttagccgga   420
accgaacgca gactagcagc gctgcgcccc catgcagcca aaccattacc cggaaaaaca   480
atcgccattc tcgacccagg acaaaactg gtggttgatg tgattccttg tgaagacggt   540
cattcccaag aacgctccaa gtttcatcag gttttggcac aagtgcaacc ccaacaggta   600
tggattgcag accgtaactt tgtaccgca ggatttctcc atactattgc caaacttgga   660
gcgttttttg tgattcgtca acacgggggt ttaggatacg agccttttgg tgagttacaa   720
gctgttgggt tgtgccaaac aggaactgtg tttgaacaac aggtggaaat tgtccatgag   780
ggagggactt ttcggtgtcg ccgtatcgta gttaagttga ctcgtcccac ccgtgaccaa   840
gagtgggaaa ttgccatttt taccaactta ccacccactg acgcagacgg cattctggtg   900
gcacaactct atcaagggcg gtggagtgtg gaaactttat ccaaactgt gacccaaaac   960 tttcatggag aaattgaaac cctagcttat cctaaagctg ccttattctc ctactgcatg  1020
gcactgtcag cctacaacct tttagcgaca cttaaagcag ttcttggcag tgtacatggg  1080
gtagacaaaa tcgatattgg gctatccgat ttttacctag tagatgatat ccattccatc  1140
tatcggggca tgatgattgc tattcctccg gttcattggc aattctttga ggagtttacc  1200
aacattcaga tggtagacgt tctccagcat ctagcaacca agtacatct caaatctttt  1260 cgcaaacacc ccagaagtcc caaaagaaa cgaccaccac tctctgttga tggcaaacat  1320
tcccactgtt ccactactcg aaagctcaag caatacaaag cagctcttga tgctatcccg  1380
tga                                                                1383

<210> SEQ ID NO 17
<211> LENGTH: 460
<212> TYPE: PRT
<213> ORGANISM: Nostoc species
```

<400> SEQUENCE: 17

```
Met Leu Ser Pro Leu Phe Asp Ala Phe Val Glu Ala Ser Pro Val Ser
  1               5                  10                  15

Val Met Met Arg Val Leu Met Glu Asn Ile Phe Asn Ser Ser Arg Met
             20                  25                  30

Asn Gln Ile Phe Asp Thr Ser Val Arg Gln Tyr Ser Gln Glu Leu
         35                  40                  45

Leu Phe Ser Thr Gln Val Asp Leu Met Ser Leu Val Val Cys Gly Met
     50                  55                  60

Tyr Pro Ser Val His Ala Ala Tyr Gln Lys Lys Ala Val Glu Val Ser
 65                  70                  75                  80

Val Ser Ala Thr Ala Leu Tyr Asn Lys Leu Gln Arg Ile Glu Leu Pro
                 85                  90                  95

Val Ser Arg Ala Leu Val His Glu Thr Ala Ser Asp Leu Gln Gln Leu
             100                 105                 110

Leu Leu Met Leu Asn Val Glu Arg Pro Ser Pro Leu Gly Lys Gln Tyr
         115                 120                 125

Arg Leu Arg Ile Val Asp Gly Ser Cys Leu Ala Gly Thr Glu Arg Arg
     130                 135                 140

Leu Ala Ala Leu Arg Pro His Ala Ala Lys Pro Leu Pro Gly Lys Thr
145                 150                 155                 160

Ile Ala Ile Leu Asp Pro Gly Thr Lys Leu Val Val Asp Val Ile Pro
                 165                 170                 175

Cys Glu Asp Gly His Ser Gln Glu Arg Ser Lys Phe His Gln Val Leu
             180                 185                 190

Ala Gln Val Gln Pro Gln Gln Val Trp Ile Ala Asp Arg Asn Phe Cys
         195                 200                 205

Thr Ala Gly Phe Leu His Thr Ile Ala Lys Leu Gly Ala Phe Phe Val
     210                 215                 220

Ile Arg Gln His Gly Gly Leu Gly Tyr Glu Pro Phe Gly Glu Leu Gln
225                 230                 235                 240

Ala Val Gly Leu Cys Gln Thr Gly Thr Val Phe Glu Gln Gln Val Glu
                 245                 250                 255

Ile Val His Glu Gly Gly Thr Phe Arg Cys Arg Arg Ile Val Val Lys
             260                 265                 270

Leu Thr Arg Pro Thr Arg Asp Gln Glu Trp Glu Ile Ala Ile Phe Thr
         275                 280                 285

Asn Leu Pro Pro Thr Asp Ala Asp Gly Ile Leu Val Ala Gln Leu Tyr
     290                 295                 300

Gln Gly Arg Trp Ser Val Glu Thr Leu Phe Gln Thr Val Thr Gln Asn
305                 310                 315                 320

Phe His Gly Glu Ile Glu Thr Leu Ala Tyr Pro Lys Ala Ala Leu Phe
                 325                 330                 335

Ser Tyr Cys Met Ala Leu Ser Ala Tyr Asn Leu Leu Ala Thr Leu Lys
             340                 345                 350

Ala Val Leu Gly Ser Val His Gly Val Asp Lys Ile Asp Ile Gly Leu
         355                 360                 365

Ser Asp Phe Tyr Leu Val Asp Ile His Ser Ile Tyr Arg Gly Met
     370                 375                 380

Met Ile Ala Ile Pro Pro Val His Trp Gln Phe Glu Glu Phe Thr
385                 390                 395                 400

Asn Ile Gln Met Val Asp Val Leu Gln His Leu Ala Thr Lys Val His
                 405                 410                 415
```

```
Leu Lys Ser Phe Arg Lys His Pro Arg Ser Pro Lys Lys Arg Pro
        420                 425                 430

Pro Leu Ser Val Asp Gly Lys His Ser His Cys Ser Thr Thr Arg Lys
        435                 440                 445

Leu Lys Gln Tyr Lys Ala Ala Leu Asp Ala Ile Pro
        450                 455                 460

<210> SEQ ID NO 18
<211> LENGTH: 942
<212> TYPE: DNA
<213> ORGANISM: Nostoc species

<400> SEQUENCE: 18
atgaacaaac caccatccag acgcaagaaa attacccctg cgacatctga ggaaccaaag    60
ctagcaactg accctgctca ggaaaatact tctttgcacg aaaatccagg gggagcaact   120
atcacggtga cggctgttga agtaacagat ttgacccagg aagaacaaag cttacgcctg   180
catttagaac accgtgtgga gagagcattt ttggaggcgg gtcaagcgtt gatggagttg   240
cgggacagac ggctgtaccg ttccacgcac cggacttttg aagaatactg ccgcgaacgc   300
ttcaattata gtcgtgacgc ggcttacttg aagatttcgg ctactgtggt ttatgagaat   360
cttcaaaagt ttttgccgac cattggtcgg caaattccaa tgccgaccaa cgaacgacaa   420
ttgcgttttt tggcgaaagc cgagttggaa ccggctgtgc aagcggatgt atggcggcag   480
gcagtggagc aagctggcaa taagattcca tccggtcgca tagtgaaaga tgttgtagat   540
aggatacgcg aaaggacgaa agtacccaat ccttaccacg ttggggagat atgcgttctt   600
ctacccaaag ataatgcaga cttgagaggt aaagcgggtt attggggcgt ggtcagccat   660
gttggagaat acagttgtac actccagata tgggacggtg actataccgt aaaaatcgaa   720
cacctgaaat cactggaatt acttgatgaa gattgccaat tcatgcagca gttatgtgtg   780
aggttacggc agttgcatca gtggacaggt cgtgacgagg ctgtggattg ctgttgcag    840 tggttgggga acaggccaa accttatctg tcatccttgc agtcaaagct gctggcgttt   900
gttgagagag agtacaacct ggtttggaag cagcagaagt ga                      942

<210> SEQ ID NO 19
<211> LENGTH: 313
<212> TYPE: PRT
<213> ORGANISM: Nostoc species

<400> SEQUENCE: 19

Met Asn Lys Pro Pro Ser Arg Arg Lys Lys Ile Thr Pro Ala Thr Ser
  1               5                  10                  15

Glu Glu Pro Lys Leu Ala Thr Asp Pro Ala Gln Glu Asn Thr Ser Leu
             20                  25                  30

His Glu Asn Pro Gly Gly Ala Thr Ile Thr Val Thr Ala Val Glu Val
         35                  40                  45

Thr Asp Leu Thr Gln Glu Glu Gln Ser Leu Arg Leu His Leu Glu His
     50                  55                  60

Arg Val Glu Arg Ala Phe Leu Glu Ala Gly Gln Ala Leu Met Glu Leu
 65                  70                  75                  80

Arg Asp Arg Arg Leu Tyr Arg Ser Thr His Arg Thr Phe Glu Glu Tyr
                 85                  90                  95

Cys Arg Glu Arg Phe Asn Tyr Ser Arg Asp Ala Ala Tyr Leu Lys Ile
            100                 105                 110
```

```
Ser Ala Thr Val Val Tyr Glu Asn Leu Gln Lys Phe Leu Pro Thr Ile
        115                 120                 125
Gly Arg Gln Ile Pro Met Pro Thr Asn Glu Arg Gln Leu Arg Phe Leu
    130                 135                 140
Ala Lys Ala Glu Leu Glu Pro Ala Val Gln Ala Asp Val Trp Arg Gln
145                 150                 155                 160
Ala Val Glu Gln Ala Gly Asn Lys Ile Pro Ser Gly Arg Ile Val Lys
                165                 170                 175
Asp Val Val Asp Arg Ile Arg Glu Arg Thr Lys Val Pro Asn Pro Tyr
            180                 185                 190
His Val Gly Glu Ile Cys Val Leu Pro Lys Asp Asn Ala Asp Leu
        195                 200                 205
Arg Gly Lys Ala Gly Tyr Trp Gly Val Val Ser His Val Gly Glu Tyr
    210                 215                 220
Ser Cys Thr Leu Gln Ile Trp Asp Gly Asp Tyr Thr Val Lys Ile Glu
225                 230                 235                 240
His Leu Lys Ser Leu Glu Leu Asp Glu Asp Cys Gln Phe Met Gln
                245                 250                 255
Gln Leu Cys Val Arg Leu Arg Gln Leu His Gln Val Asp Arg Arg Asp
            260                 265                 270
Glu Ala Val Asp Trp Leu Leu Gln Trp Leu Gly Lys Gln Ala Lys Pro
        275                 280                 285
Tyr Leu Ser Ser Leu Gln Ser Lys Leu Leu Ala Phe Val Glu Arg Glu
    290                 295                 300
Tyr Asn Leu Val Trp Lys Gln Gln Lys
305                 310

<210> SEQ ID NO 20
<211> LENGTH: 633
<212> TYPE: DNA
<213> ORGANISM: Nostoc species

<400> SEQUENCE: 20
atgacgaagw taagatgggg atrktctygk mtcgwartat cagttataca aaatactaca      60
atcttaaaca tacaattgtt agcttcgaca actattcaat caaagtatat atttaatatg     120
gctatcaaac ccctttttt atttgcactg ttaacgctct ccattatttg tgttggtacg      180
agttctggct ctgcactact gacagatatt gctcaacaaa cagacaacca aaagtcccca     240
tcgattattt tcttcctgcc caagaacga cctcagaccg gagtcggttg ggaaatcact      300
accacttcag ggaaggcaga actagccttg gcgaagcatt tggtgtatat cggggcaaaa     360
gaatatgttt cttggtggtg tcctcactgt cacgaacaaa agttaatctt tgggaagcaa     420
gcctaccaaa taatcaacga cagtattaaa gttgagtgcg ataagagagg tatcaatccc     480
cacccagact tgtgcaatgc ggcgaaagtc ccaggtgtac caacttgggt tatcaatgga     540
catcagtata ccggcgtgca aaactttaag gatcttgcga aagcttctgg ctacaagggg     600
gatatgaact ttcgttatat ccaaagcgaa taa                                  633

<210> SEQ ID NO 21
<211> LENGTH: 210
<212> TYPE: PRT
<213> ORGANISM: Nostoc species
<220> FEATURE:
<221> NAME/KEY: VARIANT
<222> LOCATION: 4, 8, 10-13
<223> OTHER INFORMATION: Xaa= Unknown
```

<400> SEQUENCE: 21

Met Thr Lys Xaa Arg Trp Gly Xaa Ser Xaa Xaa Xaa Xaa Ser Val Ile
1               5                   10                  15

Gln Asn Thr Thr Ile Leu Asn Ile Gln Leu Leu Ala Ser Thr Thr Ile
            20                  25                  30

Gln Ser Lys Tyr Ile Phe Asn Met Ala Ile Lys His Pro Phe Leu Phe
        35                  40                  45

Ala Leu Leu Thr Leu Ser Ile Ile Cys Val Gly Thr Ser Ser Gly Ser
    50                  55                  60

Ala Leu Leu Thr Asp Ile Ala Gln Gln Thr Asp Asn Gln Lys Ser Pro
65                  70                  75                  80

Ser Ile Ile Phe Phe Leu Pro Lys Glu Arg Pro Gln Thr Gly Val Gly
                85                  90                  95

Trp Glu Ile Thr Thr Thr Ser Gly Lys Ala Glu Leu Ala Leu Ala Lys
                100                 105                 110

His Leu Val Tyr Ile Gly Ala Lys Glu Tyr Val Ser Trp Trp Cys Pro
            115                 120                 125

His Cys His Glu Gln Lys Leu Ile Phe Gly Lys Gln Ala Tyr Gln Ile
        130                 135                 140

Ile Asn Asp Ser Ile Lys Val Glu Cys Asp Lys Arg Gly Ile Asn Pro
145                 150                 155                 160

His Pro Asp Leu Cys Asn Ala Ala Lys Val Pro Gly Val Pro Thr Trp
                165                 170                 175

Val Ile Asn Gly His Gln Tyr Thr Gly Val Gln Asn Phe Lys Asp Leu
            180                 185                 190

Ala Lys Ala Ser Gly Tyr Lys Gly Asp Met Asn Phe Arg Tyr Ile Gln
        195                 200                 205

Ser Glu
    210

<210> SEQ ID NO 22
<211> LENGTH: 468
<212> TYPE: DNA
<213> ORGANISM: Nostoc species

<400> SEQUENCE: 22
atgatacagt gtaatttttc gttgccacct gagtatgttc ttcgtaaggc caagcctttt      60
gatatgtggt taatagtatt ttttgtgttt agagcaaggc tagacccag tcaattaaga     120 tggcagcaat tttgggtcat tgaatgtgat ggacatttag tagccttcgg gcagatccga     180
aactttcact tagcacaaga gctaggcagt ttatttgttg caccgacttg gcgaaaccgt     240
ggtttaggga ctgttttgat acagcattta attactcaag ctagtcaacc gctttattta     300
aaatgcttaa aatatcaatt ggtgaatttt tacattaaaa gaggctttgt atccgttaat     360
tttaaagatt taccaccatc cctcaagcca agtttggac tatcccaatt acgaaagagg     420
ttaacgaaag cttttgtgct gtttatgaag tatgaatatc ccaactga                  468

<210> SEQ ID NO 23
<211> LENGTH: 155
<212> TYPE: PRT
<213> ORGANISM: Nostoc species

<400> SEQUENCE: 23

```
Met Ile Gln Cys Asn Phe Ser Leu Pro Pro Glu Tyr Val Leu Arg Lys
 1               5                  10                  15

Ala Lys Pro Phe Asp Met Trp Leu Ile Val Phe Phe Val Phe Arg Ala
            20                  25                  30

Arg Leu Asp Pro Ser Gln Leu Arg Trp Gln Gln Phe Trp Val Ile Glu
        35                  40                  45

Cys Asp Gly His Leu Val Ala Phe Gly Gln Ile Arg Asn Phe His Leu
    50                  55                  60

Ala Gln Glu Leu Gly Ser Leu Phe Val Ala Pro Thr Trp Arg Asn Arg
65                  70                  75                  80

Gly Leu Gly Thr Val Leu Ile Gln His Leu Ile Thr Gln Ala Ser Gln
                85                  90                  95

Pro Leu Tyr Leu Lys Cys Leu Lys Tyr Gln Leu Val Asn Phe Tyr Ile
            100                 105                 110

Lys Arg Gly Phe Val Ser Val Asn Phe Lys Asp Leu Pro Pro Ser Leu
        115                 120                 125

Lys Pro Lys Phe Gly Leu Ser Gln Leu Arg Lys Arg Leu Thr Lys Ala
    130                 135                 140

Phe Val Leu Phe Met Lys Tyr Glu Tyr Pro Asn
145                 150                 155
```

<210> SEQ ID NO 24
<211> LENGTH: 2355
<212> TYPE: DNA
<213> ORGANISM: Nostoc species

<400> SEQUENCE: 24

| | |
|---|---|
| atgtcagtgc cagttagcgc acagattata ccagataaaa cactacctat taattccaat | 60 |
| gttgaacatg aaggtaatac taaccgcata gaaggtggca ctataaaagg gagcaacttg | 120 |
| ttccacagtt ttgaacaatt ytccgtgctt actggaaatg aagcttactt taacaacgat | 180 |
| ataaatatcc aaaacattat tactcgtatt actgggaagt ctatttctaa tatcgatggc | 240 |
| attctcaaag ccaatggcac ggctaatttg tttctgctca atcccaatgg cattattttt | 300 |
| ggtaataatg ccaaactaaa tattggtggt tcatttctag ctactactgc aaatcaaatt | 360 |
| aattttgctg atgatactaa atttagtaca aacaatcccc aacctaatcc tttactgaca | 420 |
| gtaagtgtgc ctataggact gcaaattgat agcaaccccg gtacaattcg catccaaggt | 480 |
| acaggtcaca atctaattgg ccctcctttt tctcctctaa tcacaagtag tagcgccgca | 540 |
| aatttacaag tgcaaccaga agaactgta gcaattgttg gtggtgatgt aatttttagag | 600 |
| ggaggtgtga taacggctag ggagggcga attgaattgg gtagcctcag caatggttca | 660 |
| gtcagtatta atcctacgac ctctggttgg aaactgggct atgaaaatgt accttatttc | 720 |
| caagatatta acctctcaaa acgcgctkta gttaatacta gtggcattgg cagtggatct | 780 |
| atacagatag agggacgcak agttacgctt acagatggct cagtaatctt aaatcaaaat | 840 |
| caaggaacac taccaggagg cacactaaac gtgaatgctt cggagtcttt gtcagtgagt | 900 |
| ggtagcgatc caattgctag dacagctggt ggtttgcgga gcgaaacttt gggattyggc | 960 |
| aaagctggag acattgcaat ttcaaccaaa caggtaatta ttaaaaatgg aggacaaata | 1020 |
| aataatttaa cctttggtgc tgcaacaagt ggcaatataa atgtgaatgc ctctgattct | 1080 |
| atacaattgc ttggggtttc gccttttgac cctgctgttt ttagtactat cagcactgca | 1140 |
| actttcaatt ctggaaacgc aaacaatatt acagtgtcaa caggacaatt cgttgccacg | 1200 |

-continued

```
gatggaggta acttgtcctc ttcaacctttt ggaactggta gaggaggaga tgtcactgta      1260
agtgcaactg actctataga aataatagga gcttcaccaa taacctttca gccaagtatt      1320
ttatcttcca tatcgctcaa tgctggcaaa gctggcagcc taacaatcag tacatcaaag      1380
ttgatggttc aagatggcgg gagggttgac gcttctactt tagcaagtgg ggagggcggt      1440
agtgttacga ttaacgcctt taaatctgta gaggtaagtg gtaagatact tggttttgga      1500
gagcctagtt tggtgatctc cagtgctaat atcgtctctc caatcttgca aaagttatac      1560 agactcccttt cagtgccttc tggaaaatct ggaaacgtga cgattaatac tggtcagttg      1620
agtgttacag acggtgctga agttaacgtg agaaatgacg ttctarcga tgctggaaca      1680 ctcagaatca atgctgtttc tgtttctttta aacaaacaaa gtgccattac agcaactact      1740
gctaacggcg aaggcggtaa tattttcgtg aatacacggt atttgcagct aagtaattac      1800
agtgttgtaa cgacgaccgc aggtagtaga ggcaatggcg gtaatataaa catcaatgca      1860
gatatattaa gtgcttgggg gaagagcagt attgctgcca atgctttcta tgggtatgga      1920
ggaaatgtac taattaatac tagaggactt tttattgctc gtgacagtca aatttctgca      1980
agttctaaat acggaattaa cggcactgtt agcattaaca atactggtgg tgaaatttat      2040
cctactaaac tcaaatcaga atcgattcca gtagctcctc aaatagcatc agtttgtcaa      2100
aaaaattcag atataccaat cagtaaattt gtgaatgttg gcaccggtgg actgccagct      2160
aattctgatg atatgccata tgaattat gaacagcaaa ataactctgt ttcaatccac       2220
aataataata acttagaggc atcgaaggca tcacaaactg aagaacctat acagataata      2280
gaagctcagg gttggataat aaatcttgat ggggaatgtc gtcttaactg cacaaaacaa      2340
tacagcaacc cctaa                                                       2355
```

<210> SEQ ID NO 25
<211> LENGTH: 784
<212> TYPE: PRT
<213> ORGANISM: Nostoc species
<220> FEATURE:
<221> NAME/KEY: VARIANT
<222> LOCATION: 47, 25, 267, 319, 556
<223> OTHER INFORMATION: Xaa= Uknown

<400> SEQUENCE: 25

```
Met Ser Val Pro Val Ser Ala Gln Ile Ile Pro Asp Lys Thr Leu Pro
  1               5                  10                  15

Ile Asn Ser Asn Val Glu His Glu Gly Asn Thr Asn Arg Ile Glu Gly
             20                  25                  30

Gly Thr Ile Lys Gly Ser Asn Leu Phe His Ser Phe Glu Gln Xaa Ser
         35                  40                  45

Val Leu Thr Gly Asn Glu Ala Tyr Phe Asn Asn Asp Ile Asn Ile Gln
     50                  55                  60

Asn Ile Ile Thr Arg Ile Thr Gly Lys Ser Ile Ser Asn Ile Asp Gly
 65                  70                  75                  80

Ile Leu Lys Ala Asn Gly Thr Ala Asn Leu Phe Leu Asn Pro Asn
             85                  90                  95

Gly Ile Ile Phe Gly Asn Asn Ala Lys Leu Asn Ile Gly Gly Ser Phe
            100                 105                 110

Leu Ala Thr Thr Ala Asn Gln Ile Asn Phe Ala Asp Asp Thr Lys Phe
        115                 120                 125

Ser Thr Asn Asn Pro Gln Pro Asn Pro Leu Leu Thr Val Ser Val Pro
    130                 135                 140
```

-continued

```
Ile Gly Leu Gln Ile Asp Ser Asn Pro Gly Thr Ile Arg Ile Gln Gly
145                 150                 155                 160

Thr Gly His Asn Leu Ile Gly Pro Pro Phe Ser Pro Leu Ile Thr Ser
                165                 170                 175

Ser Ser Ala Ala Asn Leu Gln Val Gln Pro Glu Arg Thr Val Ala Ile
            180                 185                 190

Val Gly Gly Asp Val Ile Leu Glu Gly Gly Val Ile Thr Ala Arg Gly
        195                 200                 205

Gly Arg Ile Glu Leu Gly Ser Leu Ser Asn Gly Ser Val Ser Ile Asn
    210                 215                 220

Pro Thr Thr Ser Gly Trp Lys Leu Gly Tyr Glu Asn Val Pro Tyr Phe
225                 230                 235                 240

Gln Asp Ile Asn Leu Ser Lys Arg Ala Xaa Val Asn Thr Ser Gly Ile
                245                 250                 255

Gly Ser Gly Ser Ile Gln Ile Glu Gly Arg Xaa Val Thr Leu Thr Asp
            260                 265                 270

Gly Ser Val Ile Leu Asn Gln Asn Gln Gly Thr Leu Pro Gly Gly Thr
        275                 280                 285

Leu Asn Val Asn Ala Ser Glu Ser Leu Ser Val Ser Gly Ser Asp Pro
290                 295                 300

Ile Ala Arg Thr Ala Gly Gly Leu Arg Ser Glu Thr Leu Gly Xaa Gly
305                 310                 315                 320

Lys Ala Gly Asp Ile Ala Ile Ser Thr Lys Gln Val Ile Ile Lys Asn
                325                 330                 335

Gly Gly Gln Ile Asn Asn Leu Thr Phe Gly Ala Ala Thr Ser Gly Asn
            340                 345                 350

Ile Asn Val Asn Ala Ser Asp Ser Ile Gln Leu Leu Gly Val Ser Pro
        355                 360                 365

Phe Asp Pro Ala Val Phe Ser Thr Ile Ser Thr Ala Thr Phe Asn Ser
370                 375                 380

Gly Asn Ala Asn Asn Ile Thr Val Ser Thr Gly Gln Phe Val Ala Thr
385                 390                 395                 400

Asp Gly Gly Asn Leu Ser Ser Ser Thr Phe Gly Thr Gly Arg Gly Gly
                405                 410                 415

Asp Val Thr Val Ser Ala Thr Asp Ser Ile Glu Ile Gly Ala Ser
            420                 425                 430

Pro Ile Thr Phe Gln Pro Ser Ile Leu Ser Ser Ile Ser Leu Asn Ala
        435                 440                 445

Gly Lys Ala Gly Ser Leu Thr Ile Ser Thr Ser Lys Leu Met Val Gln
450                 455                 460

Asp Gly Gly Arg Val Asp Ala Ser Thr Leu Ala Ser Gly Glu Gly Gly
465                 470                 475                 480

Ser Val Thr Ile Asn Ala Phe Lys Ser Val Glu Val Ser Gly Lys Ile
                485                 490                 495

Leu Gly Phe Gly Glu Pro Ser Leu Val Ile Ser Ser Ala Asn Ile Val
            500                 505                 510

Ser Pro Ile Leu Gln Lys Leu Tyr Arg Leu Pro Ser Val Pro Ser Gly
        515                 520                 525

Lys Ser Gly Asn Val Thr Ile Asn Thr Gly Gln Leu Ser Val Thr Asp
530                 535                 540

Gly Ala Glu Val Asn Val Arg Asn Asp Gly Ser Xaa Asp Ala Gly Thr
545                 550                 555                 560
```

```
Leu Arg Ile Asn Ala Val Ser Val Ser Leu Asn Lys Gln Ser Ala Ile
                565                 570                 575

Thr Ala Thr Thr Ala Asn Gly Glu Gly Gly Asn Ile Phe Val Asn Thr
            580                 585                 590

Arg Tyr Leu Gln Leu Ser Asn Tyr Ser Val Val Thr Thr Thr Ala Gly
        595                 600                 605

Ser Arg Gly Asn Gly Gly Asn Ile Asn Ile Asn Ala Asp Ile Leu Ser
    610                 615                 620

Ala Trp Gly Lys Ser Ser Ile Ala Ala Asn Ala Phe Gly Tyr Gly
625                 630                 635                 640

Gly Asn Val Leu Ile Asn Thr Arg Gly Leu Phe Ile Ala Arg Asp Ser
                645                 650                 655

Gln Ile Ser Ala Ser Ser Lys Tyr Gly Ile Asn Gly Thr Val Ser Ile
            660                 665                 670

Asn Asn Thr Gly Gly Glu Ile Tyr Pro Thr Lys Leu Lys Ser Glu Ser
        675                 680                 685

Ile Pro Val Ala Pro Gln Ile Ala Ser Val Cys Gln Lys Asn Ser Asp
    690                 695                 700

Ile Pro Ile Ser Lys Phe Val Asn Val Gly Thr Gly Gly Leu Pro Ala
705                 710                 715                 720

Asn Ser Asp Asp Met Pro Tyr Met Asn Tyr Glu Gln Gln Asn Asn Ser
                725                 730                 735

Val Ser Ile His Asn Asn Asn Asn Leu Glu Ala Ser Lys Ala Ser Gln
            740                 745                 750

Thr Glu Glu Pro Ile Gln Ile Glu Ala Gln Gly Trp Ile Ile Asn
        755                 760                 765

Leu Asp Gly Glu Cys Arg Leu Asn Cys Thr Lys Gln Tyr Ser Asn Pro
    770                 775                 780

<210> SEQ ID NO 26
<211> LENGTH: 399
<212> TYPE: DNA
<213> ORGANISM: Nostoc species

<400> SEQUENCE: 26
atggtgatta ttcaagccac gcagcatttc tgtagattta gtcttggtgt tttcttagca    60
caatcaagag tagagataga gcagagttta acaatgtcaa ctcctaacta tcgtcaagag   120
attgatattg taaaacgttt attttcgcaa atcctaatt tatgcgttga tattatgcta    180
gcgactgaag aaaggtgtaa tgctattagc tttttagcta aaacttacag ccgattggct   240
agactggtgg ctaggaagga tagagaggca ttaattaaag agtttgaaaa tactcaaagt   300
ttttttgaag agaaaattaa tagttttctc cagcctttaa atacaacggc tctgcaacga   360
gattttaaac cccagatgca cacaaatatt agcatttga                          399

<210> SEQ ID NO 27
<211> LENGTH: 132
<212> TYPE: PRT
<213> ORGANISM: Nostoc species

<400> SEQUENCE: 27

Met Val Ile Ile Gln Ala Thr Gln His Phe Cys Arg Phe Ser Leu Gly
  1               5                  10                  15

Val Phe Leu Ala Gln Ser Arg Val Glu Ile Glu Gln Ser Leu Thr Met
             20                  25                  30
```

Ser Thr Pro Asn Tyr Arg Gln Glu Ile Asp Ile Val Lys Arg Leu Phe
        35                  40                  45

Ser Gln Asn Pro Asn Leu Cys Val Asp Ile Met Leu Ala Thr Glu Glu
 50                  55                  60

Arg Cys Asn Ala Ile Ser Phe Leu Ala Lys Thr Tyr Ser Arg Leu Ala
 65                  70                  75                  80

Arg Leu Val Ala Arg Lys Asp Arg Glu Ala Leu Ile Lys Glu Phe Glu
                 85                  90                  95

Asn Thr Gln Ser Phe Phe Glu Glu Lys Ile Asn Ser Phe Leu Gln Pro
             100                 105                 110

Leu Asn Thr Thr Ala Leu Gln Arg Asp Phe Lys Pro Gln Met His Thr
             115                 120                 125

Asn Ile Ser Ile
            130

<210> SEQ ID NO 28
<211> LENGTH: 645
<212> TYPE: DNA
<213> ORGANISM: Nostoc species

<400> SEQUENCE: 28

```
atgctgatag atatctttca tgataccgtt tgcccttggt gcagaattgg gaaaaaacat      60
ctatttgatg cactggcaca atggcaagaa caagaagtaa atatccgatg gcatccctt     120
cttctggatg atactgttcc tgctgagggg tacgaattta gtagctttat gcaaaataga    180
aaaggcatta aagcgccaga aatgcaacag atgtttgatt atacgcaacg cgcaggggag    240
gcggctgggg ttaagctaga ttttgaaaaa atccgtttgg ctgtcaatac taagcttgct    300
caccaactga ttgcattagc accgacaaac ataaaaaatg atgtcgttga agctatttat    360
agagcttact tgaagagggg tttgaatatt ggagatatta cgttattgt tgccatcggt     420
acagcatacc agatggatgc taccgaatta aagttgcaat aaacgatcg cgatgtcgtt     480
gatacagttg ttgctgaatc ggcatttgct cgcttaaatg gcatcaacag cgtgccgttt    540
ttcatcatga ataatcaagt caaggtaaat ggttctcact cggttgaggt tttccttgaa    600
gctttgaata gtactgcact tttagatata cctgcaaaaa tatga                    645
```

<210> SEQ ID NO 29
<211> LENGTH: 214
<212> TYPE: PRT
<213> ORGANISM: Nostoc species

<400> SEQUENCE: 29

Met Leu Ile Asp Ile Phe His Asp Thr Val Cys Pro Trp Cys Arg Ile
 1               5                  10                  15

Gly Lys Lys His Leu Phe Asp Ala Leu Ala Gln Trp Gln Glu Gln Glu
             20                  25                  30

Val Asn Ile Arg Trp His Pro Phe Leu Leu Asp Asp Thr Val Pro Ala
         35                  40                  45

Glu Gly Tyr Glu Phe Ser Ser Phe Met Gln Asn Arg Lys Gly Ile Lys
 50                  55                  60

Ala Pro Glu Met Gln Gln Met Phe Asp Tyr Thr Gln Arg Ala Gly Glu
 65                  70                  75                  80

Ala Ala Gly Val Lys Leu Asp Phe Glu Lys Ile Arg Leu Ala Val Asn
                 85                  90                  95

Thr Lys Leu Ala His Gln Leu Ile Ala Leu Ala Pro Thr Asn Ile Lys
             100                 105                 110

```
Asn Asp Val Val Glu Ala Ile Tyr Arg Ala Tyr Phe Glu Glu Gly Leu
    115                 120                 125

Asn Ile Gly Asp Ile Asn Val Ile Val Ala Ile Gly Thr Ala Tyr Gln
130                 135                 140

Met Asp Ala Thr Glu Leu Lys Leu Gln Leu Asn Asp Arg Asp Val Val
145                 150                 155                 160

Asp Thr Val Val Ala Glu Ser Ala Phe Ala Arg Leu Asn Gly Ile Asn
                165                 170                 175

Ser Val Pro Phe Phe Ile Met Asn Asn Gln Val Lys Val Asn Gly Ser
            180                 185                 190

His Ser Val Glu Val Phe Leu Glu Ala Leu Asn Ser Thr Ala Leu Leu
    195                 200                 205

Asp Ile Pro Ala Lys Ile
    210

<210> SEQ ID NO 30
<211> LENGTH: 273
<212> TYPE: DNA
<213> ORGANISM: Nostoc species

<400> SEQUENCE: 30
atgatagttg acatcaagca aaaaaataga ttaattcatc aacgtgtttc ggttactttt      60
aactatgaga tttacttcac ccaaaattta tttgagttga aaaacccgac gctagcgcaa     120
gtaatttcgg cagatgagga gacaaagccg aagaaaatag ttgcggtggt agacgcagga     180
atattaaagt atcaaccgga attggtgaag caattagttg cgtataccaa gttttatgga     240
gaggtactag cgatcaatgt gcccaaatat tag                                  273

<210> SEQ ID NO 31
<211> LENGTH: 90
<212> TYPE: PRT
<213> ORGANISM: Nostoc species

<400> SEQUENCE: 31

Met Ile Val Asp Ile Lys Gln Lys Asn Arg Leu Ile His Gln Arg Val
1               5                   10                  15

Ser Val Thr Phe Asn Tyr Glu Ile Tyr Phe Thr Gln Asn Leu Phe Glu
            20                  25                  30

Leu Lys Asn Pro Thr Leu Ala Gln Val Ile Ser Ala Asp Glu Glu Thr
        35                  40                  45

Lys Pro Lys Lys Ile Val Ala Val Val Asp Ala Gly Ile Leu Lys Tyr
50                  55                  60

Gln Pro Glu Leu Val Lys Gln Leu Val Ala Tyr Thr Lys Phe Tyr Gly
65                  70                  75                  80

Glu Val Leu Ala Ile Asn Val Pro Lys Tyr
                85                  90

<210> SEQ ID NO 32
<211> LENGTH: 3690
<212> TYPE: DNA
<213> ORGANISM: Artificial Sequence
<220> FEATURE:
<223> OTHER INFORMATION: 75% sequence identity to SEQ ID NO::2

<400> SEQUENCE: 32
atggggcata gagcttgggg atatctggga gggacagtcg caggtatgtt cactttggaa      60
gattttttaa gagtgattcg tcatagtggt agaccaatgg cacaggtacc ctgaggaggc     120
```

```
gaaacgttat ctataaggag ttcaatcgta aagataagtg aagtaatcgc gccatacgct      180
ccaaacgtcg cgatctcata aattgacggg cccccaagca ctgtcaattc aggtgggcca      240
gttgcaattg gaacgcttcg aaatctctta gccgcagtag agattttgac acgacgacgg      300
gaagtatccc gcgcgttcaa tgcatatccg atgaaacgaa cgttaacgga gtttgaagca      360
gcagcaccag ccctaacgta cgatccacta aacataccat cagtaccaaa tgtatcggga      420
gcgattgcgg agcagagtat aacctgagca agcggttgcc taattcatca ccggctaccg      480
cagaaatttg cgcatagtac ggacagataa cagcacgaag gttaatacct ctgcgtagac      540
cttggaccag aaccagcttt cttaagcgtg caagacagt acccgccaga ggacgtgggt      600
ccttgggtgc gatctgtcat actaggacaa gtacactcgc atccaatgct agaaacttag      660
gctcaacttt atgcgcaagg agttaaacat gattggttac ggttcattaa agattattgt      720
ggtagtacgg aagtagtctc gacttttgcc ttccatcgcc aacgttattg gtaggagaga      780
tataatagtc tcatagataa ggaacagatt tcataaaatc atattaatct ccaagctcta      840
gtcggtaata gatcacaagt agcagcgttt gaaaagtgaa ttcggtttaa atgccaaaat      900
ggtgcttctc atccaagtta ccagctacag cagtgagtct ttcctgtacc tctttaccaa      960
gctacagatt agttggtaat acccatacca ggaggtacaa ctttatttaa gtcaggtgat     1020
agaaccctat aagatattgt aatagaaaag gcatgaattt tatcgacggt taaaattcag     1080
agaattcaaa tagtgttaat cttacggtta ctacagagat atagattaca tatttttggt     1140
ctggaaacaa atactgctac ttaagaacct agctggatac tacatgttca aggataaatg     1200
ttagtaagga acaaagtccc agaattagag accacatact tgaaagcggt caaagaaggg     1260
tataaggaaa agattttacc taatgagttt tacaagaaac atgaagaaag gcggctttat     1320
aacgctgctt ctatctaagc cgttggacaa ctgaggcaga gcgatagcaa aagactaagt     1380
ggaatttagt tgccaaaaac acaggtcata gttgcaaatt tatgacaact cgcctaaat     1440 gtttaagatg atatgttcca ggtatttcca gctgttgtgg ttagaacgga caagcatgga     1500
gcttatgtgc acttggaaag aaaccgtcaa caaatatagc ggactgttag taatggttcg     1560
tcgacagaag tataggtaga tgtagcagaa cctaagaaaa ccactttgag atgtaacgtt     1620
gattcattat atgaacgcgg aatagtatga gcaagaattc aagcttaaag tttattatgt     1680
agttcacggg aggcattgtg ttgtagtatc gagccgcaag ttaacaaggg gttataacac     1740
atccagtggc agacccgatc acttgcacca catcacgaaa caattgactt gacaaactca     1800
ggtggctagt ttttggcttc accagccacc gggatagaga atcatatggt ggaatcgttc     1860
gcactgcaaa gctgacattg tatatttgta ggaccagggc agaacttcca ggagttagaa     1920
actccacagt atcatatcga ccgcaatcaa ccagacgaat tcatggactt gatgaaagca     1980
cggttggtgc agcaacccca ggtaccagca attatgcacc tacggggttt cgactaaaca     2040
atatcactaa agactggtgc gcagcacttg ctaaattaac gagtactcgg ttgtggcaac     2100
gaactgcatc gagtcaaggc cttcgtaata gatcgagata aggagagtgc ccccttattg     2160
taagtggctc aagcctctca ttctgaggga atgaataac taccgatacc attccgacaa     2220
gcaactatgt gcgcgttatg tggagtattt gcacggggcc aaaggcaatt agaaagccag     2280
tgtttaggct tacatccatc taaggaagct tccgaaagat tagcagctat ctttgaggga     2340
ctattctctt ctgctgatga gaacgtaaat gctaactctc aatggttaag tcgcgttcct     2400
gagtaagaga ggcgataaag aatgagaaca tgtacacatt ccgaatgaga aatatcgtcg     2460
catcaatcat gtctactgca gctagcagta tatagctcat tggacaccct tatcgaactc     2520
```

-continued

| | |
|---|---|
| gaggccattt actcaattgc cgtaagtctg agagctccgg gctaaaaagc cgctaagtgg | 2580 |
| ttgataccac aagcggtaat aaatttcgtg cttactggac atacgcaggc aacagtaaga | 2640 |
| ggtctgcaaa cccttgatca aatacacatg gcagaagcgc cagtgttatt catctggtga | 2700 |
| gaaatttcgc atcaagagac tgtcgcaaga tttataaagt ccagcaaagc attattgcga | 2760 |
| gcactatcag gaaaaataca ggccgccggg aaatggttg gtggtcttct gttagatatc | 2820 |
| aagtgggtta aagttacata cgtggtggaa cataaactac atcggacttg gtatttccag | 2880 |
| aatatgactc tgaatctgcc tatggaccttt gttttatgtt ttgcctccat tgattcgatc | 2940 |
| tttggttcga ctggtcgcgg gtattaagct ggtgccattg agtttatggg tggtttatcc | 3000 |
| cataatggac gtgatatgcg ataacctggg tcgagtatta aatggcgatc atggccacta | 3060 |
| gaagcaatgg ctgcaaatat gggtagccgt cttcgagatt gagcggtgac caaggcaatg | 3120 |
| tctgttatgg tttcagagca gggaatgcag cttcgaagtc aaaaactcta agaatcatta | 3180 |
| gcacaagtgg gagtgcttcc aaatgaatgg ccagtgatcc aagggccatt aaggttcggt | 3240 |
| gatcaattag cattactctc ctaaatgggc aatggaagca aaacacacca tatagccatc | 3300 |
| gagactcaga cacagtacaa tgggttctaa gaacacctaa aagctgctgt acaaagagta | 3360 |
| agacataaga ttgtgttaaa ttacgtcaaa ggtgtaatat ctaaactatt tgttagagc | 3420 |
| atatctcgac ttgttatgga tcaccccctc aacacaatcg gtctagattc tttaaaggcc | 3480 |
| gtccaagtgc acactagtct cgaactgat ttgctcctga atatgtcgct agtcataatt | 3540 |
| gtataaaata cctgtatcgt acatataggc tctgaactgt atcagcaagt gagcctaatt | 3600 |
| acgcagactc aatgagatga gtgagacaat aatggtaaac tcgaccaaac taaaagcaac | 3660 |
| gataaagacc gcattagtag tggattacgt | 3690 |

<210> SEQ ID NO 33
<211> LENGTH: 3690
<212> TYPE: DNA
<213> ORGANISM: Artificial Sequence
<220> FEATURE:
<223> OTHER INFORMATION: 80% sequence identity to SEQ ID NO:2

<400> SEQUENCE: 33

| | |
|---|---|
| atggggcatt atgccgggga atctgtgcca gccatagtgg ctggactatt tggtctagaa | 60 |
| gacgttttaa acccgcttgc ttatatagga cgactaatcc atcaattacc atctgggagt | 120 |
| gagatcttat ctgtaattgc atctattgaa cagctaaatc agctatttgc atcatacct | 180 |
| cagagagtag tgatcgcttc gatcaacgta caccaatgca tagtcatctc tgctgatgca | 240 |
| gacgcatttg gaccgggtca acatagctaa gtagcacaag acaggaagac aacacgagtg | 300 |
| caaatatgcc acccatttca tacacatctg ctggaatcaa agttggtgga atttgacgca | 360 |
| gtcgcttcag acataacgta cgatcatcca actattcgat tagcatgaaa tgtatctgga | 420 |
| gcgagcgcag agaatcgttt agcgacagca agctctttgg gtaatcacgt ctggctaccg | 480 |
| gtgtaacttg ccaaaagaat gcacaaatta cagaatgaag gctattacat catcttataa | 540 |
| atcggaccaa aacctacatt gtaaggcatc agaagccagt gcatgtcaga acatgaggga | 600 |
| gtatgggtgc catcattgaa gctagcgcaa gacgactgac ggcacatgcc acgaagcttg | 660 |
| gcagaattat ctgtccatgg cgttatagtt cattgtttag cgttagataa cgaatattct | 720 |
| cctagaaagg gagtattacc tacttgtccc tgtcaatggc agcgctattg cattgtgaca | 780 |
| gataatcatc taattcacca gagacagttt caatcaaatc ataagagtct tcatcatcta | 840 |
| ctcagtcata cattacatat agaagcatta gatcagcata tacggtttga atgacatatt | 900 |

```
agtgcatcac taccagctta cgttcaacac cgctgcgttt tatcacaacc tgttatccta    960
gaagctgctt actaggtaat cgccttagga gcgggtacaa tattaatcaa tgcagaggat   1020
ttcatcctac atgatatatc aaactaaaaa gtagtaactt tatctaaaga agaagttaat   1080
acacttcata aaggtttaaa cttacagttt atacaaggct atcaattcct gatcttcagt   1140
atggctataa gcactaattg atccgaacct agatgcattc aacatgttga aggacagata   1200
atagtgggta atcaataccc cgaattacaa acaccaatct tcaacgcgat tacagaggag   1260
tagaactaac ggatactacc tgctgcattc taccgaacat ttgcagactg gtgtcttaac   1320
tccggtcctt cgttctaagc cgttcaacta ctgcgggaca gcgcaggata agcattagat   1380
gtaattccgt tacgagacac cgagatgaat gtaacaactt catactaact acacctaatt   1440
cgtttcgatg ctcgctgcca cgtgttcgca gcatttaggg gtaacacgca cagccatgaa   1500
tcttatatgc gattgcaaat agaacgatta cgaattcatc ggagtggtac taatcgtttc   1560
tggactcaag gagagatcgg tgcgacacaa cctagtaaac aagctttgac cggtcaagtg   1620
cgtttattcg ctgatcaagg cataggagta ggatgagttg caggtgtaac cgtattacgt   1680
gcttttcgcg cgggtttgtt gcctattatt gaagcaatat gtattaattg cttagatcac   1740
atccactggc taatccaatc attttcgccg catatccaag caatcgactg aaccaaatca   1800
ggtacgtgtc tagtgttttc ggcacccaca cgtaaaggcc aacttctggg agactcctta   1860
taacaacaag ctcggcattg tagactagta acacaacggg acatttacca ggagctagaa   1920
ccgcaacatg aacaaatcaa cctcagccaa cttgaggaat cgggcaccc atggcaatcc    1980
agctcggagg agtaaccccc aggacgaggc attgttcacc tgcggacttg gtactcaacc   2040
ataccactaa ccactggggg acacgagttg ctacaatccc atgagctggc cggtggcagc   2100
gtacgacatt tagacgaagg attagtaaag attcaagata cgcaaagtgg gccattatgg   2160
taattgactc aatgctgaca ctctgggggt aataactccc tgcatataca attgcatcag   2220
acatctttac gcgggttagg tcgcggaatc gcccaagaat acagggaatt actattccgc   2280
tttttagaca tatatccaag tatagaagat cccaaaacag caggtgcttc gttataggat   2340
ctatcatctc atggtcatgt taaccaaata gtttactgtc atgaggtacg tcactttacc   2400
atgttagagc ggcaatagag aacgagtacg tctatacagt cggcattacc attttcctcg   2460
ctacaagcat atcagctgaa gctagcagct tacaagtctt aagtcaacct agtcctagcc   2520
gatgcgagtt acgtagttag cggatgtctg gcagtactgg ggttaattac ggccgagtgg   2580
acggtagaac atggggtgag atgtttagta ctcacccgac gtcgggagcg atcagaaaag   2640
ggtcaacaat ccagtgaacc attgcagaag ccaggggcgg aaatattagt ccagtggggc   2700
ggtatttccc gacacgaaag tgtgacaagg attctagaga cattcaaagg atccttgccg   2760
gccttacgag aaatgattcc tactgctggc atattagatc atgatttgcg gtcaaacatg   2820
actgggaac catttacacg ggtaatggcg cccaaagtac taggtgcttg tcatgtgcat    2880
accttgactc ataatgtacc gtgggacttt gttctttgtt cttgctctat gccttgaata   2940
atcggttcgc gtggccaagg gactaatgcg gctactaatg catacatggt tagtttagcc   3000
gatcaccgac gaggtacggg cttagctggc tggaggatta tctgggaacc atggacacga   3060
gcggaaatgg cacctaattt gcattgtcct catcgacata gtatgctgtc catgggtatg   3120
actattatgt ctatagaaca gtgattccag cttataggac agttacccga acagtcgata   3180
ccacgagtcg cagtgctacc acttgaatgg tcactgatcc aagaacattt tagttgtggt   3240
actcaagtac cactgcggtc ctagttggtg acagaaagca tatcacggca ccaagccctc   3300
```

| | | |
|---|---|---|
| aattcaaaga catagcagaa tgaagttata ggatagctaa cagcagcttt accaggacaa | 3360 | |
| ggagcaaagc atatgataat gtacattata gatgcagttt cccgagtact atctctgagc | 3420 | |
| agttatcaaa gtcatatgca tcagctcctg agcagtatgg cccttgattc tcaattggct | 3480 | |
| gtccaattgc acattacgct acaagctgac atgctggtgg agataactat actcagattt | 3540 | |
| ataccagatt tcactatcgt tgctatagcc agtgatgtgc atgaggaact gaccctagtt | 3600 | |
| gcttagcatc aacgagatga gtcagcatat accgggcaac tctacgatag cattaggtaa | 3660 | |
| gcaagcgagc ggattagacg tcaataatga | 3690 | |

<210> SEQ ID NO 34
<211> LENGTH: 3690
<212> TYPE: DNA
<213> ORGANISM: Artificial Sequence
<220> FEATURE:
<223> OTHER INFORMATION: 85% sequence identity to SEQ ID NO:2

<400> SEQUENCE: 34

| | | |
|---|---|---|
| atggggcata gcgctgggga atatgttgca gcaacagtac catgaatttt tagattagga | 60 | |
| gatggttcaa aacagattgc tcagagagca agacttatgc aacaattacc gtctggcggt | 120 | |
| taaatgtttt ctgtaaaggc ttgaatcgta aaagtgaatc aactcattgc actatactct | 180 | |
| caataagtag cggtcgcatc gattgaccga cctcaaagca ttgacatgtc tggcgaggca | 240 | |
| gtagcaaatg gagcggctga aaaaagcttg gaaccagaag acataaagac aaaatgactg | 300 | |
| caagtgtcac aggcattcct ttcacgtttg ttggacccaa tgttagcgga cattgaagcg | 360 | |
| gtagcctcag aattaaccta cagtcaagca aatatttcat aaggatcaaa tgtaagggta | 420 | |
| gctaaggcag cgaatagtat ttccaaagca acctattggt tatatcgtgt ccggcaaccg | 480 | |
| gtgaattttg cgcaatgtat ggtcacaata tagcaagaag attattcctt cttgttagaa | 540 | |
| attgcacaca aatcaacttt gtaaggcgtg ggcagacagt gcttgccaga tgatgttgta | 600 | |
| gtatgggtgc ctccgttgaa accaggtcaa gaatacttgc agcagatgct ccaaagtatg | 660 | |
| gcttaaccat ttgtgcatgc agtttaagtt gattggtttg ggtttaataa ggattattct | 720 | |
| cctagtaaag tagtatggcc gatttatccc tatcaaccgc aacgatattg gagtgcgaca | 780 | |
| aattataatc taaacagca gaaacagcta ttatcaaatc ataagaatcc tcaccctcaa | 840 | |
| ctcggtgaaa gataacattc tgcagcctta gtactgcaaa ttcattttga gtgtcgaatt | 900 | |
| agtgcatctc aagcaactta cccgcaacac tactgggttt ttttcagcc tcttttctca | 960 | |
| gcagtagctt gcttcgaaaa agccttacca gcaggtgcaa ttatattcaa gtcagatgat | 1020 | |
| ttcatcctat aaggtatagc aatcccaaaa gtatttatta tatgaaacga tgaaaataat | 1080 | |
| gcaattccga tagtattgaa attacattta gtgcaaagcc ataaatacca aattctcagt | 1140 | |
| ttggatgtaa tcactagttc tccaaaaccc aaatggattc tacgtattga aagaaaatta | 1200 | |
| ttagaaggta gtaaagcctc ccaattaaaa acaacaaact tagaagcgct ttaagacggg | 1260 | |
| tattacctac agataatacc tgctgaattc tcctaaaaat ttgaaggatg cggtcttatt | 1320 | |
| tacggatcgt ctctccaagc ctttaaacaa atgtggcaca ccgaagtaaa ggcaccaggt | 1380 | |
| aaaattccgt gaccaaaaac tgaggtaaat gtggcatctt catacgaact gcacccaaat | 1440 | |
| ctattagatc ctagcttccg ggtgtttgct gcagtaatgc gtaaatcgga cagccaagaa | 1500 | |
| gctaattggc cattggaaat acaacgacta caatttatc gcaatggtgg taacagtatg | 1560 | |
| aggactcgag tagcgatagg tgctacagaa actagtacac agactttaag cggcaaggat | 1620 | |
| tgtttactgg atgaacgagg aacagtagta acaagagttc aaggtttatc tttataacgt | 1680 | |

```
actactcgcc aggcttagtt acgtgatatt caacctaaat ttaataaatg gttatgtcaa    1740
atgcataggc aaacccgatc aatctctccg cataaccaaa caattgactt gacaaattca    1800
ggaaggtggt tattgtttcc cccactcaca agtataggca agcatctcgt agtaaccttta   1860 caacgacaag gatggcattg tgtattagca acacctgggg aagattagca ccagttagaa    1920
tcactacatt atcaattcaa cccctaccat ccagagggat tcctggacct atagcaatcc    1980
agcttggaac aggaaccgcc ataacgagga gttatttacc tgtagagtta cgactcaaca    2040
attgcacaaa gggctggggc acacgacttg ctaaattccc aaggagtggg ctttggcagc    2100
gtgcttcctt tagagcaagc catagtagaa aaccaagata tggaaagttc cccattgtgg    2160
ttactgacac aacgctcaca gtctttgggt catgagtccc ttcctgtacc attccaacat    2220
acaccgttat ggggattacg tcgggtaatt gcctagggac attggaaatt acattgcccg    2280
tgttttgact taggtccaac tatataagat tgcgaaacag tagcttctta gttagaggaa    2340
atattatgtc ctggttatca aatccaaatt gattactggc aaggggtgcg tcacgtttcc    2400
cggttagggc ggcaacaaca tatgagtgca tctacatagt caggataact aatttccttg    2460
caacacccgt ttctactgaa gctagcagaa tgtaactctt taggcaacct actccatgcc    2520
ggagccagtt agttaattac aggacgtctg gtagcactgg ggttgaaaac tgctgggtgg    2580
atggtccaac aagcggttaa atttttacta ctttccggtg gtagccagcc atctgcaaaa    2640
gctcaacaaa gcattgtaca attacggaag gcaggaccgc atgtgttcgt catgtgtgga    2700
gaaaattgcc aacaagataa agtggcagca attatatagt caagcaaact atctttgcca    2760
ccattacgtg gtataattca tgctggtggg aaattgggtg atggtatgct cttaatcatg    2820
agttgggtaa aattaacaca ggtgatggca caaaaagtac aggggggcctg gcgtttgcat    2880 tatttgactg agaatgtacg ttacgacttt tttgtgtgtt attccggtat ggtttcaata    2940
ttgggtacgc ctcgtcaagg ggattattat gctgcgaatg cttccatgga tggtttagct    3000
catcgtcgac ggggtatgcg tttatttggc ttgggcatta agtgcggact atggccacag    3060
gagggattgg cagcgaattt gcatagtcct caacaaggta gaaaggtgtc caagggaatg    3120
aggttcttgt catcagaaca gggattccag cttctaggtc aaatactcga agaatctata    3180
acacaagtac gagtccaacc agtccaatgg tgagtgatcg aagagcaatt tagttgtggt    3240
aatgaaatac catagctctc ccgattggaa aaggacagca tatctcagca aaaaccctc    3300 aagaccaaga ctaagcacaa tgagtttata gaacagctta aggctgcttt accaacagaa    3360
aaaggaaagc atttgaaaat tgacactaaa gatgaagttt ctaaagtgct tactttgagc    3420
ccttctgaaa tagatatgca tcagcgcctg aactctatgg ggcttgaatc tctaatcgct    3480
gtagaagtgc acattagcct tcagactgac ttgctggtgt atatatcaag agtctaattt    3540
acagaaagta tcagtaccgt tggtttagcc actgatgtga atgggcaacc gagccaagct    3600
actcacaatc aaggtgttaa gtcaggaaat caagggcagc tttaccaaaa caatacgaaa    3660
gataacgtgc gggtaagagg tgaaatatga                                     3690
```

<210> SEQ ID NO 35
<211> LENGTH: 3690
<212> TYPE: DNA
<213> ORGANISM: Artificial Sequence
<220> FEATURE:
<223> OTHER INFORMATION: 90% sequence identity to SEQ ID NO:2

<400> SEQUENCE: 35

```
atgggcata gtggtgggga atatatcgca gccactgtag aaggaatatt taggttagaa    60
gatggcttaa aacttattgc acatagagga agactaaggc aaccgttacc ctcttgggt   120
gaaatattat ctgtgatggc ttcacttgaa aaggtaattc aaataattgc accagactct   180
caaacagtag cgatcgcatt gattaaagga ccccaaggca ttgtcacttc tgttgaggca   240
gaaacaattg gagcgggtca aaatagccta gaagctgaag acataaagac aaagcgactg   300
caactatccc acgtattcca ttcaaatttg atggagccaa tgctggcgga cttttaagca   360
gtagcaacag aaataagcta caatcaccca aatatttcat tagaatcaaa tgtgacggga   420
gctcgggcag agattagtat tgcaacagca agcgattggg taactcatgt ccgtcaaccg   480
gtaaaatttg ccgaaagtat ggccacatta catcaagaag gtaattccat cttgttagaa   540
attcgaccca aactaacttt gtaaggcatg gggagacagt gcctgccaga agttgtggga   600
gtatggttgc ctgctttgaa acccggtcaa gaatactggc agcaaaagct acaaaggttg   660
gctgacctat atgtgcttgg agtaaaagtt gatgggttag ggtctgataa agtttattct   720
cgaagcaagg taggattgcc gactcatccc tttctacggc aacgatattg gatgagaca   780
aatcataatc taattcatca aaaaaagttt ttagcaaatc ataacaatct tcactctcta   840
ctcggacaaa gattagattt agcacccta gaactgcaaa ttcgatttga atgtgaaatt   900
agtccttctc aactaactta cctacaacac cacggtgttt ttcctcaacc tgttttcca   960
gcagcaactt acttgggaat agccttcgca gcagtttcaa tattattcaa tgcagatgat  1020
tcaatcctag atgatatagc aaaccaaaaa gtgttaattt taccaaagga tgtaattaat  1080
acaatacaga tagttgtaaa tttaccgtta gtacaatgct ataaatacca aattttgagt  1140
ttggatctaa acactatttc ttcaaaacct aaagggattc tacctattga aggtaaaata  1200
ttaataggta atagagaccc ccacttagaa acatcaaact taaagagat taaagaggag  1260
tataacccac agatatttcc tactgaaatc taccaaagat ttgaagcatg gggtctttat  1320
tacggttatt ctttccaggc cgttaaccaa ctgtggtaca gcgaagaaaa agcactgggt  1380
gaaatccagt tacctgaaac tgaggagaat gttgcagctt tatcccaact gtacccaatt  1440
ctattagatg ctggcttcca ggcgttagca gctgttatgg gtaaaacaga caaccgagaa  1500
acttacttgc cattgtaaat aaaacaacta caaatgtatc ggagtcgtag taatatttg  1560
tggacacaag tagaggtagg tgcaccagaa actattaaac aaacattgag cggtgaagtt  1620
tgttcattgg atgatcaagg aataatagta gcaagggttg aaggtctaac tttattacgt  1680
acttcacgcg aggcttggtt gcgtactatt gaacctaaat ttaaaaattg gtgtatatcaa  1740
atcccttggc aaactcaatc aatatcaccc catagccaat caatcgactt aacaatatca  1800
ggtagatggt tattgtgttc cccacctaca ggtatgggca acatgtggt agaatgctta  1860
gaacagcaag gttgggattg tatatgagta acaccggggg aaaatgacca gcagtgagaa  1920
tctcagcatt atcaagtcaa ccccagccat cctggggaat tccggcacct attggaatca  1980
agctgggagc agcagccccc attaggagga attatgcacc tgtggggttt ggactgaaca  2040
atagcgctaa ggacggggc acaggggttg caaaagtccc aagaacgggg ctgtgggagc  2100
gtacttgatt tagtccgagc cttagtgaaa aatcaaggta tggaaagggc cccattaggg  2160
ttagtgagtc aaggctcgca atctgggggt aatgggtccc ttccgataca attcgaacaa  2220
acacgtttat gggggtagg tcgaggaatt gcccaagaac ataggaaatt acaaagccgg  2280
tgttaagact tagaaccaac tatgaaagat tccaaaacag tagatgcttt gttaaaggaa  2340
```

```
ctataatctc ctggagatga aaacaaaatt gcttaatgtc aagggatacg tcacgatgcc    2400
cggtaagagc ggcaaaaaaa aatgactaca tctacccagt ccggtttaca aattttctcg    2460
caacatccat ttcaattgaa gctattagaa tataattctt tagactacct aatcctagcc    2520
gaagctagtt acttatttac cggagttctg ggagctctgg ggttataaaac cgctgtgtgg    2580 atggttcaac aagggttcaa atatcttgta cttactggac gtaggtagcc atcagctaaa    2640
gctcaactaa ccattgatca attacagtag gcaggagtgc aagtatttgt cctgtgttga    2700
gatattttcc aacaagataa tgtggctaga attattgagt caatctaagt atcttttcca    2760
gcattactag gaatatttca tgctgtcggg atatttgatg atggtttgct gttaaatatg    2820
aattgggtaa aatttaaaca ggtgatagca ccaaaaatac aaggggattg catttacat     2880 aatttaactc agaatatacc tttgaacttt tttgtatgtt tttccactat ggcttaaata    2940
ttgggatcgc ctggtaaagg gaattatgct gctgcaaatg ctttcaagga aggtttagcc    3000
aatcatcgac cgggtatggg cttacctggc ctgagcatta cctggggacc ctgggcacaa    3060
cagggaatgg ccgcaaattt cgatagtcct cctcaagata caatggtgtc ccagggaatg    3120 cctttttttgt cctcagaaca cggattgcag cttctaggac cattactcga ccaatccata    3180
ccccaagtag cagtcctacc cattcaatgg ccagtgttcc cagagcaatt cagttttggt    3240
catcaaatac ccttgctgtc cccattggta caagaaagca catcacagca caaagccctc    3300
caaacaaaga ccaagcacaa cgaattttta ggacagctaa gagctgcttt gccaagagaa    3360
ggagaaaagc gtttgatatt gtacattaaa ggtgaaattt gtcaagtact gtctttgagc    3420
gcttctcaaa gtgatatgca gcagcccctg gacactatgg gggttgattc gctaatggct    3480
ggggaattgc gcaataggct gcaaactgac gtgctcgtgg gtatatctat ggtcaaattt    3540
gtagaagata gcagtatcgt ggatttagcc gctgaagtga gtgagcaact gggccaagtt    3600
ggtcagaatc agggagttga ggcagaaaat agtgggcaac tgtaccaaag gaataggaaa    3660
ggaaacgagc gggtaagagg ggaattatga                                     3690
```

<210> SEQ ID NO 36
<211> LENGTH: 3690
<212> TYPE: DNA
<213> ORGANISM: Artificial Sequence
<220> FEATURE:
<223> OTHER INFORMATION: 95% sequence identity to SEQ ID NO:2

<400> SEQUENCE: 36

```
atggggcatg gtgctgggga atatgtggca gccacagtag caggaatatt aagttaagaa      60
gattgtttaa aactgattgc tcatagagga agactcatgc aacagatacc ctctgggggt     120
aaaatgttat ctgtaatggc ttcaattgga aaggttaatc aactaattgc accatactct     180
caaaaagcag cgatcgcatc gattaacgga ccccgaagct ttgtcatttc tggtgaggca     240
gaagaaattg gagcgcttca aaaaagctta gaagcagaag acattaagac aaaacgactg     300
caagtaaccc gcgcattcct ttcacatttg atggaaccaa tgttggcggc ctttgaagca     360
ggagcatcag aaataaccta caatcaacca aatattccat tagtaacaaa tgtaacggga     420
gaaagggcag agaatagtat tgccacagca agcaattggg taaatcatgt ccggcaaccg     480
gtgaaatttg ccaaaagtat ggacacatca cagccagaag ttattccat cttcttagaa      540 attggacccc aaccacctttt gttaggcatg ggaagacagt gcttgccaga agatctggga    600
gtttggtttc cttcctttgaa tccaggtcaa gaagactggc agcaaatgtt acaatgtttg    660
gctgaactat atgtgcatgg agttaaagtt gatttgttag ggtttgataa agattattct    720
```

```
cgtagcgagg tagtattgcc gacttatccc tttcaggggc aacgtgattg gattgagaca    780
aataataatc taatacagca aaaacagttt ttatcaaaac aaaaaaatct tcaccctcta    840
ctcggacaaa gaatacattt agcagcctta gaacagcaaa ttcgtattga atgtcaaatt    900
agtgcttctc acccaactca cctgccacac cactgtgttt tttctcaacc tgtcttcccc    960
gcagcagctt acttggaaat agccttagca gcaggttcaa ttttattcga tgcagatgat   1020
ttaatcctag aagatatagc aatccaaaag gtattaattg tatcaaagga tgaaattaat   1080
acaattcaga tagttttaga tttacagtta gtataaagct ttaaattcca aattttcagt   1140
ttggatataa acacttattc ttcataacct aaatggattc tacatattga aggaataata   1200
ttagtaggtg ataaagaccc ccaattagaa acaacaaact taaaagcgag taaggacgag   1260
tataaccaac agatattacc tactgaattc tagcagaaat tagaagaatg gggtcttaat   1320
tacggttctt ctttccaagc cataaaacaa cagtggcaca gcgaaggaaa agcactaggt   1380
gaaaatcagt taccagaaac agagatgaat gttgcaactt tataccaact gcacccaata   1440
cttatagatg ctagcttcca ggtgttagca gcagttatag gtaaaacgga caaccaagaa   1500
ggggatttgc cattggaaat aaaacgacta caaatttatg ggagtggtag taatagtttg   1560
tggactcaag tagagatagg tgcaacagaa actaataaac aaattttgtg tggtaaagtt   1620
tgtttattgg ataaacaagg aatagttgta tcaagagttg aaggtttaac tttattacgt   1680
acttctcgcg aggctttgtt aaaaaaaatt gaaccaaaat ttaataattg gttatatcaa   1740
atccattggc aaacccaatc aatttcaccc cataaccaat caattgactt aacaaaatca   1800
ggtaggggt tggtgttttc cccacccaca ggtataggca aacatcgggt agaatcctta   1860
gaacaacaag gttggcattg tatattagta acaccagggg aaatttacca gcatttagaa   1920
tctcaacatt atcaaatcaa ccctaacctt cctgaggaat tcctgcacct attgcaatca   1980
agcttggagt agcaaccccc ataacgagga attattcaca tgtggagttt gaactcaaca   2040
atagcactaa ggactgaggc acaggagtag caaaaatccc aagaactggg ctgtggcagc   2100
gtccttcatt tagtccaagc cttagtacac aatcaagata tgcaacgtgc cccattatgg   2160
ttagtgactc aaggctcaca atctgtgggt aatgagtccc ttcatataca attccaacaa   2220
acacctttat gggagttagg tcaagtaatt gcccaggaac atagggaatt acaatgccgg   2280
tatttagact tagatacaac tttggaatat tcccaaacag tagctgcttt gttagaggaa   2340
ctattatctc ctggtgatga taaccatatt gcttactgtc aaggtgtacg tcacgttgcc   2400
cgtttagagc ggcaacatat aatgagtaca tctacatagt ccggattact aatttcctcg   2460
caacaaccat ttcaactgaa gctatcagaa tataagtctt aagacaacct aatccaagcc   2520
gaagccagtt aattaattac cggaggtctg ggagaactgg agttaaaaac cgctgagtgg   2580
atggtacaac aagaggtcaa atatttagta cttaccggac gtaggccgcc atcagcaaaa   2640
gcccaacaaa ccattgaaca cttacagacg gcaggagcgc aagtattagt cctgtgtgca   2700
aatatttccc aaaaagaaaa tgtggcaaga attatagagt caatcaaagt atctttgaca   2760
gcattacaag gaataattca tgctgctggg aaattggatg atggtttgct gttaaacatg   2820
aattgtgata aatttacaca ggtgatggca cctaaagtac aatggtcttg gcatttgcat   2880
aatttgactc agaatctacc attggacttt attgtttgta ttacctctat ggcttcaata   2940
ttgggttcgc ctggtcaagg gaattatgct gctgctaatg ctttcatgga tggtttagcc   3000
aatcatcgac ggggtatgga tttaccaggc ttgagcatta aatggggacc atgagcacaa   3060
gagggaatgg cagcaaattt ggatagtcct catcaagata gcatggtgtc caagggaatg   3120
```

-continued

```
actcttctgt cttcagaaca cggattgcag gttctaggac aattactcga acaatccata      3180
ccacaagtag cagtcctacc atttcaatgg tcagtgtttc aagatcaatt tagttttggt      3240
aatcaaattc cattgctgtc ccaattggta aagaaagca aatcacagca aaaagccttc       3300
caaccaaaga caaagcacaa tgaactttta gaacagctaa aagctgcttt accaagagaa      3360
agacaacagc ttttgataat ttacattaaa gatgaaattt gtcaagtact ttctttgagc      3420
acgtctcaaa ttgatatgcg acagccctg aacactaggg ggcttgatgc tctaatggct       3480
gtggaattgc acaataggct acaaactgac ttgctcgtgg ataaatctat agtcaaattt      3540
atagaagata tcaatatcgt agatatagcc actgaagtga atgagcaact gagccaagtt     3600
gctcagaatc aaggagttga gtcagataat attgggcaac tctacctaag caataggata     3660
gtaaacgagc ggataagagg tgaattatga                                     3690
```

<210> SEQ ID NO 37
<211> LENGTH: 3690
<212> TYPE: DNA
<213> ORGANISM: Artificial Sequence
<220> FEATURE:
<223> OTHER INFORMATION: 99% sequence identity to SEQ ID NO:2

<400> SEQUENCE: 37

```
atggggcata gtgctgggga atatgtggca gccacagtag caggaatatt tagtttagaa        60
gatggtttaa aactgattgc tcatagagga agactaatgc gacagttacc ctctgggggt       120
gaaatgttat ctgtaatggc ttcaattgaa aaggtaaatc aactaattgc accatactct       180
caaaaagtag cgatcgcatc gattaacgga ccccaaagca ttgtcatttc tggtgaggca       240
gaagcaattg gagcggttca aaatagctta ggagcagaag acattaagac aaaacgactg       300
gaagtatccc acgcattcca ttcacatttg atggaaccaa tgttggcgga cttttgaagca     360 gtagcatcag aaataaccta caatcaacca aatattccat gagtatcaaa tgtaacggga      420
gctagggcag agaatagtat tgccacagca agctattggg taaatcatgt ccggcaaccg      480
gtgaaatttg cccaaagtat gggcacatta cagcaagaag ttattccat cttcttagaa       540 attggaccca aaccaacttt gttaggcatg ggaagacagt gcttgccaga agatgtggga     600
ggttggttgc cttctttgaa accaggtcaa gaagactggc agcaaatgct acaaagtttg      660
gctgaactat atgtgcatgg agttaaagtt gattggttag ggtttgataa agattattct     720
cgtagcaagg tagtattgcc gacttatccc tttcaacggc aacgttattg ggttgagaca      780
aataataatc taatacatca acaacagttt ttatcaaatc ataaaaatct tcaccctcta     840
ctcggtcaaa gattcatttt agcagcctta gaacagcaaa ttcgttttga atgtcaaatt     900
cgtgcttctc aaccaactta cctgcaacac cactgtgttt tttctcaacc tgttttccca     960
gcagcagctt acttggaaat agccttagca gcaggttcaa ctttattcaa ttcagatgat    1020
ttaatcctag aagatatagc aatccaaaaa gtattaattt tatcaaagga tgaaattaat     1080
acaattcaga gagttttaaa cttacagtta gtacaaagct ataaattcca aattttcagt   1140
ttggatataa acactaattc ttcagaacct aaatggattc tacatattga aggaaaaata    1200
ctagtaggta ataagaccc ccaattagaa acaacaaact aaaagcgat taaagacgag     1260 tataaccaac agatattacc tactgaattc taccaaaaat ctgaagaatg ggtcttaat   1320 tacggttctt ctttccaagc cgttaaacaa ctgtggcaca gcgaaggaaa agcactaggt   1380
gaaattcagt taccgaaaac cgaggtgaat gttgcaactt tataccaact gcacccaatt    1440
cttttagatg ctagcttcca ggtgttagca gcagttatgg gtaaaacgga caaccaagaa    1500
```

-continued

```
ccttatttgc cattggaaat aaaacgacta caaatttatc ggagtggtag taatagtttg    1560
tggactcaag tagagatagg tgcaacagaa actaataaac caactttgag cggtaaagtt    1620
tgtctattgg atgaacaagg aatagtagta gcaagagttg aaggtttaac tttattacgt    1680
acttctcgcg aggctttgtt ccgtaatatt gaaccaaaat ttaataattg gttatatcaa    1740
atccattggc aaacccaatc aatttcaccc cataaccaat caattgactt aacaaaatca    1800
cgtagctggt tattgttttc cccacccaca ggtataggca acatctggt agaatcctta     1860 gaacaacaag gttggcattg tatattagta acaccagggg caaattacca gcagttagaa    1920
tctcaacatt atcaaatcaa ccccaaccat cctgaggaat cctgcacct attgcaatca     1980 agcttggagc agcaaccccc cttacgagga attattcacc tgtggagttt ggactcaaca    2040
atagcactaa ggactggggc acaggagttg caaaaatccc aagaactggg ctgtggcagc    2100
ctacttcatt tagtccaagc cttagtaaaa aatcaagata tggaaagtgc cccattatgg    2160
ttagtgactc aaggctcaca atctgtgggt aatgagtccc ctcctataca attccaacaa    2220
acacctttat gggggttagg tcgagtaatt gcccaggaac atagggaatt acaatgccgg    2280
tgtttagact tagatccaac catggaagat tcccaaacag tagctgcttt gttagaggaa    2340
ctattatctc ctggtgatga aaaccaaatt gcttactgtc aaggggtacg tcacgttgcc    2400
cggttagagc ggcaacaaaa aatgagtaca tctacacagt ccggattaca aatttcctcg    2460
caacaaccat tccaactgaa gctatcagaa tataagtctt cagacaacct aatccaagcc    2520
gaagccagtt acttaattac cggaggtctg ggagcactgg ggttaaaaac cgctgagtgg    2580
atggtacaac aaggggtcaa ctatttagta cttaccggac gtaggcagcc atcagcaaaa    2640
gctcaacaaa ccattgaaca attacagaag gcaggagcgc aagtattagt cctgtgtgga    2700
catatttccc aacaagaaaa tgtggcaaga attatagagt caatcaaagt atctttgcca    2760
gcgttacgag gaataattca tgctgctggg atattggatg ctggtttgct gttaaacatg    2820 aatttgggaaa aatttacaca ggtgatggca ccaaaagtac aaggggcttg gcatttgcat    2880
aatttgactc agaatctacc cttggacttt tttgtttgtt tttcctctat ggcttcaata    2940
ttgggttcgc ctggtcaagg gaattatgct gctgctaatg ctttcatgga tggtttagcc    3000
catcatcgac ggggtatggg tttacctggc ttgagcatta actggggacc atgggcacaa    3060
gagggaatgg ccgcaaattt ggatagtcct catcaagata caatggtgtc caagggaatg    3120
acttttttgt cttcagaaca gggattgcag gttctaggac aattactcga acaatccata    3180
ccacaagtag gagtcctacc cattcaatgg tcagtgttcc aagagcaatt tagttttggt    3240
aatcaaatac cattgctgtc ccaattggta aagaaagca atcacagca aaaagccctc      3300 caaacaaaga caaagcacaa tgaatttta gaacagctaa aagctgcttt accaagagaa    3360
agagaaaagc ttttgataat ttacattaaa gatgaaattt cccaagtact ttctttgagc    3420
acttctcaaa ttgatatgca acagccctg aacactatgg ggcttgattc tctaatggct     3480
gtggaattgc acaataggct ccaaactgac ttgctcgtgg atatatctat agtcaaattt    3540
atagaagata tcagtatcgt tgatttagcc actgaagtga atgagcaact gagccaagtt    3600
gctcagaatc aaggagttga gtcagaaaat aatgggcaac tctaccaaag caataggaaa    3660
gaaaacgagc ggataagagg tgaattatga                                      3690
```

<210> SEQ ID NO 38
<211> LENGTH: 20
<212> TYPE: DNA
<213> ORGANISM: Artificial Sequence

```
<220> FEATURE:
<223> OTHER INFORMATION: Oligonucleotide
<220> FEATURE:
<221> NAME/KEY: misc_feature
<222> LOCATION: 3, 12, 18
<223> OTHER INFORMATION: n= A, T, C, or G

<400> SEQUENCE: 38
gcnggyggyg cntaygtncc                                              20

<210> SEQ ID NO 39
<211> LENGTH: 17
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: 3, 12
<223> OTHER INFORMATION: n = A,T,C or G

<400> SEQUENCE: 39
ccnggdatyt tnacytg                                                 17

<210> SEQ ID NO 40
<211> LENGTH: 32
<212> TYPE: DNA
<213> ORGANISM: Artificial Sequence
<220> FEATURE:
<223> OTHER INFORMATION: Oligonucleotide

<400> SEQUENCE: 40
atttatcata tgggttccga ttccggagcc ga                                32

<210> SEQ ID NO 41
<211> LENGTH: 36
<212> TYPE: DNA
<213> ORGANISM: Artificial Sequence
<220> FEATURE:
<223> OTHER INFORMATION: Oligonucleotide

<400> SEQUENCE: 41
aaataagaat cctcatcatt tttccaattg atgggt                            36

<210> SEQ ID NO 42
<211> LENGTH: 8826
<212> TYPE: DNA
<213> ORGANISM: Nostoc species

<400> SEQUENCE: 42
atgattacac cttcacatga aaatttaggt gcaaatgtac aagcactaag taacagtggg    60
tatctgggta tgccagcaga tgctccaaaa agtttgtcag aagttttaca aagagcagtc   120
aaaaagcatt ctgggcgagg cttaacatat attaacttgg atggctctga gtataatcaa   180
tcgtatcaag atttacttga ggaagcgcaa aaatcttggg agggttaag gaaactggga    240 ctcaaacccc aagacaaagt aatttttcag ttagaacgaa atcaagattt tattgctggt   300 ttttgggggtt gtattttagg aggttttatc cctataccag ttcctgtgcc aattaattat   360
gaagaaggca gtaatagtac taacaagctt catcatattt ggcagctatt agaacaatgt   420
ttgatcctaa cagatattaa atcagtatcg aaaatacgac ctttgtcaaa actatttcaa   480
tcagagcagt tgagacaat cgccattgat gagttacgag agtgcgaacc agataaaaac   540
ttgtatgtca gccaaccaga agatttagca ttgctaatgc ttacttccgg tagtacaagt   600
```

```
atacccaaag cggtaaaaat ctctcatcag aacttgttaa gtatgacggc aggcacaatc    660
gtgatgaatg gctttaaccg tcaggatgta accttgaatt ggatgccgat ggatcacgtg    720
ggagcgctag tgttccttag cattatggca gtggatttgg gttgtcagca agttcacata    780
ccaacggaat acattttgca aaatcctctc aactggctag atttgattac tcgtcaccaa    840
ggaacaatta gctgggctcc gaattttgcc tttaccttat tgtgcgatcg cgccgaagaa    900
attagccgta acattggaa tttatcttcc atgaggtttt tggtaaatgc tggggaacct    960
gttatcgcca aaactgcgcg aaatttcctg aaattactgg gtcaacatgg gttaccatcc   1020
actgcactgc acccagcttt tggtatgtgc gaaacctgtt caggaatcac ttggtcaaat   1080
agtttctctt tggaaaccac ctcagacgag gataccttg tttcggttgg tggtcccata   1140
cccggagcat ctgtgcggat tgtagatgaa aatcaacaag tggtggaaga ggggacaatt   1200
ggacagctgc aacttcaggg aaaattcagta accataggct actaccaaaa tgaggaggcg   1260
aaccaagaag cttttacaaa agatggttgg tttaacacag gtgatttagg attttaaaa   1320 ggtggatgtt taacaattac aggacgacaa aaagatgtaa ttattgttaa tggagtaaat   1380
tattatagtc atgagataga agctgttgtt gaagaattag gagaggttga agtttcttat   1440
accgctgctt gtgcaatttg gaatgaaaat agaagtacag atagattagc tatattttt    1500 aacacagaaa agactattga taatggttta gtggagctaa ttaaatcaat tcgcactcac   1560
gttgtcaaat ctattgggat taatcctaat tacttaattc cgttagaaaa gacaactatt   1620
ccgaaaactt ctatcggtaa aattcaaga aaacaattaa agaacggtt tgaaaacgga   1680 gaatttaagg aaattgttgc tcaaattagc acagctttgg ctgaattaaa ggcacagaat   1740
tttgtttcgg ggaatgagtt ggaacgtgat gtagccgaga tttggcaagg agtattacag   1800
attccggaag tggggattca cgataacttt tttgagttgg gtggacattc tgtaatgcta   1860
gcacaagttc acagtaagct acaggaatta tttgacacaa ccttgtcagt tgtagattta   1920
tttaaatatc cgacaattca tacaatagtt gaatatttga caaaaaaaga ttcattagag   1980
ggatcatccc aagacggaat tgcccgtgcg aaattgcgaa catcagcagt taatcaaaga   2040
gatgtagcga tcattggcat ggcttgtcgc ttcccaggag cagaaaatat ttctcaattt   2100
tggcaaaatt tatgtgatgg agtggaatca atttctttt tctctaagga agaagtcctg   2160
aatgaaggta ttcacaagca acgattggag aataaaaact acgttaaagc tgcacctatt   2220
atcaaaaaca tcgaagaatt tgatgccaac tttttttggct atagtacacg agaggcgatg   2280
atcatagatc cccaacaacg cttattcctt gagtgtgctt gggaagcact tgaagatgct   2340
ggttacgatg gaaacaccta tgaaggtgca attggtatgt atgcaggtgc ggggatgaat   2400
acatacttca tgcacaattt attccccaat cggaatcagt ttaatgctga agatggacct   2460
aatttaatga tgctggattc tatgggagga ttccaaattc aaattgctaa tgataaagac   2520
tatttaccta caagagtatc ttataaatta aatctcaagg gtccaagtct gaatgtacaa   2580
acggcttgtt caacttcttt agtagcgatc cacacagctt atcaaagtgt ggtcagtggg   2640
gagtgcgaca tggctttagc gggggagta tcggttagtg tgccccaaaa agcaggtcat   2700
ttatatgaag atgggatgat tttgtctcct gatggacatt gtcgcgcctt tgatgctaaa   2760
gctcaaggta cgatttttgg caatggttca ggaatagttca tattgaagag attgaatgaa   2820
gccatcgccg atggggatca tatttactgt gtgattaaag ggtcagccat taataatgat   2880
ggagctatga aagtggggta ttctgctact agccaggaag gccaagctac tggtgtgact   2940
gagtcgattg ctttagcagg aattaacgct gaaactatta cttattttga aactcatggt   3000
```

```
acaggaactt ccatgggaga ccccattgaa gtggcagcta tgactcaggc ttttagatca   3060
actactaata aattaggatt ttgtgctatt ggttcggtaa aaacaaatgt aggacattta   3120
caaattgctt ccggagttgc agggttcata aaaactgcat tagctttaaa atataagaaa   3180
ataccaccaa tcttacattt tgaccaaccc aacccttga ttgattttgc caatagccca   3240
ttttatgtaa ataaaaagtt acaagactgg aaaactgatg gaattcctag acgtgcaggg   3300
gttaaatcac tgggaattgg tggtacaaat gcttgtttaa ttttggaaga accaccgaat   3360
caagtcaaaa caggtcgtgg ggagggaagc aaaaataatg attatcagga gcgttcgctt   3420
cacctgttaa ctttgtcagc taaaacacca aaagcactcg aagagttggt cagtcgttat   3480
gagcatcatc tggaaagcaa cgtagagtta gaaatagcag acatctgtta tacagctaat   3540
acaggacgta gtcattttga tcatcgatta gcaattatcg cccctgacac tcaagtttta   3600
actgatgaat tagtaaaaat tagtgcgaaa gaagaaatta atggtgtatt cacaggaaaa   3660
ccttctagta ataatcaatc atcattaatt gccttcctgt ttactggaca aggttcacag   3720
tatataaata tgggaaggca actctataaa acccaacctg tcttccgtca aaccttagag   3780
cagtgcgaac aaattctaca accatattta aaaaaatcga ttttagatat tatttaccca   3840
gaagataatc aaaaattaaa cagtagtatt attgaccaaa ccgcctatac ccaagtagct   3900
ttatttgcaa tagaatatgc tctttataaa ctatgggaat cctggggaat aaaaccggat   3960
gtggtgatgg ggcatagtgc tggggaatat gtggcagcca cagtagcagg aatatttagt   4020
ttagaagatg gtttaaaact gattgctcat agaggaagac taatgcaaca gttatcctct   4080
gggggtgaaa tgttatctgt aatggcttca attgaaaagg taaatcaact aattgcacca   4140
tactctcaaa aagtagcgat cgcatcgatt aacggacccc aaagcattgt catttctggt   4200
gaggcagaag caattggagc ggttcaaaat agcttagaag cagaagacat taagacaaaa   4260
cgactgcaag tatctcacgc attccattca catttgatgg aaccaatgtt ggcggacttt   4320
gaagcagtag catcagaaat aacctacaat caaccaaata ttccattagt atcaaatgta   4380 acggagcta gggcagagaa tagtattgcc acagcaagct attgggtaaa tcatgtccgg   4440
caaccggtga atttgcccca agtatggac gcattacagc aagaaggtta ttccatcttc   4500
ttagaaattg gacccaaacc aactttgtta ggcatgggaa gacagtgctt gccagaagat   4560
gtgggagttt ggttgccttc tttgagacca ggtcaagaag actggcagca aatgctacaa   4620
agtttggctg aactatatgt gcatggagtt aaagttgatt ggttagggtt tgataaagat   4680
tattctcgta gcaaggtagt attgccgact tatcccttc aacggcaacg ttattggatc   4740
gaggcttccc agggatatac gaaacaactg aatcaacaaa tgtatccact attgggaatt   4800
aaggtagaac taccatccac cgagcagata atttaccacc agcatatcaa tctaaccagt   4860
catccctgga ttagagacca caaactctac gagacggatg taattcccgg tgtgagctat   4920
attgccatga catttgcagc tgtgggtaca ccagtagcgg tggaggaggt taactttata   4980
caacctctaa ttttggcaac cgccaatact acccgtgaaa cagaactgtt gattcaccct   5040
gctgatacta cccagactaa acaaaaagta caagttttta gccgagatac tacctccaaa   5100
gaccaatggg agcagcatgc tgaaatgact ttagtgaaga ccccccgtc tttgccagtt   5160 ttaaacctag acatcaaagc tctcaagcaa agttgagag caattgataa tgataattta   5220
aaagaaattt acaaccaat gtatgtgaac acaggcttct ggatcggtcc gatgctggat   5280
gcaatgcgtc aggtttgggt aggcgaagga acttaccttg gggaaatcga agtgccacaa   5340
gccttggaat cccaacttgc tggggaacca atccatccag ctcttcttga tgcctgtgct   5400
```

```
cgcgcaactc ctgagatttt agattctcgt cttgatgaac caggagtatt ttggactcca    5460
tggaaggtgc aggggatgac cctgagtcgt ccagctccgc gccgtttcta tgcctatgtt    5520
aatcaaccca ctcgattcaa tgaacaattg cagacccgta cttttgatat gcatctacta    5580
gatgaaaagg gtcagtcctt tggtcgcatt gacggtttta cccttcgacg tgctcccgt     5640 gaaaaatttt tgaggagttt gcaacttaca caaacggaat caattacaga ttggttgtat    5700
tctgtggaat ggagaagcaa aggtcttttg ggtaggctgc cagcccctga tttcctgtta    5760
acaccagtag aaatagagca aaaactgacg aaggaccttta cagaattagt tactcagata   5820
gatgacaata gtactttgct tttcgcaaga agcttagagg aattaagcgt agattatata    5880
gtgcaaggac tgctgtcaat gggttggtca tacaaactgg gagagacttt tgactccgat    5940
acagcagccc aacgcttagg agtagttcca actcagcagc gattattcaa gcgtttatta    6000
caaatattat cagaagcggg cattcttgag tgcaaacaac aacagtggaa ggttggacaa    6060
accttggaaa aagtcaaccc cacgggaaaa aaccagaatt tacttcgcca agctccagat    6120
gaagctgcaa cattgacatt attagaccgt tgtggtactc aactgtatgg ggtactgcga    6180
ggagcagtag acccagtgca actggttttc ccccaaggag atttaactac agcaacccaa    6240
ctgtatgaag attcaagtgc agccaaggtg atgaacacta ttgtgcaaaa agtcatcacc    6300
caaggcaccg agaaactacc tccgacaaga ggaatacggt tattggaaat tggagctgga    6360
acaggaggaa ccactagtta tgttctaccc aatctaaatc caagccaggc acaatatctg    6420
ttcacagata ttggagcatt attcactggt aaagcccaag aaaaattccg tgattataaa    6480
tttttaaaat atcaaacctt agatattgaa gaagacccag caacccaagg atttgaatat    6540
tatcaatatg atgtaattat tgcagccaat gtcctccatg caacaactaa tatcaagcaa    6600
acactatcca atgtgaagca attgttagca ccaggggaa tgttagtttt gtatgaagca     6660
acaactcgca caagttgggt ggatttagtc tttggattgt tagaaggatg gtggaagttc    6720
caagattatc aattaagacc agactatcct ctgctaagtc gtagtaattg aagaaaagtg    6780
ttagaggata caggttttac tcaggtagtt accttgccag aagttcaagg aatgccagaa    6840
atattgtctc aacaagcagt aattatagct caagcacctc aaacaattga gtgcactgga    6900
tcaacagcga agagttggtt gctattcgca gatgataaag gagttgctca acaactagca    6960
agacaactaa attctcatgg agatgtttgt accttagtat ttgctgggga caaatatgaa    7020
caaattgccc caacagagtt tactattaac cccaataacc tatcagaata tgagctactc    7080
ataagggaac tagcaacatc ttcaccatca ttaaacggag tagtgcaatg ttggagtatc    7140
tcttcaggag taagtaaaac tatcaattct gacgaattag aaaagttatc tttcaatggg    7200
tgtggcacca cctttatttt gctacaggca ttagtcaaag gggggttatc tcaaccaccc    7260
tggttatggt tagtaacttc tggttctcaa ccagtaccga cgaatcaccc agtcatacca    7320
ggagttgccc aatcttcact atggggaatg ggtaaagtga ttaacttaga acacccagaa    7380
ctcaactgtg tacgcataga tttagaccca ctgcaggcca tagaagatca agtaaatgca    7440
ctatttaatg aaatctggtc tctggataag gaagaccagg tagcatggcg tggtaattct    7500
cgttatgtag ctaggttggt gcccagttct tataggcaaa ccttgatcga aggacgacag    7560
tcatcatcag ataatgtaaa tactcaaaag cctttaagtt ccgctccga tgctacctac    7620 ttaattaccg gaggtatggg aggtttgggc ttactagtag cccattggat ggtatccaag    7680
ggagccaaga atttagtctt ggtagggcgc agttcaccgg atgaagccgc caagaaaaaa    7740
ctcacggagt tggaaatggc cggagcggca gtggtagtag aaaaggcaga tgtgtctgat    7800
```

-continued

```
attacagcta ttacaagagt gctgcataac attgagaact ccaagatacc attagcgggg    7860
ataattcatt ctgcgggaat gttatctgat cgggtattgg caaatcaaac ttggtcaagc    7920
tttgagaaag tgatggctgc caaagtccag ggagcttggc atctgcatca attaactcaa    7980
aatcagtcat tggactttt tgtgttgttt tcttctgttg catccctgtt gggttcttct    8040
ggtcaaggaa attattctgc agccaatggg tttcttgatg gtttagccca ttatcgtcaa    8100
gctatgggac taccaggatt gagcttgcat tgggggcag tttctcaagt gggagaggct    8160
gcagaacgag gtgtcgaaac taggattcat caacagggta tgggtgtgat atctccgaac    8220
cagatgttag aatgcctaga attactaatg agtggtaatg ctagaccgga aggtaagcta    8280
tcagacgctg aagtagggat tgtgccaatt gagtggtcag catggcaaga gaaagtagcc    8340
aattggacat ttttgtcaga ttggcaaaaa attatccaaa caactatgg tgtaactggc    8400 tcggaatttc tgtctaagtt ggaagctgca gcgaccgagg agcgtcgttc cctattagtg    8460
gctcatatcc gtcgtcaatt atccttagtc gtgggaatca ataatcccga atctatttca    8520
ttagaaactg gcttttttga cctgggtatg gattctttaa cttctgtgga gttgaggaat    8580
aagttgcaaa ctagtttgag ttgttcggta ccatctactt tggcttttga ttatcctaca    8640
gttggtaagc tagtagatta tctagtatca aatgttcttt ctatggaatt tgtaattta    8700 tctgatgatt tggagttgca aaacgagaat gaaactgaat taacaattcc tgcagagcta    8760
gaagaacttt cggaatcaga cgctgaagtt ttgcttcttg agaaacttag aaatattagt    8820
tactga                                                                 8826
```

<210> SEQ ID NO 43
<211> LENGTH: 2941
<212> TYPE: PRT
<213> ORGANISM: Nostoc species

<400> SEQUENCE: 43

```
Met Ile Thr Pro Ser His Glu Asn Leu Gly Ala Asn Val Gln Ala Leu
  1               5                  10                  15

Ser Asn Ser Gly Tyr Leu Gly Met Pro Ala Asp Ala Pro Lys Ser Leu
                 20                  25                  30

Ser Glu Val Leu Gln Arg Ala Val Lys Lys His Ser Gly Arg Gly Leu
             35                  40                  45

Thr Tyr Ile Asn Leu Asp Gly Ser Glu Tyr Asn Gln Ser Tyr Gln Asp
         50                  55                  60

Leu Leu Glu Glu Ala Gln Lys Ile Leu Gly Gly Leu Arg Lys Leu Gly
 65                  70                  75                  80

Leu Lys Pro Gln Asp Lys Val Ile Phe Gln Leu Glu Arg Asn Gln Asp
                 85                  90                  95

Phe Ile Ala Gly Phe Trp Gly Cys Ile Leu Gly Gly Phe Ile Pro Ile
                100                 105                 110

Pro Val Pro Val Pro Ile Asn Tyr Glu Glu Gly Ser Asn Ser Thr Asn
            115                 120                 125

Lys Leu His His Ile Trp Gln Leu Leu Glu Gln Cys Leu Ile Leu Thr
        130                 135                 140

Asp Ile Lys Ser Val Ser Lys Ile Arg Pro Leu Ser Lys Leu Phe Gln
145                 150                 155                 160

Ser Glu Gln Phe Glu Thr Ile Ala Ile Asp Glu Leu Arg Glu Cys Glu
                165                 170                 175

Pro Asp Lys Asn Leu Tyr Val Ser Gln Pro Glu Asp Leu Ala Leu Leu
            180                 185                 190
```

-continued

```
Met Leu Thr Ser Gly Ser Thr Ser Ile Pro Lys Ala Val Lys Ile Ser
            195                 200                 205

His Gln Asn Leu Leu Ser Met Thr Ala Gly Thr Ile Val Met Asn Gly
            210                 215                 220

Phe Asn Arg Gln Asp Val Thr Leu Asn Trp Met Pro Met Asp His Val
225                 230                 235                 240

Gly Ala Leu Val Phe Leu Ser Ile Met Ala Val Asp Leu Gly Cys Gln
                245                 250                 255

Gln Val His Ile Pro Thr Glu Tyr Ile Leu Gln Asn Pro Leu Asn Trp
            260                 265                 270

Leu Asp Leu Ile Thr Arg His Gln Gly Thr Ile Ser Trp Ala Pro Asn
            275                 280                 285

Phe Ala Phe Thr Leu Leu Cys Asp Arg Ala Glu Glu Ile Ser Arg Lys
290                 295                 300

His Trp Asn Leu Ser Ser Met Arg Phe Leu Val Asn Ala Gly Glu Pro
305                 310                 315                 320

Val Ile Ala Lys Thr Ala Arg Asn Phe Leu Lys Leu Leu Gly Gln His
                325                 330                 335

Gly Leu Pro Ser Thr Ala Leu His Pro Ala Phe Gly Met Cys Glu Thr
            340                 345                 350

Cys Ser Gly Ile Thr Trp Ser Asn Ser Phe Ser Leu Glu Thr Thr Ser
            355                 360                 365

Asp Glu Asp Thr Phe Val Ser Val Gly Gly Pro Ile Pro Gly Ala Ser
            370                 375                 380

Val Arg Ile Val Asp Glu Asn Gln Gln Val Val Glu Glu Gly Thr Ile
385                 390                 395                 400

Gly Gln Leu Gln Leu Gln Gly Asn Ser Val Thr Ile Gly Tyr Tyr Gln
                405                 410                 415

Asn Glu Glu Ala Asn Gln Glu Ala Phe Thr Lys Asp Gly Trp Phe Asn
            420                 425                 430

Thr Gly Asp Leu Gly Phe Leu Lys Gly Gly Cys Leu Thr Ile Thr Gly
            435                 440                 445

Arg Gln Lys Asp Val Ile Ile Val Asn Gly Val Asn Tyr Tyr Ser His
            450                 455                 460

Glu Ile Glu Ala Val Val Glu Leu Gly Glu Val Glu Val Ser Tyr
465                 470                 475                 480

Thr Ala Ala Cys Ala Ile Trp Asn Glu Asn Arg Ser Thr Asp Arg Leu
                485                 490                 495

Ala Ile Phe Phe Asn Thr Glu Lys Thr Ile Asp Asn Gly Leu Val Glu
            500                 505                 510

Leu Ile Lys Ser Ile Arg Thr His Val Val Lys Ser Ile Gly Ile Asn
            515                 520                 525

Pro Asn Tyr Leu Ile Pro Leu Glu Lys Thr Thr Ile Pro Lys Thr Ser
            530                 535                 540

Ile Gly Lys Ile Gln Arg Lys Gln Leu Lys Glu Arg Phe Glu Asn Gly
545                 550                 555                 560

Glu Phe Lys Glu Ile Val Ala Gln Ile Ser Thr Ala Leu Ala Glu Leu
                565                 570                 575

Lys Ala Gln Asn Phe Val Ser Gly Asn Glu Leu Glu Arg Asp Val Ala
            580                 585                 590

Glu Ile Trp Gln Gly Val Leu Gln Ile Pro Glu Val Gly Ile His Asp
            595                 600                 605
```

-continued

```
Asn Phe Phe Glu Leu Gly Gly His Ser Val Met Leu Ala Gln Val His
    610                 615                 620

Ser Lys Leu Gln Glu Leu Phe Asp Thr Thr Leu Ser Val Val Asp Leu
625                 630                 635                 640

Phe Lys Tyr Pro Thr Ile His Thr Ile Val Glu Tyr Leu Thr Lys Lys
                645                 650                 655

Asp Ser Leu Glu Gly Ser Ser Gln Asp Gly Ile Ala Arg Ala Lys Leu
            660                 665                 670

Arg Thr Ser Ala Val Asn Gln Arg Asp Val Ala Ile Ile Gly Met Ala
        675                 680                 685

Cys Arg Phe Pro Gly Ala Glu Asn Ile Ser Gln Phe Trp Gln Asn Leu
    690                 695                 700

Cys Asp Gly Val Glu Ser Ile Ser Phe Phe Ser Lys Glu Glu Val Leu
705                 710                 715                 720

Asn Glu Gly Ile His Lys Gln Arg Leu Glu Asn Lys Asn Tyr Val Lys
                725                 730                 735

Ala Ala Pro Ile Ile Lys Asn Ile Glu Glu Phe Asp Ala Asn Phe Phe
            740                 745                 750

Gly Tyr Ser Thr Arg Glu Ala Met Ile Ile Asp Pro Gln Gln Arg Leu
        755                 760                 765

Phe Leu Glu Cys Ala Trp Glu Ala Leu Glu Asp Ala Gly Tyr Asp Gly
    770                 775                 780

Asn Thr Tyr Glu Gly Ala Ile Gly Met Tyr Ala Gly Ala Gly Met Asn
785                 790                 795                 800

Thr Tyr Phe Met His Asn Leu Phe Pro Asn Arg Asn Gln Phe Asn Ala
                805                 810                 815

Glu Asp Gly Pro Asn Leu Met Met Leu Asp Ser Met Gly Gly Phe Gln
            820                 825                 830

Ile Gln Ile Ala Asn Asp Lys Asp Tyr Leu Pro Thr Arg Val Ser Tyr
        835                 840                 845

Lys Leu Asn Leu Lys Gly Pro Ser Leu Asn Val Gln Thr Ala Cys Ser
    850                 855                 860

Thr Ser Leu Val Ala Ile His Thr Ala Tyr Gln Ser Val Val Ser Gly
865                 870                 875                 880

Glu Cys Asp Met Ala Leu Ala Gly Gly Val Ser Val Ser Val Pro Gln
                885                 890                 895

Lys Ala Gly His Leu Tyr Glu Asp Gly Met Ile Leu Ser Pro Asp Gly
            900                 905                 910

His Cys Arg Ala Phe Asp Ala Lys Ala Gln Gly Thr Ile Phe Gly Asn
        915                 920                 925

Gly Ser Gly Ile Val Leu Leu Lys Arg Leu Asn Glu Ala Ile Ala Asp
    930                 935                 940

Gly Asp His Ile Tyr Cys Val Ile Lys Gly Ser Ala Ile Asn Asn Asp
945                 950                 955                 960

Gly Ala Met Lys Val Gly Tyr Ser Ala Thr Ser Gln Glu Gly Gln Ala
                965                 970                 975

Thr Gly Val Thr Glu Ser Ile Ala Leu Ala Gly Ile Asn Ala Glu Thr
            980                 985                 990

Ile Thr Tyr Phe Glu Thr His Gly Thr Gly Thr Ser Met Gly Asp Pro
        995                 1000                1005

Ile Glu Val Ala Ala Met Thr Gln Ala Phe Arg Ser Thr Thr Asn Lys
    1010                1015                1020
```

-continued

```
Leu Gly Phe Cys Ala Ile Gly Ser Val Lys Thr Asn Val Gly His Leu
1025                1030                1035                1040

Gln Ile Ala Ser Gly Val Ala Gly Phe Ile Lys Thr Ala Leu Ala Leu
            1045                1050                1055

Lys Tyr Lys Lys Ile Pro Pro Ile Leu His Phe Asp Gln Pro Asn Pro
        1060                1065                1070

Leu Ile Asp Phe Ala Asn Ser Pro Phe Tyr Val Asn Lys Lys Leu Gln
    1075                1080                1085

Asp Trp Lys Thr Asp Gly Ile Pro Arg Arg Ala Gly Val Lys Ser Leu
1090                1095                1100

Gly Ile Gly Gly Thr Asn Ala Cys Leu Ile Leu Glu Glu Pro Pro Asn
1105                1110                1115                1120

Gln Val Lys Thr Gly Arg Gly Glu Gly Ser Lys Asn Asn Asp Tyr Gln
            1125                1130                1135

Glu Arg Ser Leu His Leu Leu Thr Leu Ser Ala Lys Thr Pro Lys Ala
        1140                1145                1150

Leu Glu Glu Leu Val Ser Arg Tyr Glu His His Leu Glu Ser Asn Val
    1155                1160                1165

Glu Leu Glu Ile Ala Asp Ile Cys Tyr Thr Ala Asn Thr Gly Arg Ser
1170                1175                1180

His Phe Asp His Arg Leu Ala Ile Ile Ala Pro Asp Thr Gln Val Leu
1185                1190                1195                1200

Thr Asp Glu Leu Val Lys Ile Ser Ala Lys Glu Glu Ile Asn Gly Val
            1205                1210                1215

Phe Thr Gly Lys Pro Ser Ser Asn Asn Gln Ser Ser Leu Ile Ala Phe
        1220                1225                1230

Leu Phe Thr Gly Gln Gly Ser Gln Tyr Ile Asn Met Gly Arg Gln Leu
    1235                1240                1245

Tyr Lys Thr Gln Pro Val Phe Arg Gln Thr Leu Glu Gln Cys Glu Gln
1250                1255                1260

Ile Leu Gln Pro Tyr Leu Lys Lys Ser Ile Leu Asp Ile Ile Tyr Pro
1265                1270                1275                1280

Glu Asp Asn Gln Lys Leu Asn Ser Ser Ile Ile Asp Gln Thr Ala Tyr
            1285                1290                1295

Thr Gln Val Ala Leu Phe Ala Ile Glu Tyr Ala Leu Tyr Lys Leu Trp
        1300                1305                1310

Glu Ser Trp Gly Ile Lys Pro Asp Val Val Met Gly His Ser Ala Gly
    1315                1320                1325

Glu Tyr Val Ala Ala Thr Val Ala Gly Ile Phe Ser Leu Glu Asp Gly
1330                1335                1340

Leu Lys Leu Ile Ala His Arg Gly Arg Leu Met Gln Gln Leu Ser Ser
1345                1350                1355                1360

Gly Gly Glu Met Leu Ser Val Met Ala Ser Ile Glu Lys Val Asn Gln
            1365                1370                1375

Leu Ile Ala Pro Tyr Ser Gln Lys Val Ala Ile Ala Ser Ile Asn Gly
        1380                1385                1390

Pro Gln Ser Ile Val Ile Ser Gly Glu Ala Glu Ala Ile Gly Ala Val
    1395                1400                1405

Gln Asn Ser Leu Glu Ala Glu Asp Ile Lys Thr Lys Arg Leu Gln Val
1410                1415                1420

Ser His Ala Phe His Ser His Leu Met Glu Pro Met Leu Ala Asp Phe
1425                1430                1435                1440
```

```
Glu Ala Val Ala Ser Glu Ile Thr Tyr Asn Gln Pro Asn Ile Pro Leu
                1445                1450                1455

Val Ser Asn Val Thr Gly Ala Arg Ala Glu Asn Ser Ile Ala Thr Ala
            1460                1465                1470

Ser Tyr Trp Val Asn His Val Arg Gln Pro Val Lys Phe Ala Gln Ser
        1475                1480                1485

Met Asp Ala Leu Gln Gln Glu Gly Tyr Ser Ile Phe Leu Glu Ile Gly
    1490                1495                1500

Pro Lys Pro Thr Leu Leu Gly Met Gly Arg Gln Cys Leu Pro Glu Asp
1505                1510                1515                1520

Val Gly Val Trp Leu Pro Ser Leu Arg Pro Gly Gln Glu Asp Trp Gln
            1525                1530                1535

Gln Met Leu Gln Ser Leu Ala Glu Leu Tyr Val His Gly Val Lys Val
        1540                1545                1550

Asp Trp Leu Gly Phe Asp Lys Asp Tyr Ser Arg Ser Lys Val Val Leu
    1555                1560                1565

Pro Thr Tyr Pro Phe Gln Arg Gln Arg Tyr Trp Ile Glu Ala Ser Gln
        1570                1575                1580

Gly Tyr Thr Lys Gln Leu Asn Gln Gln Met Tyr Pro Leu Leu Gly Ile
1585                1590                1595                1600

Lys Val Glu Leu Pro Ser Thr Glu Gln Ile Ile Tyr His Gln His Ile
            1605                1610                1615

Asn Leu Thr Ser His Pro Trp Ile Arg Asp His Lys Leu Tyr Glu Thr
        1620                1625                1630

Asp Val Ile Pro Gly Val Ser Tyr Ile Ala Met Thr Phe Ala Ala Val
    1635                1640                1645

Gly Thr Pro Val Ala Val Glu Glu Val Asn Phe Ile Gln Pro Leu Ile
    1650                1655                1660

Leu Ala Thr Ala Asn Thr Thr Arg Glu Thr Glu Leu Leu Ile His Pro
1665                1670                1675                1680

Ala Asp Thr Thr Gln Thr Lys Gln Lys Val Gln Val Phe Ser Arg Asp
            1685                1690                1695

Thr Thr Ser Lys Asp Gln Trp Glu Gln His Ala Glu Met Thr Leu Val
        1700                1705                1710

Lys Thr Pro Pro Ser Leu Pro Val Leu Asn Leu Asp Ile Lys Ala Leu
    1715                1720                1725

Lys Gln Lys Leu Arg Ala Ile Asp Asn Asp Asn Leu Lys Glu Ile Tyr
        1730                1735                1740

Asn Gln Met Tyr Val Asn Thr Gly Phe Trp Ile Gly Pro Met Leu Asp
1745                1750                1755                1760

Ala Met Arg Gln Val Trp Val Gly Glu Gly Thr Tyr Leu Gly Glu Ile
            1765                1770                1775

Glu Val Pro Gln Ala Leu Glu Ser Gln Leu Ala Gly Glu Pro Ile His
        1780                1785                1790

Pro Ala Leu Leu Asp Ala Cys Ala Arg Ala Thr Pro Glu Ile Leu Asp
    1795                1800                1805

Ser Arg Leu Asp Glu Pro Gly Val Phe Trp Thr Pro Trp Lys Val Gln
    1810                1815                1820

Gly Met Thr Leu Ser Arg Pro Ala Pro Arg Arg Phe Tyr Ala Tyr Val
1825                1830                1835                1840

Asn Gln Pro Thr Arg Phe Asn Glu Gln Leu Gln Thr Arg Thr Phe Asp
            1845                1850                1855
```

```
Met His Leu Leu Asp Glu Lys Gly Gln Ser Phe Gly Arg Ile Asp Gly
            1860                1865                1870

Phe Thr Leu Arg Arg Ala Pro Arg Glu Lys Phe Leu Arg Ser Leu Gln
        1875                1880                1885

Leu Thr Gln Thr Glu Ser Ile Thr Asp Trp Leu Tyr Ser Val Glu Trp
    1890                1895                1900

Arg Ser Lys Gly Leu Leu Gly Arg Leu Pro Ala Pro Asp Phe Leu Leu
1905                1910                1915                1920

Thr Pro Val Glu Ile Glu Gln Lys Leu Thr Lys Asp Leu Thr Glu Leu
                1925                1930                1935

Val Thr Gln Ile Asp Asp Asn Ser Thr Leu Leu Phe Ala Arg Ser Leu
            1940                1945                1950

Glu Glu Leu Ser Val Asp Tyr Ile Val Gln Gly Leu Leu Ser Met Gly
        1955                1960                1965

Trp Ser Tyr Lys Leu Gly Glu Thr Phe Asp Ser Asp Thr Ala Ala Gln
    1970                1975                1980

Arg Leu Gly Val Val Pro Thr Gln Gln Arg Leu Phe Lys Arg Leu Leu
1985                1990                1995                2000

Gln Ile Leu Ser Glu Ala Gly Ile Leu Glu Cys Lys Gln Gln Gln Trp
                2005                2010                2015

Lys Val Gly Gln Thr Leu Glu Lys Val Asn Pro Thr Gly Lys Asn Gln
            2020                2025                2030

Asn Leu Leu Arg Gln Ala Pro Asp Glu Ala Ala Thr Leu Thr Leu Leu
        2035                2040                2045

Asp Arg Cys Gly Thr Gln Leu Tyr Gly Val Leu Arg Gly Ala Val Asp
    2050                2055                2060

Pro Val Gln Leu Val Phe Pro Gln Gly Asp Leu Thr Thr Ala Thr Gln
2065                2070                2075                2080

Leu Tyr Glu Asp Ser Ser Ala Ala Lys Val Met Asn Thr Ile Val Gln
                2085                2090                2095

Lys Val Ile Thr Gln Gly Thr Glu Lys Leu Pro Pro Thr Arg Gly Ile
            2100                2105                2110

Arg Leu Leu Glu Ile Gly Ala Gly Thr Gly Gly Thr Thr Ser Tyr Val
        2115                2120                2125

Leu Pro Asn Leu Asn Pro Ser Gln Ala Gln Tyr Leu Phe Thr Asp Ile
    2130                2135                2140

Gly Ala Leu Phe Thr Gly Lys Ala Gln Glu Lys Phe Arg Asp Tyr Lys
2145                2150                2155                2160

Phe Leu Lys Tyr Gln Thr Leu Asp Ile Glu Glu Asp Pro Ala Thr Gln
                2165                2170                2175

Gly Phe Glu Tyr Tyr Gln Tyr Asp Val Ile Ile Ala Ala Asn Val Leu
            2180                2185                2190

His Ala Thr Thr Asn Ile Lys Gln Thr Leu Ser Asn Val Lys Gln Leu
        2195                2200                2205

Leu Ala Pro Gly Gly Met Leu Val Leu Tyr Glu Ala Thr Thr Arg Thr
    2210                2215                2220

Ser Trp Val Asp Leu Val Phe Gly Leu Leu Glu Gly Trp Trp Lys Phe
2225                2230                2235                2240

Gln Asp Tyr Gln Leu Arg Pro Asp Tyr Pro Leu Leu Ser Arg Ser Asn
                2245                2250                2255

Trp Lys Lys Val Leu Glu Asp Thr Gly Phe Thr Gln Val Val Thr Leu
            2260                2265                2270
```

-continued

Pro Glu Val Gln Gly Met Pro Glu Ile Leu Ser Gln Gln Ala Val Ile
    2275                2280                2285

Ile Ala Gln Ala Pro Gln Thr Ile Glu Cys Thr Gly Ser Thr Ala Lys
    2290                2295                2300

Ser Trp Leu Leu Phe Ala Asp Asp Lys Gly Val Ala Gln Gln Leu Ala
2305                2310                2315                2320

Arg Gln Leu Asn Ser His Gly Asp Val Cys Thr Leu Val Phe Ala Gly
        2325                2330                2335

Asp Lys Tyr Glu Gln Ile Ala Pro Thr Glu Phe Thr Ile Asn Pro Asn
            2340                2345                2350

Asn Leu Ser Glu Tyr Glu Leu Leu Ile Arg Glu Leu Ala Thr Ser Ser
        2355                2360                2365

Pro Ser Leu Asn Gly Val Val Gln Cys Trp Ser Ile Ser Ser Gly Val
    2370                2375                2380

Ser Lys Thr Ile Asn Ser Asp Glu Leu Glu Lys Leu Ser Phe Asn Gly
2385                2390                2395                2400

Cys Gly Thr Thr Leu Phe Leu Gln Ala Leu Val Lys Gly Gly Leu
            2405                2410                2415

Ser Gln Pro Pro Trp Leu Trp Leu Val Thr Ser Gly Ser Gln Pro Val
    2420                2425                2430

Pro Thr Asn His Pro Val Ile Pro Gly Val Ala Gln Ser Ser Leu Trp
        2435                2440                2445

Gly Met Gly Lys Val Ile Asn Leu Glu His Pro Glu Leu Asn Cys Val
    2450                2455                2460

Arg Ile Asp Leu Asp Pro Leu Gln Ala Ile Glu Asp Gln Val Asn Ala
2465                2470                2475                2480

Leu Phe Asn Glu Ile Trp Ser Leu Asp Lys Glu Asp Gln Val Ala Trp
        2485                2490                2495

Arg Gly Asn Ser Arg Tyr Val Ala Arg Leu Val Pro Ser Ser Tyr Arg
            2500                2505                2510

Gln Thr Leu Ile Glu Gly Arg Gln Ser Ser Ser Asp Asn Val Asn Thr
        2515                2520                2525

Gln Lys Pro Leu Ser Phe Arg Ser Asp Ala Thr Tyr Leu Ile Thr Gly
    2530                2535                2540

Gly Met Gly Gly Leu Gly Leu Leu Val Ala His Trp Met Val Ser Lys
2545                2550                2555                2560

Gly Ala Lys Asn Leu Val Leu Val Gly Arg Ser Ser Pro Asp Glu Ala
            2565                2570                2575

Ala Lys Lys Lys Leu Thr Glu Leu Glu Met Ala Gly Ala Ala Val Val
        2580                2585                2590

Val Glu Lys Ala Asp Val Ser Asp Ile Thr Ala Ile Thr Arg Val Leu
    2595                2600                2605

His Asn Ile Glu Asn Ser Lys Ile Pro Leu Ala Gly Ile Ile His Ser
    2610                2615                2620

Ala Gly Met Leu Ser Asp Arg Val Leu Ala Asn Gln Thr Trp Ser Ser
2625                2630                2635                2640

Phe Glu Lys Val Met Ala Ala Lys Val Gln Gly Ala Trp His Leu His
            2645                2650                2655

Gln Leu Thr Gln Asn Gln Ser Leu Asp Phe Phe Val Leu Phe Ser Ser
        2660                2665                2670

Val Ala Ser Leu Leu Gly Ser Ser Gly Gln Gly Asn Tyr Ser Ala Ala
    2675                2680                2685

```
Asn Gly Phe Leu Asp Gly Leu Ala His Tyr Arg Gln Ala Met Gly Leu
    2690                2695                2700

Pro Gly Leu Ser Leu His Trp Gly Ala Val Ser Gln Val Gly Glu Ala
2705            2710                2715                2720

Ala Glu Arg Gly Val Glu Thr Arg Ile His Gln Gln Gly Met Gly Val
                2725                2730                2735

Ile Ser Pro Asn Gln Met Leu Glu Cys Leu Glu Leu Leu Met Ser Gly
            2740                2745                2750

Asn Ala Arg Pro Glu Gly Lys Leu Ser Asp Ala Glu Val Gly Ile Val
                2755                2760                2765

Pro Ile Glu Trp Ser Ala Trp Gln Glu Lys Val Ala Asn Trp Thr Phe
    2770                2775                2780

Leu Ser Asp Trp Gln Lys Ile Ile Gln Thr Thr Tyr Gly Val Thr Gly
2785                2790                2795                2800

Ser Glu Phe Leu Ser Lys Leu Glu Ala Ala Thr Glu Glu Arg Arg
                2805                2810                2815

Ser Leu Leu Val Ala His Ile Arg Arg Gln Leu Ser Leu Val Val Gly
                2820                2825                2830

Ile Asn Asn Pro Glu Ser Ile Ser Leu Glu Thr Gly Phe Phe Asp Leu
    2835                2840                2845

Gly Met Asp Ser Leu Thr Ser Val Glu Leu Arg Asn Lys Leu Gln Thr
    2850                2855                2860

Ser Leu Ser Cys Ser Val Pro Ser Thr Leu Ala Phe Asp Tyr Pro Thr
2865                2870                2875                2880

Val Gly Lys Leu Val Asp Tyr Leu Val Ser Asn Val Leu Ser Met Glu
                2885                2890                2895

Phe Cys Asn Leu Ser Asp Asp Leu Glu Leu Gln Asn Glu Asn Glu Thr
                2900                2905                2910

Glu Leu Thr Ile Pro Ala Glu Leu Glu Glu Leu Ser Glu Ser Asp Ala
                2915                2920                2925

Glu Val Leu Leu Leu Glu Lys Leu Arg Asn Ile Ser Tyr
                2930                2935                2940
```

<210> SEQ ID NO 44
<211> LENGTH: 10410
<212> TYPE: DNA
<213> ORGANISM: Nostoc species

<400> SEQUENCE: 44

| | | |
|---|---|---|
| atggacatga atattaatag gcgtaatact tctaactcaa acaagctga ctctctatcg | 60 |
| ccaactaaac aagcgctact tgccttagag aggatgcaat ccaaactgga cgctttagaa | 120 |
| tatgccaaga ctgaaccaat agcaatcatt ggaatgggct gccgcttccc cggaggtgca | 180 |
| tctactccga aagggttttg ggaagtttta aaaaacggag tagatgccat cactcaagta | 240 |
| cccccaaatc gatggaatct tgataattac tatgacccaa acccagaatc tcctggtaaa | 300 |
| atttatactc cttatggggg attcattgag cttctagatc agtttgatgc taatttgttc | 360 |
| ggtatttctc ctagagaagc gattcattta gaccctcaac agcgattact attagaagtt | 420 |
| acttgggaag ccatagagaa tgctctaata aatccgactg aacttaacgg aagccaaaca | 480 |
| agtgttttta ctggcatttg tggcaatgat tattaccaac gcgtaattgc tcaagactca | 540 |
| gaacaaattg atgcttatgt tgtatcaggt aatgctcata gtacggcatc ggggcgaatt | 600 |
| tcctatattt tagggttact cggaccttct ttagcagtag acacagcctg ctcctcttct | 660 |
| ttggtaagtg tgcatttagc ttgctccagt ttaagaagag gagaatctaa cctagcattg | 720 |

```
gcaggaggag tgaatagaat aatttctcca gaggtgagta tagcttttc taaagcccgt      780 atgttgtcct ttaatgggcg atgtaagact tttgacgcta gtgcagatgg ttttgttcgt    840
ggtgaaggat gcggtgttgt tgtactcaaa cgtttatcag atgcattaac tgataaagac    900
aatatcttgg ctgtgattcg gggaagcgcc attaaccaag atggtcacac cagtggttta   960
acggttccta acggtccttc tcaacaagca gtaattcgcc aagctttgga aaatgggga    1020 gtagaaccgg caaatattag ttattttgaa gctcatggta cagggacatc cttgggagat   1080
ccgattgaag ttggagccct agggactgta tttggcacaa gccactctaa agagcaacct   1140
ttaatagttg gctcagtaaa aactaacatt ggacacttag aggcagcagc aggagttgct   1200
ggtttgatca aaatagtcct acaactgcaa aatcaacaaa tagtaccatc actgcatttt   1260
aaccagccta atccttatat taattggtcg gaattaccag taaaaattcc gacgcagatt   1320
agcccttggc caacaaatgg aaaaagccgt atagctggag ttagttcttt tgggtttagt   1380
ggaactaatg ctcatgtaat tttagaagaa gctccgactc aacagtccca ggttaaggat   1440
tctgatttgg gtaagcatcc ttggcacata ctaaccttat ctgccaaatg tgaaaaagca   1500
ctgcaagaaa tgatccaaag ctatgaagaa ttttaagta atgataatac agcaacaatt   1560
gctgatatat gttttagtgc tcatataagt cgcagccatt ttgactatcg ccttgcttta   1620
atagctccat caaccgagaa attgcgccaa aaattaaagg ttttcaaaa aaacccggaa    1680 gatactctag gagtggtgag gggtcaagtt gacagtaaaa agttagcgaa aatagtattt   1740
ttattcactg gtcagggctc ccaatatatc aatatgggaa gacaactata tgaaacacaa   1800
cctgtcttcc gtcaaacctt agagcagtgc gaacaaattc tacaaccata tttaaaaaaa   1860
tcgattttag atattattta cccagaagat aatcaaaaat taaacagtag tattattgac   1920
caaaccgcct atacccaagt agctttattt gcaatagaat atgctcttta taaactatgg   1980
gaatcctggg aataaaaacc ggatgtggtg atggggcata gtgttgggga atatgtggca   2040
gccacagtag caggaatatt tagtttagaa gatggtttaa aactgattgc tcatagagga   2100
agactaatgc aacagttatc ctctgggggt gaaatgttat ctgtaatggc ttcaattgaa   2160
aaggtaaatc aactaattgc accatactct caaaaagtag cgatcgcatc gattaacgga   2220 cccaaagca ttgtcatttc tggtgaggca gaagcaattg gagcggttca aaatagctta    2280
gaagcagaag acattaagac aaaacgactg caagtatccc acgcattcca ttcacatttg   2340
atggaaccaa tgttggcgga cttgaagca gtagcatcag aaataaccta caatcaacca    2400
aatattccat tagtatcaaa tgtaacggga gctagggcag agaatagtat tgccacagca   2460
agctattggg taaatcatgt ccggcaaccg gtaaaatttg cccaaagtat ggacacatta   2520
cagcaagaag gttattccat cttcttagaa attggaccca aaccaacttt gttaggcatg   2580
ggaagacagt gcttgccaga agatgtggga gtttggttgc cttctttgag accaggtcaa   2640
gaagactggc agcaaatgct acaaagtttg gctgaactat atgtgcatgg agttaaagtt   2700
gattggttag ggtttgataa agattattct cgtagcaagg tagtattgcc gacttatccc   2760
tttcaacggc aacgttattg gattgagagc acggaaagtc aaagccaaaa agcagcttat   2820
tcctcttgtg aaacaaagag tactccaatt ttcgatttgc taatccatgg gaatatccaa   2880
cagttggctc aacaaataga aaaaattggt aaattttctc cagaacaagt caatctcctg   2940
ccagaatttc tagaagtatt agtaaaacag caccagaaac aactaattat agaaactacc   3000
aaagatttct gtaccaagt acagtggaaa cctttagttg atcccaacc caagacaagc    3060 attaaaccta gccattggtt aatttttgca gacaccaccg cagtagggga aaaattagtt   3120
```

```
cagcaattgc aatcgcacca ttgtgaatgt agtttagttt atcgaagtga ttgctaccga    3180
aaactagacg aaggtactta tcaactcaat cccacagagg ctcaagagtt tgaacaacta    3240
attcaagcta tcggggaaaa tagcaaatta cccttactcc atgtgattaa tttgtggagt    3300
ttagatattc aaggaacgca agacttaaca accacaactt taaaacaagc acaactttgg    3360
ggatgtggca cggtgctaca actagtgaaa gtgctaacta aaaccaaaag tgtagccaaa    3420
ctgtggttag tgactcgagg tgctcaatta gtcaaatccc aaaccgaatc agtctgtgtg    3480
gctgcatcac ccttgtgggg aatggggcga gtaatatctc tggagcatcc ccaactgtgg    3540
ggtggaatgg tagatttaga cccaatttct ccagaatcag aagcatacac actactacaa    3600
cttctagtaa attctaacca attagaagac catctagctt tacgggcaga taatttatac    3660
tttgctcgtt tagtcaagca atctctcaaa ccatatgatt ctgtgtcact caaggataat    3720
gcgacatatt taataacagg aggattggga gctttaggat tacacacagc gcggtggatg    3780
gttcaacaag gagcaagaca tttagtactc accggacgta agcagcctaa ccttgaagct    3840
caacaaatca ttgaagaact gcaaaagcta ggggcacaaa tattagtctt atgtggggat    3900
atctccgatg aagttgatgc gactacaatt ttttcagaaa ttgaagcatc tttaccgacc    3960
ctaaaaggtg taattaatgc tgctggggta ttagatgatg ccttgctcca ctctatgagt    4020
tgggaacaat ttacacaggt gatggcaccg aaagtacaag gggcttggca tcttcataat    4080
ttaactcaga ataaagcttt ggacttttt gtttgtttct cctcgatggc ttcattggta    4140
ggttcacccg gtcaaggaaa ttatgccgca gctaatgctt ttatggatgc tttagcccat    4200
catcgacggg gaatgggttt accaggttta agtattaact ggggaccttg gcacaagca    4260 ggaatggcag caagcttaga taatcgtaat agagatcgaa tggttgcctc tggaatcact    4320
cctttgactc cagagcaggg attgcaggtt ctaggacaac tactcgaaca gtccttacca    4380
caggtaggag ttttatcggt tcaatggtca gtgttccaag agaaatttag ttttggtaat    4440
caaataccat tacttttgga attgctagga gaaaccgaat cacaacaaaa agcctttaga    4500
acaaagacaa agcaaaatga gcttttaaaa cgattggaat ctttgccttg taaagagcgc    4560
tactatgtat tgagaactga aattcagagt gaagtagcca aagtattggc gctcaatgat    4620
tcccaactac ctggttttga gcaaggattc tttgacttgg gtatggactc attaatggca    4680
gtggaattac gtaaccgcat cacccaatta ctaaaggtga cattaccctc aaccctaagc    4740
tttgactttc ccaatattga caactaact aagtatataa gctctcaaat actagacctg    4800
agtacctcga atgatggtca gcagccagaa caaaaagtaa aagctgcaga acatgaaccc    4860
atagcgatta taggtatggg atgttcctta cctggtggag caaacacccc agaaaaattc    4920
tgggaattat tgcattcagg tactagtgcc cgtgaagaaa ttccagcaca gcgatgggac    4980
gtcaatagct actatgaccc agaccgagaa gccgcaggta aaatggtcac ccgttacggt    5040
cactttatta gtggagtaga tcaatttgac ccagaatttt ttggcatctc tccgagggaa    5100
gcaacagcca tggatcccca acatcggttg ctactggaag taagttggca agccttagag    5160
cgagccggac aaaaggtgga acgtctatca tccgaacccg ttggggtatt tgtgggtaac    5220
gatggacatg actacgaaca actgatgcaa aagcatttag agcaagagcc caacagtacc    5280
tttggcacct atacatgcac tggtaacagt ccttcgagtg cgtcaggacg tttggcttat    5340
acatttgggt tcacgggacc aacagtaacc attgataccg cctgttcttc ttccttagtg    5400
gcgattcatc aagcttgcaa cagcatacgc ctggagaat gtcagatggc aattgctggg    5460
ggagtgaaac tccatctaac tcctagtagc tatattttta cttcccgagc cggaatgatt    5520
```

```
tccccagacg gattgtgcaa aacctttgat atatcagcgg atggttatgg tcggggagaa    5580
ggctgtggta tggtggtgct caagtctttg agtcaagccc aagcagacgg tgacccaatt    5640
ttagccttga ttctgggcag tgcggtgaac caagatggac ccagtagtgg cttaacagtg    5700
cctaatggcc agtcccaaca aaaattgatt ttacaagcac tcaaacaagc tcgggtagaa    5760
ccggcagata ttagctactt agaagccat ggtacgggta catctttggg agacccata     5820 gaggtaaatg cagcagcagc agtactaggg ctccaacgtt caccaagtca gcccttgtgg    5880
ataggtacgg taaagacaaa tattgggcat ttggagtcgg cagcgggggt atcgggacta    5940
attaaggtag tactatctct acagcatcag caaatacctg ccaatttaca tctgcaagag    6000 cctaaccccca agattgactg gcaaccttgg ttacaggtac ctcaagcttt gacccccttgg  6060 gttgggtcga aggtaggtt ggcgggggta agttcttttg ggtttacggg tactaatgcc     6120
catgtggtgc tatcggaaac ccctgctgcc attgccagtt ctacagtaga gtatgagcgt    6180
ccactacatc tgttgcagtt gtcagccaaa atgacttgg ctttggcaca gctagcccaa     6240
cgctatagtg accatttaaa aacgcaccta gagcaggact taagggatat ctgctttact    6300
gccaatagta gtaggttggc tcacaagcat cgtctggcgg tggtcgcgag caatcgaaaa    6360
gagttgcaac aaaagctggg taactttggt acagattcag aaaggatgga tttggtaact    6420
ggacaagtca gtagtagtca gttgaccaaa gttgcaatgc ttttcactgg tcaagggtct    6480
caatatgtgg gtatgggtcg ccagctttac caaacccaac cgaccttcaa acaatttgtg    6540
gatcaatgtg cccaaatatt agaaaactac ttagacaaac ctttattaga aatacttgat    6600
gtcgctcaag tacaggaaaa tgtcctagct caaaccgcct atacccaagt agctttattt    6660
gcaatagaat atgctctta taaactatgg gaatcctggg aataaaaacc ggatgtggtt    6720
atggggcata gtgctgggga atatgtggca gccacagtag caggaatatt tagtttagaa    6780
gatggtttaa aactgattgc tcatagagga agactaatgc aacagttacc ctctgggggt    6840
gaaatgttat ctgtaatggc ttcaattgaa aaggtaaatc aactaattgc accatactct    6900
caaaaagtag cgatcgcatc gattaacgga ccccaaagca ttgtcatttc tggtgaggca    6960
gaagcaattg gagcggttca aaatagctta gaagcagaag acattaagac aaaacgactg    7020
caagtatccc acgcattcca ttcacatttg atggaaccaa tgttggcgga ctttgaagca    7080
gtagcatcag aaataaccta caatcaacca aatattccat tagtatcaaa tgtaacggga    7140
gctagggcag agaatagtat tgccacagca agctattggg taaatcatgt ccggcaaccg    7200
gtgaaatttg cccaaagtat ggacacatta cagcaagaag gttattccat cttcttagaa    7260
attggaccca aaccaacttt gttaggcatg ggaagacagt gcttgccaga agatgtggga    7320
gtttggttgc cttctttgaa accaggtcaa gaagactggc agcaaatgct acaaagtttg    7380
gctgaactat atgtgcatgg agttaaagtt gattggttag ggtttgataa agattattct    7440
cgtagcaagg tagtattgcc gacttatccc tttcaacggc aacgttattg gattgagaca    7500
aataataatc taatacatca aaaacagttt ttatcaaatc ataaaaatct tcaccctcta    7560
ctcggtcaaa gattacattt agcagcctta gaacagcaaa ttcgtttttga atgtcaaatt   7620 agtgcttctc aaccaactta cctgcaacac cactgtgttt tttctcaacc tgttttccca    7680
gcagcagctt acttggaaat agccttagca gcaggttcaa ttttattcaa ttcagatgat    7740
ttaatcctag aagatatagc aatccaaaaa gtattaattt tatcaaagga tgaaattaat    7800
acaattcaga tagtttttaaa tttacagtta gtacaaagct ataaattcca aattttcagt    7860
ttggatataa acactaattc ttcagaacct aaatggattc tacatattga aggaaaaata    7920
```

```
ttagtaggta ataaagaccc ccaattagaa acaacaaact taaaagcgat taaagacgag    7980
tataaccaac agatattacc tactgaattc taccaaaaat ttgaagaatg gggtcttaat    8040
tacggttctt ctttccaagc cgttaaacaa ctgtggcaca gcgaaggaaa agcactaggt    8100
gaaattcagt taccagaaac tgaggtgaat gttgcaactt tataccaact gcacccaatt    8160
cttttagatg ctagcttcca ggtgttagca gcagttatgg gtaaaacgga caaccaagaa    8220
acttatttgc cattggaaat aaaacgacta caaatttatc ggagtggtag taatagtttg    8280
tggactcaag tagagatagg tgcaacagaa actaataaac aaactttgag cggtaaagtt    8340
tgtttattgg atgaacaagg aatagtagta gcaagagttg aaggtttaac tttattacgt    8400
acttctcgcg aggctttgtt gcgtaatatt gaaccaaaat ttaataattg gttatatcaa    8460
atccattggc aaacccaatc aatttcaccc cataaccaat caattgactt aacaaaatca    8520
ggtagctggt tattgttttc cccacccaca ggtataggca acatctggt agaatcctta    8580
gaacaacaag gttggcattg tatattagta acaccagggg aaaattacca gcagttagaa    8640
tctcaacatt atcaaatcaa ccccaaccat cctgaggaat tcctgcacct attgcaatca    8700
agcttggagc agcaaccccc attacgagga attattcacc tgtggagttt ggactcaaca    8760
atagcactaa ggactggggc acaggagttg caaaaatccc aagaactggg ctgtggcagc    8820
gtacttcatt tagtccaagc cttagtaaaa aatcaagata tggaaagtgc cccattatgg    8880
ttagtgactc aaggctcaca atctgtgggt aatgagtccc ttcctataca attccaacaa    8940
acacctttat gggggttagg tcgagtaatt gcccaggaac atagggaatt acaatgccgg    9000
tgtttagact tagatccaac tatggaagat tcccaaacag tagctgcttt gttagaggaa    9060
ctattatctc ctggtgatga aaaccaaatt gcttactgtc aaggggtacg tcacgttgcc    9120
cggttagagc ggcaacaaaa aatgagtaca tctacacagt ccggattaca aatttcctcg    9180
caacaaccat ttcaactgaa gctatcagaa tataagtctt tagacaacct aatccaagcc    9240
gaagccagtt acttaattac cggaggtctg ggagcactgg ggttaaaaac cgctgagtgg    9300
atggtacaac aaggggtcaa atatttagta cttaccggac gtaggcagcc atcagcaaaa    9360
gctcaacaaa ccattgaaca attacagaag gcaggagcgc aagtattagt cctgtgtgga    9420
gatatttccc aacaagaaaa tgtggcaaga attatagagt caatcaaagt atctttgcca    9480
gcattacgag gaataattca tgctgctggg atattggatg atgggtttgct gttaaacatg    9540
aattgggaaa aatttacaca ggtgatggca ccaaaagtac aagggggcttg gcatttgcat    9600
aatttgactc agaatctacc tttggacttt tttgtttgtt tttcctctat ggcttcaata    9660
ttgggttcgc ctggtcaagg gaattatgct gctgctaatg ctttcatgga tggtttagcc    9720
catcatcgac ggggtatggg tttacctggc ttgagcatta actggggacc atgggcacaa    9780
gagggaatgg cagcaaattt ggatagtcct catcaagata gaatggtgtc caagggaatg    9840
acttttttgt cttcagaaca gggattgcag gttctaggac aattactcga caatccata    9900
ccacaagtag gagtcctacc aattcaatgg tcagtgttcc aagagcaatt tagttttggt    9960
aatcaaatac cattgctgtc ccaattggta aagaaaagca aatcacagca aaaagccctc    10020
aaaacaaaga caaagcacaa tgaattttta gaacagctaa agctgctttt accaagagaa    10080
agagaaaagc ttttgataat ttacattaaa gatgaaattt ctcaagtact ttctttgagc    10140
acttctcaaa ttgatatgca acagcccctg aacactatgg ggcttgattc tctaatggct    10200
gtggaattgc acaataggct tcaaactgac ttgctcgtgg atatatctat agtcaaattt    10260
atagaagata tcagtatcgt tgatttagcc actgaagtga atgagcaact gagccaagtt    10320
```

```
gctcagaatc aaggagttga gtcagaaaat aatgggcaac tctaccaaag caataggaaa    10380
gaaaacgagc ggataagagg tgaattatga                                     10410
```

<210> SEQ ID NO 45
<211> LENGTH: 3469
<212> TYPE: PRT
<213> ORGANISM: Nostoc species

<400> SEQUENCE: 45

```
Met Asp Met Asn Ile Asn Arg Arg Asn Thr Ser Asn Ser Lys Gln Ala
 1               5                  10                  15

Asp Ser Leu Ser Pro Thr Lys Gln Ala Leu Leu Ala Leu Glu Arg Met
            20                  25                  30

Gln Ser Lys Leu Asp Ala Leu Glu Tyr Ala Lys Thr Glu Pro Ile Ala
        35                  40                  45

Ile Ile Gly Met Gly Cys Arg Phe Pro Gly Gly Ala Ser Thr Pro Lys
    50                  55                  60

Gly Phe Trp Glu Val Leu Lys Asn Gly Val Asp Ala Ile Thr Gln Val
65                  70                  75                  80

Pro Pro Asn Arg Trp Asn Leu Asp Asn Tyr Tyr Asp Pro Asn Pro Glu
                85                  90                  95

Ser Pro Gly Lys Ile Tyr Thr Pro Tyr Gly Gly Phe Ile Glu Leu Leu
            100                 105                 110

Asp Gln Phe Asp Ala Asn Leu Phe Gly Ile Ser Pro Arg Glu Ala Ile
        115                 120                 125

His Leu Asp Pro Gln Gln Arg Leu Leu Leu Glu Val Thr Trp Glu Ala
    130                 135                 140

Ile Glu Asn Ala Leu Ile Asn Pro Thr Glu Leu Asn Gly Ser Gln Thr
145                 150                 155                 160

Ser Val Phe Thr Gly Ile Cys Gly Asn Asp Tyr Tyr Gln Arg Val Ile
                165                 170                 175

Ala Gln Asp Ser Glu Gln Ile Asp Ala Tyr Val Val Ser Gly Asn Ala
            180                 185                 190

His Ser Thr Ala Ser Gly Arg Ile Ser Tyr Ile Leu Gly Leu Leu Gly
        195                 200                 205

Pro Ser Leu Ala Val Asp Thr Ala Cys Ser Ser Ser Leu Val Ser Val
    210                 215                 220

His Leu Ala Cys Ser Ser Leu Arg Arg Gly Glu Ser Asn Leu Ala Leu
225                 230                 235                 240

Ala Gly Gly Val Asn Arg Ile Ile Ser Pro Glu Val Ser Ile Ala Phe
                245                 250                 255

Ser Lys Ala Arg Met Leu Ser Phe Asn Gly Arg Cys Lys Thr Phe Asp
            260                 265                 270

Ala Ser Ala Asp Gly Phe Val Arg Gly Glu Gly Cys Gly Val Val Val
        275                 280                 285

Leu Lys Arg Leu Ser Asp Ala Leu Thr Asp Lys Asp Asn Ile Leu Ala
    290                 295                 300

Val Ile Arg Gly Ser Ala Ile Asn Gln Asp Gly His Thr Ser Gly Leu
305                 310                 315                 320

Thr Val Pro Asn Gly Pro Ser Gln Gln Ala Val Ile Arg Gln Ala Leu
                325                 330                 335

Glu Asn Gly Gly Val Glu Pro Ala Asn Ile Ser Tyr Phe Glu Ala His
            340                 345                 350
```

```
Gly Thr Gly Thr Ser Leu Gly Asp Pro Ile Glu Val Gly Ala Leu Gly
            355                 360                 365

Thr Val Phe Gly Thr Ser His Ser Lys Glu Gln Pro Leu Ile Val Gly
        370                 375                 380

Ser Val Lys Thr Asn Ile Gly His Leu Glu Ala Ala Gly Val Ala
385                 390                 395                 400

Gly Leu Ile Lys Ile Val Leu Gln Leu Gln Asn Gln Gln Ile Val Pro
                405                 410                 415

Ser Leu His Phe Asn Gln Pro Asn Pro Tyr Ile Asn Trp Ser Glu Leu
                420                 425                 430

Pro Val Lys Ile Pro Thr Gln Ile Ser Pro Trp Pro Thr Asn Gly Lys
                435                 440                 445

Ser Arg Ile Ala Gly Val Ser Ser Phe Gly Phe Ser Gly Thr Asn Ala
            450                 455                 460

His Val Ile Leu Glu Glu Ala Pro Thr Gln Ser Gln Val Lys Asp
465                 470                 475                 480

Ser Asp Leu Gly Lys His Pro Trp His Ile Leu Thr Leu Ser Ala Lys
                485                 490                 495

Cys Glu Lys Ala Leu Gln Glu Met Ile Gln Ser Tyr Glu Glu Phe Leu
                500                 505                 510

Ser Asn Asp Asn Thr Ala Thr Ile Ala Asp Ile Cys Phe Ser Ala His
                515                 520                 525

Ile Ser Arg Ser His Phe Asp Tyr Arg Leu Ala Leu Ile Ala Pro Ser
                530                 535                 540

Thr Glu Lys Leu Arg Gln Lys Leu Lys Val Phe Gln Lys Asn Pro Glu
545                 550                 555                 560

Asp Thr Leu Gly Val Val Arg Gly Gln Val Asp Ser Lys Lys Leu Ala
                565                 570                 575

Lys Ile Val Phe Leu Phe Thr Gly Gln Gly Ser Gln Tyr Ile Asn Met
                580                 585                 590

Gly Arg Gln Leu Tyr Glu Thr Gln Pro Val Phe Arg Gln Thr Leu Glu
            595                 600                 605

Gln Cys Glu Gln Ile Leu Gln Pro Tyr Leu Lys Lys Ser Ile Leu Asp
            610                 615                 620

Ile Ile Tyr Pro Glu Asp Asn Gln Lys Leu Asn Ser Ser Ile Ile Asp
625                 630                 635                 640

Gln Thr Ala Tyr Thr Gln Val Ala Leu Phe Ala Ile Glu Tyr Ala Leu
                645                 650                 655

Tyr Lys Leu Trp Glu Ser Trp Gly Ile Lys Pro Asp Val Val Met Gly
                660                 665                 670

His Ser Val Gly Glu Tyr Val Ala Ala Thr Val Ala Gly Ile Phe Ser
                675                 680                 685

Leu Glu Asp Gly Leu Lys Leu Ile Ala His Arg Gly Arg Leu Met Gln
                690                 695                 700

Gln Leu Ser Ser Gly Gly Glu Met Leu Ser Val Met Ala Ser Ile Glu
705                 710                 715                 720

Lys Val Asn Gln Leu Ile Ala Pro Tyr Ser Lys Val Ala Ile Ala
                725                 730                 735

Ser Ile Asn Gly Pro Gln Ser Ile Val Ile Ser Gly Glu Ala Glu Ala
                740                 745                 750

Ile Gly Ala Val Gln Asn Ser Leu Glu Ala Glu Asp Ile Lys Thr Lys
            755                 760                 765
```

-continued

```
Arg Leu Gln Val Ser His Ala Phe His Ser His Leu Met Glu Pro Met
    770                 775                 780

Leu Ala Asp Phe Glu Ala Val Ala Ser Glu Ile Thr Tyr Asn Gln Pro
785                 790                 795                 800

Asn Ile Pro Leu Val Ser Asn Val Thr Gly Ala Arg Ala Glu Asn Ser
            805                 810                 815

Ile Ala Thr Ala Ser Tyr Trp Val Asn His Val Arg Gln Pro Val Lys
        820                 825                 830

Phe Ala Gln Ser Met Asp Thr Leu Gln Gln Glu Gly Tyr Ser Ile Phe
    835                 840                 845

Leu Glu Ile Gly Pro Lys Pro Thr Leu Leu Gly Met Gly Arg Gln Cys
    850                 855                 860

Leu Pro Glu Asp Val Gly Val Trp Leu Pro Ser Leu Arg Pro Gly Gln
865                 870                 875                 880

Glu Asp Trp Gln Gln Met Leu Gln Ser Leu Ala Glu Leu Tyr Val His
                885                 890                 895

Gly Val Lys Val Asp Trp Leu Gly Phe Asp Lys Asp Tyr Ser Arg Ser
            900                 905                 910

Lys Val Val Leu Pro Thr Tyr Pro Phe Gln Arg Gln Arg Tyr Trp Ile
        915                 920                 925

Glu Ser Thr Glu Ser Gln Ser Gln Lys Ala Ala Tyr Ser Ser Cys Glu
    930                 935                 940

Thr Lys Ser Thr Pro Ile Phe Asp Leu Leu Ile His Gly Asn Ile Gln
945                 950                 955                 960

Gln Leu Ala Gln Gln Ile Glu Lys Ile Gly Lys Phe Ser Pro Glu Gln
                965                 970                 975

Val Asn Leu Leu Pro Glu Phe Leu Glu Val Leu Val Lys Gln His Gln
            980                 985                 990

Lys Gln Leu Ile Ile Glu Thr Thr Lys Asp Phe Leu Tyr Gln Val Gln
        995                 1000                1005

Trp Lys Pro Leu Val Asp Thr Gln Pro Lys Thr Ser Ile Lys Pro Ser
    1010                1015                1020

His Trp Leu Ile Phe Ala Asp Thr Thr Ala Val Gly Glu Lys Leu Val
1025                1030                1035                1040

Gln Gln Leu Gln Ser His His Cys Glu Cys Ser Leu Val Tyr Arg Ser
                1045                1050                1055

Asp Cys Tyr Arg Lys Leu Asp Glu Gly Thr Tyr Gln Leu Asn Pro Thr
            1060                1065                1070

Glu Ala Gln Glu Phe Glu Gln Leu Ile Gln Ala Ile Gly Glu Asn Ser
        1075                1080                1085

Lys Leu Pro Leu Leu His Val Ile Asn Leu Trp Ser Leu Asp Ile Gln
    1090                1095                1100

Gly Thr Gln Asp Leu Thr Thr Thr Thr Leu Lys Gln Ala Gln Leu Trp
1105                1110                1115                1120

Gly Cys Gly Thr Val Leu Gln Leu Val Lys Val Leu Thr Lys Thr Lys
                1125                1130                1135

Ser Val Ala Lys Leu Trp Leu Val Thr Arg Gly Ala Gln Leu Val Lys
            1140                1145                1150

Ser Gln Thr Glu Ser Val Cys Val Ala Ala Ser Pro Leu Trp Gly Met
        1155                1160                1165

Gly Arg Val Ile Ser Leu Glu His Pro Gln Leu Trp Gly Gly Met Val
    1170                1175                1180
```

```
Asp Leu Asp Pro Ile Ser Pro Glu Ser Glu Ala Tyr Thr Leu Leu Gln
1185                1190                1195                1200

Leu Leu Val Asn Ser Asn Gln Leu Glu Asp His Leu Ala Leu Arg Ala
            1205                1210                1215

Asp Asn Leu Tyr Phe Ala Arg Leu Val Lys Gln Ser Leu Lys Pro Tyr
        1220                1225                1230

Asp Ser Val Ser Leu Lys Asp Asn Ala Thr Tyr Leu Ile Thr Gly Gly
    1235                1240                1245

Leu Gly Ala Leu Gly Leu His Thr Ala Arg Trp Met Val Gln Gln Gly
1250                1255                1260

Ala Arg His Leu Val Leu Thr Gly Arg Lys Gln Pro Asn Leu Glu Ala
1265                1270                1275                1280

Gln Gln Ile Ile Glu Glu Leu Gln Lys Leu Gly Ala Gln Ile Leu Val
                1285                1290                1295

Leu Cys Gly Asp Ile Ser Asp Glu Val Asp Ala Thr Thr Ile Phe Ser
            1300                1305                1310

Glu Ile Glu Ala Ser Leu Pro Thr Leu Lys Gly Val Ile Asn Ala Ala
        1315                1320                1325

Gly Val Leu Asp Asp Ala Leu Leu His Ser Met Ser Trp Glu Gln Phe
    1330                1335                1340

Thr Gln Val Met Ala Pro Lys Val Gln Gly Ala Trp His Leu His Asn
1345                1350                1355                1360

Leu Thr Gln Asn Lys Ala Leu Asp Phe Phe Val Cys Phe Ser Ser Met
                1365                1370                1375

Ala Ser Leu Val Gly Ser Pro Gly Gln Gly Asn Tyr Ala Ala Ala Asn
            1380                1385                1390

Ala Phe Met Asp Ala Leu Ala His His Arg Arg Gly Met Gly Leu Pro
        1395                1400                1405

Gly Leu Ser Ile Asn Trp Gly Pro Trp Ala Gln Ala Gly Met Ala Ala
    1410                1415                1420

Ser Leu Asp Asn Arg Asn Arg Asp Arg Met Val Ala Ser Gly Ile Thr
1425                1430                1435                1440

Pro Leu Thr Pro Glu Gln Gly Leu Gln Val Leu Gly Gln Leu Leu Glu
                1445                1450                1455

Gln Ser Leu Pro Gln Val Gly Val Leu Ser Val Gln Trp Ser Val Phe
            1460                1465                1470

Gln Glu Lys Phe Ser Phe Gly Asn Gln Ile Pro Leu Leu Glu Leu
        1475                1480                1485

Leu Gly Glu Thr Glu Ser Gln Gln Lys Ala Phe Arg Thr Lys Thr Lys
    1490                1495                1500

Gln Asn Glu Leu Leu Lys Arg Leu Glu Ser Leu Pro Cys Lys Glu Arg
1505                1510                1515                1520

Tyr Tyr Val Leu Arg Thr Glu Ile Gln Ser Glu Val Ala Lys Val Leu
                1525                1530                1535

Ala Leu Asn Asp Ser Gln Leu Pro Gly Phe Glu Gln Gly Phe Phe Asp
            1540                1545                1550

Leu Gly Met Asp Ser Leu Met Ala Val Glu Leu Arg Asn Arg Ile Thr
        1555                1560                1565

Gln Leu Leu Lys Val Thr Leu Pro Ser Thr Leu Ser Phe Asp Phe Pro
    1570                1575                1580

Asn Ile Glu Gln Leu Thr Lys Tyr Ile Ser Ser Gln Ile Leu Asp Leu
1585                1590                1595                1600
```

-continued

```
Ser Thr Ser Asn Asp Gly Gln Gln Pro Glu Gln Lys Val Lys Ala Ala
            1605                1610                1615
Glu His Glu Pro Ile Ala Ile Ile Gly Met Gly Cys Ser Leu Pro Gly
            1620                1625                1630
Gly Ala Asn Thr Pro Glu Lys Phe Trp Glu Leu Leu His Ser Gly Thr
            1635                1640                1645
Ser Ala Arg Glu Glu Ile Pro Ala Gln Arg Trp Asp Val Asn Ser Tyr
            1650                1655                1660
Tyr Asp Pro Asp Arg Glu Ala Ala Gly Lys Met Val Thr Arg Tyr Gly
1665                1670                1675                1680
His Phe Ile Ser Gly Val Asp Gln Phe Asp Pro Glu Phe Phe Gly Ile
                1685                1690                1695
Ser Pro Arg Glu Ala Thr Ala Met Asp Pro Gln His Arg Leu Leu Leu
            1700                1705                1710
Glu Val Ser Trp Gln Ala Leu Glu Arg Ala Gly Gln Lys Val Glu Arg
            1715                1720                1725
Leu Ser Ser Glu Pro Val Gly Val Phe Val Gly Asn Asp Gly His Asp
            1730                1735                1740
Tyr Glu Gln Leu Met Gln Lys His Leu Glu Gln Glu Pro Asn Ser Thr
1745                1750                1755                1760
Phe Gly Thr Tyr Thr Cys Thr Gly Asn Ser Pro Ser Ser Ala Ser Gly
                1765                1770                1775
Arg Leu Ala Tyr Thr Phe Gly Phe Thr Gly Pro Thr Val Thr Ile Asp
            1780                1785                1790
Thr Ala Cys Ser Ser Ser Leu Val Ala Ile His Gln Ala Cys Asn Ser
            1795                1800                1805
Ile Arg Leu Gly Glu Cys Gln Met Ala Ile Ala Gly Gly Val Lys Leu
            1810                1815                1820
His Leu Thr Pro Ser Ser Tyr Ile Phe Thr Ser Arg Ala Gly Met Ile
1825                1830                1835                1840
Ser Pro Asp Gly Leu Cys Lys Thr Phe Asp Ile Ser Ala Asp Gly Tyr
            1845                1850                1855
Gly Arg Gly Glu Gly Cys Gly Met Val Val Leu Lys Ser Leu Ser Gln
            1860                1865                1870
Ala Gln Ala Asp Gly Asp Pro Ile Leu Ala Leu Ile Leu Gly Ser Ala
            1875                1880                1885
Val Asn Gln Asp Gly Pro Ser Ser Gly Leu Thr Val Pro Asn Gly Gln
            1890                1895                1900
Ser Gln Gln Lys Leu Ile Leu Gln Ala Leu Lys Gln Ala Arg Val Glu
1905                1910                1915                1920
Pro Ala Asp Ile Ser Tyr Leu Glu Ala His Gly Thr Gly Thr Ser Leu
            1925                1930                1935
Gly Asp Pro Ile Glu Val Asn Ala Ala Ala Val Leu Gly Leu Gln
            1940                1945                1950
Arg Ser Pro Ser Gln Pro Leu Trp Ile Gly Thr Val Lys Thr Asn Ile
            1955                1960                1965
Gly His Leu Glu Ser Ala Ala Gly Val Ser Gly Leu Ile Lys Val Val
            1970                1975                1980
Leu Ser Leu Gln His Gln Gln Ile Pro Ala Asn Leu His Leu Gln Glu
1985                1990                1995                2000
Pro Asn Pro Lys Ile Asp Trp Gln Pro Trp Leu Gln Val Pro Gln Ala
            2005                2010                2015
```

-continued

Leu Thr Pro Trp Val Gly Ser Lys Gly Arg Leu Ala Gly Val Ser Ser
         2020                2025                2030

Phe Gly Phe Thr Gly Thr Asn Ala His Val Val Leu Ser Glu Thr Pro
         2035                2040            2045

Ala Ala Ile Ala Ser Ser Thr Val Glu Tyr Glu Arg Pro Leu His Leu
         2050                2055            2060

Leu Gln Leu Ser Ala Lys Asn Asp Leu Ala Leu Ala Gln Leu Ala Gln
2065            2070                2075                2080

Arg Tyr Ser Asp His Leu Lys Thr His Leu Glu Gln Asp Leu Arg Asp
             2085                2090                2095

Ile Cys Phe Thr Ala Asn Ser Ser Arg Leu Ala His Lys His Arg Leu
             2100                2105                2110

Ala Val Val Ala Ser Asn Arg Lys Glu Leu Gln Gln Lys Leu Gly Asn
         2115                2120            2125

Phe Gly Thr Asp Ser Glu Arg Met Asp Leu Val Thr Gly Gln Val Ser
         2130                2135            2140

Ser Ser Gln Leu Thr Lys Val Ala Met Leu Phe Thr Gly Gln Gly Ser
2145            2150                2155                2160

Gln Tyr Val Gly Met Gly Arg Gln Leu Tyr Gln Thr Gln Pro Thr Phe
             2165                2170                2175

Lys Gln Phe Val Asp Gln Cys Ala Gln Ile Leu Glu Asn Tyr Leu Asp
             2180                2185                2190

Lys Pro Leu Leu Glu Ile Leu Asp Val Ala Gln Val Gln Glu Asn Val
         2195                2200            2205

Leu Ala Gln Thr Ala Tyr Thr Gln Val Ala Leu Phe Ala Ile Glu Tyr
         2210                2215            2220

Ala Leu Tyr Lys Leu Trp Glu Ser Trp Gly Ile Lys Pro Asp Val Val
2225            2230                2235                2240

Met Gly His Ser Ala Gly Glu Tyr Val Ala Ala Thr Val Ala Gly Ile
             2245                2250                2255

Phe Ser Leu Glu Asp Gly Leu Lys Leu Ile Ala His Arg Gly Arg Leu
             2260                2265                2270

Met Gln Gln Leu Pro Ser Gly Gly Glu Met Leu Ser Val Met Ala Ser
             2275                2280                2285

Ile Glu Lys Val Asn Gln Leu Ile Ala Pro Tyr Ser Gln Lys Val Ala
         2290                2295            2300

Ile Ala Ser Ile Asn Gly Pro Gln Ser Ile Val Ile Ser Gly Glu Ala
2305            2310                2315                2320

Glu Ala Ile Gly Ala Val Gln Asn Ser Leu Glu Ala Glu Asp Ile Lys
             2325                2330                2335

Thr Lys Arg Leu Gln Val Ser His Ala Phe His Ser His Leu Met Glu
             2340                2345                2350

Pro Met Leu Ala Asp Phe Glu Ala Val Ala Ser Glu Ile Thr Tyr Asn
             2355                2360                2365

Gln Pro Asn Ile Pro Leu Val Ser Asn Val Thr Gly Ala Arg Ala Glu
         2370                2375            2380

Asn Ser Ile Ala Thr Ala Ser Tyr Trp Val Asn His Val Arg Gln Pro
2385            2390                2395                2400

Val Lys Phe Ala Gln Ser Met Asp Thr Leu Gln Gln Glu Gly Tyr Ser
             2405                2410                2415

Ile Phe Leu Glu Ile Gly Pro Lys Pro Thr Leu Leu Gly Met Gly Arg
             2420                2425                2430

```
Gln Cys Leu Pro Glu Asp Val Gly Val Trp Leu Pro Ser Leu Lys Pro
        2435                2440                2445

Gly Gln Glu Asp Trp Gln Gln Met Leu Gln Ser Leu Ala Glu Leu Tyr
        2450                2455                2460

Val His Gly Val Lys Val Asp Trp Leu Gly Phe Asp Lys Asp Tyr Ser
2465                2470                2475                2480

Arg Ser Lys Val Val Leu Pro Thr Tyr Pro Phe Gln Arg Gln Arg Tyr
        2485                2490                2495

Trp Ile Glu Thr Asn Asn Asn Leu Ile His Gln Lys Gln Phe Leu Ser
        2500                2505                2510

Asn His Lys Asn Leu His Pro Leu Leu Gly Gln Arg Leu His Leu Ala
        2515                2520                2525

Ala Leu Glu Gln Gln Ile Arg Phe Glu Cys Gln Ile Ser Ala Ser Gln
        2530                2535                2540

Pro Thr Tyr Leu Gln His His Cys Val Phe Ser Gln Pro Val Phe Pro
2545                2550                2555                2560

Ala Ala Ala Tyr Leu Glu Ile Ala Leu Ala Ala Gly Ser Ile Leu Phe
        2565                2570                2575

Asn Ser Asp Asp Leu Ile Leu Glu Asp Ile Ala Ile Gln Lys Val Leu
        2580                2585                2590

Ile Leu Ser Lys Asp Glu Ile Asn Thr Ile Gln Ile Val Leu Asn Leu
        2595                2600                2605

Gln Leu Val Gln Ser Tyr Lys Phe Gln Ile Phe Ser Leu Asp Ile Asn
        2610                2615                2620

Thr Asn Ser Ser Glu Pro Lys Trp Ile Leu His Ile Glu Gly Lys Ile
2625                2630                2635                2640

Leu Val Gly Asn Lys Asp Pro Gln Leu Glu Thr Thr Asn Leu Lys Ala
        2645                2650                2655

Ile Lys Asp Glu Tyr Asn Gln Gln Ile Leu Pro Thr Glu Phe Tyr Gln
        2660                2665                2670

Lys Phe Glu Glu Trp Gly Leu Asn Tyr Gly Ser Ser Phe Gln Ala Val
        2675                2680                2685

Lys Gln Leu Trp His Ser Glu Gly Lys Ala Leu Gly Glu Ile Gln Leu
        2690                2695                2700

Pro Glu Thr Glu Val Asn Val Ala Thr Leu Tyr Gln Leu His Pro Ile
2705                2710                2715                2720

Leu Leu Asp Ala Ser Phe Gln Val Leu Ala Ala Val Met Gly Lys Thr
        2725                2730                2735

Asp Asn Gln Glu Thr Tyr Leu Pro Leu Glu Ile Lys Arg Leu Gln Ile
        2740                2745                2750

Tyr Arg Ser Gly Ser Asn Ser Leu Trp Thr Gln Val Glu Ile Gly Ala
        2755                2760                2765

Thr Glu Thr Asn Lys Gln Thr Leu Ser Gly Lys Val Cys Leu Leu Asp
        2770                2775                2780

Glu Gln Gly Ile Val Val Ala Arg Val Glu Gly Leu Thr Leu Leu Arg
2785                2790                2795                2800

Thr Ser Arg Glu Ala Leu Leu Arg Asn Ile Glu Pro Lys Phe Asn Asn
        2805                2810                2815

Trp Leu Tyr Gln Ile His Trp Gln Thr Gln Ser Ile Ser Pro His Asn
        2820                2825                2830

Gln Ser Ile Asp Leu Thr Lys Ser Gly Ser Trp Leu Leu Phe Ser Pro
        2835                2840                2845
```

-continued

```
Pro Thr Gly Ile Gly Lys His Leu Val Glu Ser Leu Glu Gln Gln Gly
    2850                2855                2860

Trp His Cys Ile Leu Val Thr Pro Gly Glu Asn Tyr Gln Gln Leu Glu
2865                2870                2875                2880

Ser Gln His Tyr Gln Ile Asn Pro Asn His Pro Glu Glu Phe Leu His
                2885                2890                2895

Leu Leu Gln Ser Ser Leu Glu Gln Gln Pro Pro Leu Arg Gly Ile Ile
            2900                2905                2910

His Leu Trp Ser Leu Asp Ser Thr Ile Ala Leu Arg Thr Gly Ala Gln
        2915                2920                2925

Glu Leu Gln Lys Ser Gln Glu Leu Gly Cys Gly Ser Val Leu His Leu
    2930                2935                2940

Val Gln Ala Leu Val Lys Asn Gln Asp Met Glu Ser Ala Pro Leu Trp
2945                2950                2955                2960

Leu Val Thr Gln Gly Ser Gln Ser Val Gly Asn Glu Ser Leu Pro Ile
                2965                2970                2975

Gln Phe Gln Gln Thr Pro Leu Trp Gly Leu Gly Arg Val Ile Ala Gln
            2980                2985                2990

Glu His Arg Glu Leu Gln Cys Arg Cys Leu Asp Leu Asp Pro Thr Met
        2995                3000                3005

Glu Asp Ser Gln Thr Val Ala Ala Leu Leu Glu Glu Leu Leu Ser Pro
    3010                3015                3020

Gly Asp Glu Asn Gln Ile Ala Tyr Cys Gln Gly Val Arg His Val Ala
3025                3030                3035                3040

Arg Leu Glu Arg Gln Gln Lys Met Ser Thr Ser Thr Gln Ser Gly Leu
                3045                3050                3055

Gln Ile Ser Ser Gln Gln Pro Phe Gln Leu Lys Leu Ser Glu Tyr Lys
            3060                3065                3070

Ser Leu Asp Asn Leu Ile Gln Ala Glu Ala Ser Tyr Leu Ile Thr Gly
        3075                3080                3085

Gly Leu Gly Ala Leu Gly Leu Lys Thr Ala Glu Trp Met Val Gln Gln
    3090                3095                3100

Gly Val Lys Tyr Leu Val Leu Thr Gly Arg Arg Gln Pro Ser Ala Lys
3105                3110                3115                3120

Ala Gln Gln Thr Ile Glu Gln Leu Gln Lys Ala Gly Ala Gln Val Leu
                3125                3130                3135

Val Leu Cys Gly Asp Ile Ser Gln Gln Glu Asn Val Ala Arg Ile Ile
            3140                3145                3150

Glu Ser Ile Lys Val Ser Leu Pro Ala Leu Arg Gly Ile Ile His Ala
        3155                3160                3165

Ala Gly Ile Leu Asp Asp Gly Leu Leu Leu Asn Met Asn Trp Glu Lys
    3170                3175                3180

Phe Thr Gln Val Met Ala Pro Lys Val Gln Gly Ala Trp His Leu His
3185                3190                3195                3200

Asn Leu Thr Gln Asn Leu Pro Leu Asp Phe Phe Val Cys Phe Ser Ser
                3205                3210                3215

Met Ala Ser Ile Leu Gly Ser Pro Gly Gln Gly Asn Tyr Ala Ala Ala
            3220                3225                3230

Asn Ala Phe Met Asp Gly Leu Ala His His Arg Arg Gly Met Gly Leu
        3235                3240                3245

Pro Gly Leu Ser Ile Asn Trp Gly Pro Trp Ala Gln Glu Gly Met Ala
    3250                3255                3260
```

-continued

```
Ala Asn Leu Asp Ser Pro His Gln Asp Arg Met Val Ser Lys Gly Met
3265                3270                3275                3280

Thr Phe Leu Ser Ser Glu Gln Gly Leu Gln Val Leu Gly Gln Leu Leu
                3285                3290                3295

Glu Gln Ser Ile Pro Gln Val Gly Val Leu Pro Ile Gln Trp Ser Val
            3300                3305                3310

Phe Gln Glu Gln Phe Ser Phe Gly Asn Gln Ile Pro Leu Leu Ser Gln
        3315                3320                3325

Leu Val Lys Glu Ser Lys Ser Gln Gln Lys Ala Leu Lys Thr Lys Thr
    3330                3335                3340

Lys His Asn Glu Phe Leu Glu Gln Leu Lys Ala Ala Leu Pro Arg Glu
3345                3350                3355                3360

Arg Glu Lys Leu Leu Ile Ile Tyr Ile Lys Asp Glu Ile Ser Gln Val
                3365                3370                3375

Leu Ser Leu Ser Thr Ser Gln Ile Asp Met Gln Gln Pro Leu Asn Thr
            3380                3385                3390

Met Gly Leu Asp Ser Leu Met Ala Val Glu Leu His Asn Arg Leu Gln
        3395                3400                3405

Thr Asp Leu Leu Val Asp Ile Ser Ile Val Lys Phe Ile Glu Asp Ile
    3410                3415                3420

Ser Ile Val Asp Leu Ala Thr Glu Val Asn Glu Gln Leu Ser Gln Val
3425                3430                3435                3440

Ala Gln Asn Gln Gly Val Glu Ser Glu Asn Asn Gly Gln Leu Tyr Gln
                3445                3450                3455

Ser Asn Arg Lys Glu Asn Glu Arg Ile Arg Gly Glu Leu
            3460                3465
```